United States Patent
Voss et al.

(10) Patent No.: US 12,241,081 B2
(45) Date of Patent: Mar. 4, 2025

(54) B CELL RECEPTOR MODIFICATION IN B CELLS

(71) Applicant: The Scripps Research Institute, La Jolla, CA (US)

(72) Inventors: James Even Voss, San Diego, CA (US); Raiees Andrabi, San Diego, CA (US); Dennis R. Burton, La Jolla, CA (US); Deli Huang, La Jolla, CA (US); Alicia Gonzalez-Martin, Madrid (ES)

(73) Assignee: The Scripps Research Institute, La Jolla, CA (US)

( * ) Notice: Subject to any disclaimer, the term of this patent is extended or adjusted under 35 U.S.C. 154(b) by 1081 days.

(21) Appl. No.: 16/642,810

(22) PCT Filed: Aug. 3, 2018

(86) PCT No.: PCT/US2018/045255
§ 371 (c)(1),
(2) Date: Feb. 27, 2020

(87) PCT Pub. No.: WO2019/028417
PCT Pub. Date: Feb. 7, 2019

(65) Prior Publication Data
US 2023/0060376 A1 Mar. 2, 2023

Related U.S. Application Data

(60) Provisional application No. 62/540,702, filed on Aug. 3, 2017.

(51) Int. Cl.
| | |
|---|---|
| *C12N 15/90* | (2006.01) |
| *C07K 16/10* | (2006.01) |
| *C12N 9/22* | (2006.01) |
| *C12N 15/11* | (2006.01) |
| *C12N 15/63* | (2006.01) |

(52) U.S. Cl.
CPC ........ *C12N 15/907* (2013.01); *C07K 16/1045* (2013.01); *C12N 9/22* (2013.01); *C12N 15/11* (2013.01); *C12N 15/63* (2013.01); *C07K 2317/76* (2013.01); *C12N 2310/20* (2017.05); *C12N 2800/80* (2013.01)

(58) Field of Classification Search
CPC ........ C12N 15/907; C12N 9/22; C12N 15/11; C12N 2310/20; C12N 2800/80; C12N 15/63; C07K 16/1045; C07K 2317/76; Y02A 50/30
See application file for complete search history.

(56) References Cited

U.S. PATENT DOCUMENTS 5,204,244 A 4/1993 Fell et al.
2016/0289637 A1* 10/2016 Goldberg ............. C12N 15/102

FOREIGN PATENT DOCUMENTS

WO WO-2012079000 A1 6/2012

OTHER PUBLICATIONS

Andrabi R, Voss JE, Liang CH, Briney B, McCoy LE, Wu CY, Wong CH, Poignard P, Burton DR. Identification of Common Features in Prototype Broadly Neutralizing Antibodies to HIV Envelope V2 Apex to Facilitate Vaccine Design. Immunity. Nov. 17, 2015;43(5):959-73. (Year: 2015).*
McConnell AD, Do M, Neben TY, Spasojevic V, MacLaren J, Chen AP, Altobell L 3rd, Macomber JL, Berkebile AD, Horlick RA, Bowers PM, King DJ. High affinity humanized antibodies without making hybridomas; immunization paired with mammalian cell display and in vitro somatic hypermutation. PLoS One.7(11). (Year: 2012).*
Huang D et al. Vaccine elicitation of HIV broadly neutralizing antibodies from engineered B cells. Nat Commun. Nov. 17, 2020;11(1):5850. doi: 10.1038/s41467-020-19650-8. Erratum in: Nat Commun. Dec. 7, 2020;11(1):6360. PMID: 33203876; PMCID: PMC7673113. (Year: 2020).*
Moffett HF, Harms CK, Fitzpatrick KS, Tooley MR, Boonyaratanakornkit J, Taylor JJ. B cells engineered to express pathogen-specific antibodies protect against infection. Sci Immunol. May 17, 2019;4(35):eaax0644. doi: 10.1126/sciimmunol.aax0644. PMID: 31101673; PMCID: PMC6913193. (Year: 2019).*
Peptide Definition. Scitable by Nature Education. https://www.nature.com/scitable, accessed May 9, 2024 (Year: 2014).*
Andrabi, R. et al. (2015). Identification of common features in prototype broadly neutralizing antibodies to HIV envelope V2 apex to facilitate vaccine design. *Immunity*, 43(5), 959-973.
Baughn, L. B. et al. (2011). Recombinase-mediated cassette exchange as a novel method to study somatic hypermutation in Ramos cells. *MBio*, 2(5), 10-1128.
Borchert, G. M. et al. (2010). Histone H2A and H2B are monoubiquitinated at AID-targeted loci. *PloS One*, 5(7), e11641.
Briney, B. et al. (2016). Tailored immunogens direct affinity maturation toward HIV neutralizing antibodies. *Cell*, 166(6), 1459-1470.
Carsetti, R. et al. (1995). Transitional B cells are the target of negative selection in the B cell compartment. *The Journal of Experimental Medicine*, 181(6), 2129-2140.
Decamp, A. et al. (2014). Global panel of HIV-1 Env reference strains for standardized assessments of vaccine-elicited neutralizing antibodies. *Journal of Virology*, 88(5), 2489-2507.
Dewitt, M. A. et al. (2016). Selection-free genome editing of the sickle mutation in human adult hematopoietic stem/progenitor cells. *Science Translational Medicine*, 8(360), 360ra134-360ra134.

(Continued)

*Primary Examiner* — Hong Sang
*Assistant Examiner* — Carol Ann Chase
(74) *Attorney, Agent, or Firm* — Mark S. Cohen; PEARL COHEN ZEDEK LATZER BARATZ LLP

(57) ABSTRACT

Methods and systems are described herein for generating engineered B cells with modified immunoglobulin genes. The modified immunoglobulin genes encode modified immunoglobulins that can have high affinity for antigens, including antigens that are variable such the types of antigens on various pathogens that can escape mammalian immune responses.

16 Claims, 48 Drawing Sheets

Specification includes a Sequence Listing.

(56) References Cited

OTHER PUBLICATIONS

Doudna, J. A. et al. (2014). The new frontier of genome engineering with CRISPR-Cas9. *Science*, 346(6213), 1258096.
Ebert, A. et al. (2015). Spatial regulation of V-(D) J recombination at antigen receptor loci. *Advances in Immunology*, 128, 93-121.
Escolano, A. et al. (2016). Sequential immunization elicits broadly neutralizing anti-HIV-1 antibodies in Ig knockin mice. *Cell*, 166(6), 1445-1458.
Feige, M. J. et al. (2010). How antibodies fold. *Trends in Biochemical Sciences*, 35(4), 189-198.
Ford, G. S. et al. (1998). CD40 ligand exerts differential effects on the expression of Iγ transcripts in subclones of an IgM+ human B cell lymphoma line. *The Journal of Immunology*, 160(2), 595-605.
Giudicelli, V. et al. (2005). IMGT/GENE-DB: a comprehensive database for human and mouse immunoglobulin and T cell receptor genes. *Nucleic Acids Research*, 33(suppl_1), D256-D261.
Goodnow, C. C. et al. (1989). Induction of self-tolerance in mature peripheral B lymphocytes. *Nature*, 342(6248), 385-391.
Heydarchi, B. et al. (2016). Broad neutralizing antibodies to HIV env and other complex viral antigens from vaccinated cows. *Journal of Vaccines & Vaccination*, 7, 347.
International Search Report and Written Opinion of the International Searching Authority dated Nov. 29, 2018, issued for the corresponding International Patent Application No. PCT/US2018/045255, dated Aug. 3, 2018.
Jinek, M. et al. (2012). A programmable dual-RNA-guided DNA endonuclease in adaptive bacterial immunity. *Science*, 337(6096), 816-821.
Julien, J. P. et al. (2013). Asymmetric recognition of the HIV-1 trimer by broadly neutralizing antibody PG9. *Proceedings of the National Academy of Sciences*, 110(11), 4351-4356.
June, C. H. et al. (2009). Engineering lymphocyte subsets: tools, trials and tribulations. *Nature Reviews Immunology*, 9(10), 704-716.
Jung, D. et al. (2006). Mechanism and control of V (D) J recombination at the immunoglobulin heavy chain locus. *Annu. Rev. Immunol.*, 24, 541-570.
Karlsson Hedestam, G. B. et al. (2008). The challenges of eliciting neutralizing antibodies to HIV-1 and to influenza virus. *Nature Reviews Microbiology*, 6(2), 143-155.
Kato, T. et al. (2017). Creation of mutant mice with megabase-sized deletions containing custom-designed breakpoints by means of the CRISPR/Cas9 system. *Scientific Reports*, 7(1), 59.
Kepler, T. B. et al. (2017). Genetic and structural analyses of affinity maturation in the humoral response to HIV-1. *Immunological Reviews*, 275(1), 129-144.
Kleinstiver, B. P. et al. (2015). Broadening the targeting range of *Staphylococcus aureus* CRISPR-Cas9 by modifying PAM recognition. *Nature Biotechnology*, 33(12), 1293-1298.
Kleinstiver, B. P. et al. (2015). Engineered CRISPR-Cas9 nucleases with altered PAM specificities. *Nature*, 523(7561), 481-485.
Lee, J. H. et al. (2017). A broadly neutralizing antibody targets the dynamic HIV envelope trimer apex via a long, rigidified, and anionic β-hairpin structure. *Immunity*, 46(4), 690-702.
Lefranc, M. P. et al. (2015). IMGT®, the international ImMunoGeneTics information system® 25 years on. *Nucleic Acids Research*, 43(D1), D413-D422.
Lim, W. A. et al. (2017). The principles of engineering immune cells to treat cancer. *Cell*, 168(4), 724-740.
Masella, A. P. et al. (2012). PANDAseq: paired-end assembler for illumina sequences. *BMC Bioinformatics*, 13, 1-7.
Mashiko, D. et al. (2013). Generation of mutant mice by pronuclear injection of circular plasmid expressing Cas9 and single guided RNA. *Scientific Reports*, 3(1), 3355.
McCoy, L. E. et al. (2016). Holes in the glycan shield of the native HIV envelope are a target of trimer-elicited neutralizing antibodies. *Cell Reports*, 16(9), 2327-2338.
McLellan, J. S. et al. (2011). Structure of HIV-1 gp120 V1/V2 domain with broadly neutralizing antibody PG9. *Nature*, 480(7377), 336-343.
Montefiori, L. et al. (2016). Extremely long-range chromatin loops link topological domains to facilitate a diverse antibody repertoire. *Cell Reports*, 14(4), 896-906.
Owens, G. C. et al. (2001). Identification of two short internal ribosome entry sites selected from libraries of random oligonucleotides. *Proceedings of the National Academy of Sciences*, 98(4), 1471-1476.
Pejchal, R. et al. (2010). Structure and function of broadly reactive antibody PG16 reveal an H3 subdomain that mediates potent neutralization of HIV-1. *Proceedings of the National Academy of Sciences*, 107(25), 11483-11488.
Porteus, M. (2016). Genome editing: a new approach to human therapeutics. *Annual Review of Pharmacology and Toxicology*, 56, 163-190.
Prospec, Protein Specialists (Oct. 29, 2023). IL 4 Human, CHO (Interleukin-4 Human Recombinant, CHO)—CYT-271; Retrieved online at URL: https://www.prospecbio.com/il-4_human_cho.
Prospec, Protein Specialists (Oct. 29, 2023). sCD40L Human (Soluble CD-40 Ligand/TRAP Human Recombinant)—CYT-245; Retrieved online at URL: https://www.prospecbio.com/cd40_human.
Qi, L. S. et al. (2013). Repurposing CRISPR as an RNA-guided platform for sequence-specific control of gene expression. *Cell*, 152(5), 1173-1183.
Ran, F. A. et al. (2013). Genome engineering using the CRISPR-Cas9 system. *Nature Protocols*, 8(11), 2281-2308.
Ran, F. A. et al. (2015). In vivo genome editing using *Staphylococcus aureus* Cas9. *Nature*, 520(7546), 186-191.
Russell, D. M. et al. (1991). Peripheral deletion of self-reactive B cells. *Nature*, 354(6351), 308-311.
Ryan, J. L. et al. (2006). Clonal evolution of lymphoblastoid cell lines. *Laboratory Investigation*, 86(11), 1193-1200.
Sale, J. E. et al. (1998). TdT-accessible breaks are scattered over the immunoglobulin V domain in a constitutively hypermutating B cell line. *Immunity*, 9(6), 859-869.
Schumann, K. et al. (2015). Generation of knock-in primary human T cells using Cas9 ribonucleoproteins. *Proceedings of the National Academy of Sciences*, 112(33), 10437-10442.
Schwank, G. et al. (2013). Functional repair of CFTR by CRISPR/Cas9 in intestinal stem cell organoids of cystic fibrosis patients. *Cell Stem Cell*, 13(6), 653-658.
Seaman, M. S. et al. (2010). Tiered categorization of a diverse panel of HIV-1 Env pseudoviruses for assessment of neutralizing antibodies. *Journal of Virology*, 84(3), 1439-1452.
Shaw, K. L. et al. (2017). Clinical efficacy of gene-modified stem cells in adenosine deaminase-deficient immunodeficiency. *The Journal of Clinical Investigation*, 127(5), 1689-1699.
Sok, D. et al. (2016). Priming HIV-1 broadly neutralizing antibody precursors in human Ig loci transgenic mice. *Science*, 353(6307), 1557-1560.
Sok, D. et al. (2017). Rapid elicitation of broadly neutralizing antibodies to HIV by immunization in cows. *Nature*, 548(7665), 108-111.
Sui, J. et al. (2009). Structural and functional bases for broad-spectrum neutralization of avian and human influenza A viruses. *Nature Structural & Molecular Biology*, 16(3), 265-273.
Szeto, G. L. et al. (2015). Microfluidic squeezing for intracellular antigen loading in polyclonal B-cells as cellular vaccines. *Scientific Reports*, 5(1), 10276.
Voss, J. E. et al. (2017). Elicitation of neutralizing antibodies targeting the V2 apex of the HIV envelope trimer in a wild-type animal model. *Cell Reports*, 21(1), 222-235.
Voss, J. E. et al. (2019). Reprogramming the antigen specificity of B cells using genome-editing technologies. *eLife*, 8, e42995.
Walker, L. M. et al. (2011). Broad neutralization coverage of HIV by multiple highly potent antibodies. *Nature*, 477(7365), 466-470.
Wang, C. X. et al. (2016). Clinical applications of genome editing to HIV cure. *AIDS Patient Care and STDs*, 30(12), 539-544.
Watson, C. T. et al. (2012). The immunoglobulin heavy chain locus: genetic variation, missing data, and implications for human disease. *Genes & Immunity*, 13(5), 363-373.

(56) References Cited

OTHER PUBLICATIONS

Zetsche, B. et al. (2015). Cpf1 is a single RNA-guided endonuclease of a class 2 CRISPR-Cas system. *Cell*, 163(3), 759-771.

* cited by examiner

FIG. 2A

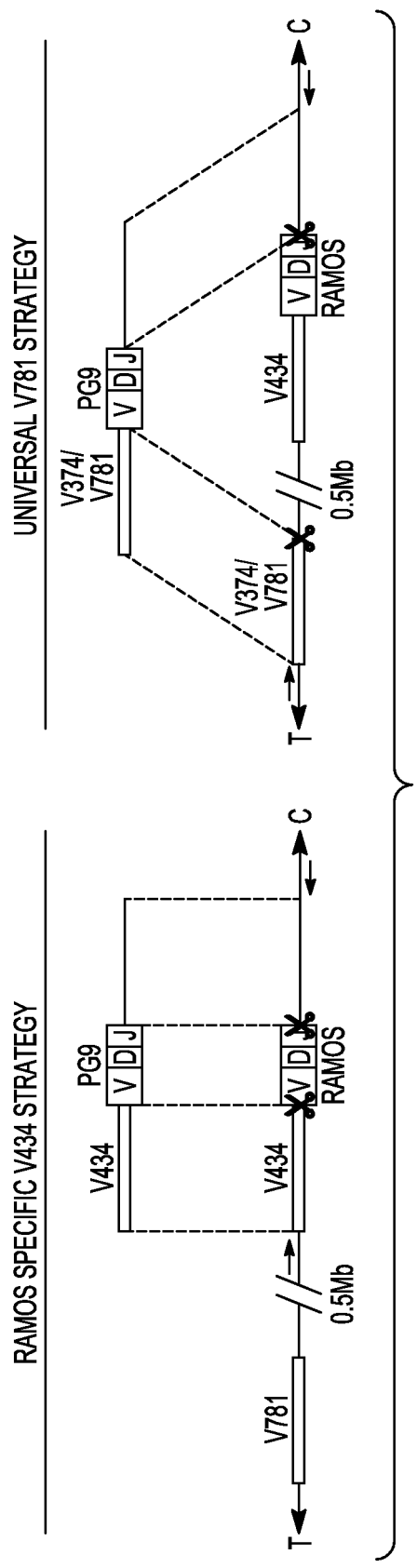
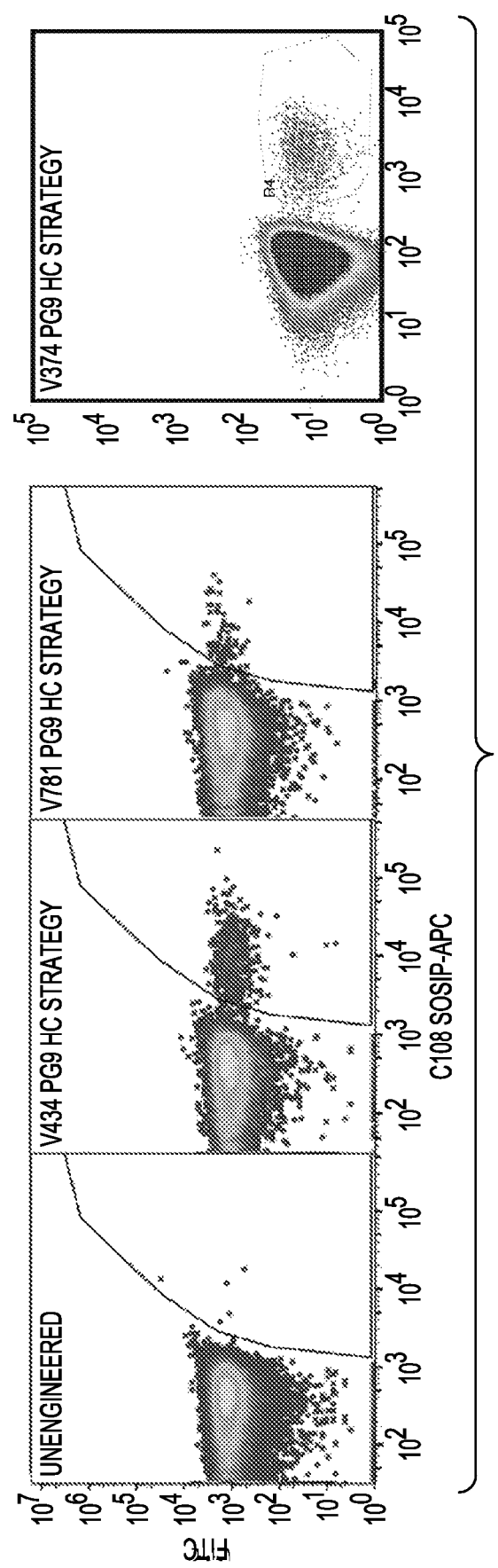
FIG. 3A
FIG. 3B

FIG. 3J-1

```
CCTACCTGGAAGAAGAGGACTCTGGGTTTGGTGTGAGGGAGGCCACAGGAAGAGAACTGAGTTCTCAGAGGGCAC
AGCCAGCATACACCTCCCAGGGTGAGCCCAAAGACTGGGCCTCCCTCATCCCTTTTACCTATCCATACAAAGG
CACCACCCACACATGCAAATCCTCACTTAGCCACCACAGGAAATGACTACACATTTCCTTAAATTCAGGGTCCAGCT
CACATGGGAAGTGCTTTCTGAGAGTCATGAGTGTCTCAGGACCTGTCATGAAACACCTGGTTCTTCCTCCTCCT
GGTGGCAGCTCCCAGATGTGAGTGTCTCAGGGGTCCCTGTGCAGGGTACAGCAGTCCAGGGCCTCTGATCCCAGGGC
TCACTGTGGGTTTCTGTTCACAGGACCCCTGTCCCCTACCTGCGGTGTTATGTGGGAAATCAATCATAGTGTTGAAG
CCTTCGGAGACCCTGTCCCCTACCTGCGGTGTTATGTGGGAAATCAATCATAGTGAAGCACCAACTACAACCCGTCCCTC
AGCCCCCAGGGAAGGGCTGAGTGGATTGGGAAATCAATCATAGTGAAGCACCAACTACAACCCGTCCCTC
AAGAGTCGAGTCACCATATCAGTAGACACGTCCAAGAAGCAGCTCTCCCTGAAGTTGAGCTCTGTGAACGCCGCG
GACACGGCTGTGTATTACTGTGCGAGAGTTATTACTAGGGCGAGTCCTGGCACAGAGGAGGTACGGTATGGAC
GTCTGGGGCCAAGGGACCACGGTCACCGTCTCCTCAGGTGAGAATGGCCACTCTAGGGCCTCTGTTCTCTGCTAC
TGCCTGTGGGGTTTCCTGAGCATTGCAGGTTGGTCCTCGGGGGACCATGTTCCGAGGGGACCTGGGCCAG
GAGGGACGGGCACTGGGTGCCTTGAGTGATGGCCCTGAGTAACTGAGCCTGTGTCTGGGGAGCCACATTTGGACGAGATGCCTGAACA
TCAGGTTGGGGTGCCTCTAGTGATGATGGCTCTGAGGAGTAACTGAGCCTGTGTCTGGGGAGCCACATTTGGACGAGATGCCTGAACA
AACCAGGGGTCTTAGTGATGATGGCTCTGAGGAGTAACTGAGCCTGTGTCTGGGGAGCCACATTTGGACGAGATGCCTGAACA
CAGGAATCGTGAAATATTTCTTTAGAATTACGAGTGCGCTGTGTGTCAACCTGCATCTTAAATTCTTATTGGCT
GGAAAGAGAACTGTCGGAGTGGGGTGAATCCAGGAGGGACGCGTAGCCCGGTTCTTGATGAGAGCAGGGTT
GGGGGCAGGGTAGCAGGGCCCAGAAACGGTGGCTGCCTCCTGACAGGGGCATGCTTACTGTTAAAGACAGGATATGTTTG
CTTGAAGCTGGTTTCCATGAGAAGAAAATGTTAAGAGAATTGTTTATCTTAGGAGGCATGCTTACTGTTAAAGACAGGATATGTTTG
AAGTGGCTTCTGAGATATTTGAAATTCTTATCATTGATTAACACCATGAGTAGTGATATGTGTCTGGAATTGTCTGGAAGCCAAAGCA
ACTGTCCAAGTAGTAAGAAATACTAGCACAGTGCTGTCGGCCCGATGCTGTTTGACCATCATAAATCAAGTT
AGCTCAGTGGCTAAGAAATACTAGCACAGTGCTGTCGGCCCGATGCTGTTTGACCATCATAAATCAAGTT
TATTTTTAATTAATTGAGCAAGCTGGAAGCTGGAAGCAGATGAATTAGAGTCTATTTTAGGAAGCAAAAACACACATTGGTAAAT
CACCCACAGCAGGTGGCAGGAAGCAGGTCACCGCGAGAGTCTATTTTAGGAAGCAAAAACACACATTGGTAAAT
TTATCACTTCTGGTTGTGAAGAGGTGTTTTGCCCAGGCCCAGATCTGAAAGTGCTCTACTGAGCAAAACAACACC
TGGACAATTTGCGTTTCTAAAATAAGGCGAGGCTGAAACTGAAAAGGCTTTTTAACTATCTGAATTTCATT
TCCAATCTTAGCTTATCAACTGCTAGTTTGTGCAAACAGCATATCAACTTCTAAACTGCATTCATTTTTAAAGTAAGA
```

FIG. 3J-2

TGTTTAAGAAATTAAACAGTCTTAGGGAGAGTTTATGACTGTATTCAAAAAGTTTTAAATTAGCTTGTTATCCCTT
CATGTGATAACTCAAATCTCAAATACTTTTCGATACCTCAGAGACATTATTTTCATAATGACTGTGTTCACAATCTTTTA
GGTTAACTCGTTTTCTCTTGATTAAGGAGAAACACTTTGATATTCTGATAGAGTGGCCTTCATTTAGTATTTTC
AAGACCACTTTTCAACTACTCACTTTAGGATAAGTTTTAGGTAAAATGTGCATCATTATCCTGAATTATTTCAGTTAA
GCATGTTAGTTGGTGGCATAAGAGAAAACTCAATCAGATAGTGCTGAAGACAGGACTGTGGAGACACCTTAGAAG
GACAGAGATTCTGTTCCGAATCACCGATGCGGGCGTCAGCAGGACTGGCCTAGCGGAGGCTCTGGGAGGGTGGCTGC
CAGGCCCGGCCCTGGGCTTTGGGTCTCCCCGACTACCCAGAGCTGGGATGCGTGGCTTCTGCCGGGCGACT
GGCTGCTCAGGCCCCAGCCCTGGTGAATGACTTGGAGGAATGATTCCATGCCAAAGCTTTGCAAGGCTCGCAGT
GACCATGCGCCCGACATGGTAAGAGACAGGCCGCCGCTGCTGCATTTGCTTCTCTCTTAAAACTTTGTATTTGAC
GTCTTATTTCCACTAGAAGGGGAACTGGTCTTAATTGCTT (SEQ ID NO:161)

FIG. 3J-3

TGGCTCCAGGCATTTTAAATTCAACAGGTTATGTAACCAGGCTTTAAATTGCACATCTCTCGTGTTACCTTCATGAC
ACAGTCAACTCCATTATGTAAGAAATGGTGAGTGCATTCCCAAGGGTCTTGCACAGTTATAAAAATAGACTTGAT
GAGGTGAGGAGTTGTTTAAATTCCCCTCGAAGAAGCAGCATCAAACCAACCACTCTCTTCCCTCTGTGACT
AGAGCTCTGTCACAGGCCACATGGACCTAAATCCTTGATGGAGATTACAGGACTACGTAAATTGGACTGATCGTTT
TTATGCTGTGTTAAATTAATAGGTGAGTCTGCACTCCCAGCCTTTGACATTTCGGATAATAATATTTCATAAACCGAATTAATTATACCCACATT
AAGATAAATTAATAGATACTGACTTTGACATTTCGGATAATAATATTTCATAAACCGAATTAATTATACCCACATT
GTTACCTACACCTTCACTGAAAAGTTCCTAGTTATGTTGAGTTCCATCAACACTCCACATGTTCAAATCTGGACATC
CAAGAGAGTCTAGAGAATAAAACGCAATGAGGGCAGTGAAACTTGCGTATATTCAGCACCTCTTAACTCAGGAGG
ACTCAATACACCCTGGAACACTCTGCTTTCTGAATGGCTCACAAATGACTCCAGCTCACTCTCCAACCTCCTCAAAC
ATCTGGCCTCTGTTTGCCCTAAGTTCACGCTCTGTCTTAGTCTATGTTCTGAAGTCTTTGTAGAGGTGAAATGAG
CTGTCAGATGGATCTTCCTTCTCACTGCAACATGGAAATTTGCTATTTCACTTAATGACCACTCTTTCCACAATGGTTG
ATTTCTTTTGGCCTGTCTTACTGGTGATTTTCAAGGAATCTCAGTTGAATCTTACTGTTTTGCATTTTGTCTCCA
TGACAAATGTTGGGAAGCTCTTTCTAGCAGCATAACATGATCTAGTGACCTGACACATTTGCAGCACACATTTGCAGCACACTCCTAGCCAT
ACAAATTCAGAACCTCTTTGGTTTCTTTCCACGCCGATAATATAATTCTGCTCTGTATGAGCACATCCTAGCCAT
CCTGTACACACCGTAGTCTACACGCCGATGAGGTACTTCTGGGTCTGCTCAAACAAATGGCCCAGAGACCACCTGGT
AATGTTCATATTCTCCTGAGGGTGAGGAAGGTACTTCTGGGTCTGCTCAAACAAATGGCCCAGAGACCACCTGGT
AGGTAGGTAAGGAGCTCACCTCGCTCTCCTAAGAAGAGAGCCCAGGTTTATCCAGATTATACAACCAGCTTCTGATGACTCTCCT
CACTTGTTCAGTCATCCATGGAGTCTCCTAAGAAGAGAGCCCCAGGTTTATCCAGATTATACAACCAGCTTCTGATGACTCTCCT
GTTACAACATCCATGGAGTATGTTCTGCAATTCAGCGGAGGAGAAATTCTTCAGAGACAGATGTCTGAATTGGTAAAT
CACACCCCTAGGGTACGAATTCTGGGCTTGAGTGTCATTGTCCAGCCATGTTCACAGGTGTGACCTGTCAGGGAAGAACCA
ATGTGGGGTACGAATTCTGGGCTTGAGTGTCATTGTCCAGCCATGTTCACAGGTGTGACCTGTCAGGGAAGAACCA
GAGTTCCTTGTCTCTCAGAGGTAGAGCTCACAGAGGTCTCTCTGGTTCCCAGGAAAGGTAATTTCACTAACTCTT
GGTGATGAGACTATCCTCCAGTGCTGATGTACTAGAGTTTCATCTGAAGCTGTCACTGTCTATCCCAATGTACA
TCTTTTCACACAGAAATGTTTAGAGGTCAGGGTACAGGCCATATTCTCAGGTTACACATTGAAGAAGGATGGAGATATATTCTA
CTACCTTCCTGAGATCTTCCACACAGGTAGCATCCTTCTAACACTCAGCATCCTAACACTCAGCTACACATTGCATG
AAATAACCACTTCCTGGGACTTAGCATCCTCTAACACTCAGGATGTTCTGAACTACAGTACACATTGCATG
GATCCAGGTTTGTCTCAATTCACTGATTATTACACTCAGTGTCTCAATATGTCTGAAGGGTAAATGACAA
TTTAGGTGACCTGGGTGTATGGTGGTTATATGAACAGTATTAACTGTATTCCAAATCTG

FIG. 3L-1

```
TCTTTGATCCATGATCACACTGTGTCCCAGACCAGCTCCTTTAAGAAGAGACTCTGG
GTTTGGTGAGGGAGGCCACAGGAGAGAACTGAGTTCTCAGAGGCCAGCATACACCTCCCAGGGTGA
GCCCAAAAGACTGGGCCTCCCTCATCCCTTTTACCTCTAAATTCCATACAAAGGCCACCACCACATGCAAATCCTCACT
TAGGCACCCACAGGAAATGACTACACACATGGGTCCAGTCTCACATGGGAAGTCCTGAGAGT
CATGGACCTCCTGCACAAGAACATGAGTGTGCACAGAACATGGATTGGTGTGCACAGGTGATTCAT
GGAGAAATAGACTGAGTGTGAGTGAGAAAAACTGATTGGTGTGGCATTTTCTGATAACGG
TGTCCTTCTGTTTGCAGGTGTCCAGTGTCAGCGATTGTCAGCGTGTCCGAGCGTCCAGCCTGGGTCGTC
CCTGAGACTCTCCTGTGCAGCGTGGCATTATTAAATATGAAGTGAGACAAGGCTCGACTCCGCCAGGCTCCAGG
CCAGGGGCTGGAGTGGGTGGCATTATTAAATATGAAGTGAGAAATATCATGGTGACTCCGTATGGGCCG
ACTCAGCATCTCCAGAGACAATTCCAAGGATACGCTTTATCTCCAAATGAATAGCCTGAGAGTCGAGGACACGGCT
ACATATTTTGTGTGAGAGAATATATGTCTGCTACTACCGTAACTGGTACACAACTATTACGATTCTATGATGGTTA
TTATAACTACCACTATATGGACGTCTGGGGCCAAAGGGACCACGTCACCGTCTCCTCAGGTAAGAATGGCCACTCT
AGGGCCCTTTGTTTCTGCTAGCCCTGTGGGGCAGGTTTCCTGAGCATTGCAGGTGGTCCTCCGGGCATGTCCGAGGT
TGGACCTGGGCGGACTGGCCAGGAGGGACGGCCACTGGGTGCCTTGAGGATCTGGGAGCCTCTGTGGATTT
CCGATGCCTTGGAGAGATGCCTGAACAAACCAGGGTCTTAGTAGTGCTTGATGAGTAACTGAGCCTGGGAGCCA
CATTTGACGAGATGCCTGAACAAACCAGGGTCTTAGTAGTGCTTGATGATGGCTCAGGAGCGGTGTCGT
AGGACTGCAAGATCGCTGCACAGCAGCGAATCGTGAAATATTTCTTAGAATATGAGGTGCGCTGTGTCAAC
CTGCATCTTAAATTCTTTATTGGCTGGAGAAAGAGACAGGGCTGGAGTGGGTGAATCCAGCCAGGACGCGTAGC
CCCGGTCTCTTGATGAGACCAGGCAGGGTTGGGCAGGGGAGCCCAGAAACGGTGGCTGCCGTCCTGACAGGGCTTA
GGGAGGCTCCAGGACCTCAGTGCCTGAAGTGTTGAAGTGGCTTCCATGAAAAATGGTTAAGAAATTATGACTTAAAAATGTGAGA
CTGTTAAAAGACAGGATATGTTGAAGTGGCTTCCAAGTATTTGAAATTCTTATCATTGATTAACACCATGAGTGATAT
GATTTCAAGTGAATTGAGGCCAAAGACAAGCTCAGTCAGCTCAAGAATACTAGCACAGTGCTGTCGGCCCCGATGCGGGACTG
GTGTCTCGAAGCAGTTATTCATAATCAAGTTTATTTTTAATTAATTGAGCGAAGCAGATGATGAATTAGAGTCA
CGTTTTGACCATCATAAATCAAGTTTATTTTTAATTAATTGAGCGAAGCAGATGATGAATTAGAGTCA
AGATGGCTGCAGGGGTCTCCGGCACCCACAGCAGGAAGCAGTCACCGCGAGAGTCTATTTAGG
AAGCAAAAAACACAATTGTAATTTATCACTTCTGGTTGTGAAGAGGTTTGCCAGCCCAGATCTGAAA
GTGCTCTACTGAGCAATTGCGTTTCTAAAATAAGGGCTGACCGAGGCTGAAAACTGAAAAG
```

FIG. 3L-2

GCTTTTTTAACTATCTGAATTTCATTTCCAATCTTAGCTTATCAACTGCTAGTTTGTGCAAACAGCATATCAACTTCT
AACTGCATTCATTTTAAAGATGTTAAGAAATTAAACAGTCTTAGGGAGAGTTTATGACTGTATTCAAAAA
GTTTTTAAATTAGCTTGTTATCCCTCATGTGATAACTAATCTCAAATACTTTTCGATACCTCAGAGCATTATTTC
ATAATGACTGTGTTCACAATCTTTTAGGTTAACTCGTTTTCTCTTTGTGATTAAGGAGAAACACTTTGATATTCTGAT
AGAGTGGCCTTCATTTAGTATTTTCAAGACCACTTTTCAACTACTCACTTTAGGTATAAGTTTTAGGTAAAATGTGC
ATCATTATCCTGAATTATTTCAGTTAAGCATGTTAGTTGGTGGCATAAGAGAAAACTCAATCAGATAGTGCTGAAGA
CAGGAC (SEQ ID NO:162)

FIG. 3L-3

```
TCTCTATTATAAAGGCATGTTGGCAAATAAAGACTACAGTTTGTATTGAATATTCATGCCAAAGAAGTTTTTCAAA
ACTTTTCAAGTAAAAAATTTATCTTGCCTAGTTTGAAATTAACAATCTAAATTCAACAAATAAGGTAATACAGTTTT
AAAAGTGATGCTGTCTATTAGTTATTCAATTATTAACAACAGACTGATATTTAAAATAAATACCATTGCACATTT
AAGTGCCATACTGTTCTGGGATTTTTAAGGAATCAGAGACCGACTCTGTTCAGGAGGATATTTATTATTTAGGT
TCAGGAGGATATTTATTATTTAGGTGCACCGGCCAAGTGCCACCGGCCAAGTGCCAAGGACTGAGCCACAGAGAACAGAGTT
CAGTTACCTTTTAAGCATTTTGTGGGTGGGAGGGGACATCTGTGCAGGGTGAAGCATACTACAGAAGTGAGA
AACAAAGACAGTTATTCAATTGAAACATGTATTACATCATTCCTTTCAAGGAAAAACATGTTTTGCGACTTGA
GTTATCTTTCTAGTGACCTTGCAGCTACACTGCAGGGAATCAGGGTCTTCAAAATGCCTGAGAAGGGAGGAGAG
GTAAGGCTCATTAGCCACAGAAAAACAGGCAGTTAGTATTTAAAGGACTCCAGTCTCTTTCTCTTTTTCAGGGAGA
ATGGGTTTTCTTACATACAGTTTCTGCTTACACATTCTTAATTCCTTTCAATACTTGACA
AGAATGGCATTTACATACAGTTTACCAAAACATGTATTTAATATATTTGTCTTTTAATATTGGAATAGGCAGACA
TACACGTAGATCAGCATTATTTGTACTAAATTTGTACTAAATTTGCAAACAATCTCAAATTGCAAACAATTTTAAAATAATTAGAATA
ATATGAAACAAATGGGTGTGTTTGGTGTGTTGTACGTATGCATTCACTTTTGCATGGGCACTATGAGTCTTTGC
TGGGCTGTGTGCACGTAGTGTGTTGTATGACCAGGAGGTTTCAAATACATCATTAAATACATAGTTATATTAA
TCTTGGCAAGGCACTCTTTCAATTCTCTGTTCTTTAATTCTGTTTCAGAAAAGTAGAACACATATTCAGTCTTAGTTCCAGT
GTAGGGAGTGCTTTCATGAGAAATACCAGAAAAAGGCAAACATGGGGCAAACTAATGTAAAATTAGCCA
CAATGTGTATGTGCGCCTACAGGTATTATCAGGTACAATAATCAACTGTCCAATGAATAGTAGGAGTTGGAGTCTCTACCAC
ATGCACCTGCGAAGAGTGTTGGGTTCTTGGGGTAGTGTTGGGTTCTTGGGGGCTACAAATCAGGGAACCCTAAAGGAATAAGAGTCCCCCA
AACCCCTGAAGAGTGTTGGGTTCTTGGGGTGATCGTTCACCATGTCCCTGCAGAGTTCGGCTGGGGTTCCTAAGGCTGATTCACTATTCAAAA
GTGATGCGTGAGATCTTTCTTGGGGTGATCGTTCACCATGTCCCTGCAGAGTTCGGCTGGGGTTCCTAAGGCTGATTCACTATTCAAAA
GATGGTGTGAGAAGCATATGTGTAAATAAGCAGAATTCTGAGCCAGGCCACAGCCACTTATACTGGGCTAGA
GACACTGGTAGGAATACACTCGTCAGCTCAGATAGAAAACCTCCCTGCAGGGTGGGGGCAGGGCTGCAGGGGGC
GCTCAGGACACATCGAGCACAGTCTTCTGCCCCAGACTCTTCTGCCCCAGAGTATTTCACAAGGTGCACATGAGGCTGGGAGAGGTTCCTCTCAGG
GCCTGGGACTTCCTTAAAAACTGGATGTTATGAAAATAAGTGCTGATGTTGTATAAATATCCTATTCAA
TGTGAGCATTATCAAACTGGATGTAATGAGAAGATTATTACTTATAAATAAGTGCAATTTTTGGAGAGACACTCATTCC
AATAATAACACATTCACATATTAAGGTTCTAGAAGTCTAGAAGTCTAGAAATGGTTCACGTTGCCCCTGAGACATTCAAATGTGGGTTCAAAG
CAAATAATAACACATTCACATATTAAGGTCTAGAAGTCTAGAAGTCTAGAAATGGTTCACGTTGCCCCTGAGACATTCAAATGTGGGTTCAAAG
TGAGGTGCTGTCCTCGGGGAGTTGTTCCTTAGTGGAGGAAGCGCTATCAACACAGAGTTCAGGTCAGGGATGGGTAGGGG
```

FIG. 3N-1

```
ATGCGTGGCCTCTAACAGGATTACGACTCGAACCCTCAGCTCCTATAATTGTCGTCCGTGTCATGGATTCTC
TTTCTCATACTGGGTCAGGAATTGGTCTATTAAATAGCATCCTTCATGAATAACTGAATAACTGAGGGAATATAGT
ATCTCTGTACCCTGAAAGCATCACCAACAACATCCCTCTAGAGCACAGCTCCTCACA
TGGAGTTTGGGCTGAGCTGGGTTTCCTCGTTGCTCTCTTTAAGAGGTGATTCATGGAGAAATAGAGACTGAGTG
TGAGTGAACATCGAGTGAGAAAACTGGATTTGTGTGGCATTTCTGATAACGGTGTCCTTCTGTTTGCAGGTGTCCA
GTGTCAGCGATTAGTGGAGTCTGGGGAGTGAGGCGTGGTCCAGCCTGGTCCCTGAGACTCTCTGTGCAGCGTC
CGGATTCGACTTCAGTAGACAAGGCATGCCACTGGGTCCGCCAGGCTCCACAGGGGCTGGAGTGGGTGGCAT
TTATTAAATATGAGAAGTGAGAAATATCATGCTGACTGGTATCCGTATGGGGCCGACTCAGCATCCAGAGACAATTC
CAAGGATATACGCTTTATCTCCAAATGAATAGCCTGAGGACACGGCTACATATTTTGTGTGAGAGAGGCT
GGTGGGCCCGACTACCCGTAATGGGTACAACTGATTTCTATGATGGTTATTATAACTACCACTATATGGACGT
CTGGGGCAAAGGGACCACGGTCACCGTCTCCTCAGGTAAGAATGGCCACTGTTGTTTCTGCTACTGC
CTGTGGGGTTCCTGAGCATTGCAGGTCCTCGGGGCACTGGGAGCCCTCATGTCCGAGGTTCCGAGACTGGCCAGG
AGGGACGGGCACTGGGGTGCCTTGATGGAGTAACTGAGCCTGGGCCACATTTGGACGAGATGCCTGAACAA
CAGGTTGGCGTCTAGTGGCTGGGAATGTGTCTCAGGAGACGGTGTCTGTGTCAACCTGCAAGATCGCTGCACAGC
ACCAGGGGTCTTAGTGGCTGATGGCTGGGAATGTGTCTCAGGAGACGGTGTCTGTGTCAACCTGCAAGATCGCTGCACAGC
AGCGAATCGTGAAATATTTTCTTTAGAATATGAGGTGCGCTGTGTGTCAACCTGCCATCTTAAATCTTATTGGCTG
GAAAGAGAACTGTGCGAGTGGGTGAATCCAGCCAGGGACGACGTAGCCGTCTTGATGAGAGCAGGGTTG
GGGGCAGGTGGTTTCCATGAGAAAATGGTTAAGAAAATTGAGAGATTTCAAGTGTTACTGAGAGATGGATGCCTCAGTGCCT
TGAAGCTGGTTTCCATGAGAAAATGGTTAAGAAAATTGAGAGATTTCAAGTGTTACTGAGAGATGGATGCCAGGACCTCAGTGCCT
GTGGCTTCTGAGTATTTGAATTTCTATCATTGATTAACACCCATGAGTGATGATGTCTGGAATTGAGGCCAAGCAAG
TGTCCAAGTATTTGAATTTCTATCATTGATTAACACCCATGAGTGATGATGTCTGGAATTGAGGCCAAGCAAG
CTCAGCTAAGAATACTAGCACACGTCGTGTCGGCGACTGCTGTGAAGATGTCGAAGATGGGGTCTCCGGCA
TTTTTTAATTAATTGAGCGAAGCAGGAAGCAGGTCCACCGCGAGACAGTCTATTTAGGAAGCAAAAACACAATTGGTAAATTT
CCCACAGCAGGTGGCAGGAAGCAGGTCCACCGCGAGACAGTCTATTTAGGAAGCAAAAACACAATTGGTAAATTT
ATCACTTCTGGTTGTGAAGAGGTGGTTTGCCCAGGCCCAGATCTGAAAGTCTACTGAGCAAAACACCCTG
GACAATTGCGTTTCTAAAATAAGGCGAGGCTGACCGAAACTGAAAAGGCTTTTTTAACTATCTGAATTCATTTC
```

FIG. 3N-2

CAATCTTAGCTTATCAACTGCTAGTTTGTGCAAACAGCATATCAACTTCTAAACTGCATTCATTTTAAAGTAAGATG
TTAAGAAATTAAACAGTCTTAGGGAGAGTTTATGACTGTATTCAAAAGTTTTTAAATTAGCTTGTTATCCCTTCA
TGTGATAACTAATCTCAAATACTTTTCGATACCTCAGAGCATTATTTCATAATGACTGTGTTCACAATCTTTTAG
GTTAACTCGTTTCTCTTTGTGATTAAGGAGAAACACTTTGATATTCTGATAGAGTGGCCTTCATTTAGTATTTTCA
AGACCACTTTTCAACTACTCACTTTAGGATAAGTTTAGGTAAAATGTGCATCATTATCCTGAATTATTTCAGTTAAG
CATGTTAGTTGGTGGCATAAGAGAAAACTCAATCAGATAGTGCTGAAGAC (SEQ ID NO:163)

```
TTCCTTAGTGGAGGAAGGCTATCAACACAGAGTTCAGGATGGGTAGGGATTTCAGGTGCTGGCCTCTAACAGGATTAC
GACTCGAACCCTCAGCTCCTCCTATAAATTGTGTCGTCCGTGTGTCATGGATTTCTCTTTCATACTGGGTCAGGAATTG
GTCTATTAAATAGCATCCTTCATGAATAACTGAGGGAATATAGTATCTCTGTACCCTGAAAGCATCAC
CCAACAACAACATCCCCTCCTTGGGAGAATCCCTCCTCACATGGAGTTTGGGCTGAGCTGGGTTT
TCCTCGTTGCTCTTTTAAGAGAGTGATTCATGGAGTGAGTGAACATGAGTGAGAAAAAC
TGGATTTGTGTGGCATTTCTGATAACGGTGTTCCTTCTGTTTGCAGGTGAGTGTCAGTGTCCAGGTCAGGATTAGTGGAGTCTGG
GGGAGGCGTGGTCCAGCTCGGGTCGTCCCTGACTCTCCTGCAGCGTCCGGATTCAGTAGACAAGG
CATGCACTGGGTCCGCCAGGCTCCAGGGGCTGGAGTGGGTGGCATTTATTAAATATGGAAGTGAGAA
ATATCATGCTGACTCCGTATGGGGCCGACTCAGCATCTCCAGAGACAATTCCAAGGATACGCTTTATCTCCAAATG
AATAGCCTGAGAGTCGAGGACACGGCTACATATTTTGTGTGAGAGGCTGGTGGGCCCGACTACCGTAATGGG
TACAACTATTACGATTTCTATGATGGTTATTATAACTACCACTCTAGGGCCTTTGTTCTGCTACTGCGTCAGCGTCA
CCGTCTCCTCAGGTAAGAATGGCCACTCTAGGGCCTTTGTTTCTGCTACTGCCTGTGGGTTTCCTGAGCATTGCA
GGTTGGTCCTCGGGGCATGTTCCGAGGTTGGACCTGGAGCCTGGCCAGGAGGGACGGGCACTGGGGTGCCT
TGAGGATCTCGGGGAGCCTCTGTGTGGGATTTCCGATGCCACATTTGGACGAGAGATGCCTGAACAAACCAGGGTTCAGGTTGGCGTCTCTGATGGAGT
AACTGAGCCTGGGGCTTCAGGAGGTGTCTCTTAAGCAGCAGGACTAAAACCAGGGTGAATCGTGAACAGCGCTGAACAGCAGCGAATCGTGAACTGTCGGAGTGGGT
GAATTATGAGGTGCGCTGTGTGTCAACCTGCATCTTAAATTCTTTATTGGCTGGAGAACTGTCGGAGTGGGT
GAATCCAGCAGGAGGGACGCGTAGCCCGGTTCTGATGAGACAGGGTGGGGCAGGGTAGCCCAGAAAC
GGTGGCTGCCGTCCTGACAGGGTCAGGGTCATGGGCTCCTTGAAGCTGGTTCCATGAGAAAA
GGATTGTTTATCTTAGGAGGCATGCTTACTGTTAAAAGACAGGATATTAATTTTTAACTGTCCAAGTATGTTTGAAGTGGCTTCTGAGAAATGGTTA
AGAAAATTATGACTTAAAACCCATGAGTGATATGTCTGGAATTCAAGTTATTTTTAATCAAGCAAGCTCAGTCAGTCAGTCAGCACAA
CATTTGATTAACACCCATGAGTGATATGTCTGGAATTCAAGTTATTTTTAATTAATTGAGCGAAGC
GTGCTGTCGGCCGGACTGCGGGATGATGAATTAGAGTCAAGATGGCTCCGCCACCCACAGCAGGTGGCAGGAAGC
TGGAAGCAGATGATGAATTAGAGTCAAGATGGCTCAGGCAAAATGGTAAATTATCACTTCTGGTTGTGAAGAGGT
AGGTCACCGCGAGAGTCTATTTTAGGAAGCAAAAAACACAACACCTGGACAATTTGCGTTTCTAAAATAA
GGTTTTGCCCAGGCCCCAGATCTCGAAAGTGCTCTACTGAGCAAGTGCTCTACTGAGCAAACACACCTGGACAATTTGCGTTTCTAAAATAA
```

FIG. 3P-2

GGCGAGGCTGACCGAAACTGAAAAGGCTTTTTTTAACTATCTGAATTTCATTTCCAATCTTAGCTTATCAACTGCTA
GTTTGTGCAAACAGCATATCAACTTCTAAACTGCATTCATTTTAAAGTAAGATGTTTAAGAAATTAAACAGTCTTAG
GGAGAGTTTATGACTGTATTCAAAAGTTTTTAAATTAGCTTGTTATCCCTTCATGTGATAACTAATCTCAAATACT
TTTCGATACCTCAGAGACACTTTCATAATGACTGTGTTCACAATCTTTTAGGTTAACTCGTTTCTCTTTGTGAT
TAAGGAGAAACACTTTGATATTTCATATAGAGTGGCCTTCATTTTAGTATTTTCAAGACCACTTTCAACTACTCACT
TTAGGATAAGTTTTAGGTAAAATGTGCATCATTATCCTGAATTATTCAGTTAAGCATGTTAGTTGGTGGCATAAGA
GAAAACTCAATCAGATAGTGCTGAAGACAGGACTGTGGAAGACACCTTAGAAGGACACAGATTCTGTTCCGAATCACC
GATGCGGCGTC

FIG. 3P-3

| V-GENE | D-GENE | J-GENE | CDR LENGTHS | AA JUNCTION | READ # (BEFORE ENGINEERING) | READ # (AFTER ENGINEERING, C108 SOSIP SORTED) |
|---|---|---|---|---|---|---|
| IGLV1-2*02 F | IGHD3-22*01 F | IGHJ4*02 F | 8.8.13 | CARAPFYDSNLFDYW | 37000 | 6048 |
| IGLV3-33*01 F | IGHD5-18*01 F | IGHJ4*02 F | 8.8.13 | CARDLGKHIREIDFW | 4382 | 24 |
| IGLV3-30*02 F* | IGHD3-10*01 F | IGHJ4*02 F* | 8.8.15 | CAKDPVGENSGSYYISW | 2569 | 102 |
| IGLV3-30*02 F* | IGHD5-18*01 F | IGHJ3*02 F | 8.8.14 | CAKGESYGPYDAFDMW | 616Δ | 60 |
| IGLV3-30*02 F* | IGHD5-18*01 F | IGHJ3*02 F | 8.8.14 | CAKGESYGPYDAFDMW | 55Δ | 0 |
| IGLV1-8*01 F | IGHD2-2*01 F | IGHJ6*03 F* | 8.8.16 | CARSPGYCSSNSCYPDVW | 222 | 13 |
| IGLV3-30*01 F* | IGHD3-10*01 F | IGHJ4*02 F* | 8.8.15 | CAKDPVGENSGSYYISW | 54 | 0 |
| IGLV3-33*05 F | IGHD3-1*01 F | IGHJ6*03 F* | 8.8.30 | CVREAGGPDYRNGYNYDFYDGYYNYHYMDVW | 0 | 574 |
| IGLV1-18*04 F | IGHD3-9*01 F | IGHJ6*02 F | 8.8.16 | CAARGSETVAAYSYFMDVW | 0 | 29 |

Δ: LINEAGE MEMBERS
*: ANOTHER GENE ASSIGNMENT ASSIGNMENT CLOSE TO THAT COULD BE MADE

FIG. 4C

```
                              SEQUENCE LISTING

<160> NUMBER OF SEQ ID NOS: 187

<210> SEQ ID NO 1
     <211> LENGTH: 110
     <212> TYPE: PRT
     <213> ORGANISM: Homo sapiens

<400> SEQUENCE: 1

Gln Ser Ala Leu Thr Gln Pro Ala Ser Val Ser Gly Ser Pro Gly Gln
     1               5                   10                  15

Ser Ile Thr Ile Ser Cys Asn Gly Thr Ser Asn Asp Val Gly Gly Tyr
                 20                  25                  30

Glu Ser Val Ser Trp Tyr Gln Gln His Pro Gly Lys Ala Pro Lys Val
                 35                  40                  45

Val Ile Tyr Asp Val Ser Lys Arg Pro Ser Gly Val Ser Asn Arg Phe
             50                  55                  60

Ser Gly Ser Lys Ser Gly Asn Thr Ala Ser Leu Thr Ile Ser Gly Leu
     65                  70                  75                  80

Gln Ala Glu Asp Glu Gly Asp Tyr Tyr Cys Lys Ser Leu Thr Ser Thr
                     85                  90                  95

Arg Arg Arg Val Phe Gly Thr Gly Thr Lys Leu Thr Val Leu
                 100                 105                 110

<210> SEQ ID NO 2
     <211> LENGTH: 107
     <212> TYPE: PRT
     <213> ORGANISM: Homo sapiens

<400> SEQUENCE: 2

Ser Tyr Glu Leu Thr Gln Pro Pro Ser Val Ser Val Ser Pro Gly Gln
     1               5                   10                  15

Thr Ala Ser Ile Thr Cys Ser Gly Asp Lys Leu Gly Asp Lys Tyr Ala
                 20                  25                  30

Cys Trp Tyr Gln Gln Lys Pro Gly Gln Ser Pro Val Leu Val Ile Tyr
                 35                  40                  45

Gln Asp Ser Lys Arg Pro Ser Gly Ile Pro Glu Arg Phe Ser Gly Ser
             50                  55                  60

Asn Ser Gly Asn Thr Ala Thr Leu Thr Ile Ser Gly Thr Gln Ala Met
     65                  70                  75                  80

Asp Glu Ala Asp Tyr Tyr Cys Gln Ala Trp Asp Ser Ser Thr Trp Val
                     85                  90                  95

Val Phe Gly Gly Gly Thr Lys Leu Thr Val Leu
                 100                 105

<210> SEQ ID NO 3
     <211> LENGTH: 107
     <212> TYPE: PRT
     <213> ORGANISM: Homo sapiens

<400> SEQUENCE: 3

Ser Tyr Glu Leu Thr Gln Pro Pro Ser Val Ser Val Ser Pro Gly Gln
     1               5                   10                  15

Thr Ala Ser Ile Thr Cys Ser Gly Asp Lys Leu Gly Asp Lys Tyr Ala
```

```
                20                  25                  30
Cys Trp Tyr Gln Gln Lys Pro Gly Gln Ser Pro Val Leu Val Ile Tyr
            35                  40                  45
Gln Asp Ser Lys Arg Pro Ser Gly Ile Pro Glu Arg Phe Ser Gly Ser
        50                  55                  60
Asn Ser Gly Asn Thr Ala Thr Leu Thr Ile Ser Gly Thr Gln Ala Met
65                  70                  75                  80
Asp Glu Ala Asp Tyr Tyr Cys Gln Ala Trp Asp Ser Ser Thr Trp Val
                85                  90                  95
Val Phe Gly Gly Gly Thr Lys Leu Thr Val Leu
                100                 105

<210> SEQ ID NO 4
<211> LENGTH: 111
<212> TYPE: PRT
<213> ORGANISM: Homo sapiens

<400> SEQUENCE: 4

Gln Ser Ala Leu Thr Gln Pro Ala Ser Val Ser Gly Ser Pro Gly Gln
1               5                   10                  15
Ser Ile Thr Ile Ser Cys Thr Gly Thr Ser Ser Asp Val Gly Ser Tyr
                20                  25                  30
Asn Leu Val Ser Trp Tyr Gln Gln His Pro Gly Lys Ala Pro Lys Leu
            35                  40                  45
Met Ile Tyr Glu Val Ser Lys Arg Pro Ser Gly Val Ser Asn Arg Phe
        50                  55                  60
Ser Gly Ser Lys Ser Gly Asn Thr Ala Ser Leu Thr Ile Ser Gly Leu
65                  70                  75                  80
Gln Ala Glu Asp Glu Ala Asp Tyr Tyr Cys Ser Ser Tyr Thr Ser Ser
                85                  90                  95
Ser Thr Leu Val Val Phe Gly Gly Gly Thr Lys Leu Thr Val Leu
                100                 105                 110

<210> SEQ ID NO 5
<211> LENGTH: 110
<212> TYPE: PRT
<213> ORGANISM: Homo sapiens

<400> SEQUENCE: 5

Gln Ser Ala Leu Thr Gln Pro Ala Ser Val Ser Gly Ser Pro Gly Gln
1               5                   10                  15
Ser Ile Thr Ile Ser Cys Thr Gly Thr Ser Ser Asp Val Gly Gly Tyr
                20                  25                  30
Asn Tyr Val Ser Trp Tyr Gln Gln His Pro Gly Lys Ala Pro Lys Leu
            35                  40                  45
Met Ile Tyr Glu Val Ser Asn Arg Pro Ser Gly Val Ser Asn Arg Phe
        50                  55                  60
Ser Gly Ser Lys Ser Gly Asn Thr Ala Ser Leu Thr Ile Ser Gly Leu
65                  70                  75                  80
Gln Ala Glu Asp Glu Ala Asp Tyr Tyr Cys Ser Ser Tyr Thr Ser Ser
                85                  90                  95
Ser Thr Pro Leu Phe Gly Gly Gly Thr Lys Leu Thr Val Leu
                100                 105                 110

<210> SEQ ID NO 6
<211> LENGTH: 108
<212> TYPE: PRT
```

<213> ORGANISM: Homo sapiens

<400> SEQUENCE: 6

```
Ser Tyr Glu Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu
            100                 105
```

<210> SEQ ID NO 7
<211> LENGTH: 110
<212> TYPE: PRT
<213> ORGANISM: Homo sapiens

<400> SEQUENCE: 7

```
Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln Arg Pro Gly Lys Ala Pro Lys Leu
        35                  40                  45

Met Ile Tyr Glu Val Ser Gln Arg Pro Ser Gly Val Pro Asp Arg Phe
    50                  55                  60

Ser Gly Phe Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Asn
                85                  90                  95

Asn Asn Leu Leu Phe Gly Gly Gly Thr Arg Val Thr Val Leu
            100                 105                 110
```

<210> SEQ ID NO 8
<211> LENGTH: 110
<212> TYPE: PRT
<213> ORGANISM: Homo sapiens

<400> SEQUENCE: 8

```
Ser Tyr Glu Leu Thr Gln Pro Pro Ser Val Ser Val Ser Pro Gly Gln
1               5                   10                  15

Thr Ala Arg Ile Thr Cys Trp Gly Asn Asn Phe Gly Asn Lys Ser Val
            20                  25                  30

His Trp Tyr Gln Gln Lys Pro Gly Gln Ser Pro Val Leu Val Val Tyr
        35                  40                  45

Asp Asp Ile Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95
```

```
Arg Asp Val Val Phe Gly Gly Gly Thr Lys Leu Thr Val Leu
                100                 105                 110
```

<210> SEQ ID NO 9
<211> LENGTH: 110
<212> TYPE: PRT
<213> ORGANISM: Homo sapiens

<400> SEQUENCE: 9

```
Gln Ala Val Val Thr Gln Pro Pro Ser Val Ser Glu Ala Pro Arg Gln
1               5                   10                  15

Arg Val Thr Ile Ser Cys Cys Gly Ser Ser Ser Asn Ile Gly Asn Asn
            20                  25                  30

Ala Val Asn Trp Tyr Gln Gln Val Pro Gly Arg Thr Pro Lys Leu Leu
        35                  40                  45

Ile Tyr Tyr Asp Asp Leu Leu Pro Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu
                100                 105                 110
```

<210> SEQ ID NO 10
<211> LENGTH: 112
<212> TYPE: PRT
<213> ORGANISM: Homo sapiens

<400> SEQUENCE: 10

```
Gln Ser Ala Leu Thr Gln Pro Ala Ser Val Ser Gly Ser Pro Gly Gln
1               5                   10                  15

Ser Ile Thr Ile Ser Cys Thr Gly Thr Asn Ser Asp Val Gly Asp Tyr
            20                  25                  30

Asp Ser Val Ser Trp Tyr Gln Gln His Pro Gly Lys Ala Pro Lys Leu
        35                  40                  45

Ile Ile Tyr Glu Val Ser Lys Arg Pro Ser Gly Val Pro Asp Arg Phe
    50                  55                  60

Ser Gly Ser Lys Ser Ala Asn Thr Ala Ser Leu Thr Ile Ser Gly Leu
65                  70                  75                  80

Gln Ala Glu Glu Ala Asp Tyr Tyr Cys Ser Ser Tyr Thr Ser Ser
                85                  90                  95

Thr Ser Leu Asp Tyr Val Phe Gly Thr Gly Thr Lys Val Thr Val Leu
                100                 105                 110
```

<210> SEQ ID NO 11
<211> LENGTH: 111
<212> TYPE: PRT
<213> ORGANISM: Homo sapiens

<400> SEQUENCE: 11

```
Gln Leu Val Leu Thr Gln Pro Pro Ser Val Ser Gly Ala Pro Gly Gln
1               5                   10                  15

Arg Val Thr Ile Ser Cys Thr Gly Gly Ser Ser Asn Val Gly Ala Gly
            20                  25                  30

Tyr Asp Val His Trp Tyr Gln Gln Phe Pro Gly Ala Ala Pro Lys Phe
        35                  40                  45
```

Val Ile Tyr Gly Asn Asn Arg Pro Ser Gly Val Pro Asp Arg Phe
 50                  55                  60

Ser Gly Ser Lys Ser Gly Asn Ser Ala Ser Leu Ala Ile Thr Gly Leu
 65                  70                  75                  80

Gln Ala Glu Asp Glu Ala Asp Tyr Tyr Cys Gln Ser Phe Asp Ser Ser
                 85                  90                  95

Leu Arg Gly Leu Val Phe Gly Gly Gly Thr Lys Leu Thr Val Leu
            100                 105                 110

<210> SEQ ID NO 12
<211> LENGTH: 110
<212> TYPE: PRT
<213> ORGANISM: Homo sapiens

<400> SEQUENCE: 12

Gln Ser Ala Leu Thr Gln Pro Ala Ser Val Ser Ala Ser Pro Gly Gln
 1               5                  10                  15

Ser Ile Thr Ile Ser Cys Ser Gly Thr Arg Ser Asp Val Gly Gly Tyr
             20                  25                  30

Asp Phe Val Ser Trp Tyr Gln Gln His Pro Gly Lys Val Pro Lys Leu
         35                  40                  45

Ile Ile Tyr Glu Val Thr Lys Arg Pro Ser Gly Ile Pro Gln Arg Phe
 50                  55                  60

Ser Gly Ser Lys Ser Gly Asn Thr Ala Ser Leu Thr Ile Ser Gly Leu
 65                  70                  75                  80

Gln Ala Asp Asp Glu Ala Asp Tyr Tyr Cys Cys Ser Tyr Ala Asn Tyr
                 85                  90                  95

Asp Glu Leu Ile Leu Gly Gly Gly Thr Lys Leu Thr Val Leu
            100                 105                 110

<210> SEQ ID NO 13
<211> LENGTH: 106
<212> TYPE: PRT
<213> ORGANISM: Homo sapiens

<400> SEQUENCE: 13

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Pro Thr Phe Gly Pro Gly Thr Lys Leu Glu
            100                 105

<210> SEQ ID NO 14
<211> LENGTH: 109
<212> TYPE: PRT
<213> ORGANISM: Homo sapiens

<400> SEQUENCE: 14

Asp Ile Val Met Thr Gln Ser Pro Leu Ser Leu Pro Val Thr Pro Gly

```
                1               5                   10                  15
            Glu Pro Ala Ser Ile Ser Cys Arg Ser Ser Gln Ser Leu Leu His Ser
                            20                  25                  30

Asn Gly Tyr Asn Tyr Leu Asp Trp Tyr Leu Gln Lys Pro Gly Gln Ser
                        35                  40                  45

Pro Gln Leu Leu Ile Tyr Leu Gly Ser Asn Arg Ala Ser Gly Val Pro
                50                  55                  60

Asp Arg Phe Ser Gly Ser Gly Ser Gly Thr Asp Phe Thr Leu Lys Ile
            65                  70                  75                  80

Ser Arg Val Glu Ala Glu Asp Val Gly Val Tyr Tyr Cys Met Gln Ala
                            85                  90                  95

Leu Gln Pro Tyr Thr Phe Gly Gln Gly Thr Lys Leu Glu
                            100                 105
```

<210> SEQ ID NO 15
<211> LENGTH: 107
<212> TYPE: PRT
<213> ORGANISM: Homo sapiens

<400> SEQUENCE: 15

```
            Glu Ile Val Leu Thr Gln Ser Pro Gly Thr Leu Ser Leu Ser Pro Gly
            1               5                   10                  15

Glu Arg Ala Thr Leu Ser Cys Arg Ala Ser Gln Ser Val Ser Ser Ser
                            20                  25                  30

Tyr Leu Ala Trp Tyr Gln Gln Lys Pro Gly Gln Ala Pro Arg Leu Leu
                        35                  40                  45

Ile Tyr Gly Ala Ser Ser Arg Ala Thr Gly Ile Pro Asp Arg Phe Ser
                50                  55                  60

Gly Ser Gly Ser Gly Thr Asp Phe Thr Leu Thr Ile Ser Arg Leu Glu
            65                  70                  75                  80

Pro Glu Asp Phe Ala Val Tyr Tyr Cys Gln Gln Tyr Gly Ser Ser Pro
                            85                  90                  95

Leu Tyr Ser Phe Gly Gln Gly Thr Lys Leu Glu
                            100                 105
```

<210> SEQ ID NO 16
<211> LENGTH: 106
<212> TYPE: PRT
<213> ORGANISM: Homo sapiens

<400> SEQUENCE: 16

```
            Glu Ile Val Leu Thr Gln Ser Pro Gly Thr Leu Ser Leu Ser Pro Gly
            1               5                   10                  15

Glu Arg Ala Thr Leu Ser Cys Arg Ala Ser Gln Ser Val Ser Ser Ser
                            20                  25                  30

Tyr Leu Ala Trp Tyr Gln Gln Lys Pro Gly Gln Ala Pro Arg Leu Leu
                        35                  40                  45

Ile Tyr Gly Ala Ser Ser Arg Ala Thr Gly Ile Pro Asp Arg Phe Ser
                50                  55                  60

Gly Ser Gly Ser Gly Thr Asp Phe Thr Leu Thr Ile Ser Arg Leu Glu
            65                  70                  75                  80

Pro Glu Asp Phe Ala Val Tyr Tyr Cys Gln Gln Tyr Gly Ser Ser Pro
                            85                  90                  95

Trp Thr Phe Gly Gln Gly Thr Lys Leu Glu
                            100                 105
```

```
<210> SEQ ID NO 17
<211> LENGTH: 111
<212> TYPE: PRT
<213> ORGANISM: Homo sapiens

<400> SEQUENCE: 17

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Arg Leu Thr Phe Gly Gly Gly Thr Lys Leu Glu
            100                 105                 110

<210> SEQ ID NO 18
<211> LENGTH: 110
<212> TYPE: PRT
<213> ORGANISM: Homo sapiens

<400> SEQUENCE: 18

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Leu Glu
            100                 105                 110

<210> SEQ ID NO 19
<211> LENGTH: 111
<212> TYPE: PRT
<213> ORGANISM: Homo sapiens

<400> SEQUENCE: 19

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80
```

-continued

Ser Arg Val Glu Ala Glu Asp Val Gly Val Tyr Tyr Cys Met Gln Ala
                85                  90                  95

Leu Gln Thr Leu Pro Asp Thr Phe Gly Gln Gly Thr Lys Leu Glu
            100                 105                 110

<210> SEQ ID NO 20
<211> LENGTH: 110
<212> TYPE: PRT
<213> ORGANISM: Homo sapiens

<400> SEQUENCE: 20

Asp Val Val Met Thr Gln Ser Pro Leu Phe Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Glu Thr Phe Gly Gln Gly Thr Lys Leu Glu
            100                 105                 110

<210> SEQ ID NO 21
<211> LENGTH: 106
<212> TYPE: PRT
<213> ORGANISM: Homo sapiens

<400> SEQUENCE: 21

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Asp
            100                 105

<210> SEQ ID NO 22
<211> LENGTH: 105
<212> TYPE: PRT
<213> ORGANISM: Homo sapiens

<400> SEQUENCE: 22

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

```
Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Ala Phe Gly Gln Gly Thr Lys Leu Glu
                100                 105

<210> SEQ ID NO 23
<211> LENGTH: 106
<212> TYPE: PRT
<213> ORGANISM: Homo sapiens

<400> SEQUENCE: 23

Ala Ile Arg Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Ser
                 85                  90                  95

Ile Thr Phe Gly Gln Gly Thr Arg Leu Glu
                100                 105

<210> SEQ ID NO 24
<211> LENGTH: 105
<212> TYPE: PRT
<213> ORGANISM: Homo sapiens

<400> SEQUENCE: 24

Ala Ile Arg Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Leu Trp
                 85                  90                  95

Thr Phe Gly Gln Gly Thr Lys Val Asp
                100                 105

<210> SEQ ID NO 25
<211> LENGTH: 111
<212> TYPE: PRT
<213> ORGANISM: Homo sapiens
```

<400> SEQUENCE: 25

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Arg Thr Phe Gly Gln Gly Thr Lys Val Glu
            100                 105                 110

<210> SEQ ID NO 26
<211> LENGTH: 106
<212> TYPE: PRT
<213> ORGANISM: Homo sapiens

<400> SEQUENCE: 26

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Gly Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Thr Ser Pro
                85                  90                  95

Trp Thr Phe Gly Gln Gly Thr Lys Val Asp
            100                 105

<210> SEQ ID NO 27
<211> LENGTH: 111
<212> TYPE: PRT
<213> ORGANISM: Homo sapiens

<400> SEQUENCE: 27

Asp Ile Val Met Thr Gln Ser Pro Asp Ser Leu Ala Val Ser Leu Gly
1               5                   10                  15

Glu Arg Ala Thr Leu Asn Cys Lys Ser Ser Gln Ser Ile Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Pro Thr Phe Gly Gln Gly Thr Lys Val Glu

<210> SEQ ID NO 28
<211> LENGTH: 105
<212> TYPE: PRT
<213> ORGANISM: Homo sapiens

<400> SEQUENCE: 28

Ala Ile Arg Met Thr Gln Ser Pro Ser Ser Val Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Thr Ala Pro Lys Leu Leu Ile
        35                  40                  45

Tyr Thr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Tyr
                85                  90                  95

Thr Phe Gly Gln Gly Thr Lys Leu Glu
            100                 105

<210> SEQ ID NO 29
<211> LENGTH: 101
<212> TYPE: PRT
<213> ORGANISM: Homo sapiens

<400> SEQUENCE: 29

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Arg Ala Phe Gly Pro
                85                  90                  95

Gly Thr Lys Val Asp
            100

<210> SEQ ID NO 30
<211> LENGTH: 105
<212> TYPE: PRT
<213> ORGANISM: Homo sapiens

<400> SEQUENCE: 30

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Cys Ala Ala Ser Ser Leu Gln Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Tyr
                 85                  90                  95

Thr Phe Gly Gln Gly Thr Lys Leu Glu
            100                 105

<210> SEQ ID NO 31
<211> LENGTH: 105
<212> TYPE: PRT
<213> ORGANISM: Homo sapiens

<400> SEQUENCE: 31

Asp Ile Val Met Thr Gln Ser Pro Ser Ser Leu Ser Ala Ser Val Gly
 1               5                  10                  15

Asp Arg Val Thr Val Thr Cys Arg Ala Ser Gln Gly Ile Ser Asn Tyr
                20                  25                  30

Leu Ala Trp Tyr Gln Gln Lys Pro Gly Lys Val Pro Lys Leu Leu Ile
             35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Gly Leu Gln Ser
 65                  70                  75                  80

Gly Asp Phe Ala Ile Tyr Tyr Cys Gln Gln Tyr Tyr Arg Phe Pro Gln
                 85                  90                  95

Thr Phe Gly Gln Gly Thr Lys Leu Glu
            100                 105

<210> SEQ ID NO 32
<211> LENGTH: 106
<212> TYPE: PRT
<213> ORGANISM: Homo sapiens

<400> SEQUENCE: 32

Glu Ile Val Leu Ala Gln Ser Pro Gly Thr Leu Ser Leu Ser Pro Gly
 1               5                  10                  15

Glu Arg Ala Thr Leu Ser Cys Arg Ala Ser His Asn Val His Pro Lys
                20                  25                  30

Tyr Phe Ala Trp Tyr Gln Gln Lys Pro Gly Gln Ser Pro Arg Leu Leu
             35                  40                  45

Ile Tyr Gly Gly Ser Thr Arg Ala Ala Gly Ile Pro Gly Lys Phe Ser
 50                  55                  60

Gly Ser Gly Ser Gly Thr Asp Phe Thr Leu Thr Ile Ser Arg Val Asp
 65                  70                  75                  80

Pro Glu Asp Phe Ala Val Tyr Tyr Cys Gln Gln Tyr Gly Gly Ser Pro
                 85                  90                  95

Tyr Thr Phe Gly Gln Gly Thr Lys Val Glu
            100                 105

<210> SEQ ID NO 33
<211> LENGTH: 110
<212> TYPE: PRT
<213> ORGANISM: Homo sapiens

<400> SEQUENCE: 33

Asp Ile Val Met Thr Gln Thr Pro Leu Ser Leu Ser Val Thr Pro Gly
 1               5                  10                  15
```

```
Gln Pro Ala Ser Ile Ser Cys Lys Ser Ser Glu Ser Leu Arg Gln Ser
                20                  25                  30

Asn Gly Lys Thr Ser Leu Tyr Trp Tyr Arg Gln Lys Pro Gly Gln Ser
            35                  40                  45

Pro Gln Leu Leu Val Phe Glu Val Ser Asn Arg Phe Ser Gly Val Ser
50                      55                  60

Asp Arg Phe Val Gly Ser Gly Ser Gly Thr Asp Phe Thr Leu Arg Ile
65                  70                  75                  80

Ser Arg Val Glu Ala Glu Asp Val Gly Phe Tyr Tyr Cys Met Gln Ser
                85                  90                  95

Lys Asp Phe Pro Leu Thr Phe Gly Gly Gly Thr Lys Val Asp
                100                 105                 110

<210> SEQ ID NO 34
<211> LENGTH: 106
<212> TYPE: PRT
<213> ORGANISM: Homo sapiens

<400> SEQUENCE: 34

Glu Ile Val Leu Thr Gln Ser Pro Gly Thr Leu Ser Leu Ser Pro Gly
1               5                   10                  15

Glu Arg Ala Thr Phe Ser Cys Arg Ser Ser His Ser Ile Arg Ser Arg
                20                  25                  30

Arg Val Ala Trp Tyr Gln His Lys Pro Gly Gln Ala Pro Arg Leu Val
            35                  40                  45

Ile His Gly Val Ser Asn Arg Ala Ser Gly Ile Ser Asp Arg Phe Ser
50                  55                  60

Gly Ser Gly Ser Gly Thr Asp Phe Thr Leu Thr Ile Thr Arg Val Glu
65                  70                  75                  80

Pro Glu Asp Phe Ala Leu Tyr Tyr Cys Gln Val Tyr Gly Ala Ser Ser
                85                  90                  95

Tyr Thr Phe Gly Gln Gly Thr Lys Leu Glu
                100                 105

<210> SEQ ID NO 35
<211> LENGTH: 110
<212> TYPE: PRT
<213> ORGANISM: Homo sapiens

<400> SEQUENCE: 35

Glu Val Val Ile Thr Gln Ser Pro Leu Phe Leu Pro Val Thr Pro Gly
1               5                   10                  15

Glu Ala Ala Ser Leu Ser Cys Lys Cys Ser His Ser Leu Gln His Ser
                20                  25                  30

Thr Gly Ala Asn Tyr Leu Ala Trp Tyr Leu Gln Arg Pro Gly Gln Thr
            35                  40                  45

Pro Arg Leu Leu Ile His Leu Ala Thr His Arg Ala Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ser Asp Asp Val Gly Thr Tyr Tyr Cys Met Gln Gly
                85                  90                  95

Leu His Ser Pro Trp Thr Phe Gly Gln Gly Thr Lys Val Glu
                100                 105                 110

<210> SEQ ID NO 36
<211> LENGTH: 101
```

```
<212> TYPE: PRT
<213> ORGANISM: Homo sapiens

<400> SEQUENCE: 36

Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Pro Asp Tyr Asn Leu Thr Ile Ser Asn Leu Glu Ser Gly Asp
65                  70                  75                  80

Phe Gly Val Tyr Tyr Cys Gln Gln Tyr Glu Phe Phe Gly Gln Gly Thr
                85                  90                  95

Lys Val Gln Val Asp
            100

<210> SEQ ID NO 37
<211> LENGTH: 99
<212> TYPE: PRT
<213> ORGANISM: Homo sapiens

<400> SEQUENCE: 37

Glu Ile Val Leu Thr Gln Ser Pro Gly Thr Leu Ser Leu Ser Pro Gly
1               5                   10                  15

Glu Thr Ala Ser Leu Ser Cys Thr Ala Ala Ser Tyr Gly His Met Thr
            20                  25                  30

Trp Tyr Gln Lys Lys Pro Gly Gln Pro Pro Lys Leu Leu Ile Phe Ala
        35                  40                  45

Thr Ser Lys Arg Ala Ser Gly Ile Pro Asp Arg Phe Ser Gly Ser Gln
    50                  55                  60

Phe Gly Lys Gln Tyr Thr Leu Thr Ile Thr Arg Met Glu Pro Glu Asp
65                  70                  75                  80

Phe Ala Arg Tyr Tyr Cys Gln Gln Leu Glu Phe Phe Gly Gln Gly Thr
                85                  90                  95

Arg Leu Glu

<210> SEQ ID NO 38
<211> LENGTH: 111
<212> TYPE: PRT
<213> ORGANISM: Homo sapiens

<400> SEQUENCE: 38

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln Asn Pro Gly Lys Ala Pro Glu Leu
        35                  40                  45

Met Ile Tyr Asp Val Ser Asn Arg Pro Ser Gly Ile Ser Asn Arg Phe
    50                  55                  60

Ser Gly Ser Lys Ser Gly Asn Thr Ala Ser Leu Thr Ile Ser Gly Leu
65                  70                  75                  80

Gln Ala Asp Asp Glu Ala Asp Tyr Tyr Cys Thr Ser Tyr Thr Asn Asp
                85                  90                  95
```

```
Ser Asn Ser Gln Val Phe Gly Gly Gly Thr Lys Leu Thr Val Leu
            100                 105                 110
```

<210> SEQ ID NO 39
<211> LENGTH: 105
<212> TYPE: PRT
<213> ORGANISM: Homo sapiens

<400> SEQUENCE: 39

```
Glu Ile Val Met Thr Gln Ser Pro Asp Thr Leu Ser Val Ser Pro Gly
1               5                   10                  15

Glu Thr Val Thr Leu Ser Cys Arg Ala Ser Gln Asn Ile Asn Lys Asn
            20                  25                  30

Leu Ala Trp Tyr Gln Tyr Lys Pro Gly Gln Ser Pro Arg Leu Val Ile
        35                  40                  45

Phe Glu Thr Tyr Ser Lys Ile Val Ala Phe Pro Ala Arg Phe Val Ala
    50                  55                  60

Ser Gly Ser Gly Thr Glu Phe Thr Leu Thr Ile Asn Asn Met Gln Ser
65                  70                  75                  80

Glu Asp Val Ala Val Tyr Tyr Cys Gln Gln Tyr Glu Glu Trp Pro Arg
                85                  90                  95

Thr Phe Gly Gln Gly Thr Lys Val Asp
            100                 105
```

<210> SEQ ID NO 40
<211> LENGTH: 105
<212> TYPE: PRT
<213> ORGANISM: Homo sapiens

<400> SEQUENCE: 40

```
Asp Ile Val Met Thr Gln Ser Pro Ser Leu Leu Ser Ala Ser Thr Gly
1               5                   10                  15

Asp Arg Val Thr Ile Ser Cys Arg Met Ser Gln Gly Ile Ser Ser Tyr
            20                  25                  30

Leu Ala Trp Tyr Gln Gln Lys Pro Gly Lys Ala Pro Glu Leu Leu Ile
        35                  40                  45

Tyr Ser Ala Ser Thr Leu Gln Ser Gly Val Pro Ser Arg Phe Ser Gly
    50                  55                  60

Ser Gly Ser Gly Thr Asp Phe Thr Leu Thr Ile Ser Gly Leu Gln Ser
65                  70                  75                  80

Gly Asp Phe Ala Ile Tyr Tyr Cys Gln Gln Tyr Tyr Arg Ser Pro Gln
                85                  90                  95

Thr Phe Gly Gln Gly Thr Lys Val Asp
            100                 105
```

<210> SEQ ID NO 41
<211> LENGTH: 3123
<212> TYPE: DNA
<213> ORGANISM: Artificial Sequence
<220> FEATURE:
<223> OTHER INFORMATION: A synthetic oligonucleotide sequence

<400> SEQUENCE: 41

```
gaaatattcc ctgtaaataa aaaaagtatc tcagtttctc tcaatgttca taattctcct     60
gagggtgagg aagtacttc tgggtctgct caaacaaatg cccagagac cacctggtag     120 gtaggtaagg agctcacctc gctctggata ttgagtctgt ctctttccct ctgtcgtctc    180
atagaaggcc agcccacttg ttcagctcct aagaagagag cccaggttta ccagattat    240
```

```
acaacacaac cagcttctga tgactctcct gttacaacat ccatggagat attttgtgta    300
ttatataatt caccaaacta atgtgaaatg cccaagttgc aatactgcac accctagggt    360
atgttcttgc aattcagcgg aggagaaatt ctttcagaga cagatggatc tgaattggta    420
aatatgtggg tacgaattct gggtttgagt gtcattgtcc agccatgttt cacaggtgtg    480
acctgtcagg gaagaaccag agttccttgt tctctcagag ggtagagctc acagaggtcc    540
tctctggttc ccaggaaagg taatttcact aatcttggtg atgagactat cctccagtgc    600
tgatgtacta tagagttttc atctgaagct gtcactgcta tccccaatgt acatcttttc    660
acacagaaat gtttagaggt caggccatat tctcagggtt acacattgag aaggatggag    720
atatattcta ctaccttctc ctgagatctc acacacaatc tcaaatttca aaaggtctca    780
gaagggcagc tctcaggtac tatttaaaaa taacccactt cctgggacag gtagcatcct    840
tctaaccatg atggatgttc tgaactacag tacacattgc atggatccag gtttgtctca    900
attcactgtg attattacac tcagcagctg tttcaatatg tctgaagggg taaatgacaa    960
tttaggtgac ctgggtgtat ggttggtgtt atatgaatct ttaaatgtag aacagtatta   1020
actgtattcc aaaatctgtc tttgatccat gatcacactt gtctcccaga ccagctcctt   1080
cagcacattt cctacccttta agaagaggac tctgggtttg gtgaggggag gccacaggaa   1140
gagaactgag ttctcagagg gcacagccag catacacctc ccagggtgag cccaaaagac   1200
tggggcctcc ctcatccctt tttacctatc catacaaagg caccacccac atgcaaatcc   1260
tcacttaggc acccacagga aatgactaca catttcctta aattcagggt ccagctcaca   1320
tgggaagtgc tttctgagag tcatggacct cctgcacaag aacatggagt ttgggctgag   1380
ctgggttttc ctcgttgctc ttttaagagg tgattcatgg agaaatagag agactgagtg   1440
tgagtgaaca tgagtgagaa aaactggatt tgtgtggcat tttctgataa cggtgtcctt   1500
ctgtttgcag gtgtccagtg tcagcgatta gtggagtctg ggggaggcgt ggtccagcct   1560
gggtcgtccc tgagactctc ctgtgcagcg tccggattcg acttcagtag acaaggcatg   1620
cactgggtcc gccaggctcc aggccagggg ctggagtggg tggcatttat taaatatgat   1680
ggaagtgaga aatatcatgc tgactccgta tggggccgac tcagcatctc cagagacaat   1740
tccaaggata cgctttatct ccaaatgaat agcctgagag tcgaggacac ggctacatat   1800
ttttgtgtga gagaggctgg tgggcccgac taccgtaatg ggtacaacta ttacgatttc   1860
tatgatggtt attataacta ccactatatg gacgtctggg gcaaagggac cacggtcacc   1920
gtctcctcag gtaagaatgg ccactctagg gcctttgttt tctgctactg cctgtgggt    1980 ttcctgagca ttgcaggttg gtcctcgggg catgttccga ggttggacct gggcggactg   2040
gccaggagga gacgggcact ggggtgcctt gaggatctgg gagcctctgt ggattttccg   2100
atgcctttgg aaaatgggac tcaggttggg tgcgtctgat ggagtaactg agcctggggg   2160
cttggggagc cacatttgga cgagatgcct gaacaaacca gggtcttag tgatggctga    2220 ggaatgtgtc tcaggagcgg tgtctgtagg actgcaagat cgctgcacag cagcgaatcg   2280
tgaaatattt tctttagaat tatgaggtgc gctgtgtgtc aacctgcatc ttaaattctt   2340
tattggctgg aaagagaact gtcggagtgg gtgaatccag ccaggaggga cgcgtagccc   2400
cggtcttgat gagagcaggg ttgggggcag gggtagccca gaaacggtgg ctgccgtcct   2460
gacaggggct tagggaggct ccaggacctc agtgccttga agctggtttc catgagaaaa   2520
ggattgttta tcttaggagg catgcttact gttaaaagac aggatatgtt tgaagtggct   2580
```

```
tctgagaaaa atggttaaga aaattatgac ttaaaaatgt gagagatttt caagtatatt    2640
aattttttta actgtccaag tatttgaaat tcttatcatt tgattaacac ccatgagtga    2700
tatgtgtctg gaattgaggc caaagcaagc tcagctaaga aatactagca cagtgctgtc    2760
ggccccgatg cgggactgcg ttttgaccat cataaatcaa gtttattttt ttaattaatt    2820
gagcgaagct ggaagcagat gatgaattag agtcaagatg gctgcatggg ggtctccggc    2880
acccacagca ggtggcagga agcaggtcac cgcgagagtc tattttagga agcaaaaaaa    2940
cacaattggt aaatttatca cttctggttg tgaagaggtg gttttgccca ggcccagatc    3000
tgaaagtgct ctactgagca aaacaacacc tggacaattt gcgtttctaa aataaggcga    3060
ggctgaccga aactgaaaag ctttttttta actatctgaa tttcatttcc aatcttagct    3120
tat                                                                  3123

<210> SEQ ID NO 42
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 42
ccttcagcac atttcctacc ttt                                              23

<210> SEQ ID NO 43
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 43
tcctcggggc atgttccgag gtt                                              23

<210> SEQ ID NO 44
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 44
ttagtggagg aagcgctatc aac                                              23

<210> SEQ ID NO 45
<211> LENGTH: 47
<212> TYPE: DNA
<213> ORGANISM: Homo Sapiens

<400> SEQUENCE: 45
atggagtttg ggctgagctg gttttcctc gttgctcttt taagagg                     47

<210> SEQ ID NO 46
<211> LENGTH: 101
<212> TYPE: DNA
<213> ORGANISM: Homo sapiens

<400> SEQUENCE: 46
gtgattcatg gagaaataga gagactgagt gtgagtgaac atgagtgaga aaaactggat      60
ttgtgtggca ttttctgata acggtgtcct tctgtttgca g                         101
```

```
<210> SEQ ID NO 47
<211> LENGTH: 419
<212> TYPE: DNA
<213> ORGANISM: Homo sapiens

<400> SEQUENCE: 47
gtgtccagtg tcagcgatta gtggagtctg ggggaggcgt ggtccagcct gggtcgtccc      60
tgagactctc ctgtgcagcg tccggattcg acttcagtag acaaggcatg cactgggtcc     120
gccaggctcc aggccagggg ctggagtggg tggcatttat taaatatgat ggaagtgaga     180
aatatcatgc tgactccgta tggggccgac tcagcatctc cagagacaat tccaaggata     240
cgctttatct ccaaatgaat agcctgagag tcgaggacac ggctacatat ttttgtgtga     300
gagaggctgg tgggcccgac taccgtaatg gtacaacta ttacgatttc tatgatggtt      360
attataacta ccactatatg gacgtctggg gcaaagggac cacggtcacc gtctcctca     419

<210> SEQ ID NO 48
<211> LENGTH: 3135
<212> TYPE: DNA
<213> ORGANISM: Artificial Sequence
<220> FEATURE:
<223> OTHER INFORMATION: A synthetic oligonucleotide sequence

<400> SEQUENCE: 48
gctgggctgt tgtgcacgta tgtgtgtttg tatgaccagg aggttttcaa atacatcatt      60
aaattacata gttatattaa tcttggcaag gcacttgtat tctgttttct ttaattctgt     120
ttgcagaaag tagacacata ttcagtctta gttccagtgt agggagtgct tttcatgaga     180
aaaataccag aaaaaagggc aaacatgggg cccactaatg taaaaattag ccacaatgtg     240
tatgtgtgtg tgtgtgtgtg tgtgtgtgtg tctgagttga atagtagagt tggagtgggc     300
ttctatccac atgcacctgc gcctacaggt attatcaggt acaataatca actgcagaac     360
cctaaaggaa ataagagtcc ccccaaaccc ctgaagagtg tttgggttca ccatgtgtcc     420
aatgattcag tgcctctcga gctccaggaa acggctccct ggtgatgcgt gagatctttt     480 cttgggtgt ccctgcagag ttcgctgggt ttcctaaggc tgattcacta tttcaaaaga     540
tggtgtgaga agcatatggt gtaaataaag cagaattctg agccagggca cagccacttt     600
atactgggct agagacactg gtaggaatat actctgtcag ctcagataga aacctccctg     660
cagggtgggg gcagggctgc aggggggcgct caggacacat cgagcacagt cttctgcccc     720
agagcaggtg cacatgaggc tggggagagg ttcctctcag ggcctgggac ttcctttaaa     780
aatatctaaa ataagtattt cacaaggact gctgatgttt gtataaatat cctattcaat     840
tgtgagcatt tatcaaactg gatgttgtaa tgagaaccac ttttataatg gcgatttcaa     900
actctgctag ttatcttaat aatagcagct ggaggtcagg aagagattat tacttataaa     960
taagtgcaat ttttggagag acacactcat tcccaaaata acacattcac atattaaggt    1020
ctagaaatgg ttcacgttgc ccctgagaca ttcaaatgtg ggttcaaagt gaggtgctgt    1080
cctcggggag ttgttcctta gtggaggaag cgctatcaac acagagttca gggatgggta    1140
ggggatgcgt ggcctctaac aggattacga ctcgaaccct cagctcctat aattgtgtcg    1200
tccgtgtgtc atggatttct ctttctcata ctgggtcagg aattggtcta ttaaatagca    1260
tccttcatga atatgcaaat aactgagggg aatatagtat ctctgtaccc tgaaagcatc    1320
acccaacaac aacatccctc cttgggagaa tcccctagag cacagctcct caccatggag    1380
tttgggctga gctgggtttt cctcgttgct ctttttaagag gtgattcatg gagaaataga    1440
```

```
gagactgagt gtgagtgaac atgagtgaga aaaactggat ttgtgtggca ttttctgata    1500
acggtgtcct tctgtttgca ggtgtccagt gtcagcgatt agtggagtct gggggaggcg    1560
tggtccagcc tgggtcgtcc ctgagactct cctgtgcagc gtccggattc gacttcagta    1620
gacaaggcat gcactgggtc cgccaggctc caggccaggg gctggagtgg gtggcattta    1680
ttaaatatga tggaagtgag aaatatcatg ctgactccgt atggggccga ctcagcatct    1740
ccagagacaa ttccaaggat acgctttatc tccaaatgaa tagcctgaga gtcgaggaca    1800
cggctacata tttttgtgtg agagaggctg gtgggcccga ctaccgtaat gggtacaact    1860
attacgattt ctatgatggt tattataact accactatat ggacgtctgg ggcaaaggga    1920
ccacggtcac cgtctcctca ggtaagaatg gccactctag ggcctttgtt ttctgctact    1980
gcctgtgggg tttcctgagc attgcaggtt ggtcctcggg gcatgttccg aggttggacc    2040
tgggcggact ggccaggagg ggacgggcac tggggtgcct tgaggatctg ggagcctctg    2100
tggattttcc gatgcctttg gaaaatggga ctcaggttgg gtgcgtctga tggagtaact    2160
gagcctgggg gcttggggag ccacatttgg acgagatgcc tgaacaaacc aggggtctta    2220
gtgatggctg aggaatgtgt ctcaggagcg gtgtctgtag gactgcaaga tcgctgcaca    2280
gcagcgaatc gtgaaatatt ttcttttagaa ttatgaggtg cgctgtgtgt caacctgcat    2340
cttaaattct ttattggctg gaaagagaac tgtcggagtg ggtgaatcca gccaggaggg    2400
acgcgtagcc ccggtcttga tgagagcagg gttgggggca ggggtagccc agaaacggtg    2460
gctgccgtcc tgacaggggc ttagggaggc tccaggacct cagtgccttg aagctggttt    2520
ccatgagaaa aggattgttt atcttaggag gcatgcttac tgttaaaaga caggatatgt    2580
ttgaagtggc ttctgagaaa aatggttaag aaaattatga cttaaaaatg tgagagattt    2640
tcaagtatat taatttttt aactgtccaa gtatttgaaa ttcttatcat ttgattaaca    2700
cccatgagtg atatgtgtct ggaattgagg ccaaagcaag ctcagctaag aaatactagc    2760
acagtgctgt cggccccgat gcgggactgc gttttgacca tcataaatca gtttatttt    2820 tttaattaat tgagcgaagc tggaagcaga tgatgaatta gagtcaagat ggctgcatgg    2880
gggtctccgg cacccacagc aggtggcagg aagcaggtca ccgcgagagt ctattttagg    2940
aagcaaaaaa acacaattgg taaatttatc acttctggtt gtgaagaggt ggttttgccc    3000
aggcccagat ctgaaagtgc tctactgagc aaaacaacac ctggacaatt tgcgtttcta    3060
aaataaggcg aggctgaccg aaactgaaaa ggcttttttt aactatctga atttcatttc    3120
caatcttagc ttatc                                                    3135

<210> SEQ ID NO 49

<400> SEQUENCE: 49

000

<210> SEQ ID NO 50
<211> LENGTH: 46
<212> TYPE: DNA
<213> ORGANISM: Homo sapiens

<400> SEQUENCE: 50
atggagtttg ggctgagctg gttttcctc gttgctcttt taagag                   46

<210> SEQ ID NO 51
<211> LENGTH: 100
<212> TYPE: DNA
```

<213> ORGANISM: Homo sapiens

<400> SEQUENCE: 51

| | | | | | |
|---|---|---|---|---|---|
| gtgattcatg | gagaaataga | gagactgagt | gtgagtgaac | atgagtgaga | aaaactggat | 60 |
| ttgtgtggca | ttttctgata | acggtgtcct | tctgtttgca | | | 100 |

<210> SEQ ID NO 52

<400> SEQUENCE: 52

000

<210> SEQ ID NO 53
<211> LENGTH: 3008
<212> TYPE: DNA
<213> ORGANISM: Artificial Sequence
<220> FEATURE:
<223> OTHER INFORMATION: A synthetic oligonucleotide sequence

<400> SEQUENCE: 53

| | | | | | |
|---|---|---|---|---|---|
| aaaagtccat | tttctctgat | aacagttat | tgttgatttt | attcttgttg | taaaaaaag | 60 |
| aaattctcat | ctatgtacat | ttcaaacctg | aataacaaaa | tttttattaa | caccaaaaat | 120 |
| aataaaagaa | tccaaatatt | tatcagctgc | ctaatagaaa | aacaaatcat | ggtaacattg | 180 |
| ttcgctggaa | tattacccat | cattcataat | aagggaatgt | ctgatacaca | aaataagaag | 240 |
| ataaaattat | caagtattta | aattgagtaa | aataagccaa | acaaataaga | gtatgtatga | 300 |
| ttctatttt | aaaaattctg | gaaaatgaaa | actgatctaa | agtaatataa | agaagattag | 360 |
| tagtttcctg | ggaatatgtt | ggcagaaggg | aaggagaaag | gataaggaaa | tagaaatagg | 420 |
| aagtagaagg | acagaaaaga | agttgaggga | atttcacttg | tccaccttcc | ttataatggt | 480 |
| aatagttatg | ccatgattat | cagttttaca | ctttaaatat | gtaaagtttta | taatctgtca | 540 |
| atcaaatctt | ataaaatgta | ttatgaggaa | acaagttgaa | aattagacaa | tgtaggagtg | 600 |
| acagaaagat | agatatgagt | atgttgaatg | tcagagatac | ctgaaagttt | atctacctga | 660 |
| accctagttc | tctccatagt | ttaaggtaaa | caggagagtg | caggaaaatc | atccatattc | 720 |
| tgattaggca | gtggcttctg | caaaccacac | taggcctggc | cggctgtgtc | ctggagttgg | 780 |
| ctaagggagg | agtcagggcc | agtggtgaga | agtgcaggcc | cagataccag | aactcactca | 840 |
| tcccagacat | gagctcttag | atacacagag | agcccatcca | tgtgtggatt | tatcttacat | 900 |
| ctgtaagtag | agaacattga | ctcttacaga | acataattta | cacacatagg | taaatctgaa | 960 |
| ataaggtgat | cagtgtgaag | attttatcac | agcacagttt | cataataagc | acaatttctc | 1020 |
| aaatcccatt | gttgtcaccc | atcttcctca | ggacactttc | atctgccctg | ggtcctgctc | 1080 |
| tttcttcagg | tgtctcaccc | cagagcttga | tatatagtag | gagacatgca | aatagggccc | 1140 |
| tcactctgct | gaagaaaacc | agccctgcag | ctctttgaga | ggagccccag | ccctgggatt | 1200 |
| cccagctgtt | tctgcttgct | gatcaggact | gcacacagag | aactcaccat | ggagtttggg | 1260 |
| ctgagctggg | ttttcctcgt | tgctcttttta | agaggtgatt | catggagaaa | tagagagact | 1320 |
| gagtgtgagt | gaacatgagt | gagaaaaact | ggatttgtgt | ggcattttct | gataacggtg | 1380 |
| tccttctgtt | tgcaggtgtc | cagtgtcagc | gattagtgga | gtctggggga | ggcgtggtcc | 1440 |
| agcctgggtc | gtccctgaga | ctctcctgtg | cagcgtccgg | attcgacttc | agtagacaag | 1500 |
| gcatgcactg | ggtccgccag | gctccaggcc | aggggctgga | gtgggtgca | tttattaaat | 1560 |
| atgatggaag | tgagaaatat | catgctgact | ccgtatgggg | ccgactcagc | atctccagag | 1620 |

```
acaattccaa ggatacgctt tatctccaaa tgaatagcct gagagtcgag gacacggcta    1680 catattttg tgtgagagag gctggtgggc ccgactaccg taatgggtac aactattacg    1740
atttctatga tggttattat aactaccact atatggacgt ctggggcaaa gggaccacgg    1800
tcaccgtctc ctcaggtaag aatgccact ctagggcctt tgttttctgc tactgcctgt     1860
ggggtttcct gagcattgca ggttggtcct cggggcatgt tccgaggttg gacctgggcg    1920
gactggccag gaggggacgg gcactggggt gccttgagga tctgggagcc tctgtggatt    1980
ttccgatgcc tttggaaaat gggactcagg ttgggtgcgt ctgatggagt aactgagcct    2040
gggggcttgg ggagccacat ttggacgaga tgcctgaaca aaccagggt cttagtgatg      2100 gctgaggaat gtgtctcagg agcggtgtct gtaggactgc aagatcgctg cacagcagcg    2160
aatcgtgaaa tattttcttt agaattatga ggtgcgctgt gtgtcaacct gcatcttaaa    2220
ttctttattg gctggaaaga gaactgtcgg agtgggtgaa tccagccagg agggacgcgt    2280
agccccggtc ttgatgagag cagggttggg ggcaggggta gcccagaaac ggtggctgcc    2340
gtcctgacag gggcttaggg aggctccagg acctcagtgc cttgaagctg gtttccatga    2400
gaaaaggatt gtttatctta ggaggcatgc ttactgttaa agacaggat atgtttgaag     2460 tggcttctga gaaaaatggt taagaaaatt atgacttaaa aatgtgagag attttcaagt    2520
atattaattt ttttaactgt ccaagtattt gaaattctta tcatttgatt aacacccatg    2580
agtgatatgt gtctggaatt gaggccaaag caagctcagc taagaaatac tagcacagtg    2640
ctgtcggccc cgatgcggga ctgcgttttg accatcataa atcaagttta ttttttttaat    2700 taattgagcg aagctggaag cagatgatga attagagtca agatggctgc atggggtct    2760 ccggcaccca cagcaggtgg caggaagcag gtcaccgcga gagtctattt taggaagcaa    2820
aaaaacacaa ttggtaaatt tatcacttct ggttgtgaag aggtggtttt gcccaggcc    2880 agatctgaaa gtgctctact gagcaaaaca acacctggac aatttgcgtt tctaaaataa    2940
ggcgaggctg accgaaactg aaaaggcttt ttttaactat ctgaatttca tttccaatct    3000
tagcttat                                                              3008
```

<210> SEQ ID NO 54

<400> SEQUENCE: 54

000

<210> SEQ ID NO 55
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 55

```
gaaaaccagc cctgcagctc ttt                                               23
```

<210> SEQ ID NO 56
<211> LENGTH: 101
<212> TYPE: DNA
<213> ORGANISM: Homo sapiens

<400> SEQUENCE: 56

```
gtgattcatg gagaaataga gagactgagt gtgagtgaac atgagtgaga aaaactggat      60
ttgtgtggca ttttctgata acggtgtcct tctgtttgca g                         101
```

<210> SEQ ID NO 57

<400> SEQUENCE: 57

000

<210> SEQ ID NO 58

<400> SEQUENCE: 58

000

<210> SEQ ID NO 59
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 59
tcctcggggc atgttccgag gtt                                          23

<210> SEQ ID NO 60
<211> LENGTH: 2817
<212> TYPE: DNA
<213> ORGANISM: Artificial Sequence
<220> FEATURE:
<223> OTHER INFORMATION: A synthetic oligonucleotide sequence

<400> SEQUENCE: 60

```
agatctcttc aattccattt actctctagc aatttaccta atatcaaaac atacagttat    60
gttatgttta caaatatgca cgcacctcta ttaatatgtg ttcataagta catacacatg   120
caccattacg tttacacata catgcatgta acaccaactg atgtaaaaat cattgtttta   180
tgtactcagt tttcctttga gtttaccctc ttttctctac tttttaaaat atttatttct   240
aatttgggga gctactaact gagattattt ttcatctcac tgaaaaacag ttttagaatt   300
tcctgtagag cagttctgct ggtggcaaat tccatcgggt tttgtctgaa agtagccat   360
tttctcctat tttttctgtt tattatatag aaagataact tatataaagt aaaattcaca   420
ggtcttaatt atacagtttg atggttttta caaatgcaga tgctcatgta gccaacagtc   480
cgatccattc tcacaacatc tccattactg cagaatggag acattctgtt ccagtcaatg   540
taaattatcc cattacacct accaaataga acgtgtatga gagacacctt tctcctgagg   600
acttttgcaa agtggggtgg atcatgtgtc ccgctccac tgaaaagggc taaatggaaa   660
actaaagtct gaaataaaat aggaggctgc cctgacgagg ggtcccactt tgcccttgga   720
cagagaacag gccgtggtca aggccctggt ccgggcagaa gcctctgtca ggacccactg   780
gcatctggtc acagacacga tggacctggg cctaggcaga agggggtgct gttggtctgc   840
tgctgagggc tctgtgggtt tctcagctgg gaaaccaaac acttgaactt ggtctccacg   900
cagggttcac tggggccagc agctgggctc tctctgcacc cttggagagc ctcaggccag   960
gcccagccca ggtaacccct cccagaaatg tcaccccacc actgggactg acactcaggc  1020
acacggagtg atttggttgg gcagaggaag aggagcacat ttgcatgaag ggcccctctc  1080
tcttttctgg gactacaggg tgggtaagaa ataccttgcaa ctgtcagcct cagcagagct  1140
ctggggagtc tgcaccatgg cctgggctct gctgctcctc accctcctca ctcagggcac  1200
aggtgacgcc tccaggaag gggcttcagg gacctctggg ctgatccttg gtctcctgct  1260
cctcaggctc accggggccc agcactgact cactggcatg tgtttctccc tctttccagg  1320
```

```
gtcctgggcc cagtctgccc tgactcagcc tgcctccgtg tctgggtctc ctggacagtc    1380
gatcaccatc tcctgcaatg gaaccagcaa tgatgttggt ggctatgaat ctgtctcctg    1440
gtaccaacaa catcccggca aagcccccaa agtcgtgatt tatgatgtca gtaaacggcc    1500
ctcaggggtt tctaatcgct tctctggctc caagtccggc aacacggcct ccctgaccat    1560
ctctgggctc caggctgagg acgagggtga ctattactgc aagtctctga caagcacgag    1620
acgtcgggtt ttcggcactg ggaccaagct gaccgttcta ggtaagtctc cccgcttctc    1680
tcctctttga gatcccaagt taaacacggg gagttttttcc cttcctgtc tgtcgaaggc    1740
taaggtctaa gcctgtctgg atgtctgaa tctttgcccc tccttgcctg ggctcctgcc    1800
ctcttctgtg attctgtcct ctgtgggtcc cagttacggg gctgcattaa acacagtgac    1860
aggaggcctt tgactgagga cttggagaga tgggggagga aatggcagga ggacaaagat    1920
agaggaagaa tattccgtga aaggtggcc ccacagcgct gggtcacacg ccatcccca    1980
agacaggcag gacaccacag acagggtggt gggtctcaga aaactcaggc cctaaacgtg    2040
gatgcttacc aattcctcca ctggaggaag acctcagagc agatgcccag gacagggact    2100
tctggtaggg acggtgactg ggacgggtgc ctgtttgtca gggaaaaccc actggagagt    2160
cagatccccc agataacttc tcacgacatg gagactcttt cgaacagaca aagctccacg    2220
ttcagctcag ggagtaaaaa aaaaatgcct caaatggagg cctttgatct actgaatcc    2280
agcccccagg actgacaccc tgtctcacca ggcagcccag aggggtctct gcagggaggt    2340
ggggtggggg ctgcaatgat ggcaccaggg agatgtgtgg gtaagaaacc cactccctgt    2400
gagagagaag agcctgaacc caggaccaac agctgccctg catgaagaga tgagaacaag    2460
gggaactggt aggaggtgtt cagacagaca ccccccaagat agacaaatac ccagggtgag    2520
atgtggtcct ggactccatc ccatccagtg tggagccagc accggtgggg gtctataggt    2580
gatgaaaat atgaaaaaga dacagatcca agaggggggtc tgtgacccc aagagtgggg    2640
gcaactccca tctgacagcg agtgtctcca ctcaccgctg acctgacctc agtccagcaa    2700
gggtccggcc tgaggtccct gccctgggcc ttagtcccat acccacttca agactgaggt    2760
caggggctcc ccaggtggac accaggactc tgaccccctg cccctcatcc aggatcc      2817
```

<210> SEQ ID NO 61

<400> SEQUENCE: 61

000

<210> SEQ ID NO 62
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 62
tttctgggac tacagggtgg gta                                             23

<210> SEQ ID NO 63

<400> SEQUENCE: 63

000

<210> SEQ ID NO 64

```
<400> SEQUENCE: 64

000

<210> SEQ ID NO 65
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 65
cccaagttaa acacggggag ttt                                              23

<210> SEQ ID NO 66
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 66
agccctaaaa agcatgggct                                                  20

<210> SEQ ID NO 67
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 67
cttctgcacc aagaggaggg                                                  20

<210> SEQ ID NO 68
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 68
gccctaaaaa gcatgggctg                                                  20

<210> SEQ ID NO 69
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 69
tcccctccct tctgagtctg                                                  20

<210> SEQ ID NO 70
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 70
gccattgtga gtgagcccta                                                  20

<210> SEQ ID NO 71
```

```
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 71
agtctgcagt aaacccctgc                                                   20

<210> SEQ ID NO 72
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 72
atgtgattgg ctccaggcat                                                   20

<210> SEQ ID NO 73
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 73
cttctgcacc aagaggaggg                                                   20

<210> SEQ ID NO 74
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 74
gaatgtgatt ggctccaggc                                                   20

<210> SEQ ID NO 75
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 75
agtctgcagt aaacccctgc                                                   20

<210> SEQ ID NO 76
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 76
gccagaatgt gattggctcc                                                   20

<210> SEQ ID NO 77
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 77
```

```
ccagtggggc ttggtatgtt                                              20

<210> SEQ ID NO 78
<211> LENGTH: 19
<212> TYPE: DNA
<213> ORGANISM: Artificial Sequence
<220> FEATURE:
<223> OTHER INFORMATION: A synthetic oligonucleotide sequence

<400> SEQUENCE: 78
gccattgtga gtgagccct                                               19

<210> SEQ ID NO 79
<211> LENGTH: 30
<212> TYPE: DNA
<213> ORGANISM: Artificial Sequence
<220> FEATURE:
<223> OTHER INFORMATION: A synthetic oligonucleotide sequence

<400> SEQUENCE: 79
gcatactaca gaagtgagaa acaaagacag                                   30

<210> SEQ ID NO 80
<211> LENGTH: 28
<212> TYPE: DNA
<213> ORGANISM: Artificial Sequence
<220> FEATURE:
<223> OTHER INFORMATION: A synthetic oligonucleotide sequence

<400> SEQUENCE: 80
gaataggcag acatacacgt agatcagc                                     28

<210> SEQ ID NO 81
<211> LENGTH: 34
<212> TYPE: DNA
<213> ORGANISM: Artificial Sequence
<220> FEATURE:
<223> OTHER INFORMATION: A synthetic oligonucleotide sequence

<400> SEQUENCE: 81
cctacaggta ttatcaggta caataatcaa ctgc                              34

<210> SEQ ID NO 82
<211> LENGTH: 33
<212> TYPE: DNA
<213> ORGANISM: Artificial Sequence
<220> FEATURE:
<223> OTHER INFORMATION: A synthetic oligonucleotide sequence

<400> SEQUENCE: 82
gtgagcattt atcaaactgg atgttgtaat gag                               33

<210> SEQ ID NO 83
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 83
ggagaatccc ctagagcaca gc                                           22

<210> SEQ ID NO 84
<211> LENGTH: 29
<212> TYPE: DNA
```

```
<213> ORGANISM: Artificial Sequence
<220> FEATURE:
<223> OTHER INFORMATION: A synthetic oligonucleotide sequence

<400> SEQUENCE: 84
cgactaccgt aatgggtaca actattacg                                      29

<210> SEQ ID NO 85
<211> LENGTH: 28
<212> TYPE: DNA
<213> ORGANISM: Artificial Sequence
<220> FEATURE:
<223> OTHER INFORMATION: A synthetic oligonucleotide sequence

<400> SEQUENCE: 85
ctttattggc tggaaagaga actgtcgg                                       28

<210> SEQ ID NO 86
<211> LENGTH: 30
<212> TYPE: DNA
<213> ORGANISM: Artificial Sequence
<220> FEATURE:
<223> OTHER INFORMATION: A synthetic oligonucleotide sequence

<400> SEQUENCE: 86
cagatgatga attagagtca agatggctgc                                     30

<210> SEQ ID NO 87
<211> LENGTH: 21
<212> TYPE: DNA
<213> ORGANISM: Artificial Sequence
<220> FEATURE:
<223> OTHER INFORMATION: A synthetic oligonucleotide sequence

<400> SEQUENCE: 87
gacgccgcat cggtgattcg g                                              21

<210> SEQ ID NO 88
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 88
ccacctcttc acaaccagaa gtg                                            23

<210> SEQ ID NO 89
<211> LENGTH: 24
<212> TYPE: DNA
<213> ORGANISM: Artificial Sequence
<220> FEATURE:
<223> OTHER INFORMATION: A synthetic oligonucleotide sequence

<400> SEQUENCE: 89
cccctgtcag gacggcagcc accg                                           24

<210> SEQ ID NO 90
<211> LENGTH: 21
<212> TYPE: DNA
<213> ORGANISM: Artificial Sequence
<220> FEATURE:
<223> OTHER INFORMATION: A synthetic oligonucleotide sequence

<400> SEQUENCE: 90
ggagataaag cgtatccttg g                                              21
```

<210> SEQ ID NO 91
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 91
cgtaatcctg ttagaggcca cgc                                           23

<210> SEQ ID NO 92
<211> LENGTH: 24
<212> TYPE: DNA
<213> ORGANISM: Artificial Sequence
<220> FEATURE:
<223> OTHER INFORMATION: A synthetic oligonucleotide sequence

<400> SEQUENCE: 92
gccgtttcct ggagctcgag aggc                                          24

<210> SEQ ID NO 93
<211> LENGTH: 24
<212> TYPE: DNA
<213> ORGANISM: Artificial Sequence
<220> FEATURE:
<223> OTHER INFORMATION: A synthetic oligonucleotide sequence

<400> SEQUENCE: 93
cgtaaacacc aaaacaacac accc                                          24

<210> SEQ ID NO 94
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 94
gccagaatgt gattggctcc                                               20

<210> SEQ ID NO 95
<211> LENGTH: 30
<212> TYPE: DNA
<213> ORGANISM: Artificial Sequence
<220> FEATURE:
<223> OTHER INFORMATION: A synthetic oligonucleotide sequence

<400> SEQUENCE: 95
cctagttatg ttgagttcca tcaacactcc                                    30

<210> SEQ ID NO 96
<211> LENGTH: 29
<212> TYPE: DNA
<213> ORGANISM: Artificial Sequence
<220> FEATURE:
<223> OTHER INFORMATION: A synthetic oligonucleotide sequence

<400> SEQUENCE: 96
cgactaccgt aatgggtaca actattacg                                     29

<210> SEQ ID NO 97
<211> LENGTH: 21
<212> TYPE: DNA
<213> ORGANISM: Artificial Sequence
<220> FEATURE:

-continued

<223> OTHER INFORMATION: A synthetic oligonucleotide sequence

<400> SEQUENCE: 97
gacgccgcat cggtgattcg g                                    21

<210> SEQ ID NO 98
<211> LENGTH: 26
<212> TYPE: DNA
<213> ORGANISM: Artificial Sequence
<220> FEATURE:
<223> OTHER INFORMATION: A synthetic oligonucleotide sequence

<400> SEQUENCE: 98
gcaaattcca tgttgcagtg agaagg                               26

<210> SEQ ID NO 99
<211> LENGTH: 24
<212> TYPE: DNA
<213> ORGANISM: Artificial Sequence
<220> FEATURE:
<223> OTHER INFORMATION: A synthetic oligonucleotide sequence

<400> SEQUENCE: 99
gggcaaaacc acctcttcac aacc                                 24

<210> SEQ ID NO 100
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 100
gctctttggt tttctttcca cg                                   22

<210> SEQ ID NO 101
<211> LENGTH: 24
<212> TYPE: DNA
<213> ORGANISM: Artificial Sequence
<220> FEATURE:
<223> OTHER INFORMATION: A synthetic oligonucleotide sequence

<400> SEQUENCE: 101
gcacacccta gggtatgttc ttgc                                 24

<210> SEQ ID NO 102
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 102
ggtactattt aaaataacc cac                                   23

<210> SEQ ID NO 103
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 103
gcaaatcctc acttaggcac cc                                   22

```
<210> SEQ ID NO 104
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 104
gctgactccg tatggggccg ac                                              22

<210> SEQ ID NO 105
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 105
gagcctgggg gcttggggag cc                                              22

<210> SEQ ID NO 106
<211> LENGTH: 29
<212> TYPE: DNA
<213> ORGANISM: Artificial Sequence
<220> FEATURE:
<223> OTHER INFORMATION: A synthetic oligonucleotide sequence

<400> SEQUENCE: 106
cgactaccgt aatgggtaca actattacg                                       29

<210> SEQ ID NO 107
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 107
gccagaatgt gattggctcc                                                 20

<210> SEQ ID NO 108
<211> LENGTH: 28
<212> TYPE: DNA
<213> ORGANISM: Artificial Sequence
<220> FEATURE:
<223> OTHER INFORMATION: A synthetic oligonucleotide sequence

<400> SEQUENCE: 108
ctttattggc tggaaagaga actgtcgg                                        28

<210> SEQ ID NO 109
<211> LENGTH: 30
<212> TYPE: DNA
<213> ORGANISM: Artificial Sequence
<220> FEATURE:
<223> OTHER INFORMATION: A synthetic oligonucleotide sequence

<400> SEQUENCE: 109
cagatgatga attagagtca agatggctgc                                      30

<210> SEQ ID NO 110
<211> LENGTH: 32
<212> TYPE: DNA
<213> ORGANISM: Artificial Sequence
<220> FEATURE:
<223> OTHER INFORMATION: A synthetic oligonucleotide sequence
```

<400> SEQUENCE: 110
ggttaactcg ttttctcttt gtgattaagg ag                32

<210> SEQ ID NO 111
<211> LENGTH: 21
<212> TYPE: DNA
<213> ORGANISM: Artificial Sequence
<220> FEATURE:
<223> OTHER INFORMATION: A synthetic oligonucleotide sequence

<400> SEQUENCE: 111
gacgccgcat cggtgattcg g                            21

<210> SEQ ID NO 112
<211> LENGTH: 26
<212> TYPE: DNA
<213> ORGANISM: Artificial Sequence
<220> FEATURE:
<223> OTHER INFORMATION: A synthetic oligonucleotide sequence

<400> SEQUENCE: 112
gcaaattcca tgttgcagtg agaagg                       26

<210> SEQ ID NO 113
<211> LENGTH: 24
<212> TYPE: DNA
<213> ORGANISM: Artificial Sequence
<220> FEATURE:
<223> OTHER INFORMATION: A synthetic oligonucleotide sequence

<400> SEQUENCE: 113
gggcaaaacc acctcttcac aacc                         24

<210> SEQ ID NO 114
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 114
gctctttggt tttctttcca cg                           22

<210> SEQ ID NO 115
<211> LENGTH: 24
<212> TYPE: DNA
<213> ORGANISM: Artificial Sequence
<220> FEATURE:
<223> OTHER INFORMATION: A synthetic oligonucleotide sequence

<400> SEQUENCE: 115
gcacacccta gggtatgttc ttgc                         24

<210> SEQ ID NO 116
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 116
ggtactattt aaaaataacc cac                          23

<210> SEQ ID NO 117
<211> LENGTH: 22

```
<212> TYPE: DNA
<213> ORGANISM: Artificial Sequence
<220> FEATURE:
<223> OTHER INFORMATION: A synthetic oligonucleotide sequence

<400> SEQUENCE: 117
gcaaatcctc acttaggcac cc                                              22

<210> SEQ ID NO 118
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 118
gctgactccg tatggggccg ac                                              22

<210> SEQ ID NO 119
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 119
gagcctgggg gcttggggag cc                                              22

<210> SEQ ID NO 120
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 120
cttaggagct gaacaagtgg gc                                              22

<210> SEQ ID NO 121
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 121
ccataaacac cgcaggtgag gg                                              22

<210> SEQ ID NO 122
<211> LENGTH: 24
<212> TYPE: DNA
<213> ORGANISM: Artificial Sequence
<220> FEATURE:
<223> OTHER INFORMATION: A synthetic oligonucleotide sequence

<400> SEQUENCE: 122
cccctggttt gttcaggcat ctcg                                            24

<210> SEQ ID NO 123
<211> LENGTH: 30
<212> TYPE: DNA
<213> ORGANISM: Artificial Sequence
<220> FEATURE:
<223> OTHER INFORMATION: A synthetic oligonucleotide sequence

<400> SEQUENCE: 123
```
cctagttatg ttgagttcca tcaacactcc                                         30

<210> SEQ ID NO 124
<211> LENGTH: 25
<212> TYPE: DNA
<213> ORGANISM: Artificial Sequence
<220> FEATURE:
<223> OTHER INFORMATION: A synthetic oligonucleotide sequence

<400> SEQUENCE: 124
aaacacctgt ggttcttcct cctcc                                              25

<210> SEQ ID NO 125
<211> LENGTH: 28
<212> TYPE: DNA
<213> ORGANISM: Artificial Sequence
<220> FEATURE:
<223> OTHER INFORMATION: A synthetic oligonucleotide sequence

<400> SEQUENCE: 125
gctgggtttt cctcgttgct cttttaag                                           28

<210> SEQ ID NO 126
<211> LENGTH: 21
<212> TYPE: DNA
<213> ORGANISM: Artificial Sequence
<220> FEATURE:
<223> OTHER INFORMATION: A synthetic oligonucleotide sequence

<400> SEQUENCE: 126
gcgtacttgc cccctctcag g                                                  21

<210> SEQ ID NO 127
<211> LENGTH: 27
<212> TYPE: DNA
<213> ORGANISM: Artificial Sequence
<220> FEATURE:
<223> OTHER INFORMATION: A synthetic oligonucleotide sequence

<400> SEQUENCE: 127
gcttgtgatt cacgttgcag atgtagg                                            27

<210> SEQ ID NO 128
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 128
cacacggacg accaattata gg                                                 22

<210> SEQ ID NO 129
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 129
attgtgtcgt ccgtgtgtca tgg                                                23

<210> SEQ ID NO 130
<211> LENGTH: 23
<212> TYPE: DNA
<213> ORGANISM: Artificial Sequence

```
<220> FEATURE:
<223> OTHER INFORMATION: A synthetic oligonucleotide sequence

<400> SEQUENCE: 130
gttgatagcg cttcctccac tgg                                              23

<210> SEQ ID NO 131
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 131
cgacacaatt ataggagctg agg                                              23

<210> SEQ ID NO 132
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 132
tcgagtcgta atcctgttag agg                                              23

<210> SEQ ID NO 133
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 133
tcaccctggg aggtgtatgc tgg                                              23

<210> SEQ ID NO 134
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 134
ctttgtatgg ataggtaaaa agg                                              23

<210> SEQ ID NO 135
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 135 cttttttacct atccatacaa agg                                             23

<210> SEQ ID NO 136
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 136
ccttcagcac atttcctacc tgg                                              23
```

```
<210> SEQ ID NO 137
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 137
ccaggtagga aatgtgctga agg                                          23

<210> SEQ ID NO 138
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 138
gtcctcgggg catgttccga ggg                                          23

<210> SEQ ID NO 139
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 139
ggtcctcggg gcatgttccg agg                                          23

<210> SEQ ID NO 140
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 140
ctcaggttgg gtgcgtctga tgg                                          23

<210> SEQ ID NO 141
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 141
tcctcggggc atgttccgag ggg                                          23

<210> SEQ ID NO 142
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 142
gcattgcagg ttggtcctcg ggg                                          23

<210> SEQ ID NO 143
<211> LENGTH: 23
<212> TYPE: DNA
<213> ORGANISM: Artificial Sequence
<220> FEATURE:
<223> OTHER INFORMATION: A synthetic oligonucleotide sequence
```

```
<400> SEQUENCE: 143
gctgtttctg cttgctgatc agg                                          23

<210> SEQ ID NO 144
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 144
gatcagcaag cagaaacagc tgg                                          23

<210> SEQ ID NO 145
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 145
atcagcaagc agaaacagct ggg                                          23

<210> SEQ ID NO 146
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 146
gaaaaccagc cctgcagctc tgg                                          23

<210> SEQ ID NO 147
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 147
ctgggtcctg ctctttcttc agg                                          23

<210> SEQ ID NO 148
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 148
gagacacctg aagaaagagc agg                                          23

<210> SEQ ID NO 149
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 149
gcacacggag tgatttggtt ggg                                          23

<210> SEQ ID NO 150
```

```
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 150
ctcaggcaca cggagtgatt tgg                                              23

<210> SEQ ID NO 151
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 151
ggcacacgga gtgatttggt tgg                                              23

<210> SEQ ID NO 152
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 152
tacccaccct gtagtcccag agg                                              23

<210> SEQ ID NO 153
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 153
ctcctctggg actacagggt ggg                                              23

<210> SEQ ID NO 154
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 154
ctgctgaggc tgacagttgc agg                                              23

<210> SEQ ID NO 155
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 155
gaccttagcc ttcgacagac agg                                              23

<210> SEQ ID NO 156
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 156
```

```
gagatcccaa gttaaacacg ggg                                             23

<210> SEQ ID NO 157
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 157
ttcctgtctg tcgaaggcta agg                                             23

<210> SEQ ID NO 158
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 158
ggctaaggtc taagcctgtc tgg                                             23

<210> SEQ ID NO 159
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 159
aaactccccg tgtttaactt ggg                                             23

<210> SEQ ID NO 160
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 160
aaaactcccc gtgtttaact tgg                                             23

<210> SEQ ID NO 161
<211> LENGTH: 4920
<212> TYPE: DNA
<213> ORGANISM: Homo sapiens

<400> SEQUENCE: 161
tgcacatctt cgtgttacct tcatgacaca gtcaactccc attatgtaag aaatggtgag     60
tgcattccca agggtcttgc acagttataa aaatagactt gatgaggtga ggagttgttt    120
aaattcccct ctgaagaagc agcatcaacc caacaaacca ctctcttccc tctgtgacta    180
gagctctgtc acaggccaca tggacctaaa tccttgatgg agattacagg actacgtaaa    240
ttggactgat cgttttatg ctgttaaatt aataggtgag tctgcactcc agcctgggca    300
acagaataat cttgtctgta aaatacaaaa gaaagataaa ttaatagata ctgactttga    360
catttcggat aataatattt tcataaaccg aatttaatta tacccacatt gttacctaca    420
ccttcactga aaagttccta gttatgttga gttccatcaa cactccacat gttcaaatct    480
ggacatccaa gagagtctag agaataaaac gcaatgaggg cagtgaaact tgcgtatatt    540
cagcacctct taactcagga ggactcaata caccctggaa cactctgctt ttctgaatgg    600
```

```
ctcacaatga ctccagctca ctctccaacc tcctcaaaca tctggcctct gtttgcccta    660
agttcacgct ctgctcttag tctatgttct gaagtctttg taagtgaaaa tgagctgtca    720
gatggatctt ccttctcact gcaacatgga atttgctatt tcacttaatg accactcttt    780
ccacaatggt tgatttcttt tggcctgttc attactggtg attttcaagg gaatctcagt    840
tgaatcttta ctgttttgca ttttgtctcc atgacaatgt tgggaagttt ttcttctagc    900
agcataacat gatctagtga cctgacacat ttgcagcaaa caatacctac aaattcagaa    960
gctctttggt tttctttcca cgaaatataa ttcttgctct tctgtgtatg agcacatcct   1020
agcatccctg tacacaccca cgtagatgtc tacacgccga tgaaatattc cctgtaaata   1080
aaaaaagtat ctcagtttct ctcaatgttc ataattctcc tgagggtgag gaaggtactt   1140
ctgggtctgc tcaaacaaat ggcccagaga ccacctggta ggtaggtaag gagctcacct   1200
cgctctggat attgagtctg tctctttccc tctgtcgtct catagaaggc cagcccactt   1260
gttcagctcc taagaagaga gcccaggttt atccagatta tacaacacaa ccagcttctg   1320
atgactctcc tgttacaaca tccatggaga tattttgtgt attatataat tcaccaaact   1380
aatgtgaaat gcccaagttg caatactgca cacctaggg tatgttcttg caattcagcg    1440
gaggagaaat tctttcagag acagatggat ctgaattggt aaatatgtgg gtacgaattc   1500
tgggcttgag tgtcattgtc cagccatgtt tcacaggtgt gacctgtcag ggaagaacca   1560
gagttccttg ttctctcaga gggtagagct cacagaggtc ctctctggtt cccaggaaag   1620
gtaatttcac taatcttggt gatgagacta tcctccagtg ctgatgtact atagagtttt   1680
catctgaagc tgtcactgct atccccaatg tacatctttt cacacagaaa tgtttagagg   1740
tcaggccata ttctcagggt tacacattga aaggatgga gatatattct actaccttct    1800
cctgagatct cacacacaat ctcaaatttc aaaaggtctc agaagggcag ctctcaggta   1860
ctatttaaaa ataacccact tcctgggaca ggtagcatcc ttctaaccat gatggatgtt   1920
ctgaagtaca gtacacattg catggatcca ggtttgtctc aattcactgt gattattaca   1980
ctcagcagct gtttcaatat gtctgaaggg gtaaatgaca atttaggtga cctgggtgta   2040
tggttggtgt tatatgaatc tttaaatgta gaacagtatt aactgtattc caaaatctgt   2100
ctttgatcca tgatcacact tgtctcccag accagctcct tcagcacatt tcctacctgg   2160
aagaagagga ctctgggttt ggtgagggga ggccacagga agagaactga gttctcagag   2220
ggcacagcca gcatacacct cccagggtga gcccaaaaga ctggggcctc cctcatccct   2280
ttttacctat ccatacaaag gcaccaccca catgcaaatc ctcacttagg cacccacagg   2340
aaatgactac acatttcctt aaattcaggg tccagctcac atgggaagtg ctttctgaga   2400
gtcatggacc tcctgcacaa gaacatgaaa cacctgtggt tcttcctcct cctggtggca   2460
gctcccagat gtgagtgtct caggaatgcg gatatgaaga tatgagatgc tgcctctgat   2520
cccagggctc actgtgggtt tttctgttca caggggtcct gtcccaggtg cagctacagc   2580 agtgggcgc aggactgttg aagccttcgg agaccctgtc cctcacctgc ggtgtttatg     2640
gtgggtcctt cagtggttac tactggagct ggatccgcca gcccccaggg aagggggctgg  2700 agtggattgg gaaatcaat catagtgaa gcaccaacta caacccgtcc ctcaagagtc     2760
gagtcaccat atcagtagac acgtccaaga agcagctctc cctgaagttg agctctgtga   2820
acgccgcgga cacggctgtg tattactgtg cgagagttat tactagggcg agtcctggca   2880
cagacgggag gtacggtatg gacgtctggg gccaagggac cacggtcacc gtctcctcag   2940
gtgagaatgg ccactctagg gcctctgttc tctgctactg cctgtggggt ttcctgagca   3000
```

```
ttgcaggttg gtcctcgggg catgttccga ggggacctgg gcggactggc caggagggga    3060
cgggcactgg ggtgccttga ggatctggga gcctctgtgg attttccgat gcctttggaa    3120
aatgggactc aggttgggtg cgtctgatgg agtaactgag cctggggct  tggggagcca    3180 catttggacg agatgcctga acaaaccagg ggtcttagtg atggctgagg aatgtgtctc    3240
aggagcggtg tctgtaggac tgcaagatcg ctgcacagca gcgaatcgtg aaatattttc    3300
tttagaatta cgaggtgcgc tgtgtgtcaa cctgcatctt aaattcttta ttggctggaa    3360
agagaactgt cggagtgggt gaatccagcc aggagggacg cgtagccccg gtcttgatga    3420
gagcagggtt gggggcaggg gtagcccaga aacggtggct gccgtcctga caggggctta    3480
gggaggctcc aggacctcag tgccttgaag ctggtttcca tgagaaaagg attgtttatc    3540
ttaggaggca tgcttactgt taaaagacag gatatgtttg aagtggcttc tgagaaaaat    3600
ggttaagaaa attatgactt aaaaatgtga gagattttca agtatattaa ttttttttaac   3660 tgtccaagta tttgaaattc ttatcatttg attaacaccc atgagtgata tgtgtctgga    3720
attgaggcca aagcaagctc agctaagaaa tactagcaca gtgctgtcgg ccccgatgcg    3780
ggactgcgtt ttgaccatca taaatcaagt ttatttttt  aattaattga gcgaagctgg    3840
aagcagatga tgaattagag tcaagatggc tgcatggggg tctccggcac ccacagcagg    3900
tggcaggaag caggtcaccg cgagagtcta ttttaggaag caaaaaaaca caattggtaa    3960
atttatcact tctggttgtg aagaggtggt tttgcccagg cccagatctg aaagtgctct    4020
actgagcaaa acaacacctg gacaatttgc gtttctaaaa taaggcgagg ctgaccgaaa    4080
ctgaaaaggc tttttttaac tatctgaatt tcatttccaa tcttagctta tcaactgcta    4140
gtttgtgcaa acagcatatc aacttctaaa ctgcattcat ttttaaagta agatgtttaa    4200
gaaattaaac agtcttaggg agagtttatg actgtattca aaaagttttt taaattagct    4260
tgttatccct tcatgtgata actaatctca aatactttt  cgatacctca gagcattatt    4320
ttcataatga ctgtgttcac aatcttttta ggttaactcg ttttctcttt gtgattaagg    4380
agaaacactt tgatattctg atagagtggc cttcatttta gtattttttca agaccacttt   4440 tcaactactc actttaggat aagttttagg taaaatgtgc atcattatcc tgaattattt    4500
cagttaagca tgttagttgg tggcataaga gaaaactcaa tcagatagtg ctgaagacag    4560
gactgtggag acaccttaga aggacagatt ctgttccgaa tcaccgatgc ggcgtcagca    4620
ggactggcct agcggaggct ctgggagggt ggctgccagg cccggcctgg gctttgggtc    4680
tccccggact acccagagct gggatgcgtg gcttctgctg ccgggcgact ggctgctcag    4740
gccccagccc tggtgaatgg acttggagga atgattccat gccaaagctt gcaaggctc    4800 gcagtgacca tgcgcccgac atggtaagag acaggcagcc gccgctgctg catttgcttc    4860
tcttaaaact ttgtatttga cgtcttattt ccactagaag gggaactggt cttaattgct    4920
```

<210> SEQ ID NO 162
<211> LENGTH: 4668
<212> TYPE: DNA
<213> ORGANISM: Homo sapiens

<400> SEQUENCE: 162

```
tggctccagg cattttaaat tcaacaggtt atgtaaccag gctttaaatt tgcacatctt      60
cgtgttacct tcatgacaca gtcaactccc attatgtaag aaatggtgag tgcattccca     120
agggtcttgc acagttataa aaatagactt gatgaggtga ggagttgttt aaattcccct     180
```

```
ctgaagaagc agcatcaacc caacaaacca ctctcttccc tctgtgacta gagctctgtc    240
acaggccaca tggacctaaa tccttgatgg agattacagg actacgtaaa ttggactgat    300
cgtttttatg ctgttaaatt aataggtgag tctgcactcc agcctgggca acagaataat    360
cttgtctgta aaatacaaaa gaaagataaa ttaatagata ctgactttga catttcggat    420
aataatattt tcataaaccg aatttaatta tacccacatt gttacctaca ccttcactga    480
aaagttccta gttatgttga gttccatcaa cactccacat gttcaaatct ggacatccaa    540
gagagtctag agaataaaac gcaatgaggg cagtgaaact tgcgtatatt cagcacctct    600
taactcagga ggactcaata caccctggaa cactctgctt ttctgaatgg ctcacaatga    660
ctccagctca ctctccaacc tcctcaaaca tctggcctct gtttgcccta agttcacgct    720
ctgctcttag tctatgttct gaagtctttg tagaggtgaa aatgagctgt cagatggatc    780
ttccttctca ctgcaacatg gaatttgcta tttcacttaa tgaccactct ttccacaatg    840
gttgatttct tttggcctgt tcattactgg tgattttcaa gggaatctca gttgaatctt    900
tactgttttg cattttgtct ccatgacaat gttgggaagt ttttcttcta gcagcataac    960
atgatctagt gacctgacac atttgcagca acaatacct acaaattcag aagctctttg   1020
gttttctttc cacgaaatat aattcttgct cttctgtgta tgagcacatc ctagcatccc   1080
tgtacacacc cacgtagatg tctacacgcc gatgaaatat tccctgtaaa taaaaaaagt   1140
atctcagttt ctctcaatgt tcataattct cctgagggtg aggaaggtac ttctgggtct   1200
gctcaaacaa atggcccaga gaccacctgg taggtaggta aggagctcac ctcgctctgg   1260
atattgagtc tgtctctttc cctctgtcgt ctcatagaag gccagcccac ttgttcagct   1320
cctaagaaga gagcccaggt ttatccagat tatacaacac aaccagcttc tgatgactct   1380
cctgttacaa catccatgga gatattttgt gtattatata attcaccaaa ctaatgtgaa   1440
atgcccaagt tgcaatactg cacaccctag gtatgttct tgcaattcag cggaggagaa   1500
attctttcag agacagatgg atctgaattg gtaaatatgt gggtacgaat tctgggcttg   1560
agtgtcattg tccagccatg tttcacaggt gtgacctgtc agggaagaac cagagttcct   1620
tgttctctca gagggtagag ctcacagagg tcctctctgg ttcccaggaa aggtaatttc   1680
actaatcttg gtgatgagac tatcctccag tgctgatgta ctatagagtt ttcatctgaa   1740
gctgtcactg ctatccccaa tgtacatctt ttcacacaga aatgtttaga ggtcaggcca   1800
tattctcagg gttacacatt gagaaggatg gagatatatt ctactacctt ctcctgagat   1860
ctcacacaca atctcaaatt tcaaaaggtc tcagaagggc agctctcagg tactatttaa   1920
aaataaccca cttcctggga caggtagcat ccttctaacc atgatggatg ttctgaacta   1980
cagtacacat tgcatggatc caggtttgtc tcaattcact gtgattatta cactcagcag   2040
ctgtttcaat atgtctgaag gggtaaatga caatttaggt gacctgggtg tatggttggt   2100
gttatatgaa tctttaaatg tagaacagta ttaactgtat tccaaaatct gtctttgatc   2160
catgatcaca cttgtctccc agaccagctc cttcagcaca tttcctacct ttaagaagag   2220
gactctgggt ttggtgaggg gaggccacag gaagagaact gagttctcag agggcacagc   2280
cagcatacac ctcccagggt gagcccaaaa gactggggcc tccctcatcc cttttttacct  2340
atccatacaa aggcaccacc cacatgcaaa tcctcactta ggcacccaca ggaaatgact   2400
acacatttcc ttaaattcag ggtccagctc acatgggaag tgctttctga gagtcatgga   2460
cctcctgcac aagaacatgg agtttgggct gagctgggtt ttcctcgttg ctcttttaag   2520
aggtgattca tggagaaata gagagactga gtgtgagtga acatgagtga gaaaaactgg   2580
```

```
atttgtgtgg catttttctga taacggtgtc cttctgtttg caggtgtcca gtgtcagcga    2640
ttagtggagt ctgggggagg cgtggtccag cctgggtcgt ccctgagact ctcctgtgca    2700
gcgtccggat tcgacttcag tagacaaggc atgcactggg tccgccaggc tccaggccag    2760
gggctggagt gggtggcatt tattaaatat gatggaagtg agaaatatca tgctgactcc    2820
gtatggggcc gactcagcat ctccagagac aattccaagg atacgcttta tctccaaatg    2880
aatagcctga gagtcgagga cacggctaca tattttgtg tgagagaggc tggtgggccc    2940
gactaccgta atgggtacaa ctattacgat ttctatgatg gttattataa ctaccactat    3000
atggacgtct ggggcaaagg gaccacggtc accgtctcct caggtaagaa tggccactct    3060
agggcctttg ttttctgcta ctgcctgtgg ggtttcctga gcattgcagg ttggtcctcg    3120
gggcatgttc cgaggttgga cctgggcgga ctggccagga ggggacgggc actggggtgc    3180
cttgaggatc tgggagcctc tgtggatttt ccgatgcctt tggaaaatgg gactcaggtt    3240
gggtgcgtct gatggagtaa ctgagcctgg gggcttgggg agccacattt ggacgagatg    3300
cctgaacaaa ccagggtct tagtgatggc tgaggaatgt gtctcaggag cggtgtctgt    3360
aggactgcaa gatcgctgca cagcagcgaa tcgtgaaata ttttctttag aattatgagg    3420
tgcgctgtgt gtcaacctgc atcttaaatt ctttattggc tggaaagaga actgtcggag    3480
tgggtgaatc cagccaggag ggacgcgtag ccccggtctt gatgagagca gggttggggg    3540
caggggtagc ccagaaacgg tggctgccgt cctgacaggg gcttagggag gctccaggac    3600
ctcagtgcct tgaagctggt ttccatgaga aaaggattgt ttatcttagg aggcatgctt    3660
actgttaaaa gacaggatat gtttgaagtg gcttctgaga aaaatggtta agaaaattat    3720
gacttaaaaa tgtgagagat tttcaagtat attaattttt ttaactgtcc aagtatttga    3780
aattcttatc atttgattaa cacccatgag tgatatgtgt ctggaattga ggccaaagca    3840
agctcagcta agaaatacta gcacagtgct gtcggccccg atgcgggact gcgttttgac    3900
catcataaat caagtttatt tttttaatta attgagcgaa gctggaagca gatgatgaat    3960
tagagtcaag atggctgcat gggggtctcc ggcacccaca gcaggtggca ggaagcaggt    4020
caccgcgaga gtctatttta ggaagcaaaa aaacacaatt ggtaaattta tcacttctgg    4080
ttgtgaagag gtggttttgc ccaggcccag atctgaaagt gctctactga gcaaaacaac    4140
acctggacaa tttgcgtttc taaaataagg cgaggctgac cgaaactgaa aaggcttttt    4200
ttaactatct gaatttcatt tccaatctta gcttatcaac tgctagtttg tgcaaacagc    4260
atatcaactt ctaaactgca ttcattttta agtaagatg tttaagaaat taaacagtct    4320
tagggagagt ttatgactgt attcaaaaag tttttttaaat tagcttgtta tcccttcatg    4380
tgataactaa tctcaaatac ttttttcgata cctcagagca ttattttcat aatgactgtg    4440
ttcacaatct ttttaggtta actcgttttc tctttgtgat taaggagaaa cactttgata    4500
ttctgataga gtggccttca ttttagtatt tttcaagacc acttttcaac tactcacttt    4560
aggataagtt ttaggtaaaa tgtgcatcat tatcctgaat tatttcagtt aagcatgtta    4620
gttggtggca taagagaaaa ctcaatcaga tagtgctgaa gacaggac                 4668
```

<210> SEQ ID NO 163
<211> LENGTH: 4563
<212> TYPE: DNA
<213> ORGANISM: Homo sapiens

<400> SEQUENCE: 163

```
tctctattat aaaggcatgt tggcaaataa agactacagt ttgtattgaa tattcatgcc        60
aaagaagttt ttttcaaaac ttttcaagta aaaattttta tcttgcctag tttgaaaatt       120
accatctaaa ttcaacaaat aaggtaatac agttttaaaa gtgatgcttg tcttattagt       180
tattcaattt attaacaaca gactgatatt taaaataaat accattgcac atttaagtgc       240
catactgttc tgggattttt taaggaatca gagagaccga ctctgttcag gaggatattt       300
attatttagg ttcaggagga tatttattat ttaggtgcac cggccaagtc gaattaacat       360
ccaaaggact gagcccagaa cagagttcag ttacctttta agcattttgt ggggtgggag       420
aggggacatc tgtgcaggt gaagcatact acagaagtga aaacaaaga cagttattca        480 attgaaacat gtattacatc atttcttcct tttcaaggaa aaacatgttt tgcgacttga       540
gtttatcttt ctagtgacct tgcagctaca ctgctaggga atcagggtct tcaaaatgcc       600
tgagaaggga ggagaggtaa ggctcattag ccacagaaaa acaggcagtt agtatttaa       660 aggactccag ctctttctct ttttcaggga gaattgggtt ttcttacata caactgagtt       720
tctgcttaca cattctttaa tttcttttaa ttcctgtttc aatacttgac aagaatggca       780
tttacataca gttttaccaa acatgtatt taaatatatt tgtcttttta atattggaat       840
aggcagacat acacgtagat cagcattatt ttgtactaaa atctcaaact gcaaacacaa       900
tttaaattca attaaataat tagaataata tgaaacaaat gggtgtgttg ttttggtgtt       960
tacgtatgca ttcacttttg catgggcaca tgtatgagtc tttgctgggc tgttgtgcac      1020
gtatgtgtgt ttgtatgacc aggaggtttt caaatacatc attaaattac atagttatat      1080
taatcttggc aaggcacttg tattctgttt tctttaattc tgtttgcaga agtagacac       1140 atattcagtc ttagttccag tgtagggagt gcttttcatg agaaaatac cagaaaaaag       1200 ggcaaacatg gggcccacta atgtaaaaat tagccacaat gtgtatgtgt gtgtgtgtgt      1260
gtgtgtgtgt gtgtctgagt tgaatagtag agttggagtg ggcttctatc cacatgcacc      1320
tgcgcctaca ggtattatca ggtacaataa tcaactgcag aaccctaaag gaaataagag      1380 tcccccaaa cccctgaaga gtgtttgggt tcaccatgtg tccaatgatt cagtgcctct       1440
cgagctccag gaaacggctc cctggtgatg cgtgagatct tttcttgggg tgtccctgca      1500
gagttcgctg ggtttcctaa ggctgattca ctatttcaaa agatggtgtg agaagcatat      1560
ggtgtaaata aagcagaatt ctgagccagg gcacagccac tttatactgg gctagagaca      1620
ctggtaggaa tatactctgt cagctcagat agaaacctcc ctgcagggtg ggggcagggc      1680
tgcagggggc gctcaggaca catcgagcac agtcttctgc cccagagcag gtgcacatga      1740
ggctggggag aggttcctct cagggcctgg gacttccttt aaaaatatct aaaataagta      1800
tttcacaagg actgctgatg tttgtataaa tatcctattc aattgtgagc atttatcaaa      1860
ctggatgttg taatgagaac cactttata atggcgattt caaactctgc tagttatctt       1920
aataatagca gctggaggtc aggaagagat tattacttat aaataagtgc aattttttgga     1980 gagacacact cattcccaaa ataacacatt cacatattaa ggtctagaaa tggttcacgt      2040
tgcccctgag acattcaaat gtgggttcaa agtgaggtgc tgtcctcggg gagttgttcc      2100
ttagtggagg aagcgctatc aacacagagt tcagggatgg gtaggggatg cgtggcctct      2160
aacaggatta cgactcgaac cctcagctcc tataattgtg tcgtccgtgt gtcatggatt      2220
tctctttctc atactgggtc aggaattggt ctattaaata gcatccttca tgaatatgca      2280
aataactgag gggaatatag tatctctgta ccctgaaagc atcacccaac aacaacatcc      2340
ctccttggga gaatccccta gagcacagct cctcacatgg agtttgggct gagctgggtt      2400
```

```
ttcctcgttg ctctttttaag aggtgattca tggagaaata gagagactga gtgtgagtga    2460
acatgagtga gaaaaactgg atttgtgtgg cattttctga taacggtgtc cttctgtttg    2520
caggtgtcca gtgtcagcga ttagtggagt ctgggggagg cgtggtccag cctgggtcgt    2580
ccctgagact ctcctgtgca gcgtccggat tcgacttcag tagacaaggc atgcactggg    2640
tccgccaggc tccaggccag gggctggagt gggtggcatt tattaaatat gatggaagtg    2700
agaaatatca tgctgactcc gtatgggggcc gactcagcat ctccagagac aattccaagg    2760
atacgcttta tctccaaatg aatagcctga gagtcgagga cacggctaca tattttgtg    2820 tgagagaggc tggtgggccc gactaccgta atgggtacaa ctattacgat ttctatgatg    2880
gttattataa ctaccactat atggacgtct ggggcaaagg gaccacggtc accgtctcct    2940
caggtaagaa tggccactct agggcctttg ttttctgcta ctgcctgtgg ggtttcctga    3000
gcattgcagg ttggtcctcg ggcatgttc cgaggttgga cctgggcgga ctggccagga    3060
ggggacgggc actggggtgc cttgaggatc tgggagcctc tgtggatttt ccgatgcctt    3120
tggaaaatgg gactcaggtt gggtgcgtct gatggagtaa ctgagcctgg ggcttgggg    3180 agccacattt ggacgagatg cctgaacaaa ccagggtct tagtgatggc tgaggaatgt    3240
gtctcaggag cggtgtctgt aggactgcaa gatcgctgca cagcagcgaa tcgtgaaata    3300
ttttctttag aattatgagg tgcgctgtgt gtcaacctgc atcttaaatt ctttattggc    3360
tggaaagaga actgtcggag tgggtgaatc cagccaggag ggacgcgtag ccccggtctt    3420
gatgagagca gggttggggg caggggtagc ccagaaacgg tggctgccgt cctgacaggg    3480
gcttagggag gctccaggac ctcagtgcct tgaagctggt ttccatgaga aaaggattgt    3540
ttatcttagg aggcatgctt actgttaaaa gacaggatat gtttgaagtg gcttctgaga    3600
aaaatggtta agaaaattat gacttaaaaa tgtgagagat tttcaagtat attaattttt    3660
ttaactgtcc aagtatttga aattcttatc atttgattaa cacccatgag tgatatgtgt    3720
ctggaattga ggccaaagca agctcagcta agaaatacta gcacagtgct gtcggccccg    3780
atgcgggact cgttttgac catcataaat caagtttatt ttttaatta attgagcgaa    3840 gctggaagca gatgatgaat tagagtcaag atggctgcat gggggtctcc ggcacccaca    3900
gcaggtggca ggaagcaggt caccgcgaga gtctatttta ggaagcaaaa aaacacaatt    3960
ggtaaattta tcacttctgg ttgtgaagag gtggttttgc ccaggccagg atctgaaagt    4020
gctctactga gcaaaacaac acctggacaa tttgcgtttc taaaataagg cgaggctgac    4080
cgaaactgaa aaggctttt ttaactatct gaatttcatt tccaatctta gcttatcaac    4140
tgctagtttg tgcaaacagc atatcaactt ctaaactgca ttcatttta aagtaagatg    4200 tttaagaaat taaacagtct tagggagagt ttatgactgt attcaaaaag ttttttaaat    4260
tagcttgtta tcccttcatg tgataactaa tctcaaatac ttttttcgata cctcagagca    4320 ttattttcat aatgactgtg ttcacaatct ttttaggtta actcgttttc tctttgtgat    4380
taaggagaaa cactttgata ttctgataga gtggccttca ttttagtatt tttcaagacc    4440
acttttcaac tactcacttt aggataagtt ttaggtaaaa tgtgcatcat tatcctgaat    4500
tatttcagtt aagcatgtta gttggtggca taagagaaaa ctcaatcaga tagtgctgaa    4560
gac                                                                   4563
```

<210> SEQ ID NO 164  
<211> LENGTH: 4597  
<212> TYPE: DNA

<213> ORGANISM: Homo sapiens

<400> SEQUENCE: 164

```
actacagttt gtattgaata ttcatgccaa agaagttttt ttcaaaactt ttcaagtaaa      60
aaattttatc ttgcctagtt tgaaaattac catctaaatt caacaaataa ggtaatacag     120
ttttaaaagt gatgcttgtc ttattagtta ttcaatttat taacaacaga ctgatatttta   180
acataaatac cattgcacat ttaagtgcca tactgttctg ggattttta aggaatcaga     240
gagaccgact ctgttcagga ggatatttat tatttaggtt caggaggata tttattattt    300
aggtgcaccg gccaagtcga attaacatcc aaaggactga gcccagaaca gagttcagtt   360
acctttaag cattttgtgg ggtgggagag gggacatctg tgcagggtga aacatactac     420
agaagtgaga aacaaagaca gctattcaat tgaaacatgt attacatcat ttcttccttt   480
tcaaggaaaa acatgttttg cgacttgagt ttatctttct agtgaccttg cagctacact   540
gctagggaat cagggtcttc aaaatgcctg agaagggagg agaggtaagg ctcattagcc   600
acagaaaaac aggcagttag tatttaaag gactccagct ctttctcttt ttcagggaga    660
attgggtttt cttacataca actgagtttc tgcttacaca ttctttaatt tcttttaatt   720
cctgttttcaa tacttgacaa gaatggcatt tacatacagt tttaccaaaa catgtattta  780
aatatatttg tcttttaat attggaatag gcagacatac acgtagatca gcattatttt   840
gtactaaaat ctcaaactgc aaacacaatt taaattcaat taaataatta gaataatatg   900
aaacaaatgg gtgtgttgtt ttggtgttta cgtatgcatt cacttttgca tgggcacatg   960
tatgagtctt tgctgggctg ttgtgcacgt atgtgtgttt gatgaccag gaggttttca   1020
aatacatcat taaattacat agttatatta atcttggcaa ggcacttgta ttctgttttc   1080
tttaattctg tttgcagaaa gtagacacat attcagtctt agttccagtg tagggagtgc  1140
ttttcatgag aaaaatacca gaaaaaggg caaacatggg gcccactaat gtaaaaatta   1200
gccacaatgt gtatgtgtgt gtgtgtgtgt gtgtgtgtgt gtgtgtgtgt ctgagttgaa   1260
tagtagagtt ggagtgggct tctatccaca tgcacctgcg cctacaggta ttatcaggta  1320
caataatcaa ctgcagaacc ctaaaggaaa taagagtccc cccaaacccc tgaagagtgt  1380
ttgggttcac catgtgtcca atgattcagt gcctctcgag ctccaggaaa cggctccctg   1440
gtgatgcgtg agatcttttc ttggggtgtc cctgcagagt tcgctgggtt tcctaaggct   1500
gattcactat ttcaaaagat ggtgtgagaa gcatatggtg taaataaagc agaattctga   1560
gccagggcac agccactta tactgggcta gagacactgg taggaatata ctctgtcagc    1620
tcagatagaa acctccctgc agggtggggg cagggctgca gggggcgctc aggacacatc   1680
gagcacagtc ttctgcccca gagcaggtgc acatgaggct ggggagaggt tcctctcagg   1740
gcctgggact tcctttaaaa atatctaaaa taagtatttc acaaggactg ctgatgtttg   1800
tataaatatc ctattcaatt gtgagcattt atcaaactgg atgttgtaat gagaaccact   1860
tttataatgg cgatttcaaa ctctgctagt tatcttaata atagcagctg gaggtcagga   1920
agagattatt acttataaat aagtgcaatt tttggagaga cacactcatt cccaaaataa   1980
cacattcaca tattaaggtc tagaaatggt tcacgttgcc cctgagacat tcaaatgtgg   2040
gttcaaagtg aggtgctgtc ctcggggagt tgttccttag tggaggaagc gctatcaaca   2100
cagagttcag ggatgggtag gggatgcgtg gcctctaaca ggattacgac tcgaaccctc   2160
agctcctata attgtgtcgt ccgtgtgtca tggatttctc tttctcatac tgggtcagga  2220
attggtctat taaatagcat ccttcatgaa tatgcaaata actgaggga atatagtatc   2280
```

```
tctgtaccct gaaagcatca cccaacaaca acatccctcc ttgggagaat cccctagagc  2340
acagctcctc acatggagtt tgggctgagc tgggttttcc tcgttgctct tttaagaggt  2400
gattcatgga gaaatagaga gactgagtgt gagtgaacat gagtgagaaa aactggattt  2460
gtgtggcatt ttctgataac ggtgtccttc tgtttgcagg tgtccagtgt cagcgattag  2520
tggagtctgg gggaggcgtg gtccagcctg gtcgtccct  gagactctcc tgtgcagcgt  2580
ccggattcga cttcagtaga caaggcatgc actgggtccg ccaggctcca ggccaggggc  2640
tggagtgggt ggcatttatt aaatatgatg gaagtgagaa atatcatgct gactccgtat  2700
ggggccgact cagcatctcc agagacaatt ccaaggatac gctttatctc caaatgaata  2760
gcctgagagt cgaggacacg gctacatatt tttgtgtgag agaggctggt gggcccgact  2820
accgtaatgg gtacaactat tacgatttct atgatggtta ttataactac cactatatgg  2880
acgtctgggg caaagggacc acggtcaccg tctcctcagg taagaatggc cactctaggg  2940
cctttgtttt ctgctactgc ctgtgggggtt tcctgagcat tgcaggttgg tcctcggggc  3000
atgttccgag gttggacctg gcggactgg  ccaggagggg acgggcactg gggtgccttg  3060
aggatctggg agcctctgtg gattttccga tgcctttgga aaatgggact caggttgggt  3120
gcgtctgatg gagtaactga gcctggggg  ttggggagcc acatttggac gagatgcctg  3180
aacaaaccag gggtcttagt gatggctgag gaatgtgtct caggagcggt gtctgtagga  3240
ctgcaagatc gctgcacagc agcgaatcgt gaaatatttt ctttagaatt atgaggtgcg  3300
ctgtgtgtca acctgcatct taaattcttt attggctgga aagagaactg tcggagtggg  3360
tgaatccagc caggagggac gcgtagcccc ggtcttgatg agagcagggt tggggcagg   3420
ggtagcccag aaacggtggc tgccgtcctg acagggcgtt agggaggctc caggacctca  3480
gtgccttgaa gctggtttcc atgagaaaag gattgtttat cttaggaggc atgcttactg  3540
ttaaaagaca ggatatgttt gaagtggctt ctgagaaaaa tggttaagaa aattatgact  3600
taaaaatgtg agagattttc aagtatatta atttttttaa ctgtccaagt atttgaaatt  3660
cttatcattt gattaacacc catgagtgat atgtgtctgg aattgaggcc aaagcaagct  3720
cagctaagaa atactagcac agtgctgtcg gccccgatgc gggactgcgt tttgaccatc  3780
ataaatcaag tttatttttt taattaattg agcgaagctg gaagcagatg atgaattaga  3840
gtcaagatgg ctgcatgggg gtctccggca cccacagcag gtggcaggaa gcaggtcacc  3900
gcgagagtct attttaggaa gcaaaaaaac acaattggta aatttatcac ttctggttgt  3960
gaagaggtgg ttttgcccag gcccagatct gaaagtgctc tactgagcaa acaacacct   4020
ggacaatttg cgtttctaaa ataaggcgag gctgaccgaa actgaaaagg ctttttttaa  4080
ctatctgaat ttcatttcca atcttagctt atcaactgct agtttgtgca aacagcatat  4140
caacttctaa actgcattca tttttaaagt aagatgttta agaaattaaa cagtcttagg  4200
gagagtttat gactgtattc aaaaagtttt ttaaattagc ttgttatccc ttcatgtgat  4260
aactaatctc aaatacttt  tcgataccte agagcattat tttcataatg actgtgttca  4320
caatcttttt aggttaactc gttttctctt tgtgattaag agaaacact  ttgatattct  4380
gatagagtgg ccttcatttt agtattttc  aagaccactt ttcaactact cactttagga  4440
taagttttag gtaaaatgtg catcattatc ctgaattatt tcagttaagc atgttagttg  4500
gtggcataag agaaaactca atcagatagt gctgaagaca ggactgtgga gacaccttag  4560
aaggacagat tctgttccga atcaccgatg cggcgtc                           4597
```

```
<210> SEQ ID NO 165
<211> LENGTH: 210
<212> TYPE: PRT
<213> ORGANISM: Homo sapiens

<400> SEQUENCE: 165

Gln Arg Leu Val Glu Ser Gly Gly Gly Val Gln Pro Gly Ser Ser
1               5                   10                  15

Leu Arg Leu Ser Cys Ala Ala Ser Gly Phe Asp Phe Ser Arg Gln Gly
                20                  25                  30

Met His Trp Val Arg Gln Ala Pro Gly Gln Gly Leu Glu Trp Val Ala
            35                  40                  45

Phe Ile Lys Tyr Asp Gly Ser Glu Lys Tyr His Ala Asp Ser Val Trp
        50                  55                  60

Gly Arg Leu Ser Ile Ser Arg Asp Asn Ser Lys Asp Thr Leu Tyr Leu
65                  70                  75                  80

Gln Met Asn Ser Leu Arg Val Glu Asp Thr Ala Thr Tyr Phe Cys Val
                85                  90                  95

Arg Glu Ala Gly Gly Pro Asp Tyr Arg Asn Gly Tyr Asn Tyr Tyr Asp
                100                 105                 110

Phe Tyr Asp Gly Tyr Tyr Asn Tyr His Tyr Met Asp Val Trp Gly Lys
            115                 120                 125

Gly Thr Thr Val Thr Val Ser Ser Ala Ser Thr Lys Gly Pro Ser Val
130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser
    210

<210> SEQ ID NO 166
<211> LENGTH: 198
<212> TYPE: PRT
<213> ORGANISM: Homo sapiens

<400> SEQUENCE: 166

Gln Arg Leu Val Glu Ser Gly Gly Gly Val Gln Pro Gly Ser Ser
1               5                   10                  15

Leu Arg Leu Ser Cys Ala Ala Ser Gly Phe Asp Phe Ser Arg Gln Gly
                20                  25                  30

Met His Trp Val Arg Gln Ala Pro Gly Gln Gly Leu Glu Trp Val Ala
            35                  40                  45

Phe Ile Lys Tyr Asp Gly Ser Glu Lys Tyr His Ala Asp Ser Val Trp
        50                  55                  60

Gly Arg Leu Ser Ile Ser Arg Asp Asn Ser Lys Asp Thr Leu Tyr Leu
65                  70                  75                  80

Gln Met Asn Ser Leu Arg Val Glu Asp Thr Ala Thr Tyr Phe Cys Val
                85                  90                  95

Arg Glu Ala Gly Gly Pro Asp Tyr Arg Asn Gly Tyr Asn Tyr Tyr Asp
                100                 105                 110
```

```
Phe Tyr Asp Gly Tyr Tyr Asn Tyr His Tyr Met Asp Val Trp Gly Lys
            115                 120                 125

Gly Thr Thr Val Thr Val Ser Ser Gly Ser Ala Ser Ala Pro Thr Leu
        130                 135                 140

Phe Pro Leu Val Ser Cys Glu Asn Ser Pro Ser Asp Thr Ser Ser Val
145                 150                 155                 160

Ala Val Gly Cys Leu Ala Gln Asp Phe Leu Pro Asp Ser Ile Thr Phe
                165                 170                 175

Ser Trp Lys Tyr Lys Asn Asn Ser Asp Ile Ser Ser Thr Arg Gly Phe
            180                 185                 190

Pro Ser Val Leu Arg Gly
            195

<210> SEQ ID NO 167
<211> LENGTH: 198
<212> TYPE: PRT
<213> ORGANISM: Homo sapiens

<400> SEQUENCE: 167

Gln Arg Leu Val Glu Ser Gly Gly Gly Val Val Gln Pro Gly Ser Ser
1               5                   10                  15

Leu Arg Leu Ser Cys Ala Ala Ser Gly Phe Asp Phe Ser Arg Gln Gly
            20                  25                  30

Met His Trp Val Arg Gln Ala Pro Gly Gln Gly Leu Glu Trp Val Ala
        35                  40                  45

Phe Ile Lys Tyr Asp Gly Ser Glu Lys Tyr His Ala Asp Ser Val Trp
    50                  55                  60

Gly Arg Leu Ser Ile Ser Arg Asp Asn Ser Lys Asp Thr Leu Tyr Leu
65                  70                  75                  80

Gln Met Asn Ser Leu Arg Val Glu Asp Thr Ala Thr Tyr Phe Cys Val
                85                  90                  95

Arg Glu Ala Gly Gly Pro Asp Tyr Arg Asn Gly Tyr Asn Tyr Tyr Asp
            100                 105                 110

Phe Tyr Asp Gly Tyr Tyr Asn Tyr His Tyr Met Asp Val Trp Gly Lys
            115                 120                 125

Gly Thr Thr Val Thr Val Ser Ser Gly Ser Ala Ser Ala Pro Thr Leu
        130                 135                 140

Phe Pro Leu Val Ser Cys Glu Asn Ser Pro Ser Asp Thr Ser Ser Val
145                 150                 155                 160

Ala Val Gly Cys Leu Ala Gln Asp Phe Leu Pro Asp Ser Ile Thr Phe
                165                 170                 175

Ser Trp Lys Tyr Lys Asn Asn Ser Asp Ile Ser Ser Thr Arg Gly Phe
            180                 185                 190

Pro Ser Val Leu Arg Gly
            195

<210> SEQ ID NO 168
<211> LENGTH: 186
<212> TYPE: PRT
<213> ORGANISM: Homo sapiens

<400> SEQUENCE: 168

Asp Gln Leu Gln Gln Trp Gly Ala Gly Leu Leu Lys Pro Ser Glu Thr
1               5                   10                  15

Leu Ser Leu Thr Cys Gly Val Tyr Gly Gly Ser Phe Arg Gly Tyr Tyr
            20                  25                  30
```

-continued

```
Trp Ser Trp Ile Arg Gln Pro Pro Gly Lys Gly Leu Glu Trp Ile Gly
             35                  40                  45

Glu Ile Asn His Ser Gly Ser Thr Asn Tyr Asn Pro Ser Leu Lys Ser
 50                  55                  60

Arg Val Thr Ile Ser Val Asp Thr Ser Lys Lys Gln Leu Ser Leu Lys
 65                  70                  75                  80

Leu Ser Ser Val Asn Ala Ala Asp Thr Ala Val Tyr Tyr Cys Ala Arg
                 85                  90                  95

Val Ile Thr Arg Ala Ser Pro Gly Thr Asp Gly Arg Tyr Gly Met Asp
            100                 105                 110

Val Trp Gly Gln Gly Thr Thr Val Thr Val Ser Ser Gly Ser Ala Ser
            115                 120                 125

Ala Pro Thr Leu Phe Pro Leu Val Ser Cys Glu Asn Ser Pro Ser Asp
130                 135                 140

Thr Ser Ser Val Ala Val Gly Cys Leu Ala Gln Asp Phe Leu Pro Asp
145                 150                 155                 160

Ser Ile Thr Phe Ser Trp Lys Tyr Lys Asn Asn Ser Asp Ile Ser Ser
                165                 170                 175

Thr Arg Gly Phe Pro Ser Val Leu Arg Gly
            180                 185

<210> SEQ ID NO 169
<211> LENGTH: 1368
<212> TYPE: PRT
<213> ORGANISM: Streptococcus pyogenes

<400> SEQUENCE: 169

Met Asp Lys Lys Tyr Ser Ile Gly Leu Asp Ile Gly Thr Asn Ser Val
 1               5                  10                  15

Gly Trp Ala Val Ile Thr Asp Glu Tyr Lys Val Pro Ser Lys Lys Phe
             20                  25                  30

Lys Val Leu Gly Asn Thr Asp Arg His Ser Ile Lys Lys Asn Leu Ile
             35                  40                  45

Gly Ala Leu Leu Phe Asp Ser Gly Glu Thr Ala Glu Ala Thr Arg Leu
 50                  55                  60

Lys Arg Thr Ala Arg Arg Arg Tyr Thr Arg Arg Lys Asn Arg Ile Cys
 65                  70                  75                  80

Tyr Leu Gln Glu Ile Phe Ser Asn Glu Met Ala Lys Val Asp Asp Ser
                 85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
            130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
210                 215                 220
```

```
Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
            245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640
```

```
His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala Lys
    1010                1015                1020

Ser Glu Gln Glu Ile Gly Lys Ala Thr Ala Lys Tyr Phe Phe Tyr Ser
1025                1030                1035                1040

Asn Ile Met Asn Phe Phe Lys Thr Glu Ile Thr Leu Ala Asn Gly Glu
                1045                1050                1055

Ile Arg Lys Arg Pro Leu Ile Glu Thr Asn Gly Glu Thr Gly Glu Ile
```

```
                    1060                1065                1070
Val Trp Asp Lys Gly Arg Asp Phe Ala Thr Val Arg Lys Val Leu Ser
        1075                1080                1085

Met Pro Gln Val Asn Ile Val Lys Lys Thr Glu Val Gln Thr Gly Gly
        1090                1095                1100

Phe Ser Lys Glu Ser Ile Leu Pro Lys Arg Asn Ser Asp Lys Leu Ile
1105                1110                1115                1120

Ala Arg Lys Lys Asp Trp Asp Pro Lys Lys Tyr Gly Gly Phe Asp Ser
        1125                1130                1135

Pro Thr Val Ala Tyr Ser Val Leu Val Val Ala Lys Val Glu Lys Gly
        1140                1145                1150

Lys Ser Lys Lys Leu Lys Ser Val Lys Glu Leu Leu Gly Ile Thr Ile
        1155                1160                1165

Met Glu Arg Ser Ser Phe Glu Lys Asn Pro Ile Asp Phe Leu Glu Ala
        1170                1175                1180

Lys Gly Tyr Lys Glu Val Lys Lys Asp Leu Ile Ile Lys Leu Pro Lys
1185                1190                1195                1200

Tyr Ser Leu Phe Glu Leu Glu Asn Gly Arg Lys Arg Met Leu Ala Ser
        1205                1210                1215

Ala Gly Glu Leu Gln Lys Gly Asn Glu Leu Ala Leu Pro Ser Lys Tyr
        1220                1225                1230

Val Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys His
        1250                1255                1260

Tyr Leu Asp Glu Ile Ile Glu Gln Ile Ser Glu Phe Ser Lys Arg Val
1265                1270                1275                1280

Ile Leu Ala Asp Ala Asn Leu Asp Lys Val Leu Ser Ala Tyr Asn Lys
        1285                1290                1295

His Arg Asp Lys Pro Ile Arg Glu Gln Ala Glu Asn Ile Ile His Leu
        1300                1305                1310

Phe Thr Leu Thr Asn Leu Gly Ala Pro Ala Ala Phe Lys Tyr Phe Asp
        1315                1320                1325

Thr Thr Ile Asp Arg Lys Arg Tyr Thr Ser Thr Lys Glu Val Leu Asp
        1330                1335                1340

Ala Thr Leu Ile His Gln Ser Ile Thr Gly Leu Tyr Glu Thr Arg Ile
1345                1350                1355                1360

Asp Leu Ser Gln Leu Gly Gly Asp
                1365

<210> SEQ ID NO 170
<211> LENGTH: 4101
<212> TYPE: DNA
<213> ORGANISM: Streptococcus pyogenes

<400> SEQUENCE: 170
gacaagaagt acagcatcgg cctggacatc ggcaccaact ctgtgggctg ggccgtgatc     60
accgacgagt acaaggtgcc cagcaagaaa ttcaaggtgc tgggcaacac cgaccggcac    120
agcatcaaga gaaacctgat cggagccctg ctgttcgaca gcggcgaaac agccgaggcc    180
acccggctga agagaaccgc cagaagaaga taccaccagac ggaagaaccg gatctgctat    240
ctgcaagaga tcttcagcaa cgagatggcc aaggtggacg acagcttctt ccacagactg    300
gaagagtcct tcctggtgga agaggataag aagcacgagc ggcaccccat cttcggcaac    360
```

```
atcgtggacg aggtggccta ccacgagaag taccccacca tctaccacct gagaaagaaa    420
ctggtggaca gcaccgacaa ggccgacctg cggctgatct atctggccct ggcccacatg    480
atcaagttcc ggggccactt cctgatcgag ggcgacctga accccgacaa cagcgacgtg    540
gacaagctgt tcatccagct ggtgcagacc tacaaccagc tgttcgagga aaacccatc     600
aacgccagcg gcgtggacgc caaggccatc ctgtctgcca gactgagcaa gagcagacgg    660
ctggaaaatc tgatcgccca gctgcccggc gagaagaaga tggcctgtt cggaaacctg     720
attgccctga gcctgggcct gacccccaac ttcaagagca acttcgacct ggccgaggat    780
gccaaactgc agctgagcaa ggacacctac gacgacgacc tggacaacct gctggcccag    840
atcggcgacc agtacgccga cctgtttctg gccgccaaga acctgtccga cgccatcctg    900
ctgagcgaca tcctgagagt gaacaccgag atcaccaagg cccccctgag cgcctctatg    960
atcaagagat acgacgagca ccaccaggac ctgaccctgc tgaaagctct cgtgcggcag   1020
cagctgcctg agaagtacaa agagatttttc ttcgaccaga gcaagaacgg ctacgccggc   1080
tacattgacg gcggagccag ccaggaagag ttctacaagt tcatcaagcc catcctggaa   1140
aagatggacg gcaccgagga actgctcgtg aagctgaaca gagaggacct gctgcggaag   1200
cagcggacct tcgacaacgg cagcatcccc caccagatcc acctgggaga gctgcacgcc   1260
attctgcggc ggcaggaaga ttttttaccca ttcctgaagg acaaccggga aaagatcgag   1320
aagatcctga ccttccgcat ccctactac gtgggccctc tggccagggg aaacagcaga   1380
ttcgcctgga tgaccagaaa gagcgaggaa accatcaccc cctggaactt cgaggaagtg   1440
gtggacaagg gcgcttccgc ccagagcttc atcgagcgga tgaccaactt cgataagaac   1500
ctgcccaacg agaaggtgct gcccaagcac agcctgctgt acgagtactt caccgtgtat   1560
aacgagctga ccaaagtgaa atacgtgacc gagggaatga gaaagcccgc cttcctgagc   1620
ggcgagcaga aaaaggccat cgtggacctg ctgttcaaga ccaaccggaa agtgaccgtg   1680
aagcagctga aagaggacta cttcaagaaa atcgagtgct tcgactccgt ggaaatctcc   1740
ggcgtggaag atcggttcaa cgcctccctg ggcacatacc acgatctgct gaaaattatc   1800
aaggacaagg acttcctgga caatgaggaa aacgaggaca ttctggaaga tatcgtgctg   1860
accctgacac tgtttgagga cagagagatg atcgaggaac ggctgaaaac ctatgcccac   1920
ctgttcgacg acaaagtgat gaagcagctg aagcggcgga gatacaccgg ctggggcagg   1980
ctgagccgga agctgatcaa cggcatccgg gacaagcagt ccggcaagac aatcctggat   2040
ttcctgaagt ccgacggctt cgccaacaga aacttcatgc agctgatcca cgacgacagc   2100
ctgacctttta agaggacat ccagaaagcc caggtgtccg gccagggcga tagcctgcac   2160
gagcacattg ccaatctggc cggcagcccc gccattaaga agggcatcct gcagacagtg   2220
aaggtggtgg acgagctcgt gaaagtgatg ggccggcaca gcccgagaa catcgtgatc   2280
gaaatggcca gagagaacca gaccacccag aagggacaga gaacagccg cgagagaatg   2340
aagcggatcg aagagggcat caaagagctg ggcagccaga tcctgaaaga acaccccgtg   2400
gaaaacaccc agctgcagaa cgagaagctg tacctgtact acctgcagaa tgggcgggat   2460
atgtacgtgg accaggaact ggacatcaac cggctgtccg actacgatgt ggaccatatc   2520
gtgcctcaga gctttctgaa ggacgactcc atcgacaaca aggtgctgac cagaagcgac   2580
aagaaccggg gcaagagcga caacgtgccc tccgaagagg tcgtgaagaa gatgaagaac   2640
tactggcggc agctgctgaa cgccaagctg attccccaga aaagttcga caatctgacc   2700
aaggccgaga gaggcggcct gagcgaactg gataaggccg gcttcatcaa gagacagctg   2760
```

```
gtggaaaccc ggcagatcac aaagcacgtg gcacagatcc tggactcccg gatgaacact      2820
aagtacgacg agaatgacaa gctgatccgg gaagtgaaag tgatcaccct gaagtccaag      2880
ctggtgtccg atttccggaa ggatttccag ttttacaaag tgcgcgagat caacaactac      2940
caccacgccc acgacgccta cctgaacgcc gtcgtgggaa ccgccctgat caaaaagtac      3000
cctaagctgg aaagcgagtt cgtgtacggc gactacaagg tgtacgacgt gcggaagatg      3060
atcgccaaga gcgagcagga aatcggcaag gctaccgcca agtacttctt ctacagcaac      3120
atcatgaact ttttcaagac cgagattacc ctggccaacg gcgagatccg gaagcggcct      3180
ctgatcgaga caaacggcga aaccggggag atcgtgtggg ataagggccg ggattttgcc      3240
accgtgcgga aagtgctgag catgccccaa gtgaatatcg tgaaaaagac cgaggtgcag      3300
acaggcggct tcagcaaaga gtctatcctg cccaagagga cagcgataaa gctgatcgcc      3360
agaaagaagg actgggaccc taagaagtac ggcggcttcg acagccccac cgtggcctat      3420
tctgtgctgg tggtggccaa agtggaaaag gcaagtccaa agaaactgaa gagtgtgaaa      3480
gagctgctgg ggatcaccat catggaaaga agcagcttcg agaagaatcc catcgacttt      3540
ctggaagcca agggctacaa agaagtgaaa aaggacctga tcatcaagct gcctaagtac      3600
tccctgttcg agctggaaaa cggccggaag agaatgctgg cctctgccgg cgaactgcag      3660
aagggaaacg aactggccct gccctccaaa tatgtgaact tcctgtacct ggccagccac      3720
tatgagaagc tgaagggctc ccccgaggat aatgagcaga acagctgtt tgtggaacag      3780 cacaagcact acctggacga gatcatcgag cagatcagcg agttctccaa gagagtgatc      3840
ctggccgacg ctaatctgga caaagtgctg tccgcctaca caagcaccg gataagccc      3900 atcagagagc aggccgagaa tatcatccac ctgtttaccc tgaccaatct gggagcccct      3960
gccgccttca gtactttga caccaccatc gaccggaaga ggtacaccag caccaaagag      4020
gtgctggacg ccacccctgat ccaccagagc atcaccggcc tgtacgagac acggatcgac      4080
ctgtctcagc tgggaggcga c                                                4101
```

<210> SEQ ID NO 171
<211> LENGTH: 1395
<212> TYPE: PRT
<213> ORGANISM: Artificial Sequence
<220> FEATURE:
<223> OTHER INFORMATION: A synthetic amino acid sequence

<400> SEQUENCE: 171

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
```

```
            115                 120                 125
His Glu Lys Tyr Pro Thr Ile Tyr His Leu Arg Lys Lys Leu Val Asp
            130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
            210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
            290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
            370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540
```

-continued

```
Lys Lys Ala Ile Val Asp Leu Leu Phe Lys Thr Asn Arg Lys Val Thr
545                 550                 555                 560

Val Lys Gln Leu Lys Glu Asp Tyr Phe Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960
```

-continued

Lys Leu Val Ser Asp Phe Arg Lys Asp Phe Gln Phe Tyr Lys Val Arg
             965                 970                 975

Glu Ile Asn Asn Tyr His His Ala His Asp Ala Tyr Leu Asn Ala Val
             980                 985                 990

Val Gly Thr Ala Leu Ile Lys Lys Tyr Pro Lys Leu Glu Ser Glu Phe
             995                 1000                1005

Val Tyr Gly Asp Tyr Lys Val Tyr Asp Val Arg Lys Met Ile Ala Lys
             1010                1015                1020

Ser Glu Gln Glu Ile Gly Lys Ala Thr Ala Lys Tyr Phe Phe Tyr Ser
1025             1030                1035                1040

Asn Ile Met Asn Phe Phe Lys Thr Glu Ile Thr Leu Ala Asn Gly Glu
             1045                1050                1055

Ile Arg Lys Arg Pro Leu Ile Glu Thr Asn Gly Glu Thr Gly Glu Ile
             1060                1065                1070

Val Trp Asp Lys Gly Arg Asp Phe Ala Thr Val Arg Lys Val Leu Ser
             1075                1080                1085

Met Pro Gln Val Asn Ile Val Lys Lys Thr Glu Val Gln Thr Gly Gly
             1090                1095                1100

Phe Ser Lys Glu Ser Ile Leu Pro Lys Arg Asn Ser Asp Lys Leu Ile
1105             1110                1115                1120

Ala Arg Lys Lys Asp Trp Asp Pro Lys Lys Tyr Gly Gly Phe Asp Ser
             1125                1130                1135

Pro Thr Val Ala Tyr Ser Val Leu Val Val Ala Lys Val Glu Lys Gly
             1140                1145                1150

Lys Ser Lys Lys Leu Lys Ser Val Lys Glu Leu Leu Gly Ile Thr Ile
             1155                1160                1165

Met Glu Arg Ser Ser Phe Glu Lys Asn Pro Ile Asp Phe Leu Glu Ala
             1170                1175                1180

Lys Gly Tyr Lys Glu Val Lys Lys Asp Leu Ile Ile Lys Leu Pro Lys
1185             1190                1195                1200

Tyr Ser Leu Phe Glu Leu Glu Asn Gly Arg Lys Arg Met Leu Ala Ser
             1205                1210                1215

Ala Gly Glu Leu Gln Lys Gly Asn Glu Leu Ala Leu Pro Ser Lys Tyr
             1220                1225                1230

Val Asn Phe Leu Tyr Leu Ala Ser His Tyr Glu Lys Leu Lys Gly Ser
             1235                1240                1245

Pro Glu Asp Asn Glu Gln Lys Gln Leu Phe Val Glu Gln His Lys His
             1250                1255                1260

Tyr Leu Asp Glu Ile Ile Glu Gln Ile Ser Glu Phe Ser Lys Arg Val
1265             1270                1275                1280

Ile Leu Ala Asp Ala Asn Leu Asp Lys Val Leu Ser Ala Tyr Asn Lys
             1285                1290                1295

His Arg Asp Lys Pro Ile Arg Glu Gln Ala Glu Asn Ile Ile His Leu
             1300                1305                1310

Phe Thr Leu Thr Asn Leu Gly Ala Pro Ala Ala Phe Lys Tyr Phe Asp
             1315                1320                1325

Thr Thr Ile Asp Arg Lys Arg Tyr Thr Ser Thr Lys Glu Val Leu Asp
             1330                1335                1340

Ala Thr Leu Ile His Gln Ser Ile Thr Gly Leu Tyr Glu Thr Arg Ile
1345             1350                1355                1360

Asp Leu Ser Gln Leu Gly Gly Asp Glu Gly Ala Asp Pro Lys Lys Lys
             1365                1370                1375

Arg Lys Val Asp Pro Lys Lys Lys Arg Lys Val Asp Pro Lys Lys Lys

Arg Lys Val
    1395

<210> SEQ ID NO 172
<211> LENGTH: 3156
<212> TYPE: DNA
<213> ORGANISM: Artificial Sequence
<220> FEATURE:
<223> OTHER INFORMATION: A synthetic oligonucleotide sequence

<400> SEQUENCE: 172

| | | | | | |
|---|---|---|---|---|---|
| aagcggaact | acatcctggg | cctggacatc | ggcatcacca | gcgtgggcta | cggcatcatc | 60 |
| gactacgaga | cacgggacgt | gatcgatgcc | ggcgtgcggc | tgttcaaaga | ggccaacgtg | 120 |
| gaaaacaacg | agggcaggcg | gagcaagaga | ggcgccagaa | ggctgaagcg | gcggaggcgg | 180 |
| catagaatcc | agagagtgaa | gaagctgctg | ttcgactaca | acctgctgac | cgaccacagc | 240 |
| gagctgagcg | gcatcaaccc | ctacgaggcc | agagtgaagg | gcctgagcca | gaagctgagc | 300 |
| gaggaagagt | tctctgccgc | cctgctgcac | ctggccaaga | gaagaggcgt | gcacaacgtg | 360 |
| aacgaggtgg | aagaggacac | cggcaacgag | ctgtccacca | aagagcagat | cagccggaac | 420 |
| agcaaggccc | tgaagagaaa | atacgtggcc | gaactgcagc | tggaacggct | gaagaaagac | 480 |
| ggcgaagtgc | ggggcagcat | caacagattc | aagaccagcg | actacgtgaa | agaagccaaa | 540 |
| cagctgctga | aggtgcagaa | ggcctaccac | cagctggacc | agagcttcat | cgacacctac | 600 |
| atcgacctgc | tggaaacccg | gcggacctac | tatgagggac | ctggcgaggg | cagccccttc | 660 |
| ggctggaagg | acatcaaaga | atggtacgag | atgctgatgg | gccactgcac | ctacttcccc | 720 |
| gaggaactgc | ggagcgtgaa | gtacgcctac | aacgccgacc | tgtacaacgc | cctgaacgac | 780 |
| ctgaacaatc | tcgtgatcac | cagggacgag | aacgagaagc | tggaatatta | cgagaagttc | 840 |
| cagatcatcg | agaacgtgtt | caagcagaag | aagaagccca | ccctgaagca | gatcgccaaa | 900 |
| gaaatcctcg | tgaacgaaga | ggatattaag | ggctacagag | tgaccagcac | cggcaagccc | 960 |
| gagttcacca | acctgaaggt | gtaccacgac | atcaaggaca | ttaccgcccg | gaaagagatt | 1020 |
| attgagaacg | ccgagctgct | ggatcagatt | gccaagatcc | tgaccatcta | ccagagcagc | 1080 |
| gaggacatcc | aggaagaact | gaccaatctg | aactccgagc | tgacccagga | agagatcgag | 1140 |
| cagatctcta | atctgaaggg | ctataccggc | acccacaacc | tgagcctgaa | ggccatcaac | 1200 |
| ctgatcctgg | acgagctgtg | gcacaccaac | gacaaccaga | tcgctatctt | caaccggctg | 1260 |
| aagctggtgc | caagaaggt | ggacctgtcc | cagcagaaag | agatccccac | caccctggtg | 1320 |
| gacgacttca | tcctgagccc | cgtcgtgaag | agaagcttca | tccagagcat | caaagtgatc | 1380 |
| aacgccatca | tcaagaagta | cggcctgccc | aacgacatca | ttatcgagct | ggcccgcgag | 1440 |
| aagaactcca | aggacgccca | gaaaatgatc | aacgagatgc | agaagcggaa | ccggcagacc | 1500 |
| aacgagcgga | tcgaggaaat | catccggacc | accggcaaag | agaacgccaa | gtacctgatc | 1560 |
| gagaagatca | agctgcacga | catgcaggaa | ggcaagtgcc | tgtacagcct | ggaagccatc | 1620 |
| cctctggaag | atctgctgaa | caaccccttc | aactatgagg | tggaccacat | catccccaga | 1680 |
| agcgtgtcct | tcgacaacag | cttcaacaac | aaggtgctcg | tgaagcagga | agaaacagc | 1740 |
| aagaagggca | accggacccc | attccagtac | ctgagcagca | gcgacagcaa | gatcagctac | 1800 |
| gaaaccttca | gaagcacat | cctgaatctg | gccaagggca | agggcagaat | cagcaagacc | 1860 |
| aagaaagagt | atctgctgga | agaacggac | atcaacaggt | tctccgtgca | gaaagacttc | 1920 |

```
atcaaccgga acctggtgga taccagatac gccaccagag gcctgatgaa cctgctgcgg    1980
agctacttca gagtgaacaa cctggacgtg aaagtgaagt ccatcaatgg cggcttcacc    2040
agctttctgc ggcggaagtg gaagtttaag aaagagcgga acaaggggta caagcaccac    2100
gccgaggacg ccctgatcat tgccaacgcc gatttcatct tcaaagagtg gaagaaactg    2160
gacaaggcca aaaagtgat ggaaaaccag atgttcgagg aaaagcaggc cgagagcatg    2220
cccgagatcg aaaccgagca ggagtacaaa gagatcttca tccccccca ccagatcaag    2280 cacattaagg acttcaagga ctacaagtac agccaccggg tggacaagaa gcctaataga    2340
gagctgatta cgacaccct gtactccacc cggaaggacg acaagggcaa cacccctgatc   2400 gtgaacaatc tgaacggcct gtacgacaag gacaatgaca agctgaaaaa gctgatcaac    2460
aagagccccg aaaagctgct gatgtaccac cacgaccccc agacctacca gaaactgaag    2520
ctgattatgg aacagtacgg cgacgagaag aatcccctgt acaagtacta cgaggaaacc    2580
gggaactacc tgaccaagta ctccaaaaag gacaacggcc ccgtgatcaa gaagattaag    2640
tattacggca caaactgaa cgcccatctg gacatcaccg acgactaccc caacagcaga    2700
aacaaggtcg tgaagctgtc cctgaagccc tacagattcg acgtgtacct ggacaatggc    2760
gtgtacaagt tcgtgaccgt gaagaatctg gatgtgatca aaaaagaaaa ctactacgaa    2820
gtgaatagca gtgctatga ggaagctaag aagctgaaga agatcagcaa ccaggccgag    2880
tttatcgcct ccttctacaa caacgatctg atcaagatca acggcgagct gtatagagtg    2940
atcggcgtga caacgacct gctgaaccgg atcgaagtga acatgatcga catcacctac    3000
cgcgagtacc tggaaaacat gaacgacaag aggcccccca ggatcattaa gacaatcgcc    3060
tccaagaccc agagcattaa gaagtacagc acagacattc tgggcaacct gtatgaagtg    3120
aaatctaaga agcaccctca gatcatcaaa aagggc    3156
```

<210> SEQ ID NO 173
<211> LENGTH: 1307
<212> TYPE: PRT
<213> ORGANISM: Francisella novicida

<400> SEQUENCE: 173

```
Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160
```

```
Ser Phe Asp Lys Phe Thr Thr Tyr Phe Ser Gly Phe Tyr Glu Asn Arg
            165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
            195                 200                 205

Thr Arg Leu Ile Thr Ala Val Pro Ser Leu Arg Glu His Phe Glu Asn
            210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
            245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
            275                 280                 285

Asp Glu Thr Ala His Ile Ile Ala Ser Leu Pro His Arg Phe Ile Pro
            290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
            325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
            355                 360                 365

Lys Lys Leu Glu Thr Ile Ser Ser Ala Leu Cys Asp His Trp Asp Thr
            370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
            405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
            435                 440                 445

Ala Leu Asp Gln Pro Leu Pro Thr Thr Leu Lys Lys Gln Glu Glu Lys
450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
            485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
            515                 520                 525

Glu Lys Phe Lys Leu Asn Phe Gln Met Pro Thr Leu Ala Ser Gly Trp
            530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
            565                 570                 575
```

-continued

```
Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Glu Pro Lys Lys Phe Gln
            645                 650                 655

Thr Ala Tyr Ala Lys Lys Thr Gly Asp Gln Lys Gly Tyr Arg Glu Ala
        660                 665                 670

Leu Cys Lys Trp Ile Asp Phe Thr Arg Asp Phe Leu Ser Lys Tyr Thr
    675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
            725                 730                 735

Thr Gly Lys Leu Tyr Leu Phe Gln Ile Tyr Asn Lys Asp Phe Ala Lys
        740                 745                 750

Gly His His Gly Lys Pro Asn Leu His Thr Leu Tyr Trp Thr Gly Leu
    755                 760                 765

Phe Ser Pro Glu Asn Leu Ala Lys Thr Ser Ile Lys Leu Asn Gly Gln
770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
            805                 810                 815

Pro Ile Pro Asp Thr Leu Tyr Gln Glu Leu Tyr Asp Tyr Val Asn His
        820                 825                 830

Arg Leu Ser His Asp Leu Ser Asp Glu Ala Arg Ala Leu Leu Pro Asn
    835                 840                 845

Val Ile Thr Lys Glu Val Ser His Glu Ile Ile Lys Asp Arg Arg Phe
850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
            885                 890                 895

Lys Glu His Pro Glu Thr Pro Ile Ile Gly Ile Asp Arg Gly Glu Arg
        900                 905                 910

Asn Leu Ile Tyr Ile Thr Val Ile Asp Ser Thr Gly Lys Ile Leu Glu
    915                 920                 925

Gln Arg Ser Leu Asn Thr Ile Gln Gln Phe Asp Tyr Gln Lys Lys Leu
930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
            965                 970                 975

His Glu Ile Val Asp Leu Met Ile His Tyr Gln Ala Val Val Val Leu
        980                 985                 990

Glu Asn Leu Asn Phe Gly Phe Lys Ser Lys Arg Thr Gly Ile Ala Glu
```

```
                995            1000           1005
Lys Ala Val Tyr Gln Gln Phe Glu Lys Met Leu Ile Asp Lys Leu Asn
       1010            1015           1020

Cys Leu Val Leu Lys Asp Tyr Pro Ala Glu Lys Val Gly Gly Val Leu
1025            1030           1035           1040

Asn Pro Tyr Gln Leu Thr Asp Gln Phe Thr Ser Phe Ala Lys Met Gly
       1045            1050           1055

Thr Gln Ser Gly Phe Leu Phe Tyr Val Pro Ala Pro Tyr Thr Ser Lys
       1060            1065           1070

Ile Asp Pro Leu Thr Gly Phe Val Asp Pro Phe Val Trp Lys Thr Ile
       1075            1080           1085

Lys Asn His Glu Ser Arg Lys His Phe Leu Glu Gly Phe Asp Phe Leu
       1090            1095           1100

His Tyr Asp Val Lys Thr Gly Asp Phe Ile Leu His Phe Lys Met Asn
1105           1110           1115           1120

Arg Asn Leu Ser Phe Gln Arg Gly Leu Pro Gly Phe Met Pro Ala Trp
       1125           1130           1135

Asp Ile Val Phe Glu Lys Asn Glu Thr Gln Phe Asp Ala Lys Gly Thr
       1140           1145           1150

Pro Phe Ile Ala Gly Lys Arg Ile Val Pro Val Ile Glu Asn His Arg
       1155           1160           1165

Phe Thr Gly Arg Tyr Arg Asp Leu Tyr Pro Ala Asn Glu Leu Ile Ala
       1170           1175           1180

Leu Leu Glu Glu Lys Gly Ile Val Phe Arg Asp Gly Ser Asn Ile Leu
1185           1190           1195           1200

Pro Lys Leu Leu Glu Asn Asp Asp Ser His Ala Ile Asp Thr Met Val
       1205           1210           1215

Ala Leu Ile Arg Ser Val Leu Gln Met Arg Asn Ser Asn Ala Ala Thr
       1220           1225           1230

Gly Glu Asp Tyr Ile Asn Ser Pro Val Arg Asp Leu Asn Gly Val Cys
       1235           1240           1245

Phe Asp Ser Arg Phe Gln Asn Pro Glu Trp Pro Met Asp Ala Asp Ala
       1250           1255           1260

Asn Gly Ala Tyr His Ile Ala Leu Lys Gly Gln Leu Leu Leu Asn His
1265           1270           1275           1280

Leu Lys Glu Ser Lys Asp Leu Lys Leu Gln Asn Gly Ile Ser Asn Gln
       1285           1290           1295

Asp Trp Leu Ala Tyr Ile Gln Glu Leu Arg Asn
       1300           1305

<210> SEQ ID NO 174
<211> LENGTH: 3921
<212> TYPE: DNA
<213> ORGANISM: Francisella novicida

<400> SEQUENCE: 174
atgacacagt tcgagggctt taccaacctg tatcaggtga gcaagacact gcggtttgag    60
ctgatcccac agggcaagac cctgaagcac atccaggagc agggcttcat cgaggaggac   120
aaggcccgca atgatcacta caaggagctg aagcccatca tcgatcggat ctacaagacc   180
tatgccgacc agtgcctgca gctggtgcag ctggattggg agaacctgag cgccgccatc   240
gactcctata gaaaggagaa aaccgaggag acaaggaacg ccctgatcga ggagcaggcc   300
acatatcgca atgccatcca cgactacttc atcggccgga cagacaacct gaccgatgcc   360
```

```
atcaataaga gacacgccga gatctacaag ggcctgttca aggccgagct gtttaatggc    420
aaggtgctga agcagctggg caccgtgacc acaaccgagc acgagaacgc cctgctgcgg    480
agcttcgaca agtttacaac ctacttctcc ggcttttatg agaacaggaa gaacgtgttc    540
agcgccgagg atatcagcac agccatccca caccgcatcg tgcaggacaa cttccccaag    600
tttaaggaga attgtcacat cttcacacgc ctgatcaccg ccgtgcccag cctgcgggag    660
cactttgaga acgtgaagaa ggccatcggc atcttcgtga gcacctccat cgaggaggtg    720
ttttccttcc ctttttataa ccagctgctg acacagaccc agatcgacct gtataaccag    780
ctgctgggag gaatctctcg ggaggcaggc accgagaaga tcaagggcct gaacgaggtg    840
ctgaatctgg ccatccagaa gaatgatgag acagcccaca tcatcgcctc cctgccacac    900
agattcatcc cctgtttaa gcagatcctg tccgatagga acaccctgtc tttcatcctg    960
gaggagttta agagcgacga ggaagtgatc cagtccttct gcaagtacaa gacactgctg   1020
agaaacgaga acgtgctgga cagccgag gccctgttta cgagctgaa cagcatcgac   1080 ctgacacaca tcttcatcag ccacaagaag ctggagacaa tcagcagcgc cctgtgcgac   1140
cactgggata cactgaggaa tgccctgtat gagcggagaa tctccgagct gacaggcaag   1200
atcaccaagt ctgccaagga aaggtgcag cgcagcctga agcacgagga tatcaacctg   1260
caggagatca tctctgccgc aggcaaggag ctgagcgagg ccttcaagca gaaaaccagc   1320
gagatcctgt cccacgcaca cgccgccctg gatcagccac tgcctacaac cctgaagaag   1380
caggaggaga aggagatcct gaagtctcag ctggacagcc tgctgggcct gtaccacctg   1440
ctggactggt ttgccgtgga tgagtccaac gaggtggacc ccgagttctc tgcccggctg   1500
accggcatca agctggagat ggagccttct ctgagcttct acaacaaggc cagaaattat   1560
gccaccaaga agccctactc cgtggagaag ttcaagctga actttcagat gcctacactg   1620
gcctctggct gggacgtgaa taaggagaag aacaatggcg ccatcctgtt tgtgaagaac   1680
ggcctgtact atctgggcat catgccaaag cagaagggca ggtataaggc cctgagcttc   1740
gagcccacag agaaaaccag cgagggcttt gataagatgt actatgacta cttccctgat   1800
gccgccaaga tgatcccaaa gtgcagcacc cagctgaagg ccgtgacagc ccactttcag   1860
acccacacaa cccccatcct gctgtccaac aatttcatcg agcctctgga gatcacaaag   1920
gagatctacg acctgaacaa tcctgagaag gagccaaaga gtttcagac agcctacgcc   1980 aagaaaaccg gcgaccagaa gggctacaga gaggccctgt gcaagtggat cgacttcaca   2040
agggattttc tgtccaagta taccaagaca acctctatcg atctgtctag cctgcggcca   2100
tcctctcagt ataaggacct gggcgagtac tatgccgagc tgaatcccct gctgtaccac   2160
atcagcttcc agagaatcgc cgagaaggag atcatggatg ccgtggagac aggcaagctg   2220
tacctgttcc agatctataa caaggacttt gccaagggcc accacggcaa gcctaatctg   2280
cacacactgt attggaccgg cctgttttct ccagagaacc tggccaagac aagcatcaag   2340
ctgaatggcc aggccgagct gttctaccgc cctaagtcca ggatgaagag gatggcacac   2400
cggctgggag agaagatgct gaacaagaag ctgaaggatc agaaaacccc aatccccgac   2460
accctgtacc aggagctgta cgactatgtg aatcacagac tgtcccacga cctgtctgat   2520
gaggccaggg ccctgctgcc caacgtgatc accaaggagg tgtctcacga gatcatcaag   2580
gataggcgct ttaccagcga caagttcttt ttccacgtgc ctatcacact gaactatcag   2640
gccgccaatt cccccatcta agttcaaccag agggtgaatg cctacctgaa ggagcacccc   2700
gagacaccta tcatcggcat cgatcggggc gagagaaacc tgatctatat cacagtgatc   2760
```

```
gcctccaccg gcaagatcct ggagcagcgg agcctgaaca ccatccagca gtttgattac    2820
cagaagaagc tggacaacag ggagaaggag agggtggcag caaggcaggc ctggtctgtg    2880
gtgggcacaa tcaaggatct gaagcagggc tatctgagcc aggtcatcca cgagatcgtg    2940
gacctgatga tccactacca ggccgtggtg gtgctggaga acctgaattt cggctttaag    3000
agcaagagga ccggcatcgc cgcgaaggcc gtgtaccagc agttcgagaa gatgctgatc    3060
gataagctga attgcctggt gctgaaggac tatccagcag agaaagtggg aggcgtgctg    3120
aacccatacc agctgacaga ccagttcacc tcctttgcca agatgggcac ccagtctggc    3180
ttcctgtttt acgtgcctgc ccatatacta tctaagatcg atcccctgac cggcttcgtg    3240
gacccctccg tgtggaaaac catcaagaat cacgagagcc gcaagcactt cctggagggc    3300
ttcgactttc tgcactacga cgtgaaaacc ggcgacttca tcctgcactt taagatgaac    3360
agaaatctgt ccttccagag gggcctgccc ggctttatgc ctgcatggga tatcgtgttc    3420
gagaagaacg agacacagtt tgacgccaag ggcacccctt tcatcgccgg caagagaatc    3480
gtgccagtga tcgagaatca cagattcacc ggcagatacc gggacctgta tcctgccaac    3540
gagctgatcg ccctgctgga ggagaagggc atcgtgttca gggatggctc caacatcctg    3600
ccaaagctgc tggagaatga cgattctcac gccatcgaca ccatggtggc cctgatccgc    3660
agcgtgctgc agatgcggaa ctccaatgcc gccacaggcg aggactatat caacagcccc    3720
gtgcgcgatc tgaatggcgt gtgcttcgac tcccggtttc agaacccaga gtggcccatg    3780
gacgccgatg ccaatggcgc ctaccacatc gccctgaagg ccagctgct gctgaatcac    3840 ctgaaggaga gcaaggatct gaagctgcag aacggcatct ccaatcagga ctggctggcc    3900
tacatccagg agctgcgcaa c                                              3921
```

<210> SEQ ID NO 175
<211> LENGTH: 1307
<212> TYPE: PRT
<213> ORGANISM: Artificial Sequence
<220> FEATURE:
<223> OTHER INFORMATION: A synthetic amino acid sequence

<400> SEQUENCE: 175

```
Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
                20                  25                  30

Glu Gln Gly Phe Ile Glu Glu Asp Lys Ala Arg Asn Asp His Tyr Lys
            35                  40                  45

Glu Leu Lys Pro Ile Ile Asp Arg Ile Tyr Lys Thr Tyr Ala Asp Gln
        50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
```

```
                145                 150                 155                 160
Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
                180                 185                 190

Ile Val Gln Asp Asn Phe Pro Lys Phe Lys Glu Asn Cys His Ile Phe
                195                 200                 205

Thr Arg Leu Ile Thr Ala Val Pro Ser Leu Arg Glu His Phe Glu Asn
        210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
        260                 265                 270

Lys Ile Lys Gly Leu Asn Glu Val Leu Asn Leu Ala Ile Gln Lys Asn
                275                 280                 285

Asp Glu Thr Ala His Ile Ile Ala Ser Leu Pro His Arg Phe Ile Pro
        290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
        340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
        370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
                420                 425                 430

Glu Ala Phe Lys Gln Lys Thr Ser Glu Ile Leu Ser His Ala His Ala
                435                 440                 445

Ala Leu Asp Gln Pro Leu Pro Thr Thr Leu Lys Lys Gln Glu Glu Lys
        450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
                500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Ser Gly Trp
        530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575
```

```
Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
            595                 600                 605

Ser Thr Gln Leu Lys Ala Val Thr Ala His Phe Gln Thr His Thr Thr
            610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Gly Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
            675                 680                 685

Lys Thr Thr Ser Ile Asp Leu Ser Ser Leu Arg Pro Ser Ser Gln Tyr
            690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
            755                 760                 765

Phe Ser Pro Glu Asn Leu Ala Lys Thr Ser Ile Lys Leu Asn Gly Gln
            770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
            835                 840                 845

Val Ile Thr Lys Glu Val Ser His Glu Ile Ile Lys Asp Arg Arg Phe
850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
            885                 890                 895

Lys Glu His Pro Glu Thr Pro Ile Ile Gly Ile Asp Arg Gly Glu Arg
            900                 905                 910

Asn Leu Ile Tyr Ile Thr Val Ile Ala Ser Thr Gly Lys Ile Leu Glu
            915                 920                 925

Gln Arg Ser Leu Asn Thr Ile Gln Gln Phe Asp Tyr Gln Lys Lys Leu
            930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990
```

-continued

Glu Asn Leu Asn Phe Gly Phe Lys Ser Lys Arg Thr Gly Ile Ala Ala
            995                 1000                1005

Lys Ala Val Tyr Gln Gln Phe Glu Lys Met Leu Ile Asp Lys Leu Asn
        1010                1015                1020

Cys Leu Val Leu Lys Asp Tyr Pro Ala Glu Lys Val Gly Gly Val Leu
1025                1030                1035                1040

Asn Pro Tyr Gln Leu Thr Asp Gln Phe Thr Ser Phe Ala Lys Met Gly
            1045                1050                1055

Thr Gln Ser Gly Phe Leu Phe Tyr Val Pro Ala Pro Tyr Thr Ser Lys
        1060                1065                1070

Ile Asp Pro Leu Thr Gly Phe Val Asp Pro Phe Val Trp Lys Thr Ile
            1075                1080                1085

Lys Asn His Glu Ser Arg Lys His Phe Leu Glu Gly Phe Asp Phe Leu
            1090                1095                1100

His Tyr Asp Val Lys Thr Gly Asp Phe Ile Leu His Phe Lys Met Asn
1105                1110                1115                1120

Arg Asn Leu Ser Phe Gln Arg Gly Leu Pro Gly Phe Met Pro Ala Trp
            1125                1130                1135

Asp Ile Val Phe Glu Lys Asn Glu Thr Gln Phe Asp Ala Lys Gly Thr
            1140                1145                1150

Pro Phe Ile Ala Gly Lys Arg Ile Val Pro Val Ile Glu Asn His Arg
        1155                1160                1165

Phe Thr Gly Arg Tyr Arg Asp Leu Tyr Pro Ala Asn Glu Leu Ile Ala
            1170                1175                1180

Leu Leu Glu Glu Lys Gly Ile Val Phe Arg Asp Gly Ser Asn Ile Leu
1185                1190                1195                1200

Pro Lys Leu Leu Glu Asn Asp Asp Ser His Ala Ile Asp Thr Met Val
            1205                1210                1215

Ala Leu Ile Arg Ser Val Leu Gln Met Arg Asn Ser Asn Ala Ala Thr
            1220                1225                1230

Gly Glu Asp Tyr Ile Asn Ser Pro Val Arg Asp Leu Asn Gly Val Cys
        1235                1240                1245

Phe Asp Ser Arg Phe Gln Asn Pro Glu Trp Pro Met Asp Ala Asp Ala
1250                1255                1260

Asn Gly Ala Tyr His Ile Ala Leu Lys Gly Gln Leu Leu Asn His
1265                1270                1275                1280

Leu Lys Glu Ser Lys Asp Leu Lys Leu Gln Asn Gly Ile Ser Asn Gln
            1285                1290                1295

Asp Trp Leu Ala Tyr Ile Gln Glu Leu Arg Asn
            1300                1305

<210> SEQ ID NO 176
<211> LENGTH: 198
<212> TYPE: PRT
<213> ORGANISM: Homo sapiens

<400> SEQUENCE: 176

Met Asp Ser Leu Leu Met Asn Arg Arg Lys Phe Leu Tyr Gln Phe Lys
1               5                   10                  15

Asn Val Arg Trp Ala Lys Gly Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

```
Ile Ser Asp Trp Asp Leu Asp Pro Gly Arg Cys Tyr Arg Val Thr Trp
 65                  70                  75                  80

Phe Thr Ser Trp Ser Pro Cys Tyr Asp Cys Ala Arg His Val Ala Asp
                 85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
            195

<210> SEQ ID NO 177
<211> LENGTH: 2791
<212> TYPE: DNA
<213> ORGANISM: Homo sapiens

<400> SEQUENCE: 177
gaaccatcat taattgaagt gagatttttc tggcctgaga cttgcaggga ggcaagaaga      60
cactctggac accactatgg acagcctctt gatgaaccgg aggaagtttc tttaccaatt     120
caaaaatgtc cgctgggcta agggtcggcg tgagacctac ctgtgctacg tagtgaagag     180
gcgtgacagt gctacatcct tttcactgga ctttggttat cttcgcaata gaacggctg     240 ccacgtggaa ttgctcttcc tccgctacat ctcggactgg acctagacc ctggccgctg     300 ctaccgcgtc acctggttca cctcctggag ccctgctac gactgtgccc gacatgtggc     360
cgactttctg cgagggaacc ccaacctcag tctgaggatc ttcaccgcgc gcctctactt     420
ctgtgaggac cgcaaggctg agcccgaggg gctgcggcgg ctgcaccgcg ccggggtgca     480
aatagccatc atgaccttca agattattt ttactgctgg atacttttg tagaaaacca     540 tgaaagaact ttcaaagcct gggaagggct gcatgaaaat tcagttcgtc tctccagaca     600
gcttcggcgc atccttttgc ccctgtatga ggttgatgac ttacgagacg catttcgtac     660
tttgggactt tgatagcaac ttccaggaat gtcacacacg atgaaatatc tctgctgaag     720
acagtggata aaaacagtc cttcaagtct tctctgtttt tattcttcaa ctctcactt      780 cttagagttt acagaaaaaa tatttatata cgactcttta aaaagatcta tgtcttgaaa     840
atagagaagg aacacaggtc tggccaggga cgtgctgcaa ttggtgcagt tttgaatgca     900
acattgtccc ctactgggaa taacagaact gcaggacctg ggagcatcct aaagtgtcaa     960 cgttttcta tgacttttag gtaggatgag agcagaaggt agatcctaaa aagcatggtg    1020
agaggatcaa atgttttat atcaacatcc tttattattt gattcatttg agttaacagt    1080
ggtgttagtg atagattttt ctattctttt cccttgacgt ttactttcaa gtaacacaaa    1140
ctcttccatc aggccatgat ctataggacc tcctaatgag agtatctggg tgattgtgac    1200
cccaaaccat ctctccaaag cattaatatc caatcatgcg ctgtatgttt taatcagcag    1260
aagcatgttt ttatgtttgt acaaaagaag attgttatgg gtggggatgg aggtatagac    1320
```

```
catgcatggt caccttcaag ctactttaat aaaggatctt aaatgggca ggaggactgt    1380 gaacaagaca ccctaataat gggttgatgt ctgaagtagc aaatcttctg gaaacgcaaa    1440
ctcttttaag gaagtcccta atttagaaac acccacaaac ttcacatatc ataattagca    1500
aacaattgga aggaagttgc ttgaatgttg gggagaggaa atctattgg ctctcgtggg    1560 tctcttcatc tcagaaatgc caatcaggtc aaggtttgct acattttgta tgtgtgtgat    1620
gcttctccca aaggtatatt aactatataa gagagttgtg acaaaacaga atgataaagc    1680
tgcgaaccgt ggcacacgct catagttcta gctgcttggg aggttgagga gggaggatgg    1740
cttgaacaca ggtgttcaag gccagcctgg gcaacataac aagatcctgt ctctcaaaaa    1800
aaaaaaaaaa aaaagaaag agagagggcc gggcgtggtg gctcacgcct gtaatcccag    1860
cactttggga ggccgagccg gcggatcac ctgtggtcag gagtttgaga ccagcctggc    1920
caacatggca aaaccccgtc tgtactcaaa atgcaaaaat tagccaggcg tggtagcagg    1980
cacctgtaat cccagctact tgggaggctg aggcaggaga tcgcttgaa cccaggaggt    2040 ggaggttgca gtaagctgag atcgtgccgt tgcactccag cctgggcgac aagagcaaga    2100
ctctgtctca gaaaaaaaaa aaaaaagag agagagagag aaagagaaca atatttggga    2160
gagaaggatg gggaagcatt gcaaggaaat tgtgctttat ccaacaaaat gtaaggagcc    2220
aataagggat ccctatttgt ctcttttggt gtctatttgt ccctaacaac tgtctttgac    2280
agtgagaaaa atattcagaa taaccatatc cctgtgccgt tattacctag caacccttgc    2340
aatgaagatg agcagatcca caggaaaact tgaatgcaca actgtcttat tttaatctta    2400
ttgtacataa gtttgtaaaa gagttaaaaa ttgttacttc atgtattcat ttatatttta    2460
tattattttg cgtctaatga tttttttatta acatgatttc cttttctgat atattgaaat    2520
ggagtctcaa agcttcataa atttataact ttagaaatga ttctaataac aacgtatgta    2580
attgtaacat tgcagtaatg gtgctacgaa gccatttctc ttgattttta gtaaactttt    2640
atgacagcaa atttgcttct ggctcacttt caatcagtta aataaatgat aaataatttt    2700
ggaagctgtg aagataaaat accaaataaa ataatataaa agtgatttat atgaagttaa    2760
aataaaaaat cagtatgatg aataaactt g                                    2791
```

<210> SEQ ID NO 178
<211> LENGTH: 15
<212> TYPE: PRT
<213> ORGANISM: Artificial Sequence
<220> FEATURE:
<223> OTHER INFORMATION: A synthetic amino acid sequence

<400> SEQUENCE: 178

Cys Ala Arg Ala Pro Phe Tyr Asp Ser Asn Leu Phe Asp Tyr Trp
1               5                   10                  15

<210> SEQ ID NO 179
<211> LENGTH: 15
<212> TYPE: PRT
<213> ORGANISM: Artificial Sequence
<220> FEATURE:
<223> OTHER INFORMATION: A synthetic amino acid sequence

<400> SEQUENCE: 179

Cys Ala Arg Asp Leu Gly Lys His Ile Arg Glu Ile Asp Phe Trp
1               5                   10                  15

<210> SEQ ID NO 180

```
<211> LENGTH: 17
<212> TYPE: PRT
<213> ORGANISM: Artificial Sequence
<220> FEATURE:
<223> OTHER INFORMATION: A synthetic amino acid sequence

<400> SEQUENCE: 180

Cys Ala Lys Asp Pro Val Gly Glu Asn Ser Gly Ser Tyr Tyr Ile Ser
1               5                   10                  15

Trp

<210> SEQ ID NO 181
<211> LENGTH: 16
<212> TYPE: PRT
<213> ORGANISM: Artificial Sequence
<220> FEATURE:
<223> OTHER INFORMATION: A synthetic amino acid sequence

<400> SEQUENCE: 181

Cys Ala Lys Gly Glu Ser Tyr Gly Pro Tyr Asp Ala Phe Asp Met Trp
1               5                   10                  15

<210> SEQ ID NO 182
<211> LENGTH: 16
<212> TYPE: PRT
<213> ORGANISM: Artificial Sequence
<220> FEATURE:
<223> OTHER INFORMATION: A synthetic amino acid sequence

<400> SEQUENCE: 182

Cys Ala Lys Gly Glu Asn Tyr Gly Pro Tyr Asp Ala Phe Asp Met Trp
1               5                   10                  15

<210> SEQ ID NO 183
<211> LENGTH: 18
<212> TYPE: PRT
<213> ORGANISM: Artificial Sequence
<220> FEATURE:
<223> OTHER INFORMATION: A synthetic amino acid sequence

<400> SEQUENCE: 183

Cys Ala Arg Ser Pro Gly Tyr Cys Ser Ser Asn Ser Cys Tyr Pro Asp
1               5                   10                  15

Val Trp

<210> SEQ ID NO 184
<211> LENGTH: 17
<212> TYPE: PRT
<213> ORGANISM: Artificial Sequence
<220> FEATURE:
<223> OTHER INFORMATION: A synthetic amino acid sequence

<400> SEQUENCE: 184

Cys Ala Lys Asp Pro Val Gly Glu Asn Ser Gly Ser Tyr Tyr Ile Ser
1               5                   10                  15

Trp

<210> SEQ ID NO 185
<211> LENGTH: 32
<212> TYPE: PRT
<213> ORGANISM: Artificial Sequence
<220> FEATURE:
<223> OTHER INFORMATION: A synthetic amino acid sequence

<400> SEQUENCE: 185
```

```
Cys Val Arg Glu Ala Gly Gly Pro Asp Tyr Arg Asn Gly Tyr Asn Tyr
1               5                   10                  15

Tyr Asp Phe Tyr Asp Gly Tyr Tyr Asn Tyr His Tyr Met Asp Val Trp
            20                  25                  30

<210> SEQ ID NO 186
<211> LENGTH: 18
<212> TYPE: PRT
<213> ORGANISM: Artificial Sequence
<220> FEATURE:
<223> OTHER INFORMATION: A synthetic amino acid sequence

<400> SEQUENCE: 186

Cys Ala Arg Gly Ser Glu Thr Val Ala Ala Tyr Ser Tyr Gly Met Asp
1               5                   10                  15

Val Trp

<210> SEQ ID NO 187
<211> LENGTH: 13
<212> TYPE: PRT
<213> ORGANISM: Artificial Sequence
<220> FEATURE:
<223> OTHER INFORMATION: A synthetic amino acid sequence
<221> NAME/KEY: MISC_FEATURE
<222> LOCATION: (8)..(8)
<223> OTHER INFORMATION: Xaa is N or S

<400> SEQUENCE: 187

Cys Thr Ser Tyr Thr Asn Asp Xaa Asn Ser Gln Val Phe
1               5                   10
```

B CELL RECEPTOR MODIFICATION IN B CELLS

CROSS-REFERENCE TO RELATED APPLICATIONS

This application is a National Phase Application of PCT International Application No. PCT/US2018/045255, International Filing Date Aug. 3, 2018, claiming the benefit of U.S. patent application Ser. No. 62/540,702, filed Aug. 3, 2017, the contents of which are hereby incorporated by reference in their entirety.

FEDERAL FUNDING

This invention was made with government support under 5R01DE025167 awarded by the National Institutes of Health. The government has certain rights in the invention.

BACKGROUND

SEQUENCE LISTING STATEMENT

The instant application contains a Sequence Listing which has been submitted electronically in ASCII format and is hereby incorporated by reference in its entirety. The ASCII copy, created on Sep. 29, 2020, is named 1816_1US_SeqListing_ST25.txt and is 164 kilobytes in size.

Some pathogens have evolved mechanisms to avoid the protective effects of most antibodies which can be elicited from the human repertoire, rendering the development of effective vaccines against these pathogens extremely difficult. Thirty-five years after the emergence of the HIV pandemic for example, no effective vaccine has yet been developed despite significant investment. Viruses such as HIV generate antigenic diversity as a part of their strategy to evade protective antibody responses capable of neutralizing the virus. Broadly neutralizing antibodies (bnAbs) to HIV do exist but such antibodies require features that are difficult to elicit from the human repertoire, because they typically derive from rare precursors and require extensive hypermutation during affinity maturation.

There are many antigenically variable pathogens like HIV, influenza and Hepatitis C for example, for which no good, broadly effective vaccine exists. In addition, human pathogens like *Plasmodium falciparum* possess neutralizing epitopes which are not easily accessed by antibodies in the natural human repertoire.

SUMMARY

Engineering strategies are described herein to introduce protective (broadly neutralizing) antibody paratopes that can target HIV into B cell receptors. The methods described herein can also be used for the introduction of paratopes into the human antibody repertoire to provide protection against many other pathogens such as influenza, Hepatitis C and *Plasmodium falciparum*, enabling the development of vaccines against all of these. In addition, the methods described herein can be used to modify antibodies to possess desired properties by harnessing antibody affinity maturation mechanisms in B cells. Hence, antibodies that are broadly neutralizing against a variety of viruses and other pathogens can be generated.

The methods described herein modify existing Ig loci in B cells while preserving somatic hypermutation and isotype switching functions. As such, engineered cells retain the genetic plasticity required for affinity maturation of long-lived, self-tolerant antibody responses that result from antigen dependent B cell maturation.

Described herein are homology directed repair (HDR) genome editing strategies that use nucleases in combination with donor nucleic acids to replace immunoglobulin variable regions of the B cell genome with selected antibody variable regions (or derivatives thereof). Both light and heavy chain replacements can be made. The novel antibodies so generated can be expressed as cell surface immunoglobulins (Ig). Other cell surface expressed, secreted, or cytoplasmic proteins can be introduced in these locations depending on the donor DNA design. The new sequences within engineered immunoglobulin loci of the modified cells can be further mutated by Activation-Induced Cytidine Deaminase (AID), to generate variants with altered properties. Variants with improved binding to a given substrate can be selected when expressed on the cell surface using fluorescence activated or magnetic cell sorting (FACS/MACS). Sorted cells can be further cultured for subsequent rounds of selection allowing this process to be used as a 'directed evolution' or 'in vitro affinity maturation' platform.

When used in primary B cells to modify B cell receptor (BCR) specificities, engineered cells can be autologously engrafted into animals or patients, and expanded in vivo through B cell receptor engagement using vaccine immunogens or in the context of natural infection. Such BCR engagement can drive the elicitation of self-tolerant, long-lived, protective antibody responses from these cells. In some cases, the cells can have multiple specificities. The methods described herein can generate in vivo antibody responses that cannot be otherwise be elicited from the natural repertoire using immunogens alone. For example, the elicitation of HIV broadly neutralizing antibody responses that are therapeutic or protective against infection by this virus can be provided using the methods described herein.

When used in animals, engineered cells can be expanded through vaccination to generate antibodies with modified properties.

Methods and systems are described herein can include:

a. introducing double-stranded breaks on either side of a replaceable genomic segment within one or more antibody producing cell wherein the replaceable genomic segment encodes a recipient immunoglobulin variable region peptide;
b. replacing the replaceable genomic segment with a segment of a donor nucleic acid, where the segment of a donor nucleic acid encodes a promoter, donor immunoglobulin variable peptide with at least one amino acid difference relative to the recipient immunoglobulin variable region peptide, or a combination thereof, to thereby generate a population of antibody producing cells comprising one or more modified antibody producing cells; and
c. selecting one or more modified antibody producing cells from the population of antibody producing cells, each modified antibody producing cell with at least one modified immunoglobulin gene comprising a segment of a donor nucleic acid.

In some cases, the replaceable genomic segment is an immunoglobulin variable region flanked on the 5' side by a functional V gene promoter and on the 3' side by a J gene intron starting close to or at the J gene splice site. The donor nucleic acid can, for example, encode an Ig VDJ/VJ recombined variable region (or derivative thereof) with at least one amino acid coding difference relative to the expressed recipient immunoglobulin variable region. The donor nucleic acid can, for example, express a modified protein as a cytoplasmic, cell surface or secreted protein depending on the donor nucleic acid design. The replacement donor nucleic acid can be flanked 3' by a homology region (HR) identical (or similar to) to a nuclease targeted J gene intron 3' of the J gene splice site. The replacement donor nucleic acid can be flanked 5' by a HR identical (or similar to) a nuclease targeted V gene 5'UTR for incorporation between cut sites by homology directed repair. The methods can thereby generate a population of antibody producing cells (e.g., B cells) having one or more modified cells expressing the novel donor nucleic acid under transcriptional control of a native cell V gene promoter and with or without splicing to native downstream constant genes.

In some cases, only a single cut site is introduced near a J gene splice site. A donor nucleic acid can still be incorporated at this cut site by host cell DNA repair mechanisms. For example, donor nucleic acid can include at least a V gene promoter followed by a replacement immunoglobulin VDJ/VJ variable region (or derivative thereof), the J gene splice site followed by a region of homology to the nuclease-targeted J gene intron in order to guide incorporation of the donor DNA at the J gene break site by homology directed repair mechanisms on the 3' side. An optional 5' HR can guide repair of the double strand break by HDR on the 5' side of the break site however incorporation by NHEJ on this side will also result in expression of the donor nucleic acid spliced to native cell constant genes and subject to somatic hypermutation.

Hence, methods and systems are also described herein that can include:
a. introducing a single double-stranded cut within a genomic segment that is adjacent to a recipient immunoglobulin variable region peptide or that is 3' to a J gene splice site in one or more antibody producing cells;
b. inserting a donor nucleic acid at the double-stranded cut site, where the donor nucleic acid includes a promoter, encodes a donor immunoglobulin variable peptide with at least one amino acid difference relative to the recipient immunoglobulin variable region peptide, or a combination thereof, to thereby generate a population of B cells comprising one or more modified antibody producing cells; and
c. selecting one or more modified antibody producing cells from the population of cells, each modified antibody producing cell with at least one modified immunoglobulin gene comprising a segment of a donor nucleic acid.

In some cases, after step (b), the method can further include inserting a donor nucleic acid at the double-stranded cut site, where the donor nucleic acid includes a promoter, cytoplasmic, cell surface expressed or secreted protein ending with a transcription termination signal.

The selecting step can involve selection for expression of a modified immunoglobulin that (selectively) binds to a specific antigen or epitope. In some cases, the selecting step can involve selection of cells that express a tag, sequence marker, or cell surface expressed protein that encoded in the modified immunoglobulin gene sequence.

In some cases, the antibody producing cell(s) are primary mammalian B cells. Such primary B cells can be engrafted (e.g., autologously) into a subject to provide the subject with B cells that can produce useful antibodies (e.g., antibodies against variable antigens). However, in some cases, the B cells are immortalized B cells, for example, from a B cell line that can reproduce for many generations in culture.

Modification of immunoglobulin variable regions of such cells can provide modified cell populations for evaluation and for other manipulations, such as in vitro antibody affinity maturation or directed evolution. Additional modifications of mutations in immunoglobulin variable regions can be generated and identified in these engineered cells, for example, that further contribute to selective binding and affinity of antibodies for a particular antigen of interest.

The engineered B cells can, for example, be subjected to additional steps such as steps (d)-(f) below.
d) culturing one or more of the modified antibody producing cells for a time and under conditions for activation-induced cytidine deaminase (AID) activity in one or more modified antibody producing cells;
e) selecting at least one modified antibody producing cell that expresses an engineered immunoglobulin with affinity (e.g., high affinity) for an antigen; and
f) optionally repeating steps (d) and (e) two to 100 times;
to thereby generate one or more separate engineered antibody producing cell(s) that express engineered antibodies and/or engineered B cell receptors having affinity for the antigen.

The engineered cell(s) generated by steps (d)-(f) can in some cases express engineered immunoglobulins having higher affinity for the antigen than the original modified immunoglobulin expressed by cells subjected only to steps (a)-(c).

At least one of the modified or engineered immunoglobulin genes can encode and/or express at a modified immunoglobulin variable peptide sequence that has at least one amino acid difference compared to the recipient immunoglobulin variable region peptide. When subjected to steps (d)-(f), cells can have modified or engineered immunoglobulin genes that encode and/or express a modified immunoglobulin variable peptide sequence that has at least one amino acid difference compared to the donor immunoglobulin variable peptide sequence.

The methods can provide new and useful cell lines for generating improved antibodies and useful fragments thereof. The methods can include directed evolution (rounds of cell culture and sorting to enrich the cell population with variants with higher affinity for the probe), as well as in vitro 'affinity maturation' of antibodies for immunogen testing. Because mutations are introduced by a process similar to what happens during an immune response, immunogens can be tested for their ability to select particular antibody evolutionary pathways given a starting antibody sequence. When used in primary cells, engineered antibody producing cells can be autologously engrafted into a mammal (or bird) where they can expand into self-tolerant long-lived antibody responses through immunization or exposure to non-self in vivo epitopes. These responses can have therapeutic benefits, and the responses can also act to prophylactically to prevent infection as vaccines. The process can also be used to modify known antibody properties via directed evolution. The methods are particularly useful in situations where normal vaccine immunogens fail to elicit antibodies with desired specivilities from the natural repertoire. For example, the methods can be used to generate antibodies capable of potent and broad HIV neutralization.

The methods are an inexpensive and expedient method for directed evolution or immunogen testing. In primary cells, the method can guide the directed evolution of antibodies or provide cell therapy vaccines that produce robust and reproducible elicitation of antibody-based protection against a spectrum of diseases in cases where immunogen alone cannot elicit protective responses from the natural repertoire after adoptive transfer and in vivo expansion.

DESCRIPTION OF THE FIGURES

FIG. 1A schematically illustrates the human immunoglobulin (Ig) heavy chain and lambda light chain loci. The heavy chain locus runs from the telomeric (T, at the left) to centromeric (C, at the right) region of the long arm of chromosome 14 at 14.q32.33. The Immunoglobulin heavy chain variable region (IGHV) is made up of a V gene region, D gene region, and J gene region spanning 1 Mb when in germline configuration. Nuclease cut sites described in this disclosure provide proof of concept data for targeting the locations indicated by the scissors depicted in FIG. 1A on extreme sides of the IgHV locus, so the intervening region can be replaced by homology directed repair in the presence of exogenous donor DNA. The Lambda light chain locus runs from the centromere (C) towards the telomere (T) on the long arm of chromosome 22 at 22q11.2. The light chain variable region (IGLV) is made up of a V gene region, and J-C gene regions spanning 1 Mb when in germline configuration. Nuclease cut sites are indicated by the scissors on extreme sides of the IGLV locus. Similar to the universal heavy chain engineering strategy, homology directed repair (HDR) is used to replace sequences between nucleases cut sites with sequence from exogenous donor DNA. FIG. 1B illustrates a method that involves use of donor DNA encoding an HIV broadly neutralizing antibody (bnAb) VDJ region flanked by sequences identical to genomic DNA. The region 5' of the 5' nuclease cut site (V7-81 or V3-74 5' UTR) and 3' of the 3' cut site (the intron after 16) are regions that would be universally present in all human B cells. The engineered bnAb VDJ region can be expressed as a transcript using regulatory sequences of the endogenous cell constant gene and when the expressed immunoglobulin protein can pair with the native light chain, a chimeric B cell receptor (BCR) will be expressed on the cell surface. B cell receptors exhibiting desirable binding and functional properties can be positively selected using an antigen of interest. Alternatively, a tag encoded within the engineered region can be used for selection. FIG. 1C illustrates further steps in an exemplary method that can involve engrafting engineered cells and boosting the cells with immunogens that engage the B cell receptor to instigate clonal expansion and affinity maturation, establishing long term protective antibody based immunity. Data illustrate proof of concept, showing that novel VDJ regions can pair ubiquitously with native cell light chains (see FIGS. 1D and 2A). FIG. 1D shows an amino acid alignment of human antibody light chain (LC) variable region sequences expressed as chimeras in 293 cells with mature PG9 heavy chain IgG (SEQ ID NOs:1-40; also shown in Table 2). Sequences named 1-31 were cloned from a human donor. Other clones included the light chains derived from select HIV bnAbs or the Ramos B cells. PGT135 and K31 did not express. The top line shows the locations for the complementarity determining regions (CDRs) (numbering is based on PG9 LC). PG9 light chain residues that make contact with the heavy chain in the crystal structure (PDB:3U2S) are indicated immediately below the top line with buried surface area in angstroms (Å). Light chains from PG9 chimeras neutralizing five or more viruses on the 12-virus global panel are highlighted in boxes. Regions of sequence similarity are underlined. FIG. IE illustrates CRISPR/cas9 guide RNA selection (SEQ ID NOs: 128-142: see Table 3). The human reference genome (GenBank: AB019437, L33851. AB019439 and AL122127) at the immunoglobulin heavy chain variable (ICHV) gene locus in the International Immunogenetics Information System (see website at www.imgt.org) was used to design CRISPR/cas9 guide RNAs using the Zhang lab-optimized CRISPR Design online platform (see website at crispr.mit.edu). Primers were ordered and cloned into the pX330-U6-chimeric_BB-CBh-hSpCas9 vector as described in Example 1. Target DNA (e.g., the genomic DNA sequences to be cleaved by these nucleases) were either synthesized or amplified from 293T or Ramos B-cell gDNA as 250-300 bp products that could be cloned into the pCAG-eGxxFP vector. The pX330 vectors were then co-transfected with their respective target pCAG vectors into 293T cells as described in Example 1. If the target DNA was cut by the CRISPR/cas9/gRNA complex expressed in the cell, the pCAG vector underwent homologous recombination to express a GFP protein. Two days after transfection, guide RNAs were scored visually based on GFP expression in the 293 cells according to the sample confocal microscopic images shown to the right of the chart (where the pattern shown in the box to the right of the chart relates to the pattern scored in the chart). The highest scoring guide RNAs which could achieve cutting against the target DNA sequences derived from all three sources were chosen for B-cell engineering experiments to insert PG9 mature HC VDJ genes by homologous recombination. The same methods were used to test Lambda locus directed guide RNAs using target sequences synthesized based on the IMGT reference sequence (Genbank D86993 and D87017), or cloned from Ramos B cells (FIG. 1E).

Figure 2A:
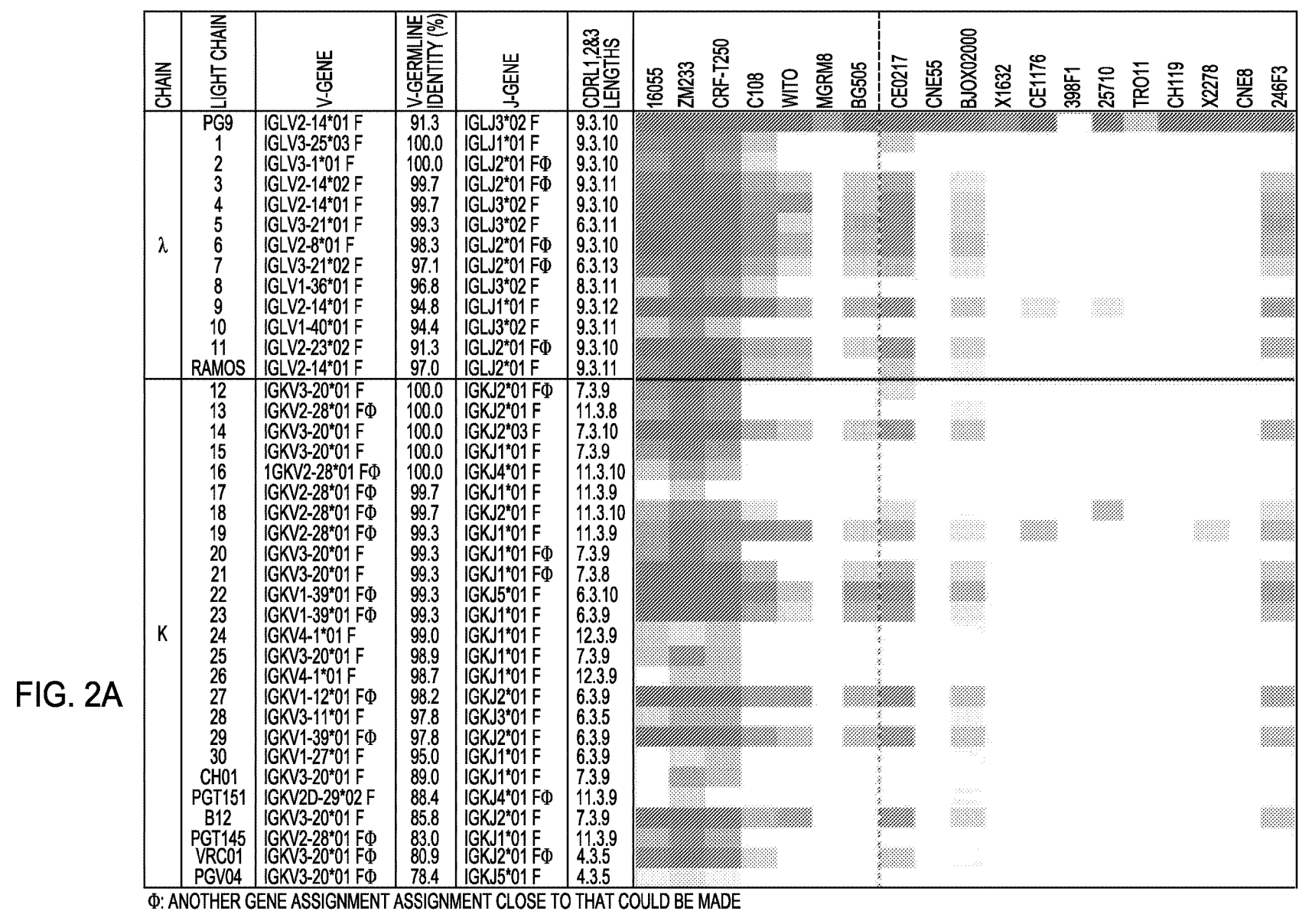

FIG. 2A-2C illustrates how an HIV broadly neutralizing antibody, PG9 (heavy chain IgG), neutralizes HIV when paired with diverse light chains (e.g., generated using methods illustrated in FIGS. 1A-ID). FIG. 2A shows the sensitivity of nineteen different HIV isolates to PG9 HC-chimeric LC antibodies. Viruses including: six strains especially sensitive to PG9 (leftmost) and 12 viruses representative of the global diversity of HIV (rightmost). The PG9 chimeras are grouped according to lambda and kappa gene usage in order of least to most mutated (sequences are in FIG. 1D, Table 2). A diversity of light chains was chosen including several derived from other bnAbs. Light chain features are provided including V and gene usage, the identity of the V-gene to germline, and the CDRL (1, 2 and 3) amino acid lengths as determined using IMGT. Dark to white heat map represents 100% to 10% or less neutralization at a concentration of 10 ug/ml of PG9 chimera IgG as described in Example 1. FIG. 2B-1 to 2B-3 graphically illustrate the relative binding of PG9 chimera IgG to HIV Envelope (SOSIP) by a series of Biolayer interferometry plots. PG9 chimeric IgGs were bound to protein G optical sensors. PGT145 purified soluble recombinant HIV Envelope trimers (color legend at bottom of page) were then bound at 500 nM for 120 s (180-300) and then dissociated in PBS for 250 s (300-550). Association and dissociation curves are shown with bound SOSIP-IgG complex measured as response units (RU) vs time in seconds (s). PG9HC/LC control is the first plot. FIG. 2C-1 to 2C-2 show images of cells illustrating results from PG9 chimeric IgG autoreactivity testing. Purified IgGs were incubated with HEp-2 cells mounted on glass slides. Antibodies that bind human antigens were detected with anti-human IgG-GFP and visualized. Negative (−) and positive (+) controls are included at the bottom right of FIG. 2C-2 along with PG9 (HC/LC) IgG. Fourteen chimeras out of 37: LLC-3,4,6, KLC 12,14-17,24,26,27, CHO1, PGT151 and Ramos LC compare with the PG9 HC/LC control which is not autoreactive.

FIG. 3A-3Q illustrate engineering of B cell receptor immunoglobulin loci to generate PG9 variants with HIV neutralizing activity. FIG. 3A schematically illustrates universal vs. Ramos specific VDJ editing in human Ramos B cell lines. The Ramos specific strategy uses cut sites after the V4-34 promoter and J6 genes to replace only the native Ramos VDJ region (400 bp) with the PG9 VDJ from a donor with homology regions (HRs) upstream and downstream of these cut sites. The universal editing strategy uses cut sites after the V7-81 or V3-74 promoter and J6 gene to replace approximately 0.5 Mb in the Ramos B cell line with PG9 bnAb from a donor DNA with homology regions (IRs) upstream and downstream of these cut sites. PCR amplification primer annealing sites to amplify the locus for confirmation of correct gene insertion are shown as small arrows above and below the line representing the chromosome. Note that these sites lay outside of donor DNA homology regions (HRs). FIG. 3B shows FACS plots of engineered Ramos B-cells (RA1), where the engineering involved using either the V78/V374 or V434 HDR strategies. Successfully engineered cells expressing chimeric PG9 BCR bind to a soluble recombinant HIV envelope native trimer probe (strain C108) labeled with allophycocyanin (APC) conjugated streptavidin. APC-positive selection gates were set against the FITC channel to eliminate autofluorescent cells using WT Ramos cells stained with the same probe (Example 1). FIGS. 3C-1 and 3C-2 illustrate the reproducibility of V781/V434 strategies. Each experiment was reproduced 12 times. FIG. 3C-1 graphically illustrates that the average percentage of cells able to bind C108 Env (SOSIP) after engineering was 0.21% (SD=0.03) and 1.75% (SD=0.20) using the V7-81 and V4-34 strategies respectively. FIG. 3C-2 graphically illustrates the average fluorescence values of APC+ cells from the 12 transfections using the V7-81 and V4-34 strategies (results for the V3-74 strategy are not shown). FIGS. 3D-1 and 3D-2 show PCR products of genomic DNA analysis confirming that the native VDJ is replaced with PG9 in engineered cells. PCR reactions were done on engineered cell genomic DNA using three sets of forward and reverse primer sets designed to amplify across the entire engineered site, including sequences outside of the homology regions (HRs) to ensure that new PG9 gene was in the expected context in the engineered cell genomes. Approximate primer annealing sites are indicated by arrows in FIG. 3A. PCR products are shown from amplification reactions using V4-34 promoter/J6 intron primers sets to yield an approximate 5.5 Kb fragment in both V4-34 engineered cells as well as in WIT cells (outlined in rectangular boxes). Note that the V781 promoter/J6 intron primer sets amplified a 5.5 Kb fragment in V7-81 engineered cells but not in WT cells in FIG. 3D-2. Sequences of these PCR products are shown in (FIGS. 3I-3Q). These results show that both strategies engineered the IGHV site as expected (V3-74 is not shown). FIG. 3E-1 to 3E-5 illustrate that engineered cells produce PG9 mRNA transcripts as IgM or as IgG in cytokine-stimulated cells. Ramos CG6 engineered cell mRNA and C108 Env selected cell mRNA was purified and cDNA libraries were made. Primer sets designed to amplify either the wild type or engineered (PG9) heavy chains (IgG or IgM) were used for PCR amplification. Bands can be identified by amplification primers: P=PG9 specific, R=Ramos VDJ specific, M=IgM specific G=IgG specific, (f)=forward primer, (rc)=reverse compliment primer. Only V4-34 or V7-81 engineered, but not WT samples, contained PG9-IgM. PG9-IgG could be amplified from CD40L/Il-2/Il-4 stimulated cells. Sequencing chromatograms for the PCR products outlined with rectangular boxes are given in FIG. 3Q. FIGS. 3H-1 and 3H-2 graphically illustrate binding of WT and CDRL3 variant Abs enriched by cell sorting with Env trimers. The wild type PG9HC/RamosLC chimera as well as representative mutants moving the LC glycan to position 97, S97N. or eliminating it, S97G, were expressed as IgGs and characterized for their binding to various HIV Env trimers using Biolayer interferometry (BLI). PG9 chimera-saturated sensors were exposed to 500 mM SOSIP Env trimer (180-250 s) and then PBS (250-500 s) for assessing binding and dissociation kinetics, measured as response units (RU; FIG. 3H-1). FIG. 3H-2 illustrates neutralization by WT and CDRL3 (S97G, S97N) variant Abs. The PG9HC/RamosLC WT chimera and the CDRL3 mutant IgGs were tested for neutralization against the panel of pseudoviruses listed in FIG. 2A. Differences between WT and mutant Abs are shown as neutralization titrations, where the percent neutralization (y-axis) is plotted as a function of IgG concentration (log µg/ml) on the x-axis. Despite improved affinity for MGRM8 SOSIP, neutralization was not detected against this virus by the engineered chimeras. FIG. 3I shows a schematic diagram of an assembled 5.5 kb genomic human immunoglobulin heavy chain variable DNA sequence that was isolated by PCR amplification from wild type Ramos lymphoma B cells. FIG. 3J-1 to 3J-3 show the 5.5 kb genomic human immunoglobulin heavy chain variable DNA sequence (SEQ ID NO: 161) schematically illustrated in FIG. 3I. The 5.5 Kb PCR product was obtained (box FIGS. 3D-1 and 3D-2), gel purified and Sanger sequenced using a series of primers to give overlapping sequence reads as indicated by the Contig arrows above the linear diagram in FIG. 3I. Annotations are represented by font color in the original and correspond to the linear diagram shown in FIG. 3I. The PCR product encompasses gDNA sequences from the V434 5 UTR (5' of the donor DNA HR) to the intron after J6 (3' of the donor DNA HR) to ensure the gene was placed in the correct location in the genome. Discrepancies between expected sequence (IMGT reference sequence and donor DNA design) are annotated in the text below the FIG. 3I linear diagram and the shaded nucleotides in FIG. 3J-1 to 3J-3. FIG. 3L-1 to 3L-3 shows the 5.5 kb genomic human immunoglobulin heavy chain variable DNA sequence (SEQ ID NO: 162) schematically diagrammed in FIG. 3K that was derived from Ramos B cells engineered using the 'V434' strategy and selected using C108 HIV Env in FACS. A 5.5 Kb PCR product was obtained (box FIG. 3D), gel purified, and Sanger sequenced using a series of primers to give overlapping sequence reads indicated by the Contig arrows above the FIG. 3K linear diagram. Annotations are represented by font color in the original and correspond to the linear diagram in FIG. 3K. The PCR product encompasses genomic DNA sequence from the V434 5'UTR (5' of the donor DNA homology region (HR)) to the intron after J6 (3' of the donor DNA homology region (HR)) to ensure the gene is placed in the correct location in the genome. Discrepancies between expected sequence (IMGT reference sequence and donor DNA design) are annotated below the linear diagram and the highlighted by shading in the nucleotide sequence. FIG. 3N1-3N3 show the 5.5 kb genomic human immunoglobulin heavy chain variable genomic DNA sequence (SEQ ID NO: 163) schematically diagrammed in FIG. 3M that was derived from Ramos B cells engineered using the 'V781' strategy and selected using C108 HIV Env in FACS. A 5.5 Kb PCR product was obtained (box FIG. 3D), gel purified and Sanger sequenced using a series of primers to give overlapping sequence reads indicated by the Contig arrows above the linear diagram in FIG. 3M. Annotations are represented by font color in the original and correspond to the FIG. 3M linear diagram. The PCR product encompasses genomic DNA sequence from the V781 5UTR (5' of the donor DNA homology region (HR)) to the intron after J6 (3' of the donor DNA HR) to ensure the gene is placed in the correct location in the genome. Discrepancies between expected sequence (IMGT reference sequence and donor DNA design) are annotated (T to C) in the FIG. 3M linear diagram and the highlighted by shading in the nucleotide sequence. FIG. 3P-1 to 3P-3 shows the 5.5 kb genomic human immunoglobulin heavy chain variable genomic DNA sequence (SEQ ID NO: 164) schematically diagrammed in FIG. 3O that was derived from EBV transformed polyclonal cells engineered using the 'V781' strategy and selected using C108 HIV Env in FACS. A 5.5 Kb PCR product was obtained (box FIG. 3D), gel purified and Sanger sequenced using a series of primers to give overlapping sequence reads indicated by the Contig arrows above the linear diagram in FIG. 3O. Annotations are represented by font color in the original and correspond to the FIG. 3O linear diagram. The PCR product encompasses genomic DNA sequence from the V781 5'UTR (5' of the donor DNA HR) to the intron after J6 (3' of the donor DNA HR) to ensure the gene is placed in the correct location in the genome. Discrepancies between expected sequence (IMGT reference sequence and donor DNA design) are annotated in below the linear diagram in the FIG. 3O aid highlighted by shading within the nucleotide sequence. FIG. 3Q (SEQ ID NOs: 164-168) shows sequences of PCR products amplified from the cDNA derived from different Ramos cell lines and translated in the correct frame into amino acid sequence. The cell line is indicated to the left of the sequence along with the PG9 VDJ reference. Either Ramos VDJ specific or PG9 VDJ forward primers were used with either IgM or IgG specific reverse primers, also indicated to the left of the sequence. HC VDJ numbering and CDRs are indicated in the linear diagram above the sequences.

FIG. 4A-4C illustrates isolation and characteristics of engineered EBV-transformed polyclonal B cells. FIG. 4A illustrates sorting of polyclonal cells engineered with universal editing strategy. Polyclonal B-cells from healthy donors (EBV transformed) were engineered using the V7-81 (universal) strategy and sorted. Cells positive for both FITC labeled and APC labeled C108 HIV envelope probes were selected. The PE channel was used to eliminate autofluorescent cells from the gate. Negative control sorts of the parental line stained with the above probes are shown as insets on the bottom right with % of live single cells contained in positive gates written in the gate. FIG. 4B illustrates that native VDJ genomic DNA was replaced with a PG9 heavy chain sequence in the engineered EBV-transformed polyclonal B cells. To show that the engineered cells had the genomic modifications, PCR amplification reactions were performed on engineered cell genomic DNA using reaction procedures like those used to obtain the results shown for FIG. 3D. A 5.5 Kb fragment was observed in polyclonal EBV engineered cells (box) but was not observed in the parental line. The sequencing chromatogram for this product is given in FIG. 3O-3P and is consistent with PG9 being correctly incorporated into the genome between universal homology regions. FIG. 4C illustrates next generation sequences of heavy chain mRNA in unengineered and in engineered C108-selected cells (SEQ ID NOs: 178-186). C108-FITC and C108-APC double positive cells were cultured before harvesting mRNA. cDNA was made and amplified with IgG and IgM variable region-specific primers, and the amplicons were sequenced using the Illumina MiSeq. Sequences with the highest numbers of reads are given in the table along with their genetic and sequence properties. PG9 HCs were detected in the engineered but not unengineered mRNA (boxed row).

FIG. 5A illustrates replacement of the Ig variable region by cutting with nucleases on the 5' and 3' sides (scissors) in the presence of donor DNA encoding the replacement ORF flanked 5' by a region of homology 5' of the 5' cut and flanked 3' by a region of homology 3' of the 3' cut. The new ORF uses a natural V gene promoter and a J gene intron splice site for expression. FIG. 5B illustrates introduction of a V gene promoter and ORF from a donor DNA into a single cut site near the 3' most J gene cut site. A 3' homology region grafts the new gene at the break site to retain intron splicing to downstream constant regions. An optional 5' homology region (HR) can encourage repair by homology directed repair (HDR); when not present the repair can be made by non-homologous end joining (NHEJ) when the donor DNA is double stranded (and preferably linear).

FIG. 6A-6C illustrate replacement of the human Ramos B cell line HC variable locus with the PG9 HIV bnAb VDJ ORF and generation of variants in the engineered cells by Activation-Induced Cytidine Deaminase (AID). FIG. 6A illustrates replacement of the human Ramos B cell line HC variable locus with the PG9 HIV bnAb VDJ ORF by the 'universal' strategy using nucleases and HRs to the 5' most V gene promoter (V781) as well as the J6 intron (3' of the splice site). The V781 promoter drove expression of the PG9 heavy chain using the native cell IgM constant gene and Ramos lambda light chain (LLC). Engineered cell surface receptors could be detected with HIV Env probes using FACS. FIGS. 6B-1 (SEQ ID NO: 187), 6B-2 and 6B-3 illustrate that AID in engineered cells generated variants of the PG9 IgM/Ramos LLC B cell receptor with higher affinity to the MGRM8 strain of HIV Env that can be selected by FACS. Three rounds of selection with MGRM8 probe highly enriched a light chain mutation at position 97 which deleted (N97G for example) or shifted (S97N) an N-linked glycan from position 95 to position 97. FIG. 6B-1 shows consensus sequences from Ig cDNA after each round of three selection steps. FIG. 6B-2 illustrates that these mutations improved binding as assessed by the on rates and off rates shown for select strains of HIV Env as detected by SOSIPS using Biolayer interferometry. FIG. 6B-3 illustrates that these mutations improved binding as assessed by virus neutralization for selected strains shown as a function of antibody concentration. FIG. 6C graphically illustrates that accumulation of mutations occurred in the new PG9 VDJ region in a cell line that was selected three times with MGRM8 (dark shaded peaks) or passaged after initial enrichment of engineered cells without further selection (clear peaks), as detected by next generation sequencing of barcoded cDNA. The graph shows the percent divergence from the initial PG9 VDJ sequence across the length of the gene (X axis) with AID hotspot motifs highlighted in stripes enclosed with dashed lines.

FIG. 7A illustrates a universal strategy that was first used to engineer the light chain where an HA epitope tag was included just after the leader with a signal sequence cleavage site for selection of successfully engineered cells. The enriched light chain engineered cells were subjected to a second round of engineering of the heavy chain using the universal strategy. Antigen specific for the antibody engineered into this line was used to enrich fully engineered cells (in this case eOD-GT8 to bind the precursor of the VRC01 HIV bnAb). FIG. 7B illustrates enrichment of antigen-specific antibodies after several rounds of engineering and/or selection by such a method.

FIG. 8A shows a schematic diagram of the donor construct designed to introduce both light and heavy chains of an antibody into the HC locus of B cells by the universal BCR editing strategy. The light chain (in this case VRC01) including constant region is to the left, followed by a furin cleavage and ribosomal slip site, followed by the heavy chain VDJ. FIG. 8B shows sorting of mouse pro-B cells 3 days post nucleofection with reagents designed to introduce the VRC01 at the HC variable locus using the universal BCR editing strategy. 10.7% of cells transfected with the VRC01 donor and two corresponding nucleases were IgM+ and bound to a probe that recognizes VRC01 'eOD-GT8' (but not to one where the VRC01 epitope is knocked out 'KO11'). WT or cells transfected with donor DNA only (without other reagents) are not recognized by these probes.

FIG. 9A schematically illustrates donor DNA and genome structures. The genomic structure shown is the Ramos heavy chain region. The schematic diagram illustrates the location of the nuclease cut site (vertical arrow pointing at the gDNA) after the Ramos VDJ region which uses the J6 intron. The homology region (HR) between the donor DNA and Ramos genome is shown. The location of primers designed to amplify genome engineering events where the 5' side of the donor is introduced through NHEJ and the 3' region is introduced by HDR are shown as thick arrows with the forward primer located in the donor DNA plasmid backbone and the reverse compliment primer is located in the J6 intron/enhancer region downstream of the HR. FIG. 9B shows that the amount of the engineered product is enriched in engineered cells selected for PG9 HC expression using HIV envelope probes. These PCR products were sequenced to confirm that the selected amplicon had the expected engineered structure.

FIG. 10A shows that only a few unengineered control cells were APC+, Pacific blue-negative. FIG. 10A shows that more of the engineered cells were APC+ and Pacific blue-negative. FIG. 10C shows PCR products from amplification of cDNA from the control unengineered cells (lanes 1 and 3) and from amplification of cDNA from engineered cells (lanes 2 and 4; APC+, FITC+, Pacific blue-negative cells). The primers for the amplification of PG9-IgM were used in lanes 1 and 2, and primers for amplification of PG9-IgG1 were used in lanes 3 and 4. FIG. 10D illustrates that only 0.02% of the unengineered controls appeared in the PG9 BCR gate as APC+. FITC+, Pacific blue-negative cells. FIG. 10E shows that more than 5-fold (0.13%) of live cells transfected with engineering reagents appeared in the PG9 BCR gate (as APC+, FITC+. Pacific blue-negative engineered cells). Live cells that bound to the PG9 probe but not to a mutant knocked out for the PG9 HC epitope (Pacific blue) were selected (FIG. 10A-10B). Of these, cells that bound to a second PG9 binding probe (FITC) were selected to remove non-specific binders (FIG. 10D-10E).

DETAILED DESCRIPTION

Methods and systems for modifying genomic immunoglobulin variable gene segments in antibody producing cells (e.g., B cells) are described herein. These methods and systems are useful for generating populations of modified or engineered cells that encode antibodies with desired features (e.g., protective features that are difficult to elicit from the natural human antibody repertoire). For example, the methods describe herein can generate B cells that encode antibodies with affinities for antigenically variable epitopes or for epitopes whose access is restricted amongst antibodies in the natural repertoire.

Figure 5A:
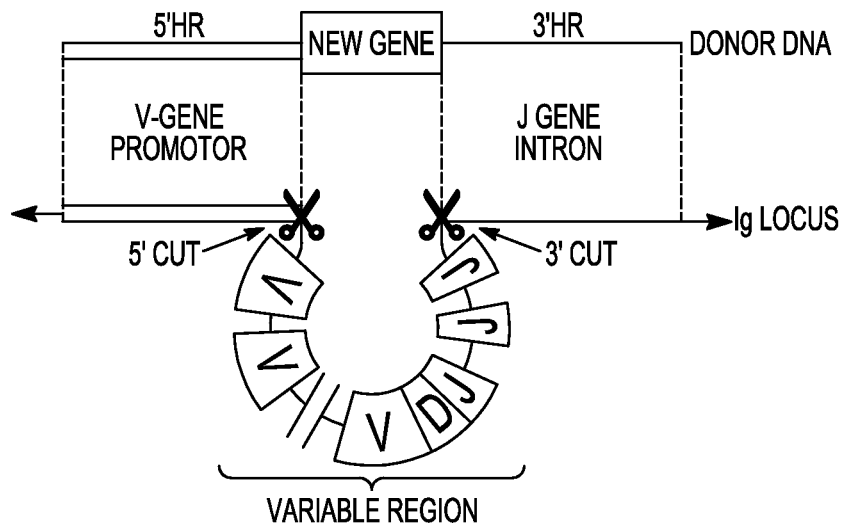
FIG. 5A-5B illustrate replacement of an Ig variable region or introduction of a V gene promoter and open reading frame from a donor DNA.

In some cases, the variable portion of an antibody can be replaced. For example, variable region replacement can be accomplished by:
1) Direct replacement of a segment, or of the entire variable region, in heavy or light chain loci. One or two DNA cuts are introduced in the genome. When two cuts are introduced they can be on either side of a 'replaceable' region to be replaced in the presence of donor DNA that includes a section to 'donated' to the recipient genome. Such a section of the donor DNA can be a regulatory sequence, a peptide coding region, or a combination thereof. The ends of the donor DNA that flank the section to be donated can include regions of sequence homology (HR) relative to the cell genome. For example, a 5' homology region can have homology to the region in the genome that is 5' genome cut site, while a 3' homology region can have homology to the region in the genome that is 3' to the 3' genome cut site (see, e.g., FIG. 5A). The donor DNA and cut sites can have a structure, for example, that grafts a replacement open reading frame (ORF) between a V gene promoter and a J gene splice site, where the encoded protein will be expressed after being spliced to downstream constant genes. In another example, donor DNA and cut sites can have a structure, for example, that includes stop codons and terminator sequences so that the encoded protein is expressed autonomously. Grafting the new donor DNA after the 5' most V gene promoter and before the 3' most J gene splice site will allow for engineering in any B cell from a particular species because both cut sites and homology arms will be universally present regardless of prior VDJ events in the cell (hereafter termed the 'Universal BCR editing' strategy).

Figure 5B:
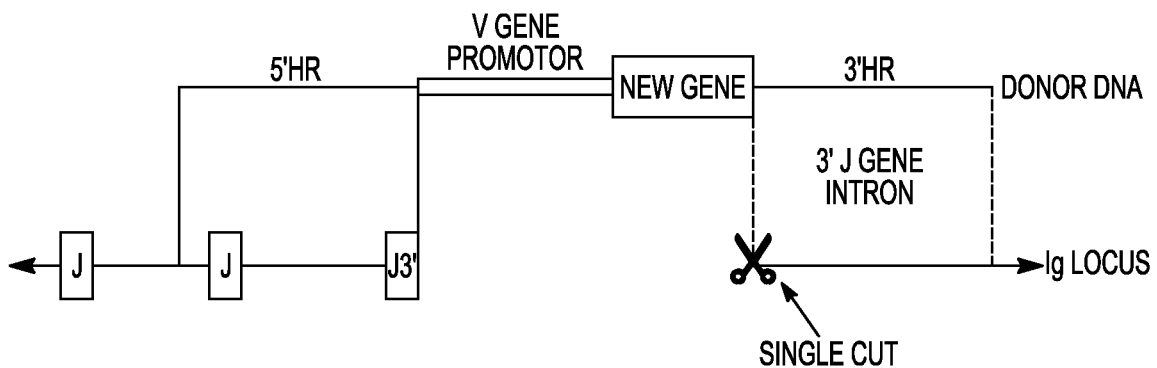

2) A V-gene promoter and open reading frame (ORF) encoded by the donor DNA can be inserted at a single cut site near the 3' J gene splice site. The donor DNA can be flanked on at least the 3' side with an HR from the J gene intron 3' of the splice site for integration by HDR allowing AID mutation of the newly inserted modified DNA to occur and for this modified DNA to be expressed and spliced to downstream constant genes (hereafter termed the 'single cut BCR editing' strategy; see, e.g., FIG. 5B). If present, a 5' homology region containing upstream J gene regions (in germline configuration) is available for HDR in any B cell from a species which has undergone VDJ recombination events using more 5' J genes but not those using the most 3' J gene.

Experiments in human and mouse B cell lines illustrate that the methods described herein are effective. For example, experiments described herein show that the entire heavy chain variable region (from the 5' most V gene promoter, V7-81, to the J6 splice site), can be replaced with the HIV broadly neutralizing antibody PG9 VDJ gene using the universal B cell editing strategy (FIG. 6A) in the human Ramos B cell lymphoma cell line. Nuclease and donor DNA reagents were introduced into cells by nucleofection. Engineered cells expressing PG9 HC as cell surface IgM using the native Ramos light chain and heavy chain constant genes can be enriched using soluble HIV native trimer probes which are recognized by the PG9 paratope. Three rounds of selection with a low affinity HIV trimer probe (MGRM8) enriched a S97N mutation in the light chain which improved affinity and HIV neutralization breadth of the immunoglobulin (Ig) (see, e.g., FIG. 6B-1 to 6B-3). Next generation sequencing of Ig heavy chain variable region cDNA from engineered cells showed an accumulation of mutations within the new heavy chain PG9 gene which preferentially occurred at AID hotspots (highlighted in FIG. 6C as stripes enclosed with dashed lines) confirming the activity of this enzyme on the new gene (FIG. 6C).

Figure 7A:
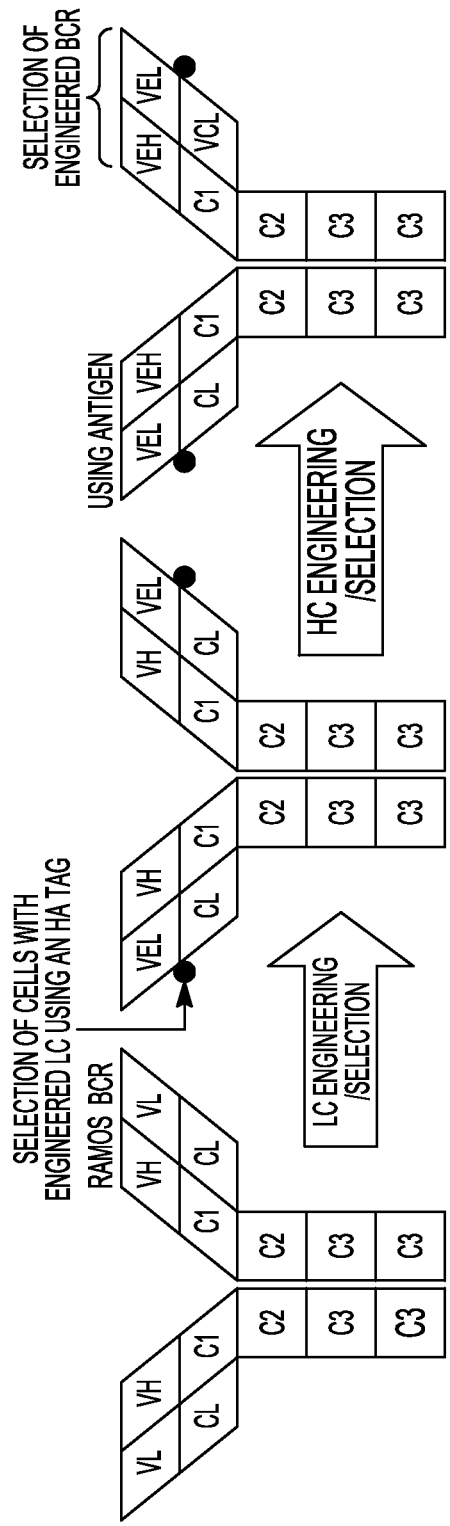
FIG. 7A-7B illustrate a two-step strategy for engineering both the light and heavy chains in the Ramos B cell line.
Figure 7B:
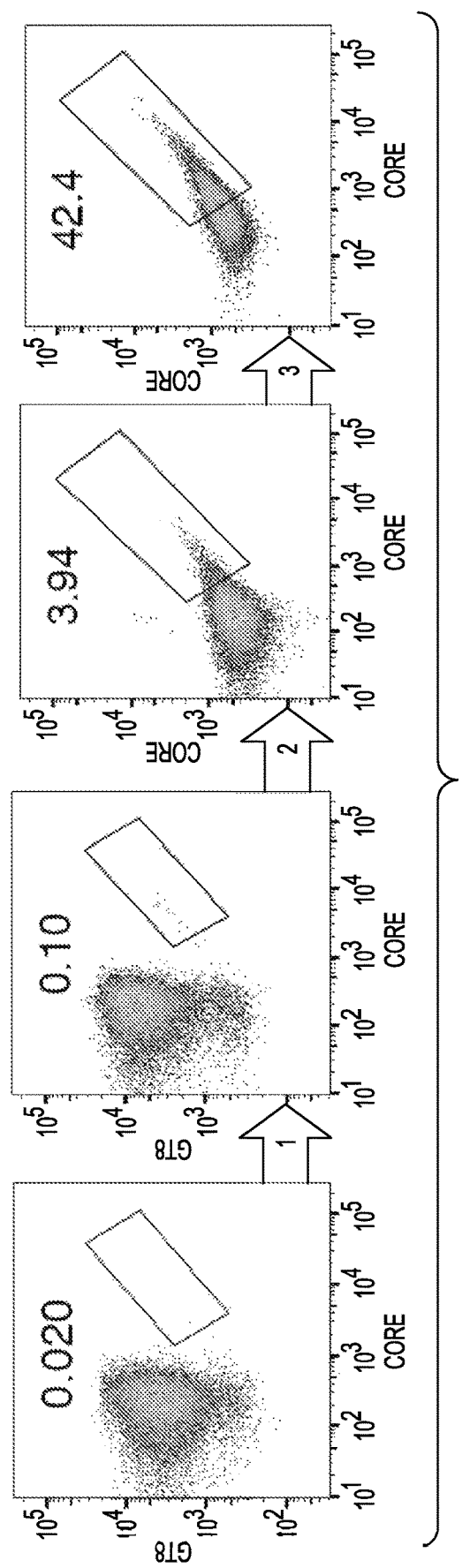

The experiments described herein therefore illustrate that the universal B cell editing strategy can graft the precursor light chain variable (VJ) region sequence from an HIV broadly neutralizing antibody (VRC01) into the lambda locus. An epitope tag was included after the leader and signal cleavage site to provide a locus for the enrichment of light chain engineered cells by FACS. The light chain engineered cells were then subjected to a second round of engineering to graft the precursor variable (VDJ) region of VRC01 DNA between a V gene promoter and the J6 splice site in the heavy chain locus. Nuclease and donor DNA engineering reagents were introduced using nucleofection. Successfully engineered cells were enriched by selection using the precursor VRC01 binding immunogen 'eOD-GT8' but no binding was observed with the VRC01 boosting immunogen 'GT3-core' when used as a probe in FACS (FIG. 7A). While enriched cells were initially unable to bind to the 'GT3-core' boosting immunogen, the accumulation of mutations in the new variable regions introduced by AID in these cells created variant B cell receptors (BCRs) that were able to bind and be enriched by the VRC01 'GT3-core' boosting immunogen (FIG. 7B).

Also as illustrated herein, donor DNA (FIG. 8A) including the mature HIV broadly neutralizing antibody VRC01 light chain followed by a furin cleavage site, the 2A ribosomal slip sequence, and finally the VRC01 heavy chain VDJ region has been incorporated into the mouse HC variable locus in a mouse pro-B cell line using a universal B cell editing strategy. Surface expression of the VRC01 antibody as IgM using mouse constant genes, was detected by IgM staining (FIG. 8B). These cells could also be stained with the soluble HIV envelope probe eOD-GT8, but not with a version of the eOD-GT8 (KO11) probe that has a mutation to disrupt binding of VRC01 antibody.

Figure 10C:
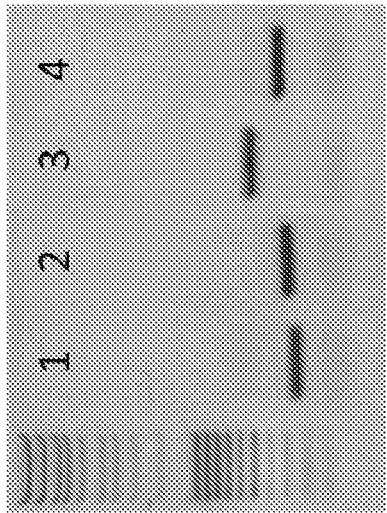
FIG. 10A-10E illustrate engineering of human primary B cells to express PG9 IgG as detected by FACS.
Figure 10B:
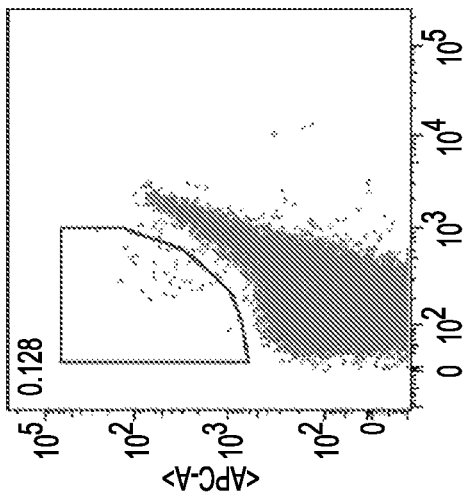
Figure 10A:
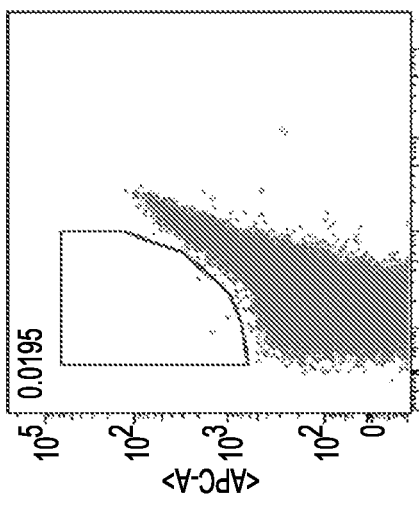
Figure 10E:
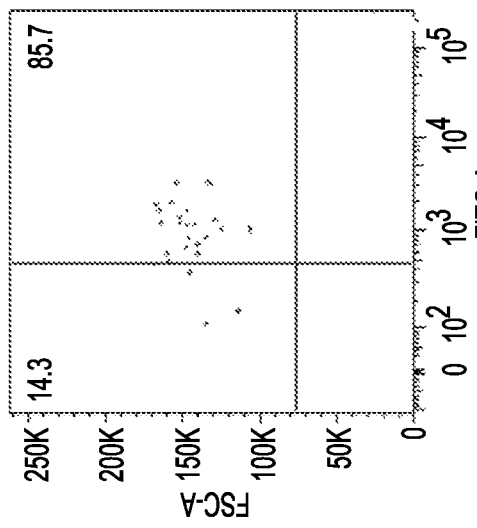
Figure 10D:
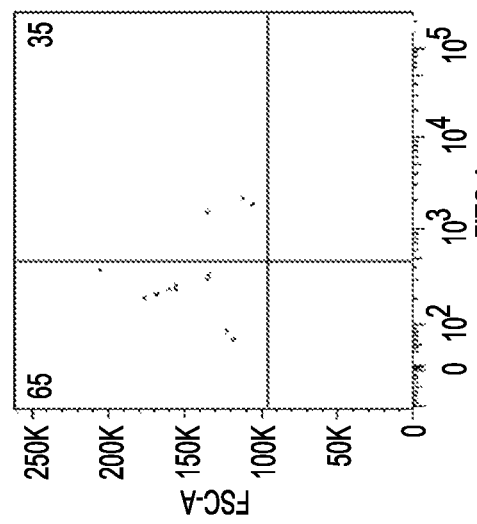

As shown herein, engineering can be achieved in primary cells through experiments performed in human B cells obtained from blood samples. B cells were purified by magnetic activated cell sorting (MACS) and cultured for activation using CD40L and IL-4. In dividing cells, the universal BCR editing strategy was used to modify primary cell heavy chains to encode the HIV bnAb PG9 antigen binding region. Nuclease and donor DNA engineering reagents were introduced by nucleofection. After culturing to allow engineering and expression of the new B cell receptor with endogenous cell light chains, cells that bound to the HIV Envelope probe 'ZM233-SOSIP' but not 'ZM233 ΔN160 SOSIP' (which knocks out PG9 HC binding), could be reproducibly detected as 0.13% of the live cell gate as compared with 0.02% in unengineered controls (FIG. 10D-10E). PCR products corresponding to PG9 Ig mRNA were amplified from engineered cell cDNA but not unengineered controls (FIG. 10C).

The methods can include these and the following components and procedures.

Target (Recipient) Immunoglobulin Loci

The methods and systems described herein can target and modify genomic loci that encode variable immunoglobulin segments. These genomic loci that encode variable immunoglobulin segments are referred to as 'recipient' nucleic acids. The recipient nucleic acids can be deleted and replaced with a nucleic acid segment that has a sequence different from the recipient nucleic acids. The nucleic acids that modify (e.g., replace) the recipient genomic nucleic acids are referred to as 'donor' nucleic acids.

The recipient nucleic acids are cellular nucleic acids within the genome of one or more animal cells. The cells can be from any type of animal, for example, a human, a domesticated animal, an animal involved in experimental research, or a zoo animal.

Figure 1A:
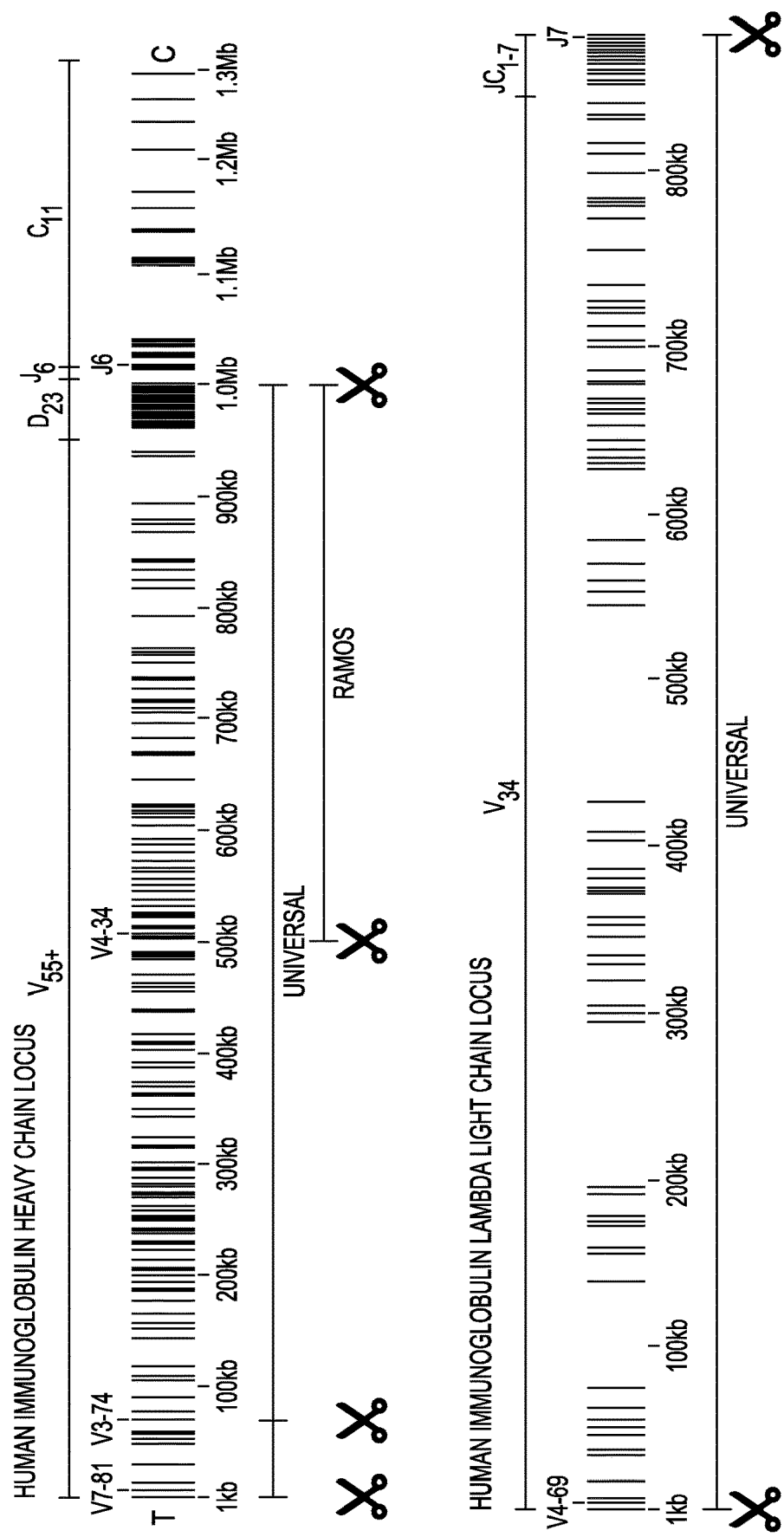
FIG. 1A-1E schematically illustrate the human Immunoglobulin (Ig) heavy chain locus as well as B cell engineering an immunization steps in humans as an example.

In some cases, the recipient nucleic acids are variable heavy chain immunoglobulin genomic nucleic acid segments. In some cases, the recipient nucleic acids are variable light chain immunoglobulin genomic nucleic acid segments. For example, the recipient nucleic acids can include any of the chromosomal segments removed as shown in FIG. 1A. For example, the recipient nucleic acids can be about 1.0 Mb of genomic heavy chain immunoglobulin DNA, or about 0.95 Mb, or about 0.9 Mb, or about 0.5 Mb of genomic heavy chain immunoglobulin DNA. For example, the recipient nucleic acids can be the Ramos segment of the heavy immunoglobulin region of the genome shown in FIG. 1A, which can include at least a portion of the V4-34 (V), D3-10 (D) and J6 (J) genes. The V4-34 locus lies halfway through the immunoglobulin heavy chain (IGHV) locus with the 5' most V-gene promoter (V7-81) about 0.5 Mb upstream (FIG. 1A). In another example, recipient nucleic acids can be a segment of light immunoglobulin genome (referred to as a 'universal' light chain segment) shown in FIG. 1A, which can include at least a portion of the V4-69 to J7 region.

In some cases, the recipient immunoglobulin nucleic acid loci can include (e.g., replaceable) segments that are smaller. For example, the recipient immunoglobulin nucleic acid loci can include (e.g., replaceable) segments that less than are less than 300,000 nucleotides in length, or less than 200,000 nucleotides in length, or less than 100,000 nucleotides in length, or less than 75,000 nucleotides in length or less than 50,000 nucleotides in length, or less than 40.000 nucleotides in length, or less than 30,000 nucleotides in length, or less than 20,000 nucleotides in length, or less than 15,000 nucleotides in length, or less than 10,000 nucleotides in length, or less than 5000 nucleotides in length, or less than 1000 nucleotides in length, or less than 900 nucleotides in length, or less than 800 nucleotides in length, or less than 700 nucleotides in length, or less than 600 nucleotides in length, or less than 500 nucleotides in length, or less than 450 nucleotides in length, or less than 400 nucleotides in length.

Recipient genomic loci that encode variable immunoglobulin segments can vary in sequence. However, any human cell can be modified using the universal cut sites and homology regions described herein. The methods described herein can also include analysis (sequencing) of recipient genomic variable DNA sequences, for example, to select desirable sites for modification. The methods can also include analysis (sequencing) of recipient genomic variable DNA sequences, for example, to select other regions for homologous recombination, and/or to identify other recognition sites for guide RNAs.

The recipient nucleic acids can have one or two recipient 'homology' regions of sequence identity or complementarity. The donor nucleic acids can also include similar 'homology' regions of sequence identity or complementarity. Such regions of sequence identity or complementarity can, for example, provide sites for homologous recombination with the donor nucleic acids. Regions of sequence identity or complementarity can abut or flank a region of sequence divergence within the recipient nucleic acids, where the sequence diverges from a region of the donor nucleic acid sequence. The regions of sequence identity or complementarity (homology regions) can be near or can include regions near a 5' nuclease cut site (V7-81 or V3-74 5' UTR) and a 3' cut site (the intron after J6), as these regions would be universally present in all B cells.

The recipient region of sequence divergence is replaced by a segment of the donor nucleic acid. Recipient nucleic acid sequences can include heavy chain, lambda chain (depicted in FIG. 1A) or kappa chain.

Recipient immunoglobulin nucleic acid segments can in some cases include, portions or variant sequences relating to the immunoglobulin sequences. Table 2 (SEQ ID NOs:1-40) provide sequences of recipient nucleic acids developed for experimental purposes that may not be found in primary B cells or in B cell lines used in the methods described herein. However, short segments of sequence homology between the SEQ ID NO:1-40 sequences and immunoglobulin sequences in B cells or B cell lines may be present. Such short segments may be less than 500 nucleotides in length, or less than 400 nucleotides in length, or less than 300 nucleotides in length, or less than 200 nucleotides in length, or less than 150 nucleotides in length, or less than 100 nucleotides in length, or less than 90 nucleotides in length, or less than 80 nucleotides in length, or less than 70 nucleotides in length, or less than 60 nucleotides in length, or less than 50 nucleotides in length, or less than 40 nucleotides in length, or less than 30 nucleotides in length.

For example, such short chromosomal segments of primary B cell or B cell lines sequences may have at least 30%, or at least 35%, or at least 40%, or least 45%, or at least 50%,at least 55%, or at least 60%, or at least 65%, or least 70%, or at least 75%, or at least 80%, or at least 85%, or at least 90%, or at least 95%, or at least 97%, or at least 98%, or at least 99%, or at least 99.5% sequence identity to any of SEQ ID NO:1-40, 41, 48, 53, or 60.

Donor (Replacement) Nucleic Acids

Donor nucleic acids are nucleic acid segments that have regions of sequence similarity (sequence identity or complementarity) and regions of sequence divergence compared to the recipient nucleic acids. For example, the donor nucleic acids can have one or two donor regions of sequence identity or complementarity compared to the recipient nucleic acids and that can abut or flank a region of sequence divergence. Such regions of sequence identity or complementarity provide sites for homologous recombination with the recipient nucleic acids. The donor region of sequence divergence replaces a segment of the recipient nucleic acid.

Donor regions of sequence identity or complementarity can be at least about 15, or at least about 16, or at least about 17, or at least about 18, or at least about 19, or at least about 20, or at least about 21, or at least about 22, or at least about 23, or at least about 24, or at least about 25 nucleotides in length. Donor regions of sequence identity or complementarity can be quite long. For example, donor regions of sequence identity or complementarity can be longer or shorter than 5000 nucleotides in length, or longer or shorter than 4000 nucleotides in length, or longer or shorter than 3000 nucleotides in length, or longer or shorter than 2000 nucleotides in length, or longer or shorter than 1000 nucleotides in length.

Donor regions of sequence identity or complementarity have at least 95%, or at least 96%, or at least 97%, or at least 98%, or at least 99%, or at least 99.5% sequence identity or complementarity to regions of recipient nucleic acids (e.g., any of SEQ ID NO: 1-40, 41, 48, 53, or 60).

Regions of sequence divergence have at least one, or at least two, or at least three, at least four, or at least five, or at least six, or at least ten, or at least twelve, or at least fifteen, or at least eighteen, or at least twenty, or at least twenty-four, or at least twenty-seven, or at least thirty, or at least thirty-three, or at least forty, or at least fifty, or at least sixty, or at least sixty-three, at least seventy nucleotide differences compared to a recipient nucleic acid (e.g., any of SEQ ID NO: 1-40, 41, 48, 53, or 60).

In some cases, donor regions of sequence divergence are less than 5000 nucleotides in length, or less than 4000 nucleotides in length, or less than 3000 nucleotides in length, or less than 2000 nucleotides in length, or less than 1500 nucleotides in length, or less than 1000 nucleotides in length, or less than 900 nucleotides in length, or less than 800 nucleotides in length, or less than 700 nucleotides in length, or less than 600 nucleotides in length, or less than 500 nucleotides in length, or less than 450 nucleotides in length, or less than 400 nucleotides in length.

Modification of Recipient Genomic Loci

There are two types of DNA editing that are referred to as non-homologous end joining (NHEJ) and homology directed repair (HDR). NHEJ causes deletions and insertions of the DNA, due to the endogenous repair process that occurs after a DNA site has been cleaved either via a double stranded break, or via DNA nicking. In HDR, the repair involves a template (e.g., donor) DNA that shares homology to the parental (e.g., target or recipient) DNA, and a substitution, deletion, or insertion is made in the parental (target or recipient) DNA of one or more nucleotides after a cleavage by a site directed nuclease. NHEJ generally occurs more frequently than HDR.

In some cases, natural (endogenous) promoter regions are not modified, thereby allowing expression of an encoded operably linked modified immunoglobulin to be under (natural) endogenous control.

Both NHEJ and HDR can be used for editing or modification of a genomic immunoglobulin allele, and this invention covers both NHEJ and HDR. However, the methods described herein typically involve HDR.

Nuclease-gRNA Systems

A variety of nuclease-gRNAs can be employed to modify the immunoglobulin loci as described herein. Nuclease-gRNAs form complexes where each gRNA guides its complex to bind to specific (target) nucleic acid segments, and the nuclease cuts the target site so that flanking target sequences can be modified.

A variety of nuclease enzymes can be employed. For example, clustered regularly interspaced short palindromic repeats (CRISPr)/Cas nucleases, Zinc Finger Nucleases. Transcription activator-like effector nucleases (TALENs) and Meganucleases can be employed. See Porteus M., Genome Editing: A New Approach to Human Therapeutics. *Annu Rev Pharmacol Toxicol* (2015).

By way of example, the CRISPr/Cas system is discussed below.

Hundreds of Cas proteins can be employed in the methods described herein. Three species that have been best characterized are provided as examples. The most commonly used Cas protein is a *Streptococcus pyogenes* Cas9, (SpCas9). More recently described forms of Cas include *Staphylococcus aureus* Cas9 (SaCas9) and *Francisella novicida* Cas2 (FnCas2, also called FnCpf1). Jinek et al., *Science* 337:816-21 (2012); Qi et al., *Cell* 152:1173-83 (2013); Ran et al., *Nature* 520:186-91 (2015); Zetsche et al., *Cell* 163:759-71 (2015).

One example of an amino acid sequence for *Streptococcus pyogenes* Cas9 (SpCas9) is provided below (SEQ ID NO:169).

```
  1  MDKKYSIGLD IGTNSVGWAV ITDEYKVPSK KFKVLGNTDR
 41  HSIKKNLIGA LLFDSGETAE ATRLKRTARR RYTRRKNRIC
 81  YLQEIFSNEM AKVDDSFFHR LEESFLVEED KKHERHPIFG
121  NIVDEVAYHE KYPTIYHLRK KLVDSTDKAD LRLIYLALAH
161  MIKFRGHFLI EGDLNPDNSD VDKLFIQLVQ TYNQLFEENP
201  INASGVDAKA ILSARLSKSR RLENLIAQLP GEKKNGLFGN
241  LIALSLGLTP NFKSNFDLAE DAKLQLSKDT YDDDLDNLLA
281  QIGDQYADLF LAAKNLSDAI LLSDILRVNT EITKAPLSAS
321  MIKRYDEHHQ DLTLLKALVR QQLPEKYKEI FFDQSKNGYA
361  GYIDGGASQE EFYKFIKPIL EKMDGTEELL VKLNREDLLR
401  KQRTFDNGSI PHQIHLGELH AILRRQEDFY PFLKDNREKI
441  EKILTFRIPY YVGPLARGNS RFAWMTRKSE ETITPWNFEE
481  VVDKGASAQS FIERMTNFDK NLPNEKVLPK HSLLYEYFTV
521  YNELTKVKYV TEGMRKPAFT SGEQKKAIVD LLFKTNRKVT
561  VKQLKEDYFK KIECFDSVEI SGVEDRFNAS LGTYHDLLKI
601  IKDKDFLDNE ENEDILEDIV LTLTLFEDRE MIEERLKTYA
641  HLFDDKVMKQ LKRRRYTGWG RLSRKLINGI RDKQSGKTIL
681  DFLKSDGFAN RNFMQLIHDD SLTFKEDIQK AQVSGQGDSL
721  HEHIANLAGS PAIKKGILQT VKVVDELVKV MGRHKPENIV
761  IEMARENQTT QKGQKNSRER MKRIEEGIKE LGSQILKEHP
801  VENTQLQNEK LYLYYLQNGR DMYVDQELDI NRLSDYDVDH
841  IVPQSFLKDD SIDNKVLTRS DKNRGKSDNV PSEEVVKKMK
881  NYWRQLLNAK LITQRKFDNL TKAERGGLSE LDKAGFIKRQ
921  LVETRQITKH VAQILDSRMN TKYDENDKLI REVKVITLKS
961  KLVSDFRKDF QFYKVREINN YHHAHDAYLN AVVGTALIKK
1001 YPKLESEFVY GDYKVYDVRK MIAKSEQEIG KATAKYFFYS
1041 NIMNFFKTEI TLANGEIRKR PLIETNGETG EIVWDKGRDF
1081 ATVRKVLSMP QVNIVKKTEV QTGGFSKESI LPKRNSDKLI
1121 ARKKDWDPKK YGGFDSPTVA YSVLVVAKVE KGKSKKLKSV
1161 KELLGITIME RSSFEKNPID FLEAKGYKEV KKDLIIKLPK
1201 YSLFELENGR KRMLASAGEL QKGNELALPS KYVNFLYLAS
1241 HYEKLKGSPE DNEQKQLFVE QHKHYLDEII EQISEFSKRV
1281 ILADANLDKV LSAYNKHRDK PIREQAENII HLFTLTNLGA
1321 PAAFKYFDTT IDRKRYTSTK EVLDATLIHQ SITGLYETRI
1361 DLSQLGGD
```

A cDNA that encodes the *Streptococcus pyogenes* Cas9 (SpCas9) is provided below (SEQ ID NO:170).

```
  1  GACAAGAAGT ACAGCATCGG CCTGGACATC GGCACCAACT
 41  CTGTGGGCTG GGCCGTGATC ACCGACGAGT ACAAGGTGCC
 81  CAGCAAGAAA TTCAAGGTGC TGGGCAACAC CGACCGGCAC
121  AGCATCAAGA AGAACCTGAT CGGAGCCCTG CTGTTCGACA
161  GCGGCGAAAC AGCCGAGGCC ACCCGGCTGA AGAGAACCGC
201  CAGAAGAAGA TACACCAGAC GGAAGAACCG GATCTGCTAT
```

```
241   CTGCAAGAGA TCTTCAGCAA CGAGATGGCC AAGGTGGACG
281   ACAGCTTCTT CCACAGACTG AAGAGTCCT TCCTGGTGGA
321   AGAGGATAAG AAGCACGAGC GGCACCCCAT CTTCGGCAAC
361   ATCGTGGACG AGGTGGCCTA CCACGAGAAG TACCCCACCA
401   TCTACCACCT GAGAAAGAAA CTGGTGGACA GCACCGACAA
441   GGCCGACCTG CGGCTGATCT ATCTGGCCCT GGCCCACATG
481   ATCAAGTTCC GGGGCCACTT CCTGATCGAG GGCGACCTGA
521   ACCCCGACAA CAGCGACGTG GACAAGCTGT TCATCCAGCT
561   GGTGCAGACC TACAACCAGC TGTTCGAGGA AAACCCCATC
601   AACGCCAGCG GCGTGGACGC CAAGGCCATC CTGTCTGCCA
641   GACTGAGCAA GAGCAGACGG CTGGAAAATC TGATCGCCCA
681   GCTGCCCGGC GAGAAGAAGA ATGGCCTGTT CGGAAACCTG
721   ATTGCCCTGA GCCTGGGCCT GACCCCCAAC TTCAAGAGCA
761   ACTTCGACCT GGCCGAGGAT GCCAAACTGC AGCTGAGCAA
801   GGACACCTAC GACGACGACC TGGACAACCT GCTGGCCCAG
841   ATCGGCGACC AGTACGCCGA CCTGTTTCTG GCCGCCAAGA
881   ACCTGTCCGA CGCCATCCTG CTGAGCGACA TCCTGAGAGT
921   GAACACCGAG ATCACCAAGG CCCCCCTGAG CGCCTCTATG
961   ATCAAGAGAT ACGACGAGCA CCACCAGGAC CTGACCCTGC
1001  TGAAAGCTCT CGTGCGGCAG CAGCTGCCTG AGAAGTACAA
1041  AGAGATTTTC TTCGACCAGA GCAAGAACGG CTACGCCGGC
1081  TACATTGACG GCGGAGCCAG CCAGGAAGAG TTCTACAAGT
1121  TCATCAAGCC CATCCTGGAA AAGATGGACG GCACCGAGGA
1161  ACTGCTCGTG AAGCTGAACA GAGAGGACCT GCTGCGGAAG
1201  CAGCGGACCT TCGACAACGG CAGCATCCCC CACCAGATCC
1241  ACCTGGGAGA GCTGCACGCC ATTCTGCGGC GGCAGGAAGA
1281  TTTTTACCCA TTCCTGAAGG ACAACCGGGA AAAGATCGAG
1321  AAGATCCTGA CCTTCCGCAT CCCCTACTAC GTGGGCCCTC
1361  TGGCCAGGGG AAACAGCAGA TTCGCCTGGA TGACCAGAAA
1401  GAGCGAGGAA ACCATCACCC CCTGGAACTT CGAGGAAGTG
1441  GTGGACAAGG GCGCTTCCGC CCAGAGCTTC ATCGAGCGGA
1481  TGACCAACTT CGATAAGAAC CTGCCCAACG AGAAGGTGCT
1521  GCCCAAGCAC AGCCTGCTGT ACGAGTACTT CACCGTGTAT
1561  AACGAGCTGA CCAAAGTGAA ATACGTGACC GAGGGAATGA
1601  GAAAGCCCGC CTTCCTGAGC GGCGAGCAGA AAAAGGCCAT
1641  CGTGGACCTG CTGTTCAAGA CCAACCGGAA AGTGACCGTG
1681  AAGCAGCTGA AAGAGGACTA CTTCAAGAAA ATCGAGTGCT
1721  TCGACTCCGT GGAAATCTCC GGCGTGGAAG ATCGGTTCAA
1761  CGCCTCCCTG GGCACATACC ACGATCTGCT GAAAATTATC
1801  AAGGACAAGG ACTTCCTGGA CAATGAGGAA ACGAGGACA
1841  TTCTGGAAGA TATCGTGCTG ACCCTGACAC TGTTTGAGGA
1881  CAGAGAGATG ATCGAGGAAC GGCTGAAAAC CTATGCCCAC
1921  CTGTTCGACG ACAAAGTGAT GAAGCAGCTG AAGCGGCGGA
1961  GATACACCGG CTGGGGCAGG CTGAGCCGGA AGCTGATCAA
2001  CGGCATCCGG GACAAGCAGT CCGGCAAGAC AATCCTGGAT
2041  TTCCTGAAGT CCGACGGCTT CGCCAACAGA AACTTCATGC
2081  AGCTGATCCA CGACGACAGC CTGACCTTTA AGAGGACAT
2121  CCAGAAAGCC CAGGTGTCCG GCCAGGGCGA TAGCCTGCAC
2161  GAGCACATTG CCAATCTGGC CGGCAGCCCC GCCATTAAGA
2201  AGGGCATCCT GCAGACAGTG AAGGTGGTGG ACGAGCTCGT
2241  GAAAGTGATG GGCCGGCACA AGCCCGAGAA CATCGTGATC
2281  GAAATGGCCA GAGAGAACCA GACCACCCAG AAGGGACAGA
2321  AGAACAGCCG CGAGAGAATG AAGCGGATCG AAGAGGGCAT
2361  CAAAGAGCTG GGCAGCCAGA TCCTGAAAGA ACACCCCGTG
2401  GAAAACACCC AGCTGCAGAA CGAGAAGCTG TACCTGTACT
2441  ACCTGCAGAA TGGGCGGGAT ATGTACGTGG ACCAGGAACT
2481  GGACATCAAC CGGCTGTCCG ACTACGATGT GGACCATATC
2521  GTGCCTCAGA GCTTTCTGAA GGACGACTCC ATCGACAACA
2561  AGGTGCTGAC CAGAAGCGAC AAGAACCGGG GCAAGAGCGA
2601  CAACGTGCCC TCCGAAGAGG TCGTGAAGAA GATGAAGAAC
2641  TACTGGCGGC AGCTGCTGAA CGCCAAGCTG ATTACCCAGA
2681  GAAAGTTCGA CAATCTGACC AAGGCCGAGA GAGGCGGCCT
2721  GAGCGAACTG GATAAGGCCG GCTTCATCAA GAGACAGCTG
2761  GTGGAAACCC GGCAGATCAC AAAGCACGTG GCACAGATCC
2801  TGGACTCCCG GATGAACACT AAGTACGACG AGAATGACAA
2841  GCTGATCCGG GAAGTGAAAG TGATCACCCT GAAGTCCAAG
2881  CTGGTGTCCG ATTTCCGGAA GGATTTCCAG TTTTACAAAG
2921  TGCGCGAGAT CAACAACTAC CACCACGCCC ACGACGCCTA
2961  CCTGAACGCC GTCGTGGGAA CCGCCCTGAT CAAAAAGTAC
3001  CCTAAGCTGG AAAGCGAGTT CGTGTACGGC GACTACAAGG
3041  TGTACGACGT GCGGAAGATG ATCGCCAAGA GCGAGCAGGA
3081  AATCGGCAAG GCTACCGCCA AGTACTTCTT CTACAGCAAC
3121  ATCATGAACT TTTTCAAGAC CGAGATTACC CTGGCCAACG
3161  GCGAGATCCG GAAGCGGCCT CTGATCGAGA CAAACGGCGA
3201  AACCGGGGAG ATCGTGTGGG ATAAGGGCCG GGATTTTGCC
3241  ACCGTGCGGA AAGTGCTGAG CATGCCCCAA GTGAATATCG
3281  TGAAAAAGAC CGAGGTGCAG ACAGGCGGCT TCAGCAAAGA
3321  GTCTATCCTG CCCAAGAGGA ACAGCGATAA GCTGATCGCC
3361  AGAAAGAAGG ACTGGGACCC TAAGAAGTAC GGCGGCTTCG
3401  ACAGCCCCAC CGTGGCCTAT TCTGTGCTGG TGGTGGCCAA
3441  AGTGGAAAAG GGCAAGTCCA AGAAACTGAA GAGTGTGAAA
```

-continued

```
3481 GAGCTGCTGG GGATCACCAT CATGGAAAGA AGCAGCTTCG
3521 AGAAGAATCC CATCGACTTT CTGGAAGCCA AGGGCTACAA
3561 AGAAGTGAAA AAGGACCTGA TCATCAAGCT GCCTAAGTAC
3601 TCCCTGTTCG AGCTGGAAAA CGGCCGGAAG AGAATGCTGG
3641 CCTCTGCCGG CGAACTGCAG AAGGGAAACG AACTGGCCCT
3681 GCCCTCCAAA TATGTGAACT TCCTGTACCT GGCCAGCCAC
3721 TATGAGAAGC TGAAGGGCTC CCCCGAGGAT AATGAGGAGA
3761 AACAGCTGTT TGTGGAACAG CACAAGCACT ACCTGGACGA
3801 GATCATCGAG CAGATCAGCG AGTTCTCCAA GAGAGTGATC
3841 CTGGCCGACG CTAATCTGGA CAAAGTGCTG TCCGCCTACA
3881 ACAAGCACCG GGATAAGCCC ATCAGAGAGC AGGCCGAGAA
3921 TATCATCCAC CTGTTTACCC TGACCAATCT GGGAGCCCCT
3961 GCCGCCTTCA AGTACTTTGA CACCACCATC GACCGGAAGA
4001 GGTACACCAG CACCAAAGAG GTGCTGGACG CCACCCTGAT
4041 CCACCAGAGC ATCACCGGCC TGTACGAGAC ACGGATCGAC
4081 CTGTCTCAGC TGGGAGGCGA C
```

An amino acid sequence of a *Streptococcus pyogenes* Cas9 variant with D10A and H840A mutations is provided below (SEQ ID NO: 171). Note that the positions of these mutations can vary by about-1-5 nucleotides.

```
  1 MDKKYSIGLA IGTNSVGWAV ITDEYKVPSK KFKVLGNTDR
 41 HSIKKNLIGA LLFDSGETAE ATRLKRTARR RYTRRKNRIC
 81 YLQEIFSNEM AKVDDSFFHR LEESFLVEED KKHERHPIFG
121 NIVDEVAYHE KYPTIYHLRK KLVDSTDKAD LRLIYLALAH
161 MIKFRGHFLI EGDLNPDNSD VDKLFIQLVQ TYNQLFEENP
201 INASGVDAKA ILSARLSKSR RLENLIAQLP GEKKNGLFGN
241 LIALSLGLTP NFKSNFDLAE DAKLQLSKDT YDDDLDNLLA
281 QIGDQYADLF LAAKNLSDAI LLSDILRVNT EITKAPLSAS
321 MIKRYDEHHQ DLTLLKALVR QQLPEKYKEI FFDQSKNGYA
361 GYIDGGASQE EFYKFIKPIL EKMDGTEELL VKLNREDLLR
401 KQRTFDNGSI PHQIHLGELH AILRRQEDFY PFLKDNREKI
441 EKILTFRIPY YVGPLARGNS RFAWMTRKSE ETITPWNFEE
481 VVDKGASAQS FIERMTNFDK NLPNEKVLPK HSLLYEYFTV
521 YNELTKVKYV TEGMRKPAFL SGEQKKAIVD LLFKTNRKVT
561 VKQLKEDYFK KIECFDSVEI SGVEDRFNAS LGTYHDLLKI
601 IKDKDFLDNE ENEDILEDIV LTLTLFEDRE MIEERLKTYA
641 HLFDDKVMKQ LKRRRYTGWG RLSRKLINGI RDKQSGKTIL
681 DFLKSDGFAN RNFMQLIHDD SLTFKEDIQK AQVSGQGDSL
721 HEHIANLAGS PAIKKGILQT VKVVDELVKV MGRHKPENIV
761 IEMARENQTT QKGQKNSRER MKRIEEGIKE LGSQILKEHP
801 VENTQLQNEK LYLYYLQNGR DMYVDQELDI NRLSDYDVDA
```

-continued

```
 841 IVPQSFLKDD SIDNKVLTRS DKNRGKSDNV PSEEVVKKMK
 881 NYWRQLLNAK LITQRKFDNL TKAERGGLSE LDKAGFIKRQ
 921 LVETRQITKH VAQILDSRMN TKYDENDKLI REVKVITLKS
 961 KLVSDFRKDF QFYKVREINN YHHAHDAYLN AVVGTALIKK
1001 YPKLESEFVY GDYKVYDVRK MIAKSEQEIG KATAKYFFYS
1041 NIMNFFKTEI TLANGEIRKR PLIETNGETG EIVWDKGRDF
1081 ATVRKVLSMP QVNIVKKTEV QTGGFSKESI LPKRNSDKLI
1121 ARKKDWDPKK YGGFDSPTVA YSVLVVAKVE KGKSKKLKSV
1161 KELLGITIME RSSFEKNPID FLEAKGYKEV KKDLIIKLPK
1201 YSLFELENGR KRMLASAGEL QKGNELALPS KYVNFLYLAS
1241 HYEKLKGSPE DNEQKQLFVE QHKHYLDEII EQISEFSKRV
1281 ILADANLDKV LSAYNKHRDK PIREQAENII HLFTLTNLGA
1321 PAAFKYFDTT IDRKRYTSTK EVLDATLIHQ SITGLYETRI
1361 DLSQLGGDEG ADPKKKRKVD PKKKRKVDPK KKRKV
```

A cDNA that encodes the *Staphylococcus aureus* Cas9 (SaCas9) is provided below (SEQ ID NO:172).

```
   1 AAGCGGAACT ACATCCTGGG CCTGGACATC GGCATCACCA
  41 GCGTGGGCTA CGGCATCATC GACTACGAGA CACGGGACGT
  81 GATCGATGCC GGCGTGCGGC TGTTCAAAGA GGCCAACGTG
 121 GAAAACAACG AGGGCAGGCG GAGCAAGAGA GGCGCCAGAA
 161 GGCTGAAGCG GCGGAGGCGG CATAGAATCC AGAGAGTGAA
 201 GAAGCTGCTG TTCGACTACA ACCTGCTGAC CGACCACAGC
 241 GAGCTGAGCG GCATCAACCC CTACGAGGCC AGAGTGAAGG
 281 GCCTGAGCCA AAAGCTGAGC GAGGAAGAGT TCTCTGCCGC
 321 CCTGCTGCAC CTGGCCAAGA GAAGAGGCGT GCACAACGTG
 361 AACGAGGTGG AAGAGGACAC CGGCAACGAG CTGTCCACCA
 401 AAGAGCAGAT CAGCCGGAAC AGCAAGGCCC TGGAAGAGAA
 441 ATACGTGGCC GAACTGCAGC TGGAACGGCT GAAGAAAGAC
 481 GGCGAAGTGC GGGGCAGCAT CAACAGATTC AAGACCAGCG
 521 ACTACGTGAA AGAAGCCAAA CAGCTGCTGA AGGTGCAGAA
 561 GGCCTACCAC CAGCTGGACC AGAGCTTCAT CGACACCTAC
 601 ATCGACCTGC TGGAAACCCG GCGGACCTAC TATGAGGGAC
 641 CTGGCGAGGG CAGCCCCTTC GGCTGGAAGG ACATCAAAGA
 681 ATGGTACGAG ATGCTGATGG CCACTGCAC CTACTTCCCC
 721 GAGGAACTGC GGAGCGTGAA GTACGCCTAC AACGCCGACC
 761 TGTACAACGC CCTGAACGAC CTGAACAATC TCGTGATCAC
 801 CAGGGACGAG AACGAGAAGC TGGAATATTA CGAGAAGTTC
 841 CAGATCATCG AGAACGTGTT CAAGCAGAAG AAGAAGCCCA
 881 CCCTGAAGCA GATCGCCAAA GAAATCCTCG TGAACGAAGA
 921 GGATATTAAG GGCTACAGAG TGACCAGCAC CGGCAAGCCC
```

-continued

```
 961 GAGTTCACCA ACCTGAAGGT GTACCACGAC ATCAAGGACA
1001 TTACCGCCCG GAAAGAGATT ATTGAGAACG CCGAGCTGCT
1041 GGATGAGATT GCCAAGATCC TGACCATCTA CCAGAGCAGC
1081 GAGGACATCC AGGAAGAACT GACCAATCTG AACTCCGAGC
1121 TGACCCAGGA AGAGATCGAG CAGATCTCTA ATCTGAAGGG
1161 CTATACCGGC ACCCACAACC TGAGCCTGAA GGCCATCAAC
1201 CTGATCCTGG ACGAGCTGTG GCACACCAAC GACAACCAGA
1241 TCGCTATCTT CAACCGGCTG AAGCTGGTGC CCAAGAAGGT
1281 GGACCTGTCC CAGCAGAAAG AGATCCCCAC CACCCTGGTG
1321 GACGACTTCA TCCTGAGCCC CGTCGTGAAG AGAAGCTTCA
1361 TCCAGAGCAT CAAAGTGATC AACGCCATCA TCAAGAAGTA
1401 CGGCCTGCCC AACGACATCA TTATCGAGCT GGCCCGCGAG
1441 AAGAACTCCA AGGACGCCCA GAAAATGATC AACGAGATGC
1481 AGAAGCGGAA CCGGCAGACC AACGAGCGGA TCGAGGAAAT
1521 CATCCGGACC ACCGGCAAAG AGAACGCCAA GTACCTGATC
1561 GAGAAGATCA AGCTGCACGA CATGCAGGAA GGCAAGTGCC
1601 TGTACAGCCT GGAAGCCATC CCTCTGGAAG ATCTGCTGAA
1641 CAACCCCTTC AACTATGAGG TGGACCACAT CATCCCCAGA
1681 AGCGTGTCCT TCGACAACAG CTTCAACAAC AAGGTGCTCG
1721 TGAAGCAGGA AGAAAACAGC AAGAAGGGCA ACCGGACCCC
1761 ATTCCAGTAC CTGAGCAGCA GCGACAGCAA GATCAGCTAG
1801 GAAACCTTCA AGAAGCACAT CCTGAATCTG GCCAAGGGCA
1841 AGGGCAGAAT CAGCAAGACC AAGAAAGAGT ATCTGCTGGA
1881 AGAACGGGAC ATCAACAGGT TCTCCGTGCA GAAAGACTTC
1921 ATCAACCGGA ACCTGGTGGA TACCAGATAC GCCACCAGAG
1961 GCCTGATGAA CCTGCTGCGG AGCTACTTCA GAGTGAACAA
2001 CCTGGACGTG AAAGTGAAGT CCATCAATGG CGGCTTCACC
2041 AGCTTTCTGC GGCGGAAGTG GAAGTTTAAG AAAGAGCGGA
2081 ACAAGGGGTA CAAGCACCAC GCCGAGGACG CCCTGATCAT
2121 TGCCAACGCC GATTTCATCT TCAAAGAGTG GAAGAAACTG
2161 GACAAGGCCA AAAAAGTGAT GGAAAACCAG ATGTTCGAGG
2201 AAAAGCAGGC CGAGAGCATG CCCGAGATCG AAACCGAGCA
2241 GGAGTACAAA GAGATCTTCA TCACCCCCCA CCAGATCAAG
2281 CACATTAAGG ACTTCAAGGA CTACAAGTAC AGCCACCGGG
2321 TGGACAAGAA GCCTAATAGA GAGCTGATTA ACGACACCCT
2361 GTACTCCACC CGGAAGGACG ACAAGGGCAA CACCCTGATC
2401 GTGAACAATC TGAACGGCCT GTACGACAAG GACAATGACA
2441 AGCTGAAAAA GCTGATCAAC AAGAGCCCCG AAAAGCTGCT
2481 GATGTACCAC CACGACCCCC AGACCTACCA GAAACTGAAG
2521 CTGATTATGG AACAGTACGG CGACGAGAAG AATCCCCTGT
```

-continued

```
2561 ACAAGTACTA CGAGGAAACC GGGAACTACC TGACCAAGTA
2601 CTCCAAAAAG GACAACGGCC CCGTGATCAA GAAGATTAAG
2641 TATTACGGCA ACAAACTGAA CGCCCATCTG GACATCACCG
2681 ACGACTACCC CAACAGCAGA AACAAGGTCG TGAAGCTGTC
2721 CCTGAAGCCC TACAGATTCG ACGTGTACCT GGACAATGGC
2761 GTGTACAAGT TCGTGACCGT GAAGAATCTG GATGTGATCA
2801 AAAAAGAAAA CTACTACGAA GTGAATAGCA AGTGCTATGA
2841 GGAAGCTAAG AAGCTGAAGA AGATCAGCAA CCAGGCCGAG
2881 TTTATCGCCT CCTTCTACAA CAACGATCTG ATCAAGATCA
2921 ACGGCGAGCT GTATAGAGTG ATCGGCGTGA ACAACGACCT
2961 GCTGAACCGG ATCGAAGTGA ACATGATCGA CATCACCTAC
3001 CGCGAGTACC TGGAAAACAT GAACGACAAG AGGCCCCCCA
3041 GGATCATTAA GACAATCGCC TCCAAGACCC AGAGCATTAA
3081 GAAGTACAGC ACAGACATTC TGGGCAACCT GTATGAAGTG
3121 AAATCTAAGA AGCACCCTCA GATCATCAAA AAGGGC
```

An amino acid sequence for a *Francisella novicida* Cas2 (FnCas2, also called FnCpf1) is shown below (SEQ ID NO: 173).

```
  1 MTQFEGFTNL YQVSKTLRFE LIPQGKTLKH IQEQGFIEED
 41 KARNDHYKEL KPIIDRIYKT YADQCLQLVQ LDWENLSAAI
 81 DSYRKEKTEE TRNALIEEQA TYRNAIHDYF IGRTDNLTDA
121 INKRHAEIYK GLFKAELFNG KVLKQLGTVT TTEHENALLR
161 SFDKFTTYFS GFYENRKNVE SAEDISTAIP HRIVQDNFPK
201 FKENCHIFTR LITAVPSLRE HFENVKKAIG IFVSTSIEEV
241 FSFPFYNQLL TQTQIDLYNQ LLGGISREAG TEKIKGLNEV
281 LNLAIQKNDE TAHIIASLPH REIPLFKQIL SDRNTLSFIL
321 EEFKSDEEVI QSFCKYKTLL RNENVLETAE ALFNELNSID
361 LTHIFISHKK LETISSALCD HWDTLRNALY ERRISELTGK
401 ITKSAKEKVQ RSLKHEDINL QEIISAAGKE LSEAFKQKTS
441 EILSHAHAAL DQPLPTTLKK QEEKEILKSQ LDSLLGLYHL
481 LDWFAVDESN EVDPEFSARL TGIKLEMEPS LSFYNKARNY
521 ATKKPYSVEK FKLNFQMPTL ASGWDVNKEK NNGAILFVKN
561 GLYYLGIMPK QKGRYKALSF EPTEKTSEGF DKMYYDYFPD
601 AAKMIPKCST QLKAVTAHFQ THTTPILLSN NFIEPLEITK
641 EIYDLNNPEK EPKKFQTAYA KKTGDQKGYR EALCKWIDFT
681 RDFLSKYTKT TSIDLSSLRP SSQYKDLGEY YAELNPLLYH
721 ISFQRIAEKE IMDAVETGKL YLFQIYNKDF AKGHHGKPNL
761 HTLYWTGLFS PENLAKTSIK LNGQAELFYR PKSRMKRMAH
801 RLGEKMLNKK LKDQKTPIPD TLYQELYDYV NHRLSHDLSD
841 EARALLPNVI TKEVSHEIIK DRRFTSDKFE FHVPITLNYQ
881 AANSPSKFNQ RVNAYLKEHP ETPIIGIDRG ERNEIYITVI
```

```
 921  DSTGKILEQR SLNTIQQFDY QKKLDNREKE RVAARQAWSV
 961  VGTIKDLKQG YLSQVIHEIV DLMIHYQAVV VLENLNFGFK
1001  SKRTGIAEKA VYQQFEKMLI DKLNCLVLKD YPAEKVGGVL
1041  NPYQLTDQFT SFAKMGTQSG FLFYVPAPYT SKIDPLTGFV
1081  DPFVWKTIKN HESRKHFLEG FDFLHYDVKT GDFILHFKMN
1121  RNLSFQRGLP GFMPAWDIVF EKNETQFDAK GTPFIAGKRI
1161  VPVIENHRFT GRYRDLYPAN ELIALLEEKG IVFRDGSNIL
1201  PKLLENDDSH AIDTMVALIR SVLQMRNSNA ATGEDYINSP
1241  VRDLNGVCFD SRFQNPEWPM DADANGAYHI ALKGQLLLNH
1281  LKESKDLKLQ NGISNQDWLA YIQELRN
```

A cDNA that encodes the foregoing *Francisella novicida* Cas2 (FnCas2, also called dFnCpf1) polypeptide is shown below (SEQ ID NO: 174).

```
   1  ATGACACAGT TCGAGGGCTT TACCAACCTG TATCAGGTGA
  41  GCAAGACACT GCGGTTTGAG CTGATCCCAC AGGGCAAGAC
  81  CCTGAAGCAC ATCCAGGAGC AGGGCTTCAT CGAGGAGGAC
 121  AAGGCCCGCA ATGATCACTA CAAGGAGCTG AAGCCCATCA
 161  TCGATCGGAT CTACAAGACC TATGCCGACC AGTGCCTGCA
 201  GCTGGTGCAG CTGGATTGGG AGAACCTGAG CGCCGCCATC
 241  GACTCCTATA GAAAGGAGAA AACCGAGGAG ACAAGGAACG
 281  CCCTGATCGA GGAGCAGGCC ACATATCGCA ATGCCATCCA
 321  CGACTACTTC ATCGGCCGGA CAGACAACCT GACCGATGCC
 361  ATCAATAAGA GACACGCCGA GATCTACAAG GGCCTGTTCA
 401  AGGCCGAGCT GTTTAATGGC AAGGTGCTGA AGCAGCTGGG
 441  CACCGTGACC ACAACCGAGC ACGAGAACGC CCTGCTGCGG
 481  AGCTTCGACA AGTTTACAAC CTACTTCTCC GGCTTTTATG
 521  AGAACAGGAA GAACGTGTTC AGCGCCGAGG ATATCAGCAC
 561  AGCCATCCCA CACCGCATCG TGCAGGACAA CTTCCCCAAG
 601  TTTAAGGAGA ATTGTCACAT CTTCACACGC CTGATCACCG
 641  CCGTGCCCAG CCTGCGGGAG CACTTTGAGA ACGTGAAGAA
 681  GGCCATCGGC ATCTTCGTGA GCACCTCCAT CGAGGAGGTG
 721  TTTTCCTTCC CTTTTTATAA CCAGCTGCTG ACACAGACCC
 761  AGATCGACCT GTATAACCAG CTGCTGGGAG GAATCTCTCG
 801  GGAGGCAGGC ACCGAGAAGA TCAAGGGCCT GAACGAGGTG
 841  CTGAATCTGG CCATCCAGAA GAATGATGAG ACAGCCCACA
 881  TCATCGCCTC CCTGCCACAC AGATTCATCC CCCTGTTTAA
 921  GCAGATCCTG TCCGATAGGA CACCCTGTC TTTCATCCTG
 961  GAGGAGTTTA AGAGCGACGA GGAAGTGATC CAGTCCTTCT
1001  GCAAGTACAA GACACTGCTG AGAAACGAGA ACGTGCTGGA
1041  GACAGCCGAG GCCCTGTTTA ACGAGCTGAA CAGCATCGAC
1081  CTGACACACA TCTTCATCAG CCACAAGAAG CTGGAGACAA
1121  TCAGCAGCGC CCTGTGCGAC CACTGGGATA CACTGAGGAA
1161  TGCCCTGTAT GAGCGGAGAA TCTCCGAGCT GACAGGCAAG
1201  ATCACCAAGT CTGCCAAGGA GAAGGTGCAG CGCAGCCTGA
1241  AGCACGAGGA TATCAACCTG CAGGAGATCA TCTCTGCCGC
1281  AGGCAAGGAG CTGAGCGAGG CCTTCAAGCA GAAAACCAGC
1321  GAGATCCTGT CCCACGCACA CGCCGCCCTG GATCAGCCAC
1361  TGCCTACAAC CCTGAAGAAG CAGGAGGAGA AGGAGATCCT
1401  GAAGTCTCAG CTGGACAGCC TGCTGGGCCT GTACCACCTG
1441  CTGGACTGGT TTGCCGTGGA TGAGTCCAAC GAGGTGGACC
1481  CCGAGTTCTC TGCCCGGCTG ACCGGCATCA AGCTGGAGAT
1521  GGAGCCTTCT CTGAGCTTCT ACAACAAGGC CAGAAATTAT
1561  GCCACCAAGA AGCCCTACTC CGTGGAGAAG TTCAAGCTGA
1601  ACTTTCAGAT GCCTACACTG GCCTCTGGCT GGGACGTGAA
1641  TAAGGAGAAG AACAATGGCC CCATCCTGTT TGTGAAGAAC
1681  GGCCTGTACT ATCTGGGCAT CATGCCAAAG CAGAAGGGCA
1721  GGTATAAGGC CCTGAGCTTC GAGCCCACAG AGAAAACCAG
1761  CGAGGGCTTT GATAAGATGT ACTATGACTA CTTCCCTGAT
1801  GCCGCCAAGA TGATCCCAAA GTGCAGCACC CAGCTGAAGG
1841  CCGTGACAGC CCACTTTCAG ACCCACACAA CCCCCATCCT
1881  GCTGTCCAAC AATTTCATCG AGCCTCTGGA GATCACAAAG
1921  GAGATCTACG ACCTGAACAA TCCTGAGAAG GAGCCAAAGA
1961  AGTTTCAGAC AGCCTACGCC AAGAAAACCG GCGACCAGAA
2001  GGGCTACAGA GAGGCCCGT GCAAGTGGAT CGACTTCACA
2041  AGGGATTTTC TGTCCAAGTA TACCAAGACA CCTCTATCG
2081  ATCTGTCTAG CCTGCGGCCA TCCTCTCAGT ATAAGGACCT
2121  GGGCGAGTAC TATGCCGAGC TGAATCCCCT GCTGTACCAC
2161  ATCAGCTTCC AGAGAATCGC CGAGAAGGAG ATCATGGATG
2201  CCGTGGAGAC AGGCAAGCTG TACCTGTTCC AGATCTATAA
2241  CAAGGACTTT GCCAAGGGCC ACCACGGCAA GCCTAATCTG
2281  CACACACTGT ATTGGACCGG CCTGTTTTCT CCAGAGAACC
2321  TGGCCAAGAC AAGCATCAAG CTGAATGGCC AGGCCGAGCT
2361  GTTCTACCGC CCTAAGTCCA GGATGAAGAG GATGGCACAC
2401  CGGCTGGGAG AGAAGATGCT GAACAAGAAG CTGAAGGATC
2441  AGAAAACCCC AATCCCCGAC ACCCTGTACC AGGAGCTGTA
2481  CGACTATGTG AATCACAGAC TGTCCCACGA CCTGTCTGAT
2521  GAGGCCAGGG CCCTGCTGCC AACGTGATC ACCAAGGAGG
2561  TGTCTCACGA GATCATCAAG GATAGGCGCT TTACCAGCGA
2601  CAAGTTCTTT TTCCACGTGC CTATCACACT GAACTATCAG
2641  GCCGCCAATT CCCCATCTAA GTTCAACCAG AGGGTGAATG
2681  CCTACCTGAA GGAGCACCCC GAGACACCTA TCATCGGCAT
```

```
2721  CGATCGGGGC GAGAGAAACC TGATCTATAT CACAGTGATC
2761  GCCTCCACCG GCAAGATCCT GGAGCAGCGG AGCCTGAACA
2801  CCATCCAGCA GTTTGATTAC CAGAAGAAGC TGGACAACAG
2841  GGAGAAGGAG AGGGTGGCAG CAAGGCAGGC CTGGTCTGTG
2881  GTGGGCACAA TCAAGGATCT GAAGCAGGGC TATCTGAGCC
2921  AGGTCATCCA CGAGATCGTG GACCTGATGA TCCACTACCA
2961  GGCCGTGGTG GTGCTGGAGA ACCTGAATTT CGGCTTTAAG
3001  AGOAAGAGGA CCGGCATCGC CGCGAAGGCC GTGTACCAGC
3041  AGTTCGAGAA GATGCTGATC GATAAGCTGA ATTGCCTGGT
3081  GCTGAAGGAC TATCCAGCAG AGAAAGTGGG AGGCGTGCTG
3121  AACCCATACC AGCTGACAGA CCAGTTCACC TCCTTTGCCA
3161  AGATGGGCAC CCAGTCTGGC TTCCTGTTTT ACGTGCCTGC
3201  CCCATATACA TCTAAGATCG ATCCCCTGAC CGGCTTCGTG
3241  GACCCCTTCG TGTGGAAAAC CATCAAGAAT CACGAGAGCC
3281  GCAAGCACTT CCTGGAGGGC TTCGACTTTC TGCACTACGA
3321  CGTGAAAACC GGCGACTTCA TCCTGCACTT TAAGATGAAC
3361  AGAAATCTGT CCTTCCAGAG GGGCCTGCCC GGCTTTATGC
3401  CTGCATGGGA TATCGTGTTC GAGAAGAACG AGACACAGTT
3441  TGACGCCAAG GGCACCCCTT TCATCGCCGG CAAGAGAATC
3481  GTGCCAGTGA TCGAGAATCA CAGATTCACC GGCAGATACC
3521  GGGACCTGTA TCCTGCCAAC GAGCTGATCG CCCTGCTGGA
3561  GGAGAAGGGC ATCGTGTTCA GGGATGGCTC CAACATCCTG
3601  CCAAAGCTGC TGGAGAATGA CGATTCTCAC GCCATCGACA
3641  CCATGGTGGC CCTGATCCGC AGCGTGCTGC AGATGCGGAA
3681  CTCCAATGCC GCCACAGGCG AGGACTATAT CAACAGCCCC
3721  GTGCGCGATC TGAATGGCGT GTGCTTCGAC TCCCGGTTTC
3761  AGAACCCAGA GTGGCCCATG GACGCCGATG CCAATGGCGC
3801  CTACCACATC GCCCTGAAGG GCCAGCTGCT GCTGAATCAC
3841  CTGAAGGAGA GCAAGGATCT GAAGCTGCAG AACGGCATCT
3881  CCAATCAGGA CTGGCTGGCC TACATCCAGG AGCTGCGCAA
3921  C
```

An amino acid sequence for variant FnCas2 (also known as dFnCpf1), has mutations at about position 917 (e.g., D917A) and/or at about position 1006 (e.g., E1006A). See Zetsche et al., Cell 163:759-71 (2015). This sequence is shown below as SEQ ID NO: 175. Note that the positions of these mutations can vary by about 1-5 nucleotides.

```
  1  MTQFEGFTNL YQVSKTLRFE LIPQGRTLRH IQEQGFIEED
 41  KARNDHYKEL KPIIDRIYRT YADQCLQLVQ LDWENLSAAI
 81  DSYRKEKTEE TRNALIEEQA TYRNAIHDYF IGRTDNLTDA
121  INKRHAEIYK GLFKAELFNG KVLKQLGTVT TTEHENALLR
161  SFDKFTTYFS GFYENRKNVE SAEDISTAIP HRIVQDNFPR
201  FRENCHIFTR LITAVPSLRE HFENVRKAIG IFVSTSIEEV
241  FSFPFYNQLL TQTQIDLYNQ LLGGISREAG TERIRGLNEV
281  LNLAIQKNDE TAHIIASLPH RFIPLFKQIL SDRNTLSFIL
321  EEFKSDEEVI QSFCRYRTLL RNENVLETAE ALFNELNSID
361  LTHIFISHRR LETISSALCD HWDTLRNALY ERRISELTGR
401  ITKSAKEKVQ RSLRHEDINL QEIISAAGRE LSEAFRQRTS
441  EILSHAHAAL DQPLPTTLKK QEEREILRSQ LDSLLGLYHL
481  LDWFAVDESN EVDPEFSARL TGIKLEMEPS LSFYNKARNY
521  ATRRPYSVER FKLNFQMPTL ASGWDVNKEK NNGAILFVKN
561  GLYYLGIMPR QRGRYRALSF EPTERTSEGF DRMYYDYFPD
601  AAKMIPKCST QLKAVTAHFQ THTTPILLSN NFIEPLEITR
641  EIYDLNNPER EPRRFQTAYA KKTGDQKGYR EALCKWIDFT
681  RDFLSRYTRT TSIDLSSLRP SSQYRDLGEY YAELNPLLYH
721  ISFQRIAEKE IMDAVETGRL YLFQIYNRDF AKGHHGKPNL
761  HTLYWTGLFS PENLAKTSIK LNGQAELFYR PKSRMKRMAH
801  RLGEKMLNKK LKDQKTPIPD TLYQELYDYV NHRLSHDLSD
841  EARALLPNVI TKEVSHEIIK DRRFTSDRFF FHVPITLNYQ
881  AANSPSKFNQ RVNAYLREHP ETPIIGIDRG ERNLIYITVI
921  ASTGKILEQR SLNTIQQFDY QRRLDNRERE RVAARQAWSV
961  VGTIKDLKQG YLSQVIHEIV DLMIHYQAVV VLENLNFGEK
1001 SKRTGIAAKA VYQQFEKMLI DRLNCLVLRD YPAERVGGVL
1041 NPYQLTDQFT SFARMGTQSG FLFYVPAPYT SKIDPLTGFV
1081 DPFVWKTIKN HESRRHELEG FDFLHYDVKT GDFILHFKMN
1121 RNLSFQRGLP GFMPAWDIVF EKNETQFDAK GTPFIAGKRI
1161 VPVIENHRFT GRYRDLYPAN ELIALLEERG IVFRDGSNIL
1201 PRLLENDDSH AIDTMVALIR SVLQMRNSNA ATGEDYINSP
1241 VRDLNGVCFD SRFQNPEWPM DADANGAYHI ALRGQLLLNH
1281 LKESKDLKLQ NGISNQDWLA YIQELRN
```

As used herein Cas refers to all members of the Cas family that have the nuclease active (Cas). In some cases, variants of a family of de-activated Cas proteins (dCas) may be employed. There are dozens Cas and dCas proteins from various species and any of these Cas and dCas proteins can be used in the compositions and methods described herein.

Guide RNAs (gRNAs)

Different guide RNAs (gRNAs) form complexes with different nuclease proteins. By way of example, Cas-type gRNAs are discussed below.

The three species Cas (*Streptococcus pyogenes*, *Staphylococcus aureus*, and *Francisella novicida*) utilize completely different types of gRNA and PAM sites. Because the gRNAs have different hairpin structures the gRNAs for one type of Cas protein will not bind to another type of Cas protein. Therefore the gRNAs for SpCas9 do not bind to SaCas9, or FnCas2. Similarly the SaCas9, and FnCas2 gRNAs do not bind to each other or to SpCas9. The unique gRNAs make it possible to target a Cas to a first target DNA site to make a first modification while targeting another Cas enzyme that uses a different gRNA to a second target DNA site without interfering with the targeted modification of the first target site.

The Cas system can recognize any sequence in the genome that matches 20 bases of the gRNA. However, each gRNA must also be adjacent to a "Protospacer Adjacent Motif" (PAM) which is invariant for each type of Cas protein, because the PAM binds directly to the Cas protein. See Doudna et al., Science 346(6213): 1077, 1258096 (2014); and Jinek et al., Science 337:816-21 (2012). Hence, the guide RNAs used for dCas-shielding will have a sequence adjacent to a PAM site that is bound by the dCas protein.

When the Cas system was first described for Cas9, with a "NGG" PAM site, the PAM was somewhat limiting in that it required a GG in the right orientation to the site to be targeted. Different Cas9 species have now been described with different PAM sites. See Jinek et al., Science 337:816-21 (2012); Ran et al., Nature 520:186-91 (2015); and Zetsche et al., Cell 163:759-71 (2015). In addition, mutations in the PAM recognition domain (Table 1) have increased the diversity of PAM sites for SpCas9 and SaCas9. See Kleinstiver et al., Nat Biotechnol 33:1293-1298 (2015); and Kleinstiver et al., Nature 523:481-5 (2015).

Table 1 summarizes information about PAM sites.

TABLE 1

| PAM sites | |
|---|---|
| | PAM sites |
| SpCas9 | NGG |
| SpCas9 VRER variant | NGCG |
| SpCas9 EQR variant | NGAG |
| SpCas9 VQR variant | NGAN or NGNG |
| SaCas9 | NNGRRT |
| SaCas9, KKH variant | NNNRRT |
| FnCas2 (Cpf1) | TTN |

DNA annotations:
N = A, C, T or G
R = Purine, A or G

Note that the guide RNA for SpCas9, and SaCas9 covers 20 bases in the 5'direction of the PAM site, while for FnCas2 (Cpf1) the guide RNA covers 20 bases to 3' of the PAM.

It is now clear that the PAM sites available for Cas are diverse, so that virtually any part of the genome can be protected. The PAM site for the gRNA should be selected so that the Cas gRNA complex properly targets the selected site for protection. Similarly, the PAM site for the Cas nuclease gRNA should target the editing site. Hence, the PAM site for a first Cas-gRNA can be different from the PAM site for a second Cas-gRNA.

The Figures and Examples provide examples of gRNA sequences for various genomic DNA sites.

RNA-Protein Complex Delivery.

The nucleases-gRNA complex can be delivered as RNA-protein complexes (RNPs), for example, where the RNPs are pre-assembled outside of the cell. These RNPs are quite stable. One advantage of RNP delivery of nuclease-gRNA complexes is that complex formation can readily be controlled ex vivo and the selected nuclease polypeptides can independently be complexed with selected guide RNA sequences so that the structure and compositions of the desired complexes is known with certainty.

For example, nuclease-gRNA can be prepared by incubating the nuclease proteins with the selected gRNA using a molar excess of gRNA relative to protein (e.g., using about a 1:1.1 to 1: 1.4 protein to gRNA molar ratio). The buffer used during such incubation can include 20 mM HEPES (pH 7.5), 150 mM KCl, 1 mM $MgCl_2$, 10% glycerol and 1 mM TCEP. Incubation can be done at 37° C. for about 5 minutes to about 30 minutes (usually 10 minutes is sufficient).

To introduce the nuclease-gRNA complex into cells nucleofection can be employed. See Lin et al., Enhanced homology-directed human genome engineering by controlled timing of CRISPR/Cas9 delivery. For example, nucleofection reactions can involve mixing approximately $1 \times 10^4$ to $1 \times 10^7$ cells in about 10 µl to 40 µl of nucleofection reagent with about 5 s to 30 µl of nuclease-gRNA. In some instances about $2 \times 10^5$ cells are mixed with about 20 µl of nucleofection reagent and about 10 µl nuclease-gRNA. After electroporation, growth media is added and the cells are transferred to tissue culture plates for growth and evaluation. The nucleofection reagents and machines are available from Lonza (Allendale, NJ).

The B cells can be obtained from and delivered to a subject. Such a subject can be an animal such as a human, a domesticated animal, or a zoo animal. In some cases the B cells can be obtained from and delivered to a human subject or a laboratory animal. Examples of laboratory animals from whom the B cells can be obtained and/or to whom the B cells can be administered can include mice, rats, dogs, cats, goats, sheep, rabbits, and the like.

Other Delivery Routes

If nuclease-gRNA complex delivery is not feasible, there are other ways of deploying nuclease-gRNA. For example, different nuclease proteins and/or gRNAs can be expressed in a selected cell type. The nucleases and/or gRNAs can be introduced into a selected recipient cell (e.g., a primary B cell) in form of a nucleic acid molecule encoding the nucleases or gRNAs, for example, in expression cassettes or expression vectors.

The expression cassettes or expression vectors include promoter sequences that are operably linked to the nucleic acid segment encoding the guide RNAs, or nuclease proteins. Methods for ensuring expression of a functional guide RNA and/or nuclease polypeptide are available in the art. For example, the nucleic acid segments encoding the selected guide RNAs and/or nucleases can be present in a vector, such as for example a plasmid, cosmid, virus, bacteriophage or another vector available for genetic engineering. The coding sequences inserted in the vector can be synthesized by standard methods, or isolated from natural sources. The coding sequences may further be ligated to transcriptional regulatory elements, termination sequences, and/or to other amino acid encoding sequences. Such regulatory sequences are available to those skilled in the art and include, without being limiting, regulatory sequences ensuring the initiation of transcription, internal ribosomal entry sites (IRES) (Owens, Proc. Natl. Acad. Sci. USA 98 (2001), 1471-1476) and optionally regulatory elements ensuring termination of transcription and stabilization of the transcript. Non-limiting examples for regulatory elements ensuring the initiation of transcription comprise a translation initiation codon, transcriptional enhancers such as e.g. the SV40-enhancer, insulators and/or promoters, such as for example the cytomegalovirus (CMV) promoter, SV40-promoter, RSV-promoter (Rous sarcoma virus), the lacZ promoter, chicken beta-actin promoter, CAG-promoter (a combination of chicken beta-actin promoter and cytomegalovirus immediate-early enhancer), the gal10 promoter, human elongation factor 1α-promoter, AOX1 promoter, GAL 1 promoter CaM-kinase promoter, the lac, trp or tac promoter, the lacUV5 promoter, the *Autographa californica* multiple nuclear polyhedrosis virus (AcMNPV) polyhedral promoter, or a globin intron in mammalian and other animal cells. Non-limiting examples for regulatory elements ensuring transcription termination include the V40-poly-A site, the tk-poly-A site or the SV40, lacZ or AcMNPV polyhedral polyadenylation signals, which are to be included downstream of the nucleic acid sequence of the invention. Additional regulatory elements may include translational enhancers, Kozak sequences and intervening sequences flanked by donor and acceptor sites for RNA splicing. Moreover, elements such as origin of replication, drug resistance gene or regulators (as part of an inducible promoter) may also be included.

Activation-Induced Cytidine Deaminase

Activation-induced cytidine deaminase, also known as AICDA and AID, is a 24 kDa enzyme which in humans is encoded by the AICDA gene. The AID enzyme can create mutations in DNA by deamination of cytosine base to generate a uracil in the position of affected cytosine. The uracil is recognized as a thymine by the cell. In other words, it changes a C:G base pair into a U:G mismatch. Hence, a C:G is converted to a T:A base pair. During germinal center development of B lymphocytes, AID also generates other types of mutations, such as C:G to A:T.

AICDA gene expression can be induced by addition of cadmium chloride, by IL-4 ligation, by CD40 ligation, or a combination thereof. As illustrated herein AID expression was induced by CD40L and IL-4. CD40L and IL-4 can be obtained from Prospecbio (see websites at www.prospecbio.com/cd40_human and www.prospecbio.com/IL-4_Human_CHO).

An example of a human AID sequence (NCBI accession no. AB040431.1) is shown below as SEQ ID NO:176.

```
MDSLLMNRRK FLYQFKNVRW AKGRRETYLC YVVKRRDSAT

SFSLDFGYLR NKNGCHVELL FLRYISDWDL DPGRCYRVTW

FTSWSPCYDC ARHVADFLRG NPNLSLRIFT ARLYFCEDRK

AEPEGLRRLH RAGVQIAIMT FKDYFYCWNT FVENHERTFK

AWEGLHENSV RLSRQLRRIL LPLYEVDDLR DAFRTLGL
```

An example of a nucleotide sequence that encodes the SEQ ID NO: human AID sequence (accession no. AB040431.1) is shown below as SEQ ID NO:177.

```
   1  GAACCATCAT TAATTGAAGT GAGATTTTTC TGGCCTGAGA
  41  CTTGCAGGGA GGCAAGAAGA CACTCTGGAC ACCACTATGG
  81  ACAGCCTCTT GATGAACCGG AGGAAGTTTC TTTACCAATT
 121  CAAAAATGTC CGCTGGGCTA AGGGTCGGCG TGAGACCTAC
 161  CTGTGCTACG TAGTGAAGAG GCGTGACAGT GCTACATCCT
 201  TTTCACTGGA CTTTGGTTAT CTTCGCAATA AGAACGGCTG
 241  CCACGTGGAA TTGCTCTTCC TCCGCTACAT CTCGGACTGG
 281  GACCTAGACC CTGGCCGCTG CTACCGCGTC ACCTGGTTCA
 321  CCTCCTGGAG CCCCTGCTAC GACTGTGCCC GACATGTGGC
 361  CGACTTTCTG CGAGGGAACC CCAACCTCAG TCTGAGGATC
 401  TTCACCGCGC GCCTCTACTT CTGTGAGGAC CGCAAGGCTG
 441  AGCCCGAGGG GCTGCGGCGG CTGCACCGCG CCGGGGTGCA
 481  AATAGCCATC ATGACCTTCA AAGATTATTT TTACTGCTGG
 521  AATACTTTTG TAGAAACCA TGAAAGAACT TTCAAAGCCT
 561  GGGAAGGGCT GCATGAAAAT TCAGTTCGTC TCTCCAGACA
 601  GCTTCGGCGC ATCCTTTTGC CCCTGTATGA GGTTGATGAC
 641  TTACGAGACG CATTTCGTAC TTTGGGACTT TGATAGCAAC
 681  TTCCAGGAAT GTCACACACG ATGAAATATC TCTGCTGAAG
 721  ACAGTGGATA AAAACAGTC CTTCAAGTCT TCTCTGTTTT
 761  TATTCTTCAA CTCTCACTTT CTTAGAGTTT ACAGAAAAAA
 801  TATTTATATA CGACTCTTTA AAAAGATCTA TGTCTTGAAA
 841  ATAGAAGG AACACAGGTC TGGCCAGGGA CGTGCTGCAA
 881  TTGGTGCAGT TTTGAATGCA ACATTGTCCC CTACTGGGAA
 921  TAACAGAACT GCAGGACCTG GGAGCATCCT AAAGTGTCAA
 961  CGTTTTTCTA TGACTTTTAG GTAGGATGAG AGCAGAAGGT
1001  AGATCCTAAA AAGCATGGTG AGAGGATCAA ATGTTTTTAT
1041  ATCAACATCC TTTATTATTT GATTCATTTG AGTTAACAGT
1081  GGTGTTAGTG ATAGATTTTT CTATTCTTTT CCCTTGACGT
1121  TTACTTTCAA GTAACACAAA CTCTTCCATC AGGCCATGAT
1161  CTATAGGACC TCCTAATGAG AGTATCTGGG TGATTGTGAC
1201  CCCAAACCAT CTCTCCAAAG CATTAATATC CAATCATGCG
1241  CTGTATGTTT TAATCAGCAG AAGCATGTTT TTATGTTTGT
1281  ACAAAAGAAG ATTGTTATGG GTGGGGATGG AGGATATGAC
1321  CATGCATGGT CACCTTCAAG CTACTTTAAT AAAGGATCTT
1361  AAAATGGGCA GGAGGACTGT GAACAAGACA CCCTAATAAT
1401  GGGTTGATGT CTGAAGTAGC AAATCTTCTG GAAACGCAAA
1441  CTCTTTTAAG GAAGTCCCTA ATTTAGAAAC ACCCACAAAC
1481  TTCACATATC ATAATTAGCA AACAATTGGA AGGAAGTTGC
1521  TTGAATGTTG GGGAGAGGAA AATCTATTGG CTCTCGTGGG
1561  TCTCTTCATC TCAGAAATGC CAATCAGGTC AAGGTTTGCT
1601  ACATTTTGTA TGTGTGTGAT GCTTCTCCCA AAGGTATATT
1641  AACTATATAA GAGAGTTGTG ACAAAACAGA ATGATAAAGC
1681  TGCGAACCGT GGCACACGCT CATAGTTCTA GCTGCTTGGG
1721  AGGTTGAGGA GGGAGGATGG CTTGAACACA GGTGTTCAAG
1761  GCCAGCCTGG GCAACATAAC AAGATCCTGT CTCTCAAAAA
1801  AAAAAAAAAA AAAAAGAAAG AGAGAGGGCC GGGCGTGGTG
1841  GCTCACGCCT GTAATCCCAG CACTTTGGGA GGCCGAGCCG
1881  GGCGGATCAC CTGTGGTCAG GAGTTTGAGA CCAGCCTGGC
1921  CAACATGGCA AAACCCCGTC TGTACTCAAA ATGCAAAAAT
1961  TAGCCAGGCG TGGTAGCAGG CACCTGTAAT CCCAGCTACT
2001  TGGGAGGCTG AGGCAGGAGA ATCGCTTGAA CCCAGGAGGT
```

```
-continued
2041  GGAGGTTGCA GTAAGCTGAG ATCGTGCCGT TGCACTCCAG

2081  CCTGGGCGAC AAGAGCAAGA CTCTGTCTCA GAAAAAAAAA

2121  AAAAAAAGAG AGAGAGAGAG AAAGAGAACA ATATTTGGGA

2161  GAGAAGGATG GGGAAGCATT GCAAGGAAAT TGTGCTTTAT

2201  CCAACAAAAT GTAAGGAGCC AATAAGGGAT CCCTATTTGT

2241  CTCTTTTGGT GTCTATTTGT CCCTAACAAC TGTCTTTGAC

2281  AGTGAGAAAA ATATTCAGAA TAACCATATC CCTGTGCCGT

2321  TATTACCTAG CAACCCTTGC AATGAAGATG AGCAGATCCA

2361  CAGGAAAACT TGAATGCACA ACTGTCTTAT TTTAATCTTA

2401  TTGTACATAA GTTTGTAAAA GAGTTAAAAA TTGTTACTTC

2441  ATGTATTCAT TTATATTTTA TATTATTTTG CGTCTAATGA

2481  TTTTTTATTA ACATGATTTC CTTTTCTGAT ATATTGAAAT

2521  GGAGTCTCAA AGCTTCATAA ATTTATAACT TTAGAAATGA

2561  TTCTAATAAC AACGTATGTA ATTGTAACAT TGCAGTAATG

2601  GTGCTACGAA GCCATTTCTC TTGATTTTTA GTAAACTTTT

2641  ATGACAGCAA ATTTGCTTCT GGCTCACTTT CAATCAGTTA

2681  AATAAATGAT AAATAATTTT GGAAGCTGTG AAGATAAAAT

2741  ACCAAATAAA ATAATATAAA AGTGATTTAT ATGAAGTTAA

2761  AATAAAAAAT CAGTATGATG GAATAAACTT G
```

In some cases. B cells can be modified to express higher levels of the AID enzyme.

For example, the B cells can be transiently transfected with an expression cassette or expression vector that can express an AID enzyme during step (d) of a method described herein. In some cases, B cell lines can be used that can be induced to express higher levels of the AID enzyme (e.g., during step (d)) than the parental (unmodified) cells. In addition, B cell lines that can constitutively express the AID enzyme can also be used.

B cells can be transfected with an expression cassette or expression vector that includes a heterologous promoter operably linked to a nucleic acid segment that encodes an AID enzyme.

Immunoglobulin Properties

The modified or engineered immunoglobulins generated by the methods described herein can have various properties that are selected by the user. For example, the modified or engineered immunoglobulins generated by the methods described herein can have affinities of various antigens. When describing the strength of the antigen-immunoglobulin (antibody) complex, the affinity and avidity of the immunoglobulin (antibody) for an antigen can be evaluated.

Antibody affinity is typically described as a measure of the strength of interaction between an antigenic epitope and an antibody's antigen binding site. It can be defined by the same basic thermodynamic principles that govern any reversible biomolecular interaction:

$$K_A = \frac{[Ab-Ag]}{[Ab][Ag]}$$

• $K_A$ = affinity constant

• $[Ab]$ = molar concentration of unoccupied binding sites on the antibody

• $[Ag]$ = molar concentration of unoccupied binding sites on the antigen

• $[Ab-Ag]$ = molar concentration of the antibody–antigen complex

In other words, $K_A$ describes how much antibody-antigen complex exists at the point when equilibrium is reached. The time taken for this to occur depends on rate of diffusion and is similar for every antibody. However, high-affinity antibodies can bind a greater amount of antigen in a shorter period of time than low-affinity antibodies. $K_A$ can therefore vary widely for antibodies from below $10^5$ mol$^{-1}$ to above $10^{12}$ mol$^{-1}$, and can be influenced by factors including pH, temperature and buffer composition.

The affinity of a homogenous population of antibodies can be measured accurately because they are homogeneous and selective for a single epitope. Polyclonal antibodies are heterogeneous and will contain a mixture of antibodies of different affinities recognizing several epitopes —therefore only an average affinity can be determined.

The modified and/or engineered B cells described herein can have or can produce antibodies with affinity constant values of at least $10^6$ mol$^{-1}$, or at least $10^7$ mol$^{-1}$, or at least $10^8$ mol$^{-1}$, or at least $10^9$ mol$^{-1}$. In some cases, the modified and/or engineered B cells described herein can have or can produce antibodies with affinity constant values that may be less than $10^{13}$ mol$^{-1}$, or less than $10^{12}$ mol$^{-1}$. The methods described herein can improve or increase the affinity of immunoglobulins encoded at recipient loci so that the modified or engineered immunoglobulins neutralize pathogen infection.

Antibody avidity is a measure of the overall strength of an antibody-antigen complex.

It is dependent on three major parameters:
Affinity of the antibody for the epitope (see above)
Valency of both the antibody and antigen
Structural arrangement of the parts that interact All antibodies are multivalent e.g. IgG antibodies are bivalent while IgM antibodies are decavalent. The greater an immunoglobulin's valency (number of antigen binding sites), the greater the amount of antigen it can bind. Similarly, antigens can demonstrate multivalency because they can bind to more than one antibody. Multimeric interactions between an antibody and an antigen help their stabilization. A favorable structural arrangement of antibody and antigen can also lead to a more stable antibody-antigen complex.

The methods described herein can improve or increase the affinity and/or avidity of immunoglobulins encoded at recipient loci. Hence, the modified or engineered immunoglobulins expressed by the modified/engineered loci have higher affinity and/or higher avidity than the original unmodified immunoglobulins encoded by the unmodified loci.

Such immunoglobulins or antibodies can be collected from antibody producing cells and used in vitro or in vivo for a variety of purposes.

Administration

The B cells can be obtained from and delivered to a subject. Such a subject can be an animal such as a human, a domesticated animal, or a zoo animal. In some cases the B cells can be obtained from and delivered to a human subject or a laboratory animal. Examples of laboratory animals from whom the B cells can be obtained and/or to whom the B cells can be administered can include mice, rats, dogs, cats, goats, sheep, rabbits, and the like.

Similarly, antibodies produced by modified or engineered antibody producing cells can also be administered to a subject.

Modified or engineered B cells generated as described herein can be administered to subjects. Such subjects can be in need of such B cells, for example, because the subjects have been infected with a virus or other pathogen, because the subjects' immune system is compromised, or because the health of the subjects would be improved by supplementation with the modified or engineered B cells. The cells are administered in a manner that permits them to graft or migrate to a tissue site and to reconstitute or regenerate immune function.

Devices are available that can be adapted for administering cells.

An immunogen (e.g., an antigenic polypeptide, antigenic peptidoglycan, or antigenic polysaccharide) and adjuvant that can stimulate engineered cells to clonally expand and affinity mature can also be co-administered.

For therapy, modified or engineered B cells can be administered locally or systemically. A population of modified or engineered B cells can be introduced by injection, catheter, implantable device, or the like. A population of modified or engineered B cells can be administered in any physiologically acceptable excipient or carrier that does not adversely affect the cells. For example, the modified or engineered B cells can be administered intravenously. Methods of administering the modified or engineered B cells to subjects, particularly human subjects, include injection or implantation of the cells into target sites in the subjects. The modified or engineered B cells of the invention can be inserted into a delivery device which facilitates introduction of the cells after injection or implantation of the device within subjects. Such delivery devices include tubes, e.g., catheters, for injecting cells and fluids into the body of a recipient subject. The tubes can additionally include a needle. e.g., a syringe, through which the cells of the invention can be introduced into the subject at a desired location.

A population of modified or engineered B cells can be supplied in the form of a pharmaceutical composition. Such a composition can include an isotonic excipient prepared under sufficiently sterile conditions for human administration. For general principles in medicinal formulation, the reader is referred to CELL THERAPY: STEM CELL TRANSPLANTATION, GENE THERAPY, AND CELLULAR IMMUNOTHERAPY, by G. Morstyn & W. Sheridan eds, Cambridge University Press, 1996: and HEMATOPOIETIC STEM CELL THERAPY, E. D. Ball, J. Lister & P. Law, Churchill Livingstone, 2000. The choice of the cellular excipient and any accompanying constituents of the composition that includes a population of modified or engineered B cells can be adapted to optimize administration by the route and/or device employed.

As used herein, the term "solution" includes a carrier or diluent in which the modified or engineered B cells remain viable. Carriers and diluents which can be used with this aspect of the invention include saline, aqueous buffer solutions, physiologically acceptable solvents, and/or dispersion media. The use of such carriers and diluents is known in the art. The solution is preferably sterile and fluid to allow syringability. For transplantation, a solution containing a suspension of modified or engineered B cells can be drawn up into a syringe, and the solution containing the cells can be administrated to subjects. Multiple injections may be made using this procedure.

The modified or engineered B cells can also be embedded in a support matrix. A composition that includes a population of modified or engineered B cells can also include or be accompanied by one or more other ingredients that facilitate engraftment or functional mobilization of the modified or engineered B cells. Suitable ingredients include matrix proteins that support or promote adhesion of the modified or engineered B cells. In another embodiment, the composition may include physiologically acceptable matrix scaffolds. Such physiologically acceptable matrix scaffolds can be resorbable and/or biodegradable.

The population of modified or engineered B cells generated by the methods described herein can include low percentages of non-modified or non-engineered B cells. For example, a population of reprogrammed cells for use in compositions and for administration to subjects can have less than about 90% non-modified or non-engineered B cells, less than about 85% non-modified or non-engineered B cells, less than about 80% non-modified or non-engineered B cells, less than about 75% non-modified or non-engineered B cells, less than about 70% non-modified or non-engineered B cells, less than about 65% non-modified or non-engineered B cells, less than about 60% non-modified or non-engineered B cells, cells, less than about 50% non-modified or non-engineered B cells, less than about 40% non-modified or non-engineered B cells, less than about 30% non-modified or non-engineered B cells, less than about 20% non-modified or non-engineered B cells, less than about 10% non-modified or non-engineered B cells, less than about 8% non-modified or non-engineered B cells, less than about 5% non-modified or non-engineered B cells, less than about 3% non-modified or non-engineered B cells, less than about 2% non-modified or non-engineered B cells, or less than about 1% non-modified or non-engineered B cells of the total cells in the cell population.

To determine the suitability of various therapeutic administration regimens and dosages of cell compositions, the cells can first be tested in a suitable animal model. At one level, cells are assessed for their ability to survive and maintain their phenotype in vivo. Cells can also be assessed to ascertain whether they function in vivo, or to determine an appropriate dosage such as an appropriate number of cells and/or a frequency of administration of cells. Cell compositions can be administered to immunodeficient animals (such as nude mice, or animals rendered immunodeficient chemically or by irradiation). Tissues can be harvested after a period of regrowth, and assessed as to whether the administered cells or progeny thereof are still present, are alive, and/or have migrated to desired or undesired locations.

Injected cells can be traced by a variety of methods. For example, cells containing or expressing a detectable label (such as green fluorescent protein, or beta-galactosidase) can readily be detected. The cells can be pre-labeled, for example, with BrdU or [$^3$H]-thymidine, or by introduction of an expression cassette that can express green fluorescent protein, or beta-galactosidase. Alternatively, the reprogrammed cells can be detected by their expression of a cell marker that is not expressed by the animal employed for testing (for example, a human-specific antigen). The presence and phenotype of the administered population of reprogrammed cells can be assessed by fluorescence microscopy (e.g., for green fluorescent protein, or beta-galactosidase), by immunohistochemistry (e.g., using an antibody against a human antigen), by ELISA (using an antibody against a human antigen), or by RT-PCR analysis using primers and hybridization conditions that cause amplification to be specific for human polynucleotides.

The dose and the number of administrations can therefore be optimized by those skilled in the art.

The following Examples illustrate some features of the invention.

Example 1: Materials and Methods

This Example describes some of the materials and methods employed in the development of aspects of the invention.

PG9 Chimeric Light Chain IgG Expression

The anti-HIV-1 PG9 B cell from an HIV-infected patent was used for isolation of PG9 heavy and light chain IgG DNA. The PG9 heavy chain IgG and one of the light chain antibody plasmids (sequences shown in FIGS. 1D and 1n Table 2 below), were co-transfected in a 1:1 ratio into 200 mls of 293F cells (at $1 \times 1^{06}$ cells/ml) in Freestyle media (Thermo Scientific) using PEIMAX (40K) in transfectagro (Coming). Supernatants were harvested on day 5 post transfection and sterile filtered (0.22 μm) before IgG purification using Protein A/G Sepharose (1:1) (GE Healthcare). Briefly, supernatants loaded overnight onto beads were washed with PBS and eluted with 12 mls 50 mM citric acid buffer pH2.2 into 2 mls neutralization buffer (1M Tris pH 9.0). Eluted IgG was vivaspin (Sigma Aldrich) concentrated and buffer exchanged into PBS. Each antibody was purified by size exclusion on a S200 10/30 column (GE Healthcare) in PBS buffer and the 150 KDa peak pooled and concentrated. IgG concentrations were measured by Nanodrop (Thermoscientific) and stored at 4° C. Non-reducing SDS PAGE gels were run using 5 μg of protein to confirm purity and quality of the IgG produced.

TABLE 2

Sequences of PG9 heavy chain IgG and one of the light chain

| Type | Sequence |
| --- | --- |
| PG9 | QSALTQPASVSGSPGQSITISCNGTSNDVGGYESVSWYQQHPGKAPK VVIYDVSKRPSGVSNRFSGSKSGNTASLTISGLQAEDEGDYYCKSLT SIRRRVFGTGIKLTVL (SEQ ID NO: 1) |
| lambda1 | SYELTQPPSVSVSPGQTASITCSGDKLGDKYACWYQQKPGQSPVLV IYQDSKRPSGIPERFSGSNSGNTATLTISGTQAMDEADYYCQAWDS STWVVFGGGTKLTVL (SEQ ID NO: 2) |
| lambda2 | SYELTQPPSVSVSPGQTASITCSGDKLGDKYACWYQQKPGQSPVL VIYQDSKRPSGIPERFSGSNSGNTATLTISGTQAMDEADYYCQAW DSSTWVVFGGGTKLTVL (SEQ ID NO: 3) |
| lambda3 | QSALTQPASVSGSPGQSITISCTGTSSDVGSYNLVSWYQQHPGKA PKLMIYEVSKRPSGVSNRFSGSKSGNTASLTISGLQAEDEADYYC SSYTSSSTLVVFGGGTKLTVL (SEQ ID NO: 4) |
| lambda4 | QSALTQPASVSGSPGQSITISCTGTSSDVGGYNYVSWYQQHPGK APKLMIYEVSNRPSGVSNRFSGSKSGNTASLTISGLQAEDEADY YCSSYTSSSTPLFGGGTKLTVL (SEQ ID NO: 5) |
| lambda5 | SYELTQPPSVSVAPGKTARITCGGNNIGSKSVHWYQQKPGQAPV LVIYYDSDRPSGIPERFSGSNSGNTATLTISRVEAGDEADYYCQV WDSSSDHWVFGGGTKLTVL (SEQ ID NO: 6) |
| lambda6 | QSALTQPPSASGSPGQSVTISCTGTSSDVGGYNYVSWYQQRPGK APKLMIYEVSQRPSGVPDRFSGFKSGNTASLTVSGLQAEDEADY YCSSYAGNNNLLFGGGTRVTVL (SEQ ID NO: 7) |
| lambda7 | SYELTQPPSVSVSPGQTARITCWGNNFGNKSVHWQQKPGQSP VLVVYDDIDRPSGIPERFSGSNSGNTATLTISRVEAGDEADYYC QVWDSSSDHRDVVFGGGTKLTVL (SEQ ID NO: 8) |
| lambda8 | QAVVTQPPSVSEAPRQRVTISCCGSSSNIGNNAVNWYQQVPGR TPKLLIYYDDLLPSGVSDRFSGSKSGTSASLAISGLQSEDEADY YCAAWDDSLNGWVFGGGTKLTVL (SEQ ID NO: 9) |
| lambda9 | QSALTQPASVSGSPGQSITISCTGTNSDVGDYDSVSWYQQHPG KAPKLUYEVSKRPSGVPDRFSGSKSANTASLTISGLQAEEEAD YYCSSYTSSTSLDYVFGTGTKVTVL (SEQ ID NO: 10) |
| lambda10 | QLVLTQPPSVSGAPGQRVTISCTGGSSNVGAGYDVHWYQQFP GAAPKFVIYGNNNRPSGVPDRFSGSKSGNSASLAITGLQAEDE ADYYCQSFDSSLRGLVFGGGTKLTVL (SEQ ID NO: 11) |
| lambda11 | QSALTQPASVSASPGQSITISCSGTRSDVGGYDFVSWYQQHPGK VPKLIIYEVTKRPSGIPQRFSGSKSGNTASLTISGLQADDEADYY CCSYANYDELILGGGTKLTVL (SEQ ID NO: 12) |
| kappa12 | E1VLTQSPGTLSLSPGERATLSCRASQSVSSSYLAWYQQKPGQA PRLLIYGASSRATGIPDRFSGSGSGTDFTLTISRLEPEDFAVYYC QQYGSSPPTFGPGTKLE (SEQ ID NO: 13) |
| kappa13 | DIVMTQSPLSLPVTPGEPASISCRSSQSLLHSNGYNYLDWYLQ KPGQSPQLLIYLGSNRASGVPDRFSGSGSGTQFTLKISRVEAED VGVYYCMQALQPYTFGQGTKLE (SEQ ID NO: 14) |

TABLE 2-continued

Sequences of PG9 heavy chain IgG and one of the light chain

| Type | Sequence |
|---|---|
| kappa14 | EIVLTQSPGTLSLSPGERATLSCRASQSVSSSYLAWYQQKPGQ APRLLIYGASSRATGIPDRFSGSGSGTDFTLTISRLEPEDFAVY YCQQYGSSP1YSIGQGTKIE (SEQ ID NO: 15) |
| kappa15 | EIVLTQSPGTLSLSPGERATLSCRASQSVSSSYLAWYQQKPGQ APRLLIYGASSRATGIPDRFSGSGSGTDFTLTISRLEPEDFAV YYCQQYGSSPWTFGQGTKLE (SEQ ID NO: 16) |
| kappa16 | DIVMTQSPLSLPVTPGEPASISCRSSQSLLHSNGYNYLDWYLQ KPGQSPQLLIYLGSNRASGVPDRFSGSGSGTDFTLKISRVEAE DVGVYYCMQALQTPRLTFGGGTKLE (SEQ ID NO: 17) |
| kappa17 | DVVMTQSPLSLPVTPGEPASISCRSSQSLLHSNGYNYLDWYLQ KPGQSPQLLIYLGSNRASGVPDRFSGSGSGTDFTLKISRVEAED VGVYYCMQALQTPWTFGQGTKLE (SEQ ID NO: 18) |
| kappa18 | DVVMTQSPLSLPVTPGEPASISCRSSQSLLHSNGYNYLDWYLQ KPGQSPQLLIYLGSNRASGVPDRFSGSGSGTDFTLKISRVEAED VGVYYCMQALQTLPDTFGQGTKLE (SEQ ID NO: 19) |
| kappa19 | DVVMTQSPLFLPVTPGEPASISCRSSQSLIHSNGYNYLDWYLQ KPGQSPQLLIYLGSNRASGVPDRFSGSGSGTDFTLKISRVEAED VGVYYCMQALQTPETFGQGTKLE (SEQ ID NO: 20) |
| kappa20 | EIVLTQSPGTLSLSPGERATLSCRASQSVSSSYIAWYQQKPGQA PRLLIYGASSRATGIPDRFSGSGSGTDFTLTISRLEPEDFAVYC QQYGSSPLTFGQGTKVD (SEQ ID NO: 21) |
| kappa21 | EIVMTQSPGTLSLSPGERATLSCRASQSVSSSYLAWYQQKPGQ APRLLIYGASSRATGIPDRFSGSGSGTDFTLTISRLEPEDFAVYY CQQYGSSPAFGQGTKLE (SEQ ID NO: 22) |
| kappa22 | AIRMTQSPSSLSASVGDRVTITCRASQSISSYLNWYQQKPGKA PKLLIYAASSLQSGVPSRFSGSGSGTDFTLTISSLQPEDFATYY CQQSYSTPSITFGQGTRLE (SEQ ID NO: 23) |
| kappa23 | AIRMTQSPSSLSASVGDRVTITCRASQSISSYLNWYQQKPGKA PKLLIYAASSLQSGVPSRFSGSGSGTDFTLTISSLQPEDFATYY CQQSYSTIWTFGQGTKVD (SEQ ID NO: 24) |
| kappa24 | DIVMTQSPDSLAVSLGERATINCKSSQSVLYSSNNKNYLAWY QQKPGQPPKLLIYWASTRESGVPDRFSGSGSGTDFTITISSIQ AEDVAVYYCQQYYSTPRTFGQGTKVE (SEQ ID NO: 25) |
| kappa25 | EIVLTQSPGTLSLSPGERATLSCRASQSVSGSYIAWYQQKPGQ APRLLIYGASSRATGIPDRFSGSGSGTDFTLTISRLEPEDFAVYY CQQYGTSPWTFGQGTKVD (SEQ ID NO: 26) |
| kappa26 | DIVMTQSPDSLAVSLGERATLNCKSSQSILYSSNNKNYLAWYQ QKPGQPPKLLIYWASTRESGVPDRFSGSGSGTDFTLTISSLQAE DVAVYYCQQYYSTPPTFGQGTKVE (SEQ ID NO: 27) |
| kappa27 | AIRMTQSPSSVSASVGDRVTITCRASQSISSWLAWYQQKPGTA PKLLIYTASSLQSGVPSRFSGSGSGTDFTLTTSSLQPEDFATYY QQANSFPYTFGQGTKLE (SEQ ID NO: 28) |
| kappa28 | EIVLTQSPATLSLSPGERATLSCRASQSVSSYLAWYQQKPGQA PRLLIYDASNRATGIPARFSGSGSGTDFTLTISSLEPEDFAVYYC QQRRAFGPGTKVD (SEQ ID NO: 29) |
| kappa29 | DIVMTQSPSSLSASVGDRVTITCRASQGISSYLNWYQQKPGKA PKLLICAASSLQSGVPSRFSGSGSGTDFTLTISSLQPEDFATYYC QQSYSTPYTFGQGTKLE (SEQ ID NO: 30) |
| kappa30 | DIVMTQSPSSLSASVGDRVTVTCRASQGISNYLAWYQQKPGK VPKLLIYAASTLQSGVPSRFSGSGSGTDFTLTISGLQSGDFAIY YCQQYYRFPQTFGQGTKLE (SEQ ID NO: 31) |
| CH01 | EIVLAQSPGTLSLSPGERATLSCRASHNVHPKYFAWYQQKPGQ SPRLLIYGGSTRAAGIPGKFSGSGSGTDFTLTISRVDPEDFAVY CQQYGGSPYTFGQGTKVE (SEQ ID NO: 32) |
| PGT151 | DIVMTQTPLSLSVTPGQPASTSCKSSESLRQSNGKTSLYWYRQK PGQSPQLLVFEVSNRFSGVSDRFVGSGSGTDFTLRISRVEAEDV GFYYCMQSKDFPLTFGGGTKVD (SEQ ID NO: 33) |

TABLE 2-continued

Sequences of PG9 heavy chain IgG and one of the light chain

| Type | Sequence |
|---|---|
| B12 | EIVLTQSPGTLSLSPGERATFSCRSSHSIRSRRVAWYQHKPGQA PRLVIHGVSNRASGISDRFSGSGSGTDFTLTITRVEPEDFALYYC QVYGASSYTFGQGTKLE (SEQ ID NO: 34) |
| PGT145 | EVVITQSPLFLPVTPGEAASLSCKCSHSLQHSTGANYLAWYLQ RPGQTPRLLIHLATHRASGVPDRFSGSGSGTDFTLKISRVESDD VGTYYCMQGLHSPWTFGQGTKVE (SEQ ID NO: 35) |
| VRC01 | E1VLTQSPGTLSLSPGETAIISCRTSQYGSLAWYQQRPGQAPRL VIYSGSTRAAGIPDRFSGSRWGPDYNLTISNLESGDFGVYYCQ QYEFFGQGTKVQVD (SEQ ID NO: 36) |
| PGV04 | EIVLTQSPGTLSLSPGETASLSCTAASYGHMTWYQKKPGQPP KLLIFATSKRASGIPDRFSGSQFGKQYTLTITRMEPEDFARYY CQQLEFFGQGTRLE (SEQ ID NO: 37) |
| Ramos | QSALTQPASVSGSPGQSITISCTGTSSDVGGYNYVSWYQQNP GKAPELMIYDVSNRPSGISNRFSGSKSGNTASLTISGLQADD EADYYCTSYTNDSNSQVFGGGTKLTVL (SEQ ID NO: 38) |
| PGT135 | EIVMTQSPDTLSVSPGETVTLSCRASQNINKNLAWYQYKPG QSPRLVIFETYSKIVAFPARFVASGSGTEFTLTINNMQSEDV AVYYCQQYEEWPRTFGQGTKVD (SEQ ID NO: 39) |
| K31 | DIVMTQSPSLLSASTGDRVTISCRMSQGISSYLAWYQQKPG KAPELLIYSASTLQSGVPSRFSGSGSGTDFTLTISGLQSGDFA IYYCQQYYRSPQTFGQGTKVD (SEQ ID NO: 40) |

Biolayer Interferometry

Kinetic measurements were obtained with an Octet Red instrument immobilizing IgGs on previously hydrated (in PBS pH 7.4) anti-human IgG Fc sensors (Fortebio, Inc.). PGT145 purified SOSIP trimers were analyzed as free analytes in solution (PBS, pH 7.4). Briefly, the biosensors were immersed in PBS, pH 7.4, containing IgGs at a concentration of 10 µg/ml for 2 min and at 1,000 rpm prior to the encounter with the analyte. The SOSIP analytes were concentrated to 500 nM. The IgG-immobilized sensor was in contact with the analyte in solution for 120 s at 1,000 rpm and then removed from the analyte solution and placed into PBS for another 250 s. These time intervals generated the association and dissociation binding curves reported in this study.

Polyreactivity Assay: HEp-2 Cell Staining Assay

The HEp-2 cell-staining assay was performed using kits purchased from Aesku Diagnostics (Oakland, CA) according to manufacturer's instructions. These Aesku slides use optimally fixed human epithelial (HEp-2) cells (ATCC) as substrate and affinity purified, FITC-conjugated goat anti-human IgG for the detection. Briefly, 25 µl of 100 µg/ml mAb and controls were incubated on HEp-2 slides in a moist chamber at room temperature for 30 min. Slides were then rinsed and submerged in PBS and 25 µl of FITC-conjugated goat anti-human IgG was immediately applied to each well. Slides were incubated again for 30 min and washed as above before mounting on coverslips using the provided medium. Slides were viewed at 20× magnification and photographed on an EVOS fl fluorescence microscope at a 250 ms exposure with 100% intensity. Positive and negative control sera were provided by the vendor. Samples showing fluorescence greater than the negative or PG9 HC/LC control were considered positive for HEp-2 staining.

Pseudovirus Neutralization Assays

To produce pseudoviruses, plasmids were cotransfected encoding Env with an Env-deficient backbone plasmid (pSG3DEnv) in a 1:2 ratio with the transfection reagent Fugene 6 (Promega) into 293T cells. Pseudoviruses were harvested from the supernatant 48 hr post-transfection and flash frozen in aliquots at −80° C. Pseudovirus infectivity was assessed using dextran on TZM-b1 cells before neutralization assays were performed with the antibody of interest in TZM-b1 cells as described by Seaman et al., *J Virol* 84, 1439-1452 (2010) and Walker et al. *Nature* 477, 466-470 (2011). Rather than IC50 concentrations, % virus neutralization at 10 ug/ml of chimeric IgG was reported as the average value from three separate experiments. Select antibodies were also titrated in a 2-fold serial dilution with media starting at 100 ug/ml and diluting down 6 wells.

B Cell Lines

Ramos (RAI) and (2G6) cells were obtained from ATCC and cultured as directed (CRL-1596 and CRL-1923 respectively). Epstein-Barr virus (EBV) immortalized B cells derived from human blood were developed as described by Ryan et al. *Lab Invest* 86, 1193-1200 (2006). Briefly, the marmoset cell line B95-8 (ATCC CRL-1612) was cultured as directed. Supernatants containing EBV were harvested and used to infect fresh PBMCs purified from human plasma (obtained from The Scripps Research Institute's Normal Blood Donor Service). After 24 hours cells were resuspended in fresh media containing 400 ng/ml cyclosporin. Media was refreshed weekly until cell line became established.

B Cell Engineering Reagents

CRISPR/cas9 guide RNA (gRNA) sequences targeting sites within the immunoglobulin heavy chain variable (IGHV) locus of the human reference genome sequence annotated in IMGT (the international ImMunoGeneTics information system; LeFrane et al. *Nucleic Acids Res* 43, D413-422 (2015)) were identified using the Zhang Lab CRISPR design web server (see website at crispr.mit.edu). The CRISPR/cas9 guide RNA (gRNA) sequences were synthesized as primers (Valuegene), and cloned into the pX330-U6-Chimeric_BB-CBh-hSpCas9 vector (Addgene plasmid #71707) as described by Ran et al. *Nat Protoc* 8, 2281-2308 (2013). The top five gRNA targets identified were developed for each of the three target cut sites; 5' of the V781 (GenBank: AB019437) and V434 (GenBank: AB019439), genes, and 3' of the J6 gene (GenBank: AL122127). Roughly 250 bp of sequences containing the CRISPR/cas9 target sequences were synthesized based on the IMGT annotated reference sequence (Geneart), or PCR amplified from 293T or Ramos B cell gDNA samples. These CRISPR/cas9 target sequences were cloned into the pCAG-EGxxFP vector (Addgene plasmid #50716), and Sanger sequenced (Eton Bioscience). The gRNAs were tested for their efficacy in directing cas9 mediated dsDNA cleavage by cotransfection of the pX330 and corresponding pCAG targets into 293T cells using PEIMAX (40K). Target DNA cutting was scored as GFP expression because dsDNA cuts within the target will result in HDR that restores the GFP reading frame in the pCAG plasmid as described by Mashiko et al. *Sci Rep* 3, 3355 (2013).

Donor DNA was synthesized as three separate genes (Gencart): The V434, or V781 5' UTR homology regions, (5' segment) and the PG9 VDJ ORF and 3' homology region (3' segment). A functional PG9 VDJ ORF was designed by grafting the PG9 VDJ nucleotide sequence (GenBank GU272045.1), after the V3-33 start codon, leader peptide, and V-gene intron (GenBank: AB019439), because V3-33 is the germline from which PG9 evolved. The 3' segment was cloned into the HR110PA-1 donor DNA vector (System Biosciences). Either the V434 or V781 homology region was then cloned 5' of the PG9 gene using restriction enzymes. Unique restriction sites had to be added to the plasmid by site directed mutagenesis in order to avoid cutting naturally existing restriction sites within the 5 and 3' homology regions. PAM sites in CRISPR/cas9 targets within donor DNA homology regions were also mutated using Site directed mutagenesis (Agilent Technologies) to prevent donor DNA cutting in B cells also transfected with nuclease plasmids. Final nucleotide sequences for donor DNAs are shown below.

V434p PG9HC Donor DNA (SEQ ID NO: 41):
```
   1   GAAATATTCC CTGTAAATAA AAAAAGTATC TCAGTTTCTC
  41   TCAATGTTCA TAATTCTCCT GAGGGTGAGG AAGGTACTTC
  81   TGGGTCTGCT CAAACAAATG GCCCAGAGAC CACCTGGTAG
 121   GTAGGTAAGG AGCTCACCTC GCTCTGGATA TTGAGTCTGT
 161   CTCTTTCCCT CTGTCGTCTC ATAGAAGGCC AGCCCACTTG
 201   TTCAGCTCCT AAGAAGAGAG CCCAGGTTTA TCCAGATTAT
 241   ACAACACAAC CAGCTTCTGA TGACTCTCCT GTTACAACAT
 281   CCATGGAGAT ATTTTGTGTA TTATATAATT CACCAAACTA
 321   ATGTGAAATG CCCAAGTTGC AATACTGCAC ACCCTAGGGT
 361   ATGTTCTTGC AATTCAGCGG AGGAGAAATT CTTTCAGAGA
 401   CAGATGGATC TGAATTGGTA AATATGTGGG TACGAATTCT
 441   GGGTTTGAGT GTCATTGTCC AGCCATGTTT CACAGGTGTG
 481   ACCTGTCAGG GAAGAACCAG AGTTCCTTGT TCTCTCAGAG
 521   GGTAGAGCTC ACAGAGGTCC TCTCTGGTTC CCAGGAAAGG
 561   TAATTTCACT AATCTTGGTG ATGAGACTAT CCTCCAGTGC
 601   TGATGTACTA TAGAGTTTTC ATCTGAAGCT TGTCACTGCTA
 641   TCCCCAATGT ACATCTTTTC ACACAGAAAT GTTTAGAGGT
 681   CAGGCCATAT TCTCAGGGTT ACACATTGAG AAGGATGGAG
 721   ATATATTCTA CTACCTTCTC CTGAGATCTC ACACACAATC
 761   TCAAATTTCA AAAGGTCTCA GAAGGGCAGC TCTCAGGTAC
 801   TATTTAAAAA TAACCCACTT CCTGGGACAG GTAGCATCCT
 841   TCTAACCATG ATGGATGTTC TGAACTACAG TACACATTGC
 881   ATGGATCCAG GTTTGTCTCA ATTCACTGTG ATTATTACAC
 921   TCAGCAGCTG TTTCAATATG TCTGAAGGGG TAAATGACAA
 961   TTTAGGTGAC CTGGGTGTAT GGTTGGTGTT ATATGAATCT
1001   TTAAATGTAG AACAGTATTA ACTGTATTCC AAAATCTGTC
1041   TTTGATCCAT GATCACACTT GTCTCCCAGA CCAGCT*CCTT*
1081   *CAGCACATTT CCTACCTTTA* AGAAGAGGAC TCTGGGTTTG
1121   GTGAGGGGAG GCCACAGGAA GAGAACTGAG TTCTCAGAGG
1161   GCACAGCCAG CATACACCTC CCAGGGTGAG CCCAAAAGAC
1201   TGGGGCCTCC CTCATCCCTT TTTACCTATC CATACAAAGG
1241   CACCACCCAC ATGCAAATCC TCACTTAGGC ACCCACAGGA
1281   AATGACTACA CATTTCCTTA AATTCAGGGT CCAGCTCACA
1321   TGGGAAGTGC TTTCTGAGAG TCATGGACCT CCTGCACAAG
1361   AACATGGAGT TTGGGCTGAG CTGGGTTTTC CTCGTTGCTC
1401   TTTTAAGAGG *TGATTCATGG AGAAATAGAG AGACTGAGTG*
1441   *TGAGTGAACA TGAGTGAGAA AAACTGGATT TGTGTGGCAT*
1481   *TTTCTGATAA CGGTGTCCTT CTGTTTGCAG* GTGTCCAGTG
1521   TCAGCGATTA GTGGAGTCTG GGGGAGGCGT GGTCCAGCCT
1561   GGGTCGTCCC TGAGACTCTC CTGTGCAGCG TCCGGATTCG
1601   ACTTCAGTAG ACAAGGCATG CACTGGGTCC GCCAGGCTCC
1641   AGGCCAGGGG CTGGAGTGGG TGGCATTTAT TAAATATGAT
1681   GGAAGTGAGA AATATCATGC TGACTCCGTA TGGGGCCGAC
1721   TCAGCATCTC CAGAGACAAT TCCAAGGATA CGCTTTATCT
1761   CCAAATGAAT AGCCTGAGAG TCGAGGACAC GGCTACATAT
1801   TTTTGTGTGA GAGAGGCTGG TGGGCCCGAC TACCGTAATG
1841   GGTACAACTA TTACGATTTC TATGATGGTT ATTATAACTA
1881   CCACTATATG GACGTCTGGG GCAAAGGGAC CACGGTCACC
1921   GTCTCCTCAG GTAAGAATGG CCACTCTAGG GCCTTTGTTT
1961   TCTGCTACTG CCTGTGGGGT TTCCTGAGCA TTGCAGGTTG
2001   GTCCTCGGGG CATGTTCCGA GGTTGGACCT GGGCGGACTG
2041   GCCAGGAGGG GACGGGCACT GGGGTGCCTT GAGGATCTGG
2041   GAGCCTCTGT GGATTTTCCG ATGCCTTTGG AAAATGGGAC
2041   TCAGTTGGGG TGCGTCTGAT GGAGTAACTG AGCCTGGGGG
2041   CTTGGGGAGC CACATTTGGA CGAGATGCCT GAACAAACCA
2041   GGGGTCTTAG TGATGGCTGA GGAATGTGTC TCAGGAGCGG
```

```
2041  TGTCTGTAGG ACTGCAAGAT CGCTGCACAG CAGCGAATCG

2041  TGAAATATTT TCTTTAGAAT TATGAGGTGC GCTGTGTGTC

2041  AACCTGCATC TTAAATTCTT TATTGGCTGG AAAGAGAACT

2041  GTCGGAGTGG GTGAATCCAG CCAGGAGGGA CGCGTAGCCC

2041  CGGTCTTGAT GAGAGCAGGG TTGGGGGCAG GGGTAGCCCA

2041  GAAACGGTGG CTGCCGTCCT GACAGGGGCT TAGGGAGGCT

2041  CCAGGACCTC AGTGCCTTGA AGCTGGTTTC CATGAGAAAA

2041  GGATTGTTTA TCTTAGGAGG CATGCTTACT GTTAAAAGAC

2041  AGGATATGTT TGAAGTGGCT TCTGAGAAAA ATGGTTAAGA

2041  AAATTATGAC TTAAAAATGT GAGAGATTTT CAAGTATATT

2041  AATTTTTTTA ACTGTCCAAG TATTTGAAAT TCTTATCATT

2041  TGATTAACAC CCATGAGTGA TATGTGTCTG GAATTGAGGC

2041  CAAAGCAAGC TCAGCTAAGA AATACTAGCA CAGTGCTGTC

2041  GGCCCCGATG CGGGACTGCG TTTTGACCAT CATAAATCAA

2041  GTTTATTTTT TTAATTAATT GAGCGAAGCT GGAAGCAGAT

2041  GATGAATTAG AGTCAAGATG GCTGCATGGG GGTCTCCGGC

2041  ACCCACAGCA GGTGGCAGGA AGCAGGTCAC CGCGAGAGTC

2041  TATTTTAGGA AGCAAAAAAA CACAATTGGT AAATTTATCA

2041  CTTCTGGTTG TGAAGAGGTG GTTTTGCCCA GGCCCAGATC

2041  TGAAAGTGCT CTACTGAGCA AAACAACACC TGGACAATTT

2041  GCGTTTCTAA AATAAGGCGA GGCTGACCGA AACTGAAAAG

2041  GCTTTTTTTA ACTATCTGAA TTTCATTTCC AATCTTAGCT

2041  TAT
```

The foregoing sequence includes:

Human IGHV V4-34 promoter, IMGT reference sequence GenBank: AB019439
CCTTCAGCACATTTCCTACCTTT (SEQ ID NO:42): 5' crispr guide sequence and PAM site mutation
Human IGHV V3-33 Leader sequence. IMGT reference sequence GenBank: AB019439
Human IGHV V3-33 intron. IMGT reference sequence GenBank: AB019439
Human IGHV V3-33 gene, IMGT reference sequence GenBank: AB019439
PG9 heavy chain VDJ gene, GenBank GU272045.1
3' of the IGHV J6 gene (intron), IMGT reference sequence GenBank: AL122127
TCCTCGGGGCATGTTCCGAGGTT (SEQ ID NO:43): 3' crispr guide sequence and PAM site mutation
TTAGTGGAGGAAGCGCTATCAAC (SEQ ID NO:44): 5' crispr guide sequence and PAM site mutation The V434p PG9HC Donor DNA (SEQ ID NO:41) has several features including one or more promoters, crispr guide sequences (e.g., with a PAM site mutation), leader sequences, introns, immunoglobulin heavy chain variable (IGHV) sequences, or 3' sequences.

In particular, the V434p PG9HC Donor DNA (SEQ ID NO:41) has a Human immunoglobulin heavy chain variable (IGHV) V4-34 promoter (from IMGT reference sequence GenBank: AB019439; nucleotides 1-1363 of the SEQ ID NO:41 sequence) as well as a crispr guide sequences with PAM site mutation (e.g., CCTTCAGCACATTTCCTACCTTT, SEQ ID NO:42, at nucleotides 1047-1089 of the SEQ ID NO:41 sequence). In addition, the V434p PG9HC Donor DNA (SEQ ID NO:41) has a Human IGHV V3-33 Leader sequence (ATGGAGTTTGGGCTGAGCTGGGTTTTC CTCGTTGCTCTTAAGAGG SEQ ID NO:45 from IMGT reference sequence GenBank: AB019439; at nucleotides 1364-1409 of the V434p PG9HC Donor DNA (SEQ ID NO:41), as well as a Human immunoglobulin heavy chain variable (IGHV) V3-33 intron (GTGATTCATG-GAGAAATAGAGAGACTGAGTGTGAG TGAACAT-GAGTGAGAAAAACTGGATTTGTGTGGCATTTTCT-GATAACGG TGTCCTTCTGTTTGCAG SEQ ID NO:46, from IMGT reference sequence GenBank: AB019439; nucleotides 1410-1510 of the V434p PG9HC Donor DNA (SEQ ID NO:41) sequence). The V434p PG9HC Donor DNA (SEQ ID NO:41) has a Human IGHV V3-33 gene (GTGTCCAGTGTCAGCGATTAGTGGAGTCTGGGG-GAGGCGTGGTCCAGCCT GGGTCGTCCCTGA-GACTCTCCTGTGCAGCGTCCGGATTCG ACTTCAGTAGACAAGG-CATGCACTGGGTCCGCCAGGCTCCAGGCAG GGGCTGGAGTGGGTGGCATTTATTAAATATGATG-GAAGTGAGAAATATCA TGCTGACTCCGTATGGGGCCGACTCAG-CATCTCCAGAGACAAT TCCAAGGATACGCTT-TATCTCCAAATGAATAGCCTGAGAGTCGAG GACACGGCTACATATTTGTGT-GAGAGAGGCTGGTGGGCCCGACTACC GTAATGGGTACAACTATTACGATTTCTATGATGGTT-ATTATAACTACCACTATATG GACGTCTGGGGCAAAGGGACCACGGT-CACCGTCTCCTCA, SEQ ID NO:47 from IMGT reference sequence GenBank: AB019439 and PG9 heavy chain VDJ gene, GenBank GU272045.1; nucleotides 1511-1929 of the V434p PG9HC Donor DNA (SEQ ID NO:41) sequence). The V434p PG9HC Donor DNA (SEQ ID NO:41) has the 3' portion of the immunoglobulin heavy chain variable (IGHV) J6 gene (intron), from IMGT reference sequence GenBank: AL122127; nucleotides 1930-2043 of the V434p PG9HC Donor DNA (SEQ ID NO:41) sequence). The V434p PG9HC Donor DNA (SEQ ID NO:41) also has a 3' crispr guide sequence with a PAM site mutation (TCCTCGGGG-CATGTTCCGAGGTT SEQ ID NO:43).

Another nucleotide sequence, referred to as the V781p PG9HC donor DNA is shown below. The V781p PG9HC donor DNA has several features including one or more promoters, crispr guide sequences (e.g., sometimes with a PAM site mutation), leader sequences, introns, immunoglobulin heavy chain variable (IGHV) sequences, or 3' sequences.

```
V781p PG9HC Donor DNA (SEQ ID NO: 48):
   1  GCTGGGCTGT TGTGCACGTA TGTGTGTTTG TATGACCAGG

41  AGGTTTTCAA ATACATCATT AAATTACATA GTTATATTAA

81  TCTTGGCAAG GCACTTGTAT TCTGTTTTCT TTAATTCTGT

121  TTGCAGAAAG TAGACACATA TTCAGTCTTA GTTCCAGTGT

161  AGGGAGTGCT TTTCATGAGA AAAATACCAG AAAAAAGGGC

201  AAACATGGGG CCCACTAATG TAAAAATTAG CCACAATGTG

241  TATGTGTGTG TGTGTGTGTG TGTGTGTGTG TCTGAGTTGA

281  ATAGTAGAGT TGGAGTGGGC TTCTATCCAC ATGCACCTGC
```

```
 321 GCCTACAGGT ATTATCAGGT ACAATAATCA ACTGCAGAAC
 361 CCTAAAGGAA ATAAGAGTCC CCCCAAACCC CTGAAGAGTG
 401 TTTGGGTTCA CCATGTGTCC AATGATTCAG TGCCTCTCGA
 441 GCTCCAGGAA ACGGCTCCCT GGTGATGCTG GAGATCTTTT
 481 CTTGGGGTGT CCCTGCAGAG TTCGCTGGGT TTCCTAAGGC
 521 TGATTCACTA TTTCAAAAGA TGGTGTGAGA AGCATATGGT
 561 GTAAATAAAG CAGAATTCTG AGCCAGGGCA CAGCCACTTT
 601 ATACTGGGCT AGAGACACTG GTAGGAATAA ACTCTGTCAG
 641 CTCAGATAGA AACCTCCCTG CAGGGTGGGG GCAGGGCTGC
 681 AGGGGGCGCT CAGGACACAT CGAGCACAGT CTTCTGCCCC
 721 AGAGCAGGTG CACATGAGGC TGGGGAGAGG TTCCTCTCAG
 761 GGCCTGGGAC TTCCTTTAAA AATATCTAAA ATAAGTATTT
 801 CACAAGGACT GCTGATGTTT GTATAAATAT CCTATTCAAT
 841 TGTGAGCATT TATCAAACTG GATGTTGTAA TGAGAACCAC
 881 TTTTATAATG GCGATTTCAA ACTCTGCTAG TTATCTTAAT
 921 AATAGCAGCT GGAGGTCAGG AAGAGATTAT TACTTATAAA
 961 TAAGTGCAAT TTTTGGAGAG ACACACTCAT TCCCAAAATA
1001 ACACATTCAC ATATTAAGGT CTAGAAATGG TTCACGTTGC
1041 CCCTGAGACA TTCAAATGTG GGTTCAAAGT GAGGTGCTGT
1081 CCTCGGGGAG TTGITCCTTA GTGGAGGAAG CGCTATCAAC
1121 ACAGAGTTCA GGGATGGGTA GGGGATGCGT GGCCTCTAAC
1161 AGGATTACGA CTCGAACCCT CAGCTCCTAT AATTGTGTCG
1201 TCCGTGTGTC ATGGATTCT CTTTCTCATA CTGGGTCAGG
1241 AATTGGTCTA TTAAATAGCA TCCTTCATGA ATATGCAAAT
1281 AACTGAGGGG AATATAGTAT CTCTGTACCC TGAAAGCATC
1321 ACCCAACAAC AACATCCCTC CTTGGGAGAA TCCCCTAGAG
1361 CACAGCTCCT CACCATGGAG TTTGGGCTGA GCTGGGTTTT
1401 CCTCGTTGCT CTTTTAAGAG GTGATTCATG GAGAAATAGA
1441 GAGACTGAGT GTGAGTGAAC ATGAGTGAGA AAAACTGGAT
1481 TTGTGTGGCA TTTTCTGATA ACGGTGTCCT TCTGTTTGCA
1521 GGTCTCCAGT GTCAGCGATT AGTGGAGTCT GGGGGAGGCG
1561 TGGTCCAGCC TGGGTCGTCC CTGAGACTCT CCTGTGCAGC
1601 GTCCGGATTC GACTTCAGTA GACAAGGCAT GCACTGGGTC
1641 CGCCAGGCTC CAGGCCAGGG GCTGGAGTGG GTGGCATTTA
1681 TTAAATATGA TGGAAGTGAG AAATATCATG CTGACTCCGT
1721 ATGGGGCCGA CTCAGCATCT CCAGAGACAA TTCCAAGGAT
1761 ACGCTTTATC TCCAAATGAA TAGCCTGAGA GTCGAGGACA
1801 CGGCTACATA TTTTTGTGTG AGAGAGGCTG GTGGGCCCGA
1841 CTACCGTAAT GGGTACAACT ATTACGATTT CTATGATGGT
1881 TATTATAACT ACCACTATAT GGACGTCTGG GGCAAAGGGA
1921 CCACGGTCAC CGTCTCCTCA GGTAAGAATG GCCACTCTAG
1961 GGCCTTTGTT TTCTGCTACT GCCTGTGGGG TTTCCTGAGC
2001 ATTGCAGGTT GGTCCTCGGG GCATGTTCCG AGGTTGGACC
2041 TGGGCGGACT GGCCAGGAGG GGACGGGCAC TGGGGTGCCT
2081 TGAGGATCTG GGAGCCTCTG TGGATTTTCC GATGCCTTTG
2121 GAAAATGGGA CTCAGGTTGG GTGCGTCTGA TGGAGTAACT
2161 GAGCCTGGGG GCTTGGGGAG CCACATTTGG ACGAGATGCC
2201 TGAACAAACC AGGGGTCTTA GTGATGGCTG AGGAATGTGT
2241 CTCAGGAGCG GTGTCTGTAG GACTGCAAGA TCGCTGCACA
2281 GCAGCGAATC GTGAAATATT TTCTTTAGAA TTATGAGGTG
2321 CGCTGTGTGT CAACCTGCAT CTTAAATTCT TTATTGGCTG
2361 GAAAGAGAAC TGTCGGAGTG GGTGAATCCA GCCAGGAGGG
2401 ACGCGTAGCC CCGGTCTTGA TGAGAGCAGG GTTGGGGGCA
2441 GGGGTAGCCC AGAAACGGTG GCTGCCGTCC TGACAGGGGC
2481 TTAGGGAGGC TCCAGGACCT CAGTGCCTTG AAGCTGGTTT
2521 CCATGAGAAA AGGATTGTTT ATCTTAGGAG GCATGCTTAC
2561 TGTTAAAAGA CAGGATATGT TTGAAGTGGC TTCTGAGAAA
2601 AATGGTTAAG AAAATTATGA CTTAAAAATG TGAGAGATTT
2641 TCAAGTATAT TAATTTTTTT AACTGTCCAA GTATTTGAAA
2681 TTCTTATCAT TTGATTAACA CCCATGAGTG ATATGTGTCT
2721 GGAATTGAGG CCAAAGCAAG CTCAGCTAAG AAATACTAGC
2761 ACAGTGCTGT CGGCCCCGAT GCGGGACTGC GTTTTGACCA
2801 TCATAAATCA AGTTTATTTT TTTAATTAAT TGAGCGAAGC
2841 TGGAAGCAGA TGATGAATTA GAGTCAAGAT GGCTGCATGG
2881 GGGTCTCCGG CACCCACAGC AGGTGGCAGG AAGCAGGTCA
2921 CCGCGAGAGT CTATTTTAGG AAGCAAAAAA ACACAATTGG
2961 TAAATTTATC ACTTCTGGTT GTGAAGAGGT GGTTTTGCCC
3001 AGGCCCAGAT CTGAAAGTGC TCTACTGAGC AAAACAACAC
3041 CTGGACAATT TGCGTTTCTA AAATAAGGCG AGGCTGACCG
3081 AAACTGAAAA GGCTTTTTTT AACTATCTGA ATTTCATTTC
3121 CAATCTTAGC TTATC
```

This sequence includes the following:
Human IGHV V4-34 promoter, IMGT reference sequence GenBank: AB019439
CCTTCAGCACAITTCCTACCTTT (SEQ ID NO:42): 5' crispr guide sequence and PAM site mutation
Human IGHV V3-33 Leader sequence. IMGT reference sequence GenBank: AB019439
Human IGHV V3-33 intron, IMGT reference sequence GenBank: AB019439
Human IGHV V3-33 gene, IMGT reference sequence GenBank: AB019439
PG9 heavy chain VDJ gene, GenBank GU272045.1
3' of the IGHV J6 gene (intron), IMGT reference sequence GenBank: AL122127
TCCTCGGGGCATGICCGAGGTT (SEQ ID NO:43): 3' crispr guide sequence and PAM site mutation Human IGH V7-81 promoter, IMGT reference sequence GenBank: AB019437 TTAGTGGAGGAAGCGCTATCAAC (SEQ ID NO:44): 5' crispr guide sequence and PAM site mutation In particular, the V781p PG9HC donor DNA (SEQ ID NO:48) has a human IGH V7-81 promoter (SEQ ID NO:49, from IMGT reference sequence GenBank: AB019437; nucleotides 1-1374 of the V781p PG9HC donor DNA) as well as a crispr guide sequences with PAM site mutation (e.g., TTAGTGGAGGAAG CGCTATCAAC. SEQ ID NO:44, at nucleotides 1098-1120 of the V781p PG9HC donor DNA SEQ ID NO:48 sequence). In addition, the V781p PG9HC donor DNA (SEQ ID NO:48 has a human immunoglobulin heavy chain variable (IGHV) V3-33 Leader sequence (ATGGAGGGGACTGAGCTGGTTCCTCGATGCTCTTTTAAGAG, SEQ ID NO.50, which is an IMGT reference sequence GenBank: ABT19439), and a human immunoglobulin heavy chain variable V3-33 intron sequence GTGATTCATGGAGAAATAGAGAGACTGAGTGTGAGTGAACATGAGTGAGAAAAA CTGGATTTGTGTGGCATTCACTGATAACGATGTCCATCTGTATGCA, SEQ ID NO:51, which is an IMGT reference sequence GenBank: AB019439). In addition, the V781p PG9HC donor DNA (SEQ ID NO:48) has a PG9 heavy chain VDJ sequence (SEQ ID NO:52, from GenBank GU272045.1, nucleotides 1521-1920 of the V781p PG9HC donor DNA (SEQ ID NO:48) sequence. The V781p PG9HC donor DNA (SEQ ID NO:48) also has a 3' end of the IGHV J6 gene (intron, SEQ ID NO: from IMGT reference sequence GenBank: AL122127, nucleotides 1941-3135 of the V781p PG9HC donor DNA (SEQ ID NO:48)), which includes a 3' crispr guide sequence with a PAM site mutation (TCCTCGAGGCATGTFCCGAGGT; SEQ ID NO:43).

```
V374p PG9HC Donor DNA (SEQ ID NO: 53):
   1   AAAAGTCCAT TTTCTCTGAT TAACAGTTAT TGTTGATTTT
  41   ATTCTTGTTG TAAAAAAAAG AAATTCTCAT CTATGTACAT
  81   TTCAAACCTG AATAACAAAA TTTTTATTAA CACCAAAAAT
 121   AATAAAGAA TCCAAATATT TATCAGCTGC CTAATAGAAA
 161   AACAAATCAT GGTAACATTG TTCCCTGGAA TATTACCCAT
 201   CATTCATAAT AAGGGAATGT CTGATACACA AAATAAGAAG
 241   ATAAAATTAT CAAGTATTTA AATTGAGTAA AATAAGCCAA
 281   ACAAATAAGA GTATGTATGA TTCTATTTTT AAAAATTCTG
 321   GAAAATGAAA ACTGATCTAA AGTAATATAA AGAAGATTAG
 361   TAGTTTCCTG GGAATATGTT GGCAGAAGGG AAGGAGAAAG
 401   GATAAGGAAA TAGAAATAGG AAGTAGAAGG ACAGAAAAGA
 441   AGTTGAGGGA ATTTCACTTG TCCACCTTCC TTATAATGGT
 481   AATAGTTATG CCATGATTAT CAGTTTTACA CTTTAAATAT
 521   GTAAAGTTTA TAATCTGTCA ATCAAATCTT ATAAAATGTA
 561   TTATGAGGAA ACAAGTTGAA AATTAGACAA TGTAGGAGTG
 601   ACAGAAAGAT AGATATGAGT ATGTTGAATG TCAGAGATAC
 641   CTGAAAGTTT ATCTACCTGA ACCCTAGTTC TCTCCATAGT
 681   TTAAGGTAAA CAGGAGAGTG CAGGAAAATC ATCCATATTC
 721   TGATTAGGCA GTGGCTTCTG CAAACCACAC TAGGCCTGGC
 761   CGGCTGTGTC CTGGAGTTGG CTAAGGGAGG AGTCAGGGCC
 801   AGTGGTGAGA AGTGCAGGCC CAGATACCAG AACTCACTCA
 841   TCCCAGACAT GAGCTCTTAG ATACACAGAG AGCCCATCCA
 881   TGTGTGGATT TATCTTACAT CTGTAAGTAG AGAACATTGA
 921   CTCTTAGAGA ACATAATTTA CACACATAGG TAAATCTGAA
 961   ATAAGGTGAT CAGTGTGAAG ATTTTATCAC AGCACAGTTT
1001   CATAATAAGC ACAATTTCTC AAATCCCATT GTTGTCACCC
1041   ATCTTCCTCA GGACACTTTC ATCTGCCCTG GGTCCTGCTC
1081   TTTCTTCAGG TGTCTCACCC CAGAGCTTGA TATATAGTAG
1121   GAGACATGCA AATAGGGCCC TCACTCTGCT GAAGAAAACC
1161   AGCCCTGCAG CTCTTTGAGA GGAGCCCCAG CCCTGGGATT
1201   CCCAGCTGTT TCTGCTTGCT GATCAGGACT GCACACAGAG
1241   AACTCACCAT GGAGTTTGGG CTGAGCTGGG TTTTCCTCGT
1281   TGCTCTTTTA AGAGGTGATT CATGGAGAAA TAGAGAGACT
1321   GAGTGTGAGT GAACATGAGT GAGAAAAACT GGATTTGTGT
1361   GGCATTTCT GATAACGGTG TCCTTCTGTT TGCAGGTGTC
1401   CAGTGTCAGC GATTAGTGGA GTCTGGGGGA GGCGTGGTCC
1441   AGCCTGGGTC GTCCCTGAGA CTCTCCTGTG CAGCGTCCGG
1481   ATTCGACTTC AGTAGACAAG GCATGCACTG GGTCCGCCAG
1521   GCTCCAGGCC AGGGGCTGGA GTGGGTGGCA TTTATTAAAT
1561   ATGATGGAAG TGAGAAATAT CATGCTGACT CCGTATGGGG
1601   CCGACTCAGC ATCTCCAGAG ACAATTCCAA GGATACGCTT
1641   TATCTCCAAA TGAATAGCCT GAGAGTCGAG GACACGGCTA
1681   CATATTTTG TGTGAGAGAG GCTGGTGGGC CGACTACCG
1721   TAATGGGTAC AACTATTACG ATTTCTATGA TGGTTATTAT
1761   AACTACCACT ATATGGACGT CTGGGGCAAA GGGACCACGG
1801   TCACCGTCTC CTCAGGTAAG AATGGCCACT CTAGGGCCTT
1841   TGTTTTCTGC TACTGCCTGT GGGGTTTCCT GAGCATTGCA
1881   GGTTGGTCCT CGGGGCATGT TCCGAGGTTG ACCTGGGCG
1921   GACTGGCCAG GAGGGGACGG GCACTGGGGT GCCTTGAGGA
1961   TCTGGGAGCC TCTGTGGATT TTCCGATGCC TTTGGAAAAT
2001   GGGACTCAGG TTGGGTGCGT CTGATGGAGT AACTGAGCCT
2041   GGGGGCTTGG GGAGCCACAT TTGGACGAGA TGCCTGAACA
2081   AACCAGGGGT CTTAGTGATG GCTGAGGAAT GTGTCTCAGG
2121   AGCGGTGTCT GTAGGACTGC AAGATCGCTG CACAGCAGCG
2161   AATCGTGAAA TATTTCTTT AGAATTATGA GGTGCGCTGT
2201   GTGTCAACCT GCATCTTAAA TTCTTTATTG GCTGGAAAGA
2241   GAACTGTCGG AGTGGGTGAA TCCAGCCAGG AGGGACGCGT
2281   AGCCCCGGTC TTGATGAGAG CAGGGTTGGG GGCAGGGGTA
2321   GCCCAGAAAC GGTGGCTGCC GTCCTGACAG GGGCTTAGGG
```

```
2361  AGGCTCCAGG ACCTCAGTGC CTTGAAGCTG GTTTCCATGA
2401  GAAAAGGATT GTTTATCTTA GGAGGCATGC TTACTGTTAA
2441  AAGACAGGAT ATGTTTGAAG TGGCTTCTGA GAAAAATGGT
2481  TAAGAAAATT ATGACTTAAA AATGTGAGAG ATTTTCAAGT
2521  ATATTAATTT TTTTAACTGT CCAAGTATTT GAAATTCTTA
2561  TCATTTGATT AACACCCATG AGTGTATATG TCTGGAATT
2601  GAGGCCAAAG CAAGCTCAGC TAAGAAATAC TAGCACAGTG
2641  CTGTCGGCCC CGATGCGGGA CTGCGTTTTG ACCATCATAA
2681  ATCAAGTTTA TTTTTTTAAT TAATTGAGCG AAGCTGGAAG
2721  CAGATGATGA ATTAGAGTCA AGATGGCTGC ATGGGGGTCT
2761  CCGGCACCCA CAGCAGGTGG CAGGAAGCAG GTCACCGCGA
2801  GAGTCTATTT TAGGAAGCAA AAAAACACAA TTGGTAAATT
2841  TATCACTTCT GGTTGTGAAG AGGTGGTTTT GCCCAGGCCC
2881  AGATCTGAAA GTGCTCTACT GAGCAAAACA ACACCTGGAC
2921  AATTTGCGTT TCTAAAATAA GGCGAGGCTG ACCGAAACTG
2961  AAAAGGCTTT TTTTAACTAT CTGAATTTCA TTTCCAATCT
3001  TAGCTTAT
```

The V374p PG9HC Donor DNA (SEQ ID NO:53) has the following segments:
1) A Human IGHV V3-74 promoter, IMGT reference sequence (SEQ ID NO:54, from GenBank: L33851, nucleotides 1-1294 of SEQ ID NO:53,
2) A 5' crispr guide sequence (GAAAACCAGCCCTGCAGCTCTTT: SEQ ID NO:55 with a mutant PAM site (TTT) nucleotides 1154-1176 of SEQ ID NO:53);
3) A Human IGHV V3-33 intron, IMGT reference sequence (from GenBank: AB019439, nucleotides 1295-1395 of SEQ ID NO:53), shown below as SEQ ID NO:56

```
1295                GTGATT CATGGAGAAA TAGAGAGACT
1321  GAGTGTGAGT GAACATGAGT GAGAAAAACT GGATTTGTGT
1361  GGCATTTTCT GATAACGGTG TCCTTCTGTT TGCAG
```

4) PG9 heavy chain VDJ gene (SEQ ID NO:57, from GenBank GU272045.1 nucleotides 1396-1814);
5) A 3' end of the IGHV J6 gene (intron), IMGT reference sequence (SEQ ID NO:58, from GenBank: AL122127, nucleotides 1815-3008); and
6) A 3' crispr guide sequence (TCCTCGGGG-CATGTTCCGAGGTT, SEQ ID NO:59) with a mutant PAM site (GTD).

VL4-69p-VLJ7 PG9LC Donor (SEQ ID NO: 60)
```
   1  AGATCTCTTC AATTCCATTT ACTCTCTAGC AATTTACCTA
  41  ATATCAAAAC ATACAGTTAT GTTATGTTTA CAAATATGCA
  81  CGCACCTCTA TTAATATGTG TTCATAAGTA CATACACATG
 121  CACCATTACG TTTACACATA CATGCATGTA ACACCAACTG
 161  ATGTAAAAAT CATTGTTTTA TGTACTCAGT TTTCCTTTGA
 201  GTTTACCCTC TTTTCTCTAC TTTTTAAAAT ATTTATTTCT
 241  AATTTGGGGA GCTACTAACT GAGATTATTT TTCATCTCAC
 281  TGAAAAACAG TTTTAGAATT TCCTGTAGAG CAGTTCTGCT
 321  GGTGGCAAAT TCCATCGGGT TTTGTCTGAA AAGTAGCCAT
 361  TTTCTCCTAT TTTTTCTGTT TATTATATAG AAAGATAACT
 401  TATATAAAGT AAAATTCACA GGTCTTAATT ATACAGTTTG
 441  ATGGTTTTTA CAAATGCAGA TGCTCATGTA GCCAACAGTC
 481  CGATCCATTC TCACAACATC TCCATTACTG CAGAATGGAG
 521  ACATTCTGTT CCAGTCAATG TAAATTATCC CATTACACCT
 561  ACCAAATAGA ACGTGTATGA GAGACACCTT TCTCCTGAGG
 601  ACTTTTGCAA AGTGGGGTGG ATCATGTGTC CCGCTCCCAC
 641  TGAAAAGGGC TAAATGGAAA ACTAAAGTCT GAAATAAAAT
 681  AGGAGGCTGC CCTGACGAGG GGTCCCACTT TGCCCTTGGA
 721  CAGAGAACAG GCCGTGGTCA AGGCCCTGGT CCGGGCAGAA
 761  GCCTCTGTCA GGACCCACTG GCATCGGTC ACAGACACGA
 801  TGGACCTGGG CCTAGGCAGA AGGGGGTGCT GTTGGTCTGC
 841  TGCTGAGGGC TCTGTGGGTT TCTCAGCTGG GAAACCAAAC
 881  ACTTGAACTT GGTCTCCACG CAGGGTTCAC TGGGGCCAGC
 921  AGCTGGGCTC TCTCTGCACC CTTGGAGAGC CTCAGGCCAG
 961  GCCCAGCCCA GGTAACCCCT CCCAGAAATG TCACCCCACC
1001  ACTGGGACTG ACACTCAGGC ACACGGAGTG ATTTGGTTGG
1041  GCAGAGGAAG AGGAGCACAT TTGCATGAAG GCCCCTCTC
1081  TCTTTTCTGG GACTACAGGG TGGGTAAGAA ATACCTGCAA
1121  CTGTCAGCCT CAGCAGAGCT CTGGGGAGTC TGCACCATGG
1161  CCTGGGCTCT GCTGCTCCTC ACCCTCCTCA CTCAGGGCAC
1201  AGGTGACGCC TCCAGGGAAG GGGCTTCAGG GACCTCTGGG
1241  CTGATCCTTG GTCTCCTGCT CCTCAGGCTC ACCGGGGCCC
1281  AGCACTGACT CACTGGCATG TGTTTCTCCC TCTTTCCAGG
1321  GTCCTGGGCC CAGTCTGCCC TGACTCAGCC TGCCTCCGTG
1361  TCTGGGTCTC CTGGACAGTC GATCACCATC TCCTGCAATG
1401  GAACCAGCAA TGATGTTGGT GGCTATGAAT CTGTCTCCTG
1441  GTACCAACAA CATCCCGGCA AAGCCCCCAA AGTCGTGATT
1481  TATGATGTCA GTAAACGGCC CTCAGGGGTT TCTAATCGCT
1521  TCTCTGGCTC CAAGTCCGGC AACACGGCCT CCCTGACCAT
1561  CTCTGGGCTC CAGGCTGAGG ACGAGGGTGA CTATTACTGC
1601  AAGTCTCTGA CAAGCACGAG ACGTCGGGTT TTCGGCACTG
1641  GGACCAAGCT GACCGTTCTA GGTAAGTCTC CCCGCTTCTC
1681  TCCTCTTTGA GATCCCAAGT TAAACACGGG GAGTTTTTCC
1721  CTTTCCTGTC TGTCGAAGGC TAAGGTCTAA GCCTGTCTGG
```

```
1761  ATGTCTGGAA TCTTTGCCCC TCCTTGCCTG GGCTCCTGCC
1801  CTCTTCTGTG ATTCTGTCCT CTGTGGGTCC CAGTTACGGG
1841  GCTGCATTAA ACACAGTGAC AGGAGGCCTT TGACTGAGGA
1881  CTTGGAGAGA TGGGGGAGGA AATGGCAGGA GGACAAAGAT
1921  AGAGGAAGAA TATTCCGTGA GAAGGTGGCC CCACAGCGCT
1961  GGGTCACACG CCATCCCCCA AGACAGGCAG GACACCACAG
2001  ACAGGGTGGT GGGTCTCAGA AAACTCAGGC CCTAAACGTG
2041  GATGCTTACC AATTCCTCCA CTGGAGGAAG ACCTCAGAGC
2081  AGATGCCCAG GACAGGGACT TCTGGTAGGG ACGGTGACTG
2121  GGACGGGTGC CTGTTTGTCA GGGAAAACCC ACTGGAGAGT
2161  CAGATCCCCC AGATAACTTC TCACGACATG GAGACTCTTT
2221  CGAACAGACA AAGCTCCACG TTCAGCTCAG GGAGTAAAAA
2261  AAAAATGCCT CAAATGGAGG CCTTTGATCT ACTGGAATCC
2321  AGCCCCCAGG ACTGACACCC TGTCTCACCA GGCAGCCCAG
2361  AGGGGTCTCT GCAGGGAGGT CGCGTGGGGC CTGCAATGAT
2401  GGCACCAGGG AGATGTGTGG GTAAGAAACC CACTCCCTGT
2441  GAGAGAGAAG AGCCTGAACC CAGGACCAAC AGCTGCCCTG
2481  CATGAAGAGA TGAGAACAAG GGGAACTGGT AGGAGGTGTT
2521  CAGACAGACA CCCCCAAGAT AGACAAATAC CCAGGGTGAG
2561  ATGTGGTCCT GGAC1CCATC CCATCCAGTG TGGAGCCAGC
2601  ACCGGTGGGG GTCTATAGGT GATGGAAAAT ATGAAAAAGA
2641  GACAGATCCA AGAGGGGGTC TGTGACCCCC AAGAGTGGGG
2681  GCAACTCCCA TCTGACAGCG AGTGTCTCCA CTCACCGCTG
2721  ACCTGACCTC AGTCCAGCAA GGGTCCGGCC TGAGGTCCCT
2761  GCCCTGGGCC TTAGTCCCAT ACCCACTTCA AGACTGAGGT
2801  CAGGGGCTCC CCAGGTGGAC ACCAGGACTC TGACCCCCTG
2841  CCCCTCATCC AGGATCC
```

The VL4-69p-VU7 PG9LC Donor (SEQ ID NO:60) has the following segments:
1) Human VL4-69p, IMGT reference sequence (SEQ ID NO:61, from GenBank: D86993, nucleotides 1-1156 of the SEQ ID NO:60 sequence),
2) A 5' CRISPR guide sequence (TTTCTGGGACTA-CAGGGTGGGTA; SEQ ID NO: 62) with a TTT mutation;
3) Mature PG9 light chain (SEQ ID NO:63; nucleotides 1157-1661 of the SEQ ID NO:60 sequence);
4) VLJ7-Cintron, IMGT reference sequence (SEQ ID NO:64 from GenBank: D87017, nucleotides 1662-2857 of the SEQ ID NO:60 sequence); and
5) A 3' CRISPR guide sequence (CCCAAGT-TAAACACGGGGAGTTT SEQ ID NO:65 with mutation (CCC).

B Cell Engineering

Optimal nucleofection parameters for Ramos RA 1, 2G6 (from ATCC) or EBV transformed polyclonal B cell lines were identified using a GFPmax (Lonza) plasmid as described for the Neon transfection System (Life Technologies). Optimal setting were used to nucleofect 10 µg of HR110PA-1 PG9 donor DNA along with 2.5 ug each gRNA plasmid (pX330) into 5×10⁶ cells using the 100 µl tip according to the manufacturer's instructions. Cells were recovered in antibiotic fire media at normal culture conditions and grown for 72 hours.

Engineered Cell Selection

Three days post nucleofection. B cells were washed in PBS and stained in FACS buffer (PBS+1% FBS) with randomly biotinylated (EZ-Link NHS-Biotin, ThermoFisher), PGT145 purified C108.c03 HIV Env SOSIP (Voss et al. Cell Press (under review) (2017)) FITC or APC labeled streptavidin tetramers (SA1005, SA10002, ThermoFisher) as described by McCoy et al. (*Cell Rep* 16, 2327-2338 (2016)). Briefly, 2 µg of biotinylated SOSIP was mixed with 0.5 µl of streptavidin in 7.5 µl PBS and incubated 30 min. Two microliters of this solution was then incubated for 45 min with 5×10⁶ cells in 100 µl FACS buffer. Cells were again washed and single live B cells positive for APC fluorophore (or both APC and FITC in the case of engineered EBV transformed polyclonal cells), were selected for further passage using the FACSARIA III (BD Biosciences). Selection gates were made using unengineered cell controls incubated with the same probes. In the case of engineered EBV cells, selected cells were spiked into unengineered cells (to enrich engineered cell numbers) and cultured for a second round of selection.

gDNA Sequence Analysis

Genomic DNA was isolated from 3×10⁶ cells using the AllPrep DNA/RNA Mini Kit (Qiagen) for use as template in a PCR reaction using 3 forward and reverse primer sets specific for genomic regions beyond the 5' and 3' homology regions found within the donor DNAs. These primer sets were designed using the NCBI Primer BLAST server. For the V781 engineering strategy:

1 (5'-AGCCCTAAAAAGCATGGGCT-3' (SEQ ID NO: 66) and

5'-CTTCTGCACCAAGAGGAGGG-3' (SEQ ID NO: 67)), 2 (5-'GCCCTAAAAAGCATGGGCTG-3' (SEQ ID NO: 68) and 5'-TCCCCTCCCTTCTGAGTCTG-3' (SEQ ID NO: 69))
and 3 (5'-GCCATTGTGAGTGAGCCCTA-3' (SEQ ID NO: 70) and

5'-AGTCTGCAGTAAACCCCTGC-3' (SEQ ID NO: 71)).

For the V434 Strategy 1 (5'-ATGTGATTGGCTCCAGGCAT-3' (SEQ ID NO: 72) and

5'-CTTCTGCACCAAGAGGAGGG-3' (SEQ ID NO: 73)), 2 (5'-GAATGTGATTGGCTCCAGGC-3' (SEQ ID NO: 74) and 5'-AGTCTGCAGTAAACCCCTGC-3' (SEQ ID NO: 75))
and 3 (5'-GCCAGAATGTGATTGGCTCC-3' (SEQ ID NO: 76) and

5'-CCAGTGGGGCTTGGTATGTT-3' (SEQ ID NO: 77)).

The reaction was carried out using Phusion HF Polymerase (NEB), 200 ng template, 0.4 µM each primer, 200 µM each dNTP in a total volume of 100 µl. After denaturing at 98'C for 30 sec. performed 34 cycles at 98'C for 10 sec., 63'C for 30 sec., then 72'C for 3.5 min. followed by a 30 min. hold at 72TC. The 5.5 kb product was purified on 1% agarose and the DNA extracted using the QIAquick Gel Extraction Kit (Qiagen). The PCR product was sequenced using Sanger sequencing (Eton Bioscience) with many primers such that the complete 5.5 kb sequence contig could be assembled.
For V781 strategy:

```
                                    (SEQ ID NO: 78)
5'-GCCATTGTGAGTGAGCCCT-3', (SEQ ID NO: 79)
5'-GCATACTACAGAAGTGAGAAACAAAGACAG-3', (SEQ ID NO: 80)
5'-GAATAGGCAGACATACACGTAGATCAGC-3', (SEQ ID NO: 81)
5'-CCTACAGGTATTATCAGGTACAATAATCAACTGC-3', (SEQ ID NO: 82)
5'-GTGAGCATTTATCAAACTGGATGTTGTAATGAG-3', (SEQ ID NO: 83)
5'-GGAGAATCCCCTAGAGCACAGC-3', (SEQ ID NO: 84)
5'-CGACTACCGTAATGGGTACAACTATTACG-3', (SEQ ID NO: 85)
5'-CTTTATTGGCTGGAAAGAGAACTGTCGG-3', (SEQ ID NO: 86)
5'-CAGATGATGAATTAGAGTCAAGATGGCTGC-3', (SEQ ID NO: 87)
5'-GACGCCGCATCGGTGATTCGG-3', (SEQ ID NO: 88)
5'-CCACCTCTTCACAACCAGAAGTG-3', (SEQ ID NO: 89)
5'-GCCCCTGTCAGGACGGCAGCCACCG-3', (SEQ ID NO: 90)
5'-GGAGATAAAGCGTATCCTTGG-3', (SEQ ID NO: 91)
5'-CGTAATCCTGTTAGAGGCCACGC-3', (SEQ ID NO: 92)
5'-GCCGTTTCCTGGAGCTCGAGAGGC-3', (SEQ ID NO: 93)
5'-CGTAAACACCAAAACAACACACCC-3'.
```

For V434 Strategy:

```
                                    (SEQ ID NO: 94)
5'-GCCAGAATGTGATTGGCTCC-3', (SEQ ID NO: 95)
5'-CCTAGTTATGTTGAGTTCCATCAACACTCC-3', (SEQ ID NO: 96)
5'-CGACTACCGTAATGGGTACAACTATTACG-3', (SEQ ID NO: 96)
5'-CAGATGATGAATTAGAGTCAAGATGGCTGC-3', (SEQ ID NO: 97)
5'-GACGCCGCATCGGTGATTCGG-3', (SEQ ID NO: 98)
5'-GCAAATTCCATGTTGCAGTGAGAAGG-3', (SEQ ID NO: 99)
5'-GGGCAAAACCACCTCTTCACAACC-3', (SEQ ID NO: 100)
5'-GCTCTTTGGTTTTCTTTCCACG-3', (SEQ ID NO: 101)
5'-GCACACCCTAGGGTATGTTCTTGC-3', (SEQ ID NO: 102)
5'-GGTACTATTTAAAAATAACCCAC-3', (SEQ ID NO: 103)
5'-GCAAATCCTCACTTAGGCACCC-3', (SEQ ID NO: 104)
5'-GCTGACTCCGTATGGGGCCGAC-3', (SEQ ID NO: 105)
5'-GAGCCTGGGGGCTTGGGGAGCC-3', (SEQ ID NO: 106)
5'-CGACTACCGTAATGGGTACAACTATTACG-3'.
```

For WT:

```
                                    (SEQ ID NO: 107)
5'-GCCAGAATGTGATTGGCTCC-3', (SEQ ID NO: 108)
5'-CTTTATTGGCTGGAAAGAGAACTGTCGG-3', (SEQ ID NO: 109)
5'-CAGATGATGAATTAGAGTCAAGATGGCTGC-3', (SEQ ID NO: 110)
5'-GGTTAACTCGTTTTCTCTTTGTGATTAAGGAG-3', (SEQ ID NO: 111)
5'-GACGCCGCATCGGTGATTCGG-3', (SEQ ID NO: 112)
5'-GCAAATTCCATGTTGCAGTGAGAAGG-3', (SEQ ID NO: 113)
5'-GGGCAAAACCACCTCTTCACAACC-3', (SEQ ID NO: 114)
5'-GCTCTTTGGTTTTCTTTCCACG-3', (SEQ ID NO: 115)
5'-GCACACCCTAGGGTATGTTCTTGC-3', (SEQ ID NO: 116)
5'-GGTACTATTTAAAAATAACCCAC-3', (SEQ ID NO: 117)
5'-GCAAATCCTCACTTAGGCACCC-3', (SEQ ID NO: 118)
5'-GCTGACTCCGTATGGGGCCGAC-3', (SEQ ID NO: 119)
5'-GAGCCTGGGGGCTTGGGGAGCC-3', (SEQ ID NO: 120)
5'-CTTAGGAGCTGAACAAGTGGGC-3', (SEQ ID NO: 121)
5'-CCATAAACACCGCAGGTGAGGG-3', (SEQ ID NO: 122)
5'-CCCCTGGTTTGTTCAGGCATCTCG-3', (SEQ ID NO: 123)
5'-CCTAGTTATGTTGAGTTCCATCAACACTCC-3'.
```

Sanger Sequencing of mRNA

To confirm the presence of PG9 mRNA in Ramos RA 1 engineered cells and to detect isotype switching from PG9 IgM to IgG in engineered Ramnos 2G6 engineered cells, total RNA was isolated from 3×10P pelleted cells using the AllPrep DNA/RNA Mini Kit (Qiagen) then used as template for reverse transcription and amplification using the OneStep RT-PCR Kit (Qiagen) with forward primers (Integrated DNA Technologies) specific to the Ramos WT antibody variable region 5'-AAACACCTGTGGTTCTTCCTCCTCC-3' (SEQ ID NO: 124), the PG9 antibody variable region 5'-GCTGGGTTTTTCCGTTGCTCTTTTAAG-3' (SEQ ID NO: 125) and reverse primers specific to the IgM constant region 5'-GCGTACTTTGCCCCCTCTCAGG-3' (SEQ ID NO:126) and the IgG constant region 5'-GCTTGTGATTCACGTTGCAGATGTAGG-3' (SEQ ID NO127).

The reactions contained 400 μM each dNTP, 0.6 μM each forward and reverse primer, 10 ng RNA template, 5U RNasin Plus (Promega) in a total volume of 50 μl. The conditions were 50° C. for 30 min., 95° C. for 15 min. then 30 cycles of 94° C. for 30 sec., 58° C. for 40 sec. and 72° C. for 60 sec. followed by an additional 10 min. at 72° C. Products were visualized on 1% agarose and purified using the QIAquick PCR Purification Kit (QIagen). The PCR products were sequenced using Sanger sequencing with the same primers used for the PCR (ETON Bioscience).

Next Generation Sequencing of Ig mRNA

To characterize the introduction and selection of mutations in Ig heavy and light chain variable gene regions in HIV Env SOSIP selected Ramos cells, and to identify PG9 mRNA in engineered polyclonal B cells, RNA was prepared (RNEasy kit, Qiagen) from total cells and was subjected to reverse transcription using barcoding primers that contain unique Ab identifiers as described by Briney et al. (*Cell* 166, 1459-1470 (2016)). The cDNA was then amplified using a mix of gene specific primers. Illumina sequencing adapters and sample-specific indexes were added during a second round of PCR as previously described (id.). Samples were quantified using fluorimetry (Qubit, Life Technologies), pooled at approximately equimolar concentrations, and the sample pool was requantified before loading onto an Illumina MiSeq (MiSeq v3 Reagent Kit, Illumina). Paired-end MiSeq reads were merged with PANDAseq (Masella et al. *BMC Bioinformatics* 13, 31 (2012)). Germline assignment, junction identification, and other basic Ab information was determined using AbStar (see website at github.com/briney/abstar).

In Vitro Affinity Maturation

Ramos RA 1 cells engineered to replace the endogenous VDJ with PG9 VDJ using the universal (V781) strategy and selected with C108 SOSIP in FACS was passaged 8 times to allow for the introduction of mutations into the Ig variable regions. Cells were titrated with biotinylated PGT145 purified WITO, MGRM8, CRF-T250 or C108 SOSIP (Voss et al. Cell Press (under review) (2017)), APC-labeled streptavidin tetramers (described above). Cells were incubated with a range of concentrations (3-0.0015 μg/ml SOSIP as tetramer solution) for 45 minutes in FACS buffer and washed with PBS. APC+ gates were set using unengineered Ramos cells incubated with the highest concentration of SOSIP probe (3 μg/ml SOSIP as tetramer). Engineered cells in the APC+ gate at each SOSIP incubation concentration were plotted as a % of total cells against the log of the probe concentration in μg/ml to calculate the effective concentration require to stain 10% of cells (EC10). MGRM8 or WITO probes were incubated with either MGRM8 or WITO APC-labeled tetramer as previously described at their EC10 concentrations along with 1000× dilution of anti-human lambda FITC-labeled antibody (southern biotech) for 45 min. Cells were washed and live single cells with the highest APC signal (top 5%) after normalization for surface BCR levels (FITC) were selected for subsequent expansion and further sorting with WITO or MGRM8 SOSIPs. This process was repeated twice more with EC10 concentration for probes calculated before each sort. The starting C108 selected engineered line was also continually passaged throughout the experiment for final mRNA sequencing. At the end of the experiment all cell lines were titrated with C108, CRF-T250, WITO and MGRM8 probes. mRNA was harvested from cells after each sorting step and sequenced using next generation sequencing (NGS) as described above.

Example 2: Genome Editing B Cell Receptor Genomic Sequences

Figure 1C:
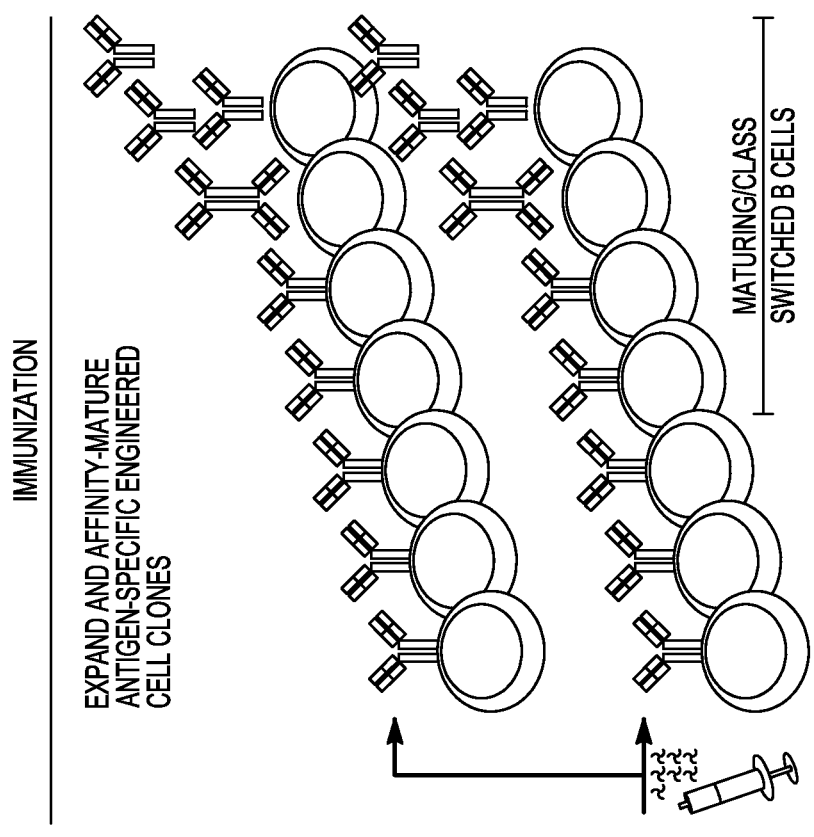
Figure 1B:
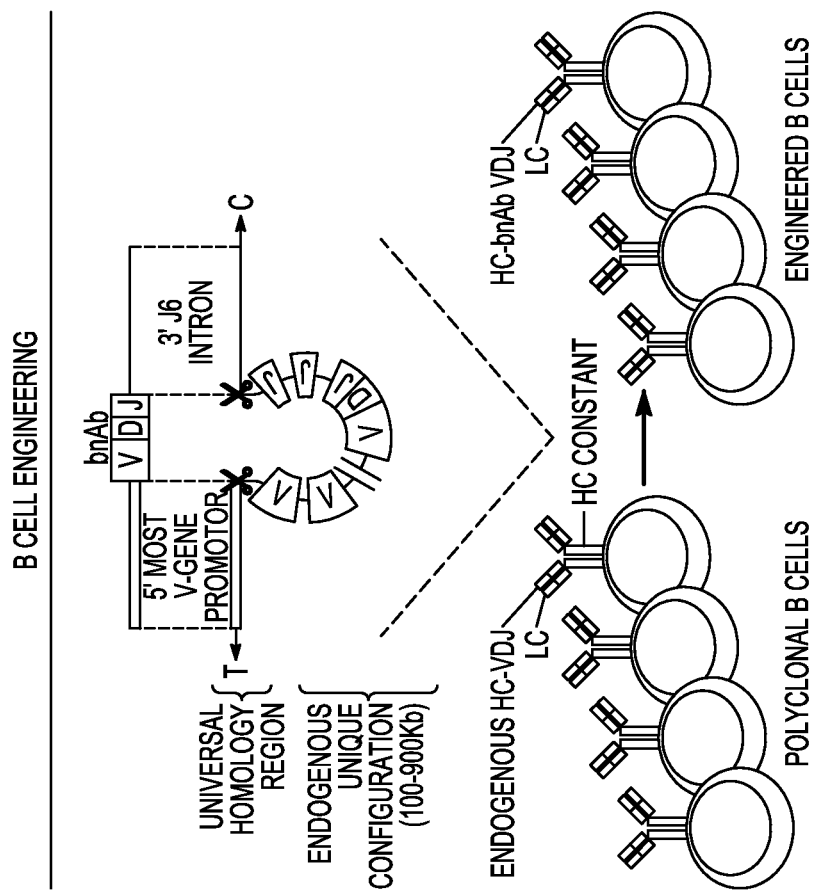
Figures 1, 2B:
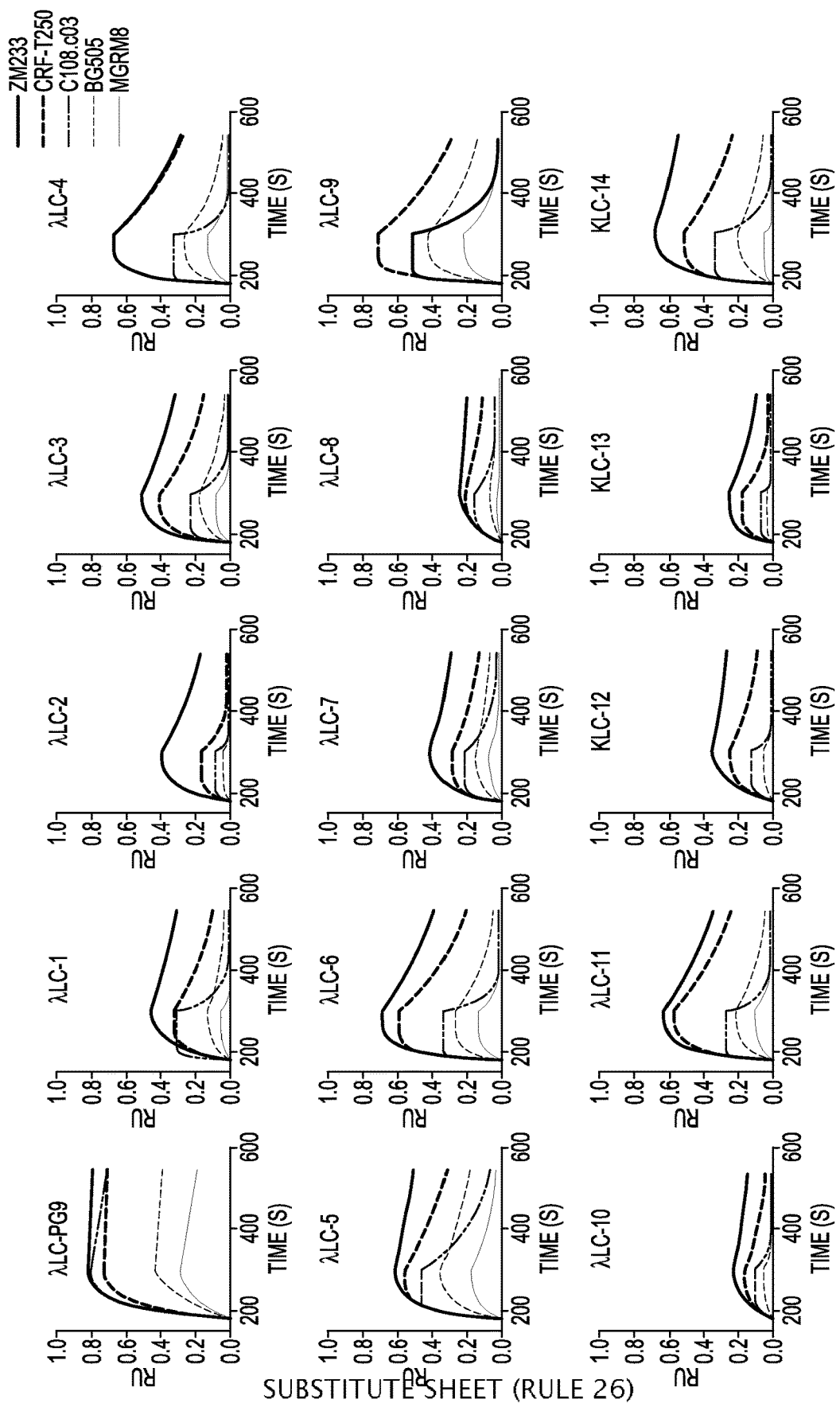

This Example describes modulation of B cell receptor specificities using genome editing technologies. The modulated region was a nearly 1 mega-base (Mb) when in germline configuration and included the immunoglobulin heavy chain variable (IGHV) locus on chromosome 14 (at 14q32.33) (see FIG. 1A).

An HDR strategy was developed that introduced dsDNA breaks after the most 5' V-gene promoter (V7-81 or V3-74), and after the distal J gene (J6), using respective homology regions (HRs) 5' and 3' to these sites that are retained in all human B cells. The distance between these cut sites can vary depending on which V and J genes were assembled in a given B cell (FIG. 1B). Thus, regardless of which V and J genes were previously assembled, the editing strategy described herein introduces the new VDJ gene in a way that allows transcription using a naturally regulated V-gene promoter from its native locus where it would be subject to hypermutation by activation-induced cytidine deaminase (AID). When paired with an endogenous cell light chain (LC), a chimeric immunoglobulin (Ig) is secreted as the isotype determined by the genomic configuration of the heavy chain (HC) constant region.

Primary B cells modified using this strategy are then autologously engrafted, expanded and subject to affinity maturation under normal control mechanisms through immunization to overcome antibody repertoire defined barriers to the elicitation of protective antibodies (FIG. 1C).

Previous studies have suggested that the breadth and neutralization potency of a number of protective broadly neutralizing antibodies (bnAbs) targeting the HIV Envelope glycoprotein (Env) apex region are largely encoded by the heavy chain variable region VDJ. This class of bnAbs possess particularly long heavy chain complementarity-determining region 3 (CDR3) loops, which form the majority of contacts with Env.

The inventors have found that the IgG heavy from the apex-targeting bnAb PG9 could successfully pair with a diversity of lambda and kappa LCs when co-transfected in HEK293 cells, including a LC endogenous to the cell line in which the inventors are providing B cell receptor engineering strategies, the Ramos (RA 1) Burkitt's lymphoma line (FIG. 1D; Table 2).

Purified PG9 chimeras were evaluated for their ability to neutralize HIV. Twelve viruses representing the global diversity of HIV-1 strains (deCamp et al. *J Virol* 88, 2489-2507 (2014)) were examined along with six viruses known to be highly sensitive to neutralization by PG9 (Andrabi et al. *Immunity* 43, 959-973 (2015)). All PG9 chimeric antibodies neutralized one or more of the PG9-sensitive viruses, and most neutralized multiple viruses from different clades in the global panel (FIG. 2A-2B). No chimeric antibody was as broadly neutralizing as the original PG9, indicating at least some light chain-dependent restriction to neutralization breadth.

Most chimeras had measurable binding to recombinantly expressed native Env trimers (SOSIPs) (FIG. 2B), although autoreactivity was detected for some antibodies (FIG. 2C). In the immunization strategy illustrated in FIG. 1C, such autoreactive antibodies would eventually be eliminated by tolerance mechanisms.

Overall, these data show that PG9 nucleic acids can be used to develop proof-of-concept engineering strategies that can confer protective antibody paratopes to B cell receptors through VDJ gene replacement.

Example 3: Replacing the VDJ Region

B cell VDJ editing was first performed in the Ramos (RA 1) B cell lymphoma line. This human monoclonal line expresses an immunoglobulin heavy chain that uses the V4-34 (V), D3-10 (D) and J6 (J) genes as IgM. The V4-34 locus lies halfway through the immunoglobulin heavy chain (IGHV) locus placing the 5' most V-gene promoter (V7-81) about 0.5 Mb upstream (FIG. 1A).

In addition to the B cell editing strategy described above, which grafts the PG9 VDJ gene between the V7-81 promoter and J6 splice site, the inventors developed an engineering strategy that specifically introduced a dsDNA cut 3' of the V4-34 promoter (instead of the V7-81), and used donor DNA with a V4-34 promoter sequence 5' homology region. This strategy replaces only the 400 bp Ramos VDJ rather than a 0.5 Mb region that is replaced using the 'universal' BCR editing strategy (FIG. 3A).

Figure 1D:
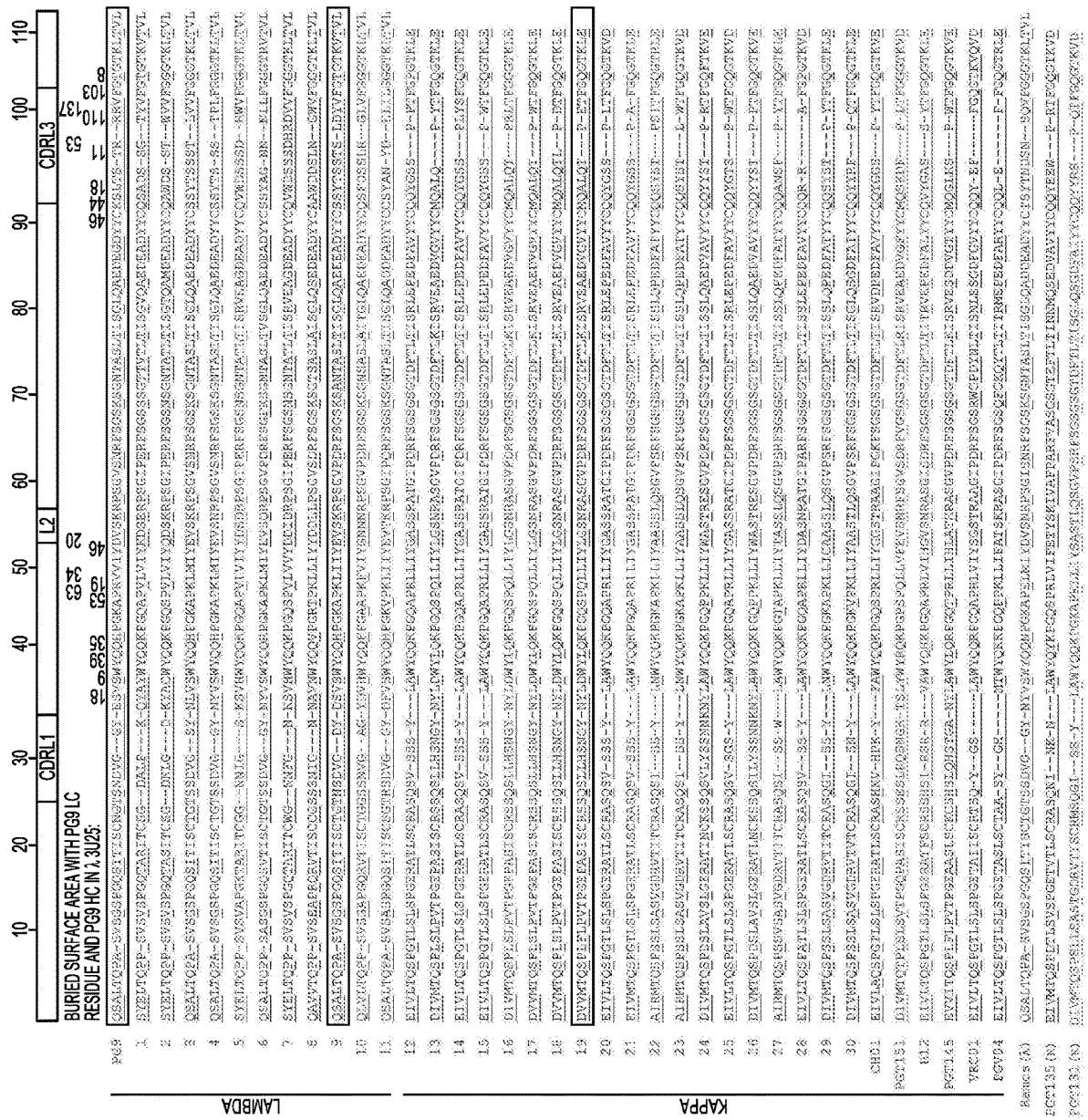
Figure 1E:
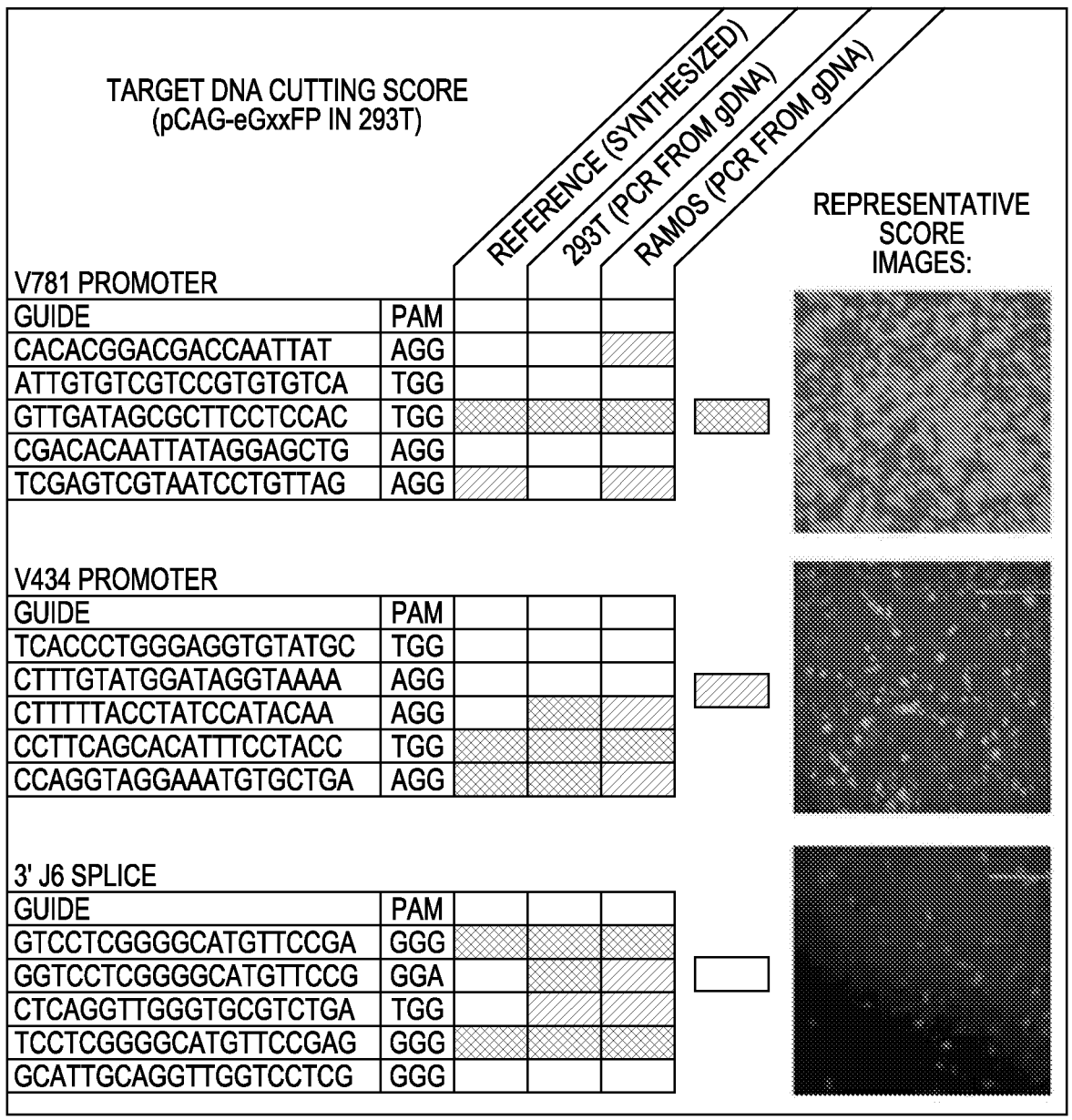

The 'V4-34/Ramos-specific' or the 'V7-81 or V3-74/ universal B cell' VDJ editing reagents were introduced into cells as two plasmids encoding 5' and 3' dsDNA cutting by CRISPR/cas9 (FIG. 1E; Table 3), and one plasmid encoding PG9 donor DNA (Example 1, SEQ ID NOs:1-40) using nucleofection. Cells were cultured for 3 days to allow for PG9 VDJ gene replacement and expression to occur.

TABLE 3

Examples of CRISPR/cas9 guide RNA Sequences

V781 promoter

| Guide | Pam | SEQ ID NO: |
|---|---|---|
| CACACGGACGACCAATTAT | AGG | SEQ ID NO: 128 |
| ATTGTGTCGTCCGTGTGTCA | TGG | SEQ ID NO: 129 |
| GTTGATAGCGCTTCCTCCAC | TGG | SEQ ID NO: 130 |
| CGACACAATTATAGGAGCTG | AGG | SEQ ID NO: 131 |
| TCGAGTCGTAATCCTGTTAG | AGG | SEQ ID NO: 132 |

V434 promoter

| Guide | PAM | SEQ ID NO: |
|---|---|---|
| TCACCCTGGGAGGTGTATGC | TGG | SEQ ID NO: 133 |
| CTTTGTATGGATAGGTAAAA | AGG | SEQ ID NO: 134 |
| CTTTTTACCTATCCATACAA | AGG | SEQ ID NO: 135 |
| CCTTCAGCACATTTCCTACC | TGG | SEQ ID NO: 136 |
| CCAGGTAGGAAATGTGCTGA | AGG | SEQ ID NO: 137 |

TABLE 3-continued

Examples of CRISPR/cas9 guide RNA Sequences

3' J6 SPLICE

| guide | PAM | SEQ ID NO: |
|---|---|---|
| GTCCTCGGGGCATGTTCCGA | GGG | SEQ ID NO: 138 |
| GGTCCTCGGGGCATGTTCCG | AGG | SEQ ID NO: 139 |
| CTCAGGTTGGGTGCGTCTGA | TGG | SEQ ID NO: 140 |
| TCCTCGGGGCATGTTCCGAG | GGG | SEQ ID NO: 141 |
| GCATTGCAGGTTGGTCCTCG | GGG | SEQ ID NO: 142 |

V374 promoter (NEW)

| guide | PAM | SEQ ID NO: |
|---|---|---|
| GCTGTTTCTGCTTGCTGATC | AGG | SEQ ID NO: 143 |
| GATCAGCAAGCAGAAACAGC | TGG | SEQ ID NO: 144 |
| ATCAGCAAGCAGAAACAGCT | GGG | SEQ ID NO: 145 |
| GAAAACCAGCCCTGCAGCTC | TGG | SEQ ID NO: 146 |
| CTGGGTCCTGCTCTTTCTTC | AGG | SEQ ID NO: 147 |
| GAGACACCTGAAGAAAGAGC | AGG | SEQ ID NO: 148 |

Lambda Light chain IGVL4-69 (NEW)

| guide | PAM | SEQ ID NO: |
|---|---|---|
| GCACACGGAGTGATTTGGTT | GGG | SEQ ID NO: 149 |
| CTCAGGCACACGGAGTGATT | TGG | SEQ ID NO: 150 |
| GGCACACGGAGTGATTTGGT | TGG | SEQ ID NO: 151 |
| TACCCACCCTGTAGTCCCAG | AGG | SEQ ID NO: 152 |
| CTCCTCTGGGACTACAGGGT | GGG | SEQ ID NO: 153 |
| CTGCTGAGGCTGACAGTTGC | AGG | SEQ ID NO: 154 |

Lambda Light chain IGVL4-69 (NEW)

| guide | PAM | SEQ ID NO: |
|---|---|---|
| GACCTTAGCCTTCGACAGAC | AGG | SEQ ID NO: 155 |
| GAGATCCCAAGTTAAACACG | GGG | SEQ ID NO: 156 |
| TTCCTGTCTGTCGAAGGCTA | AGG | SEQ ID NO: 157 |
| GGCTAAGGTCTAAGCCTGTC | TGG | SEQ ID NO: 158 |
| AAACTCCCCGTGTTTAACTT | GGG | SEQ ID NO: 159 |
| AAAACTCCCCGTGTTTAACT | TGG | SEQ ID NO: 160 |

To distinguish between the chimeric B cell receptor and the unmodified B cell receptor endogenous to the Ramos cells, fluorescently labeled HIV Env SOSIP trimer(clade AE C108.c03, Andrabi et al. *Immunity,* 43, 959-973 (2015): Voss et al., Cell Press (under review) (2017)) was used, which has been shown to be neutralized by an IgG chimera composed of PG9HC and Ramos LC (FIG. 2A).

Figures 2, 2B, 3:
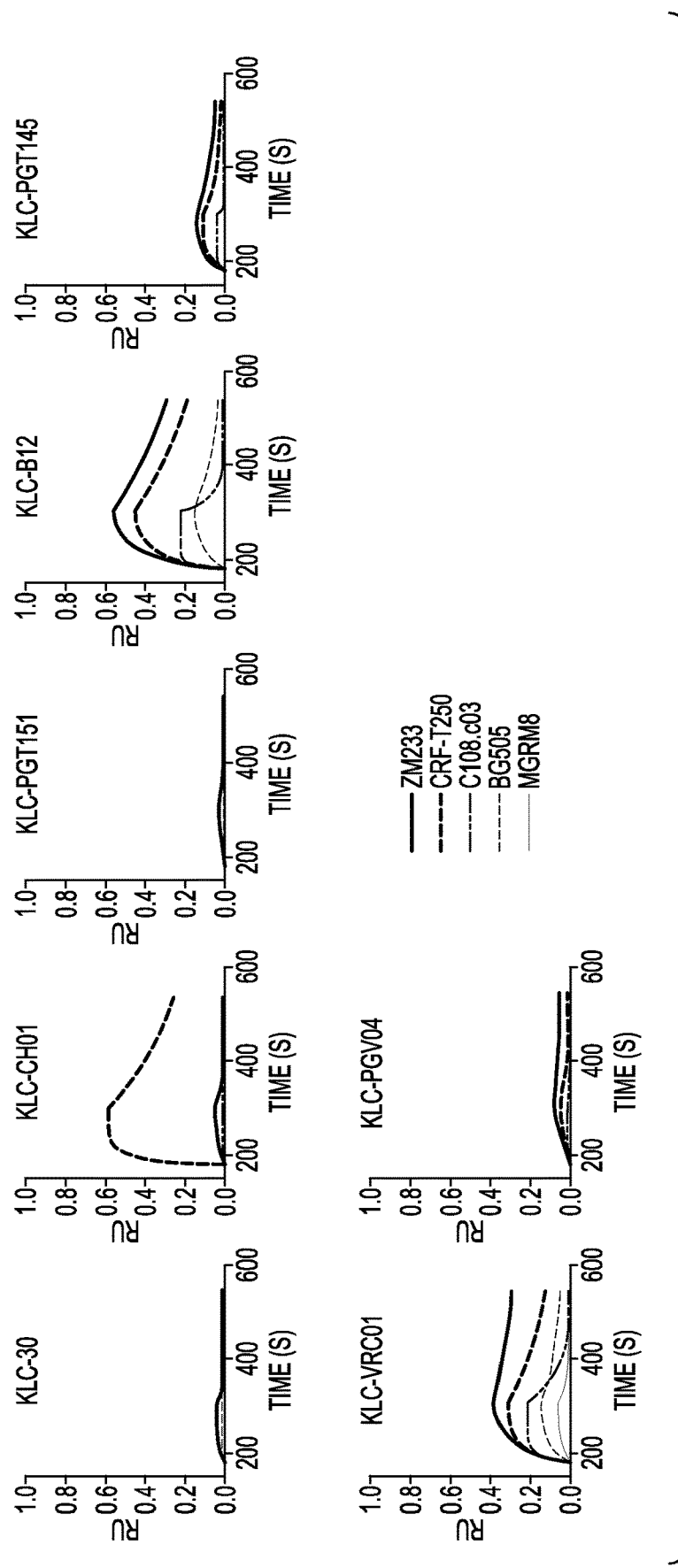
Figures 1, 3C:
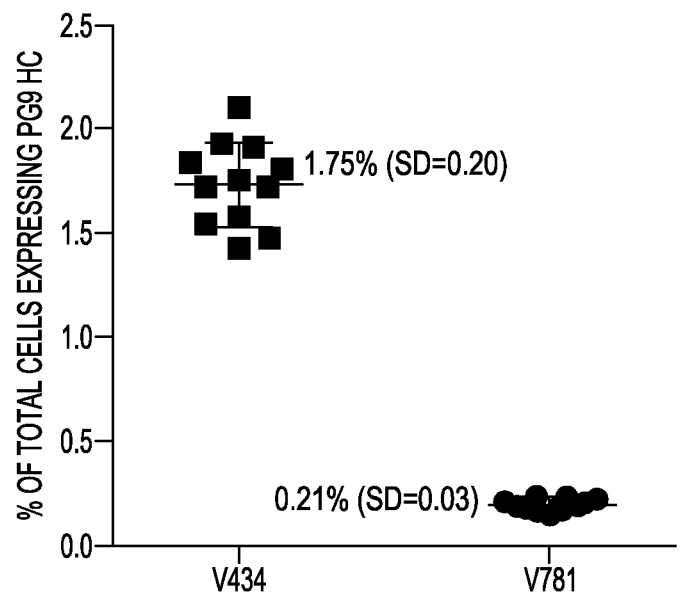
Figures 2, 3C:
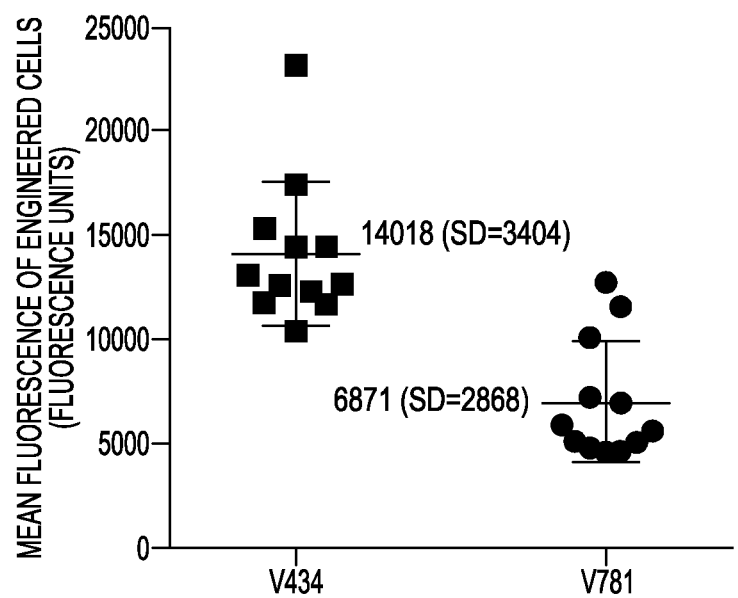

Cells positive for PG9 HC/Ramos LC chimeric IgM were detected by flow cytometry (FIG. 3B). Cells engineered by the V434 or V781 strategies reproducibly converted an average of 1.75% (SD=0.20) or 0.21% (SD=0.03), respectively, of transfected cells into Env binding cells (FIG. 3C-1).

It is remarkable that the universal editing strategy that removed 0.5 Mb of the IGHV locus was only about 8 times less efficient than the Ramos-specific strategy that replaces only 400 bp.

Interestingly, the average fluorescent intensity of engineered cells expressing PG9 from the V781 promoter was reproducibly about half that of cells expressing PG9 from the V4-34 promoter. This may be due to possible differences in promoter strengths and thus surface expression levels of the PG9 chimeric BCR (FIG. 3C-2).

Env SOSIP trimer protein was used to sort successfully engineered HIV-specific cells to produce enriched subpopulations for further experiments. Genomic DNA extracted from these PG9-engineered Ramos cells was PCR amplified using primers that annealed upstream and downstream of the expected insertion sites and outside of the donor DNA HRs. Sanger sequencing of these PCR products confirmed that that the new PG9 gene was grafted as expected between CRISPR cut sites within the IGHV locus (FIG. 3D, FIGS. 3F-3G; 3I-3P).

Figures 2, 2B:
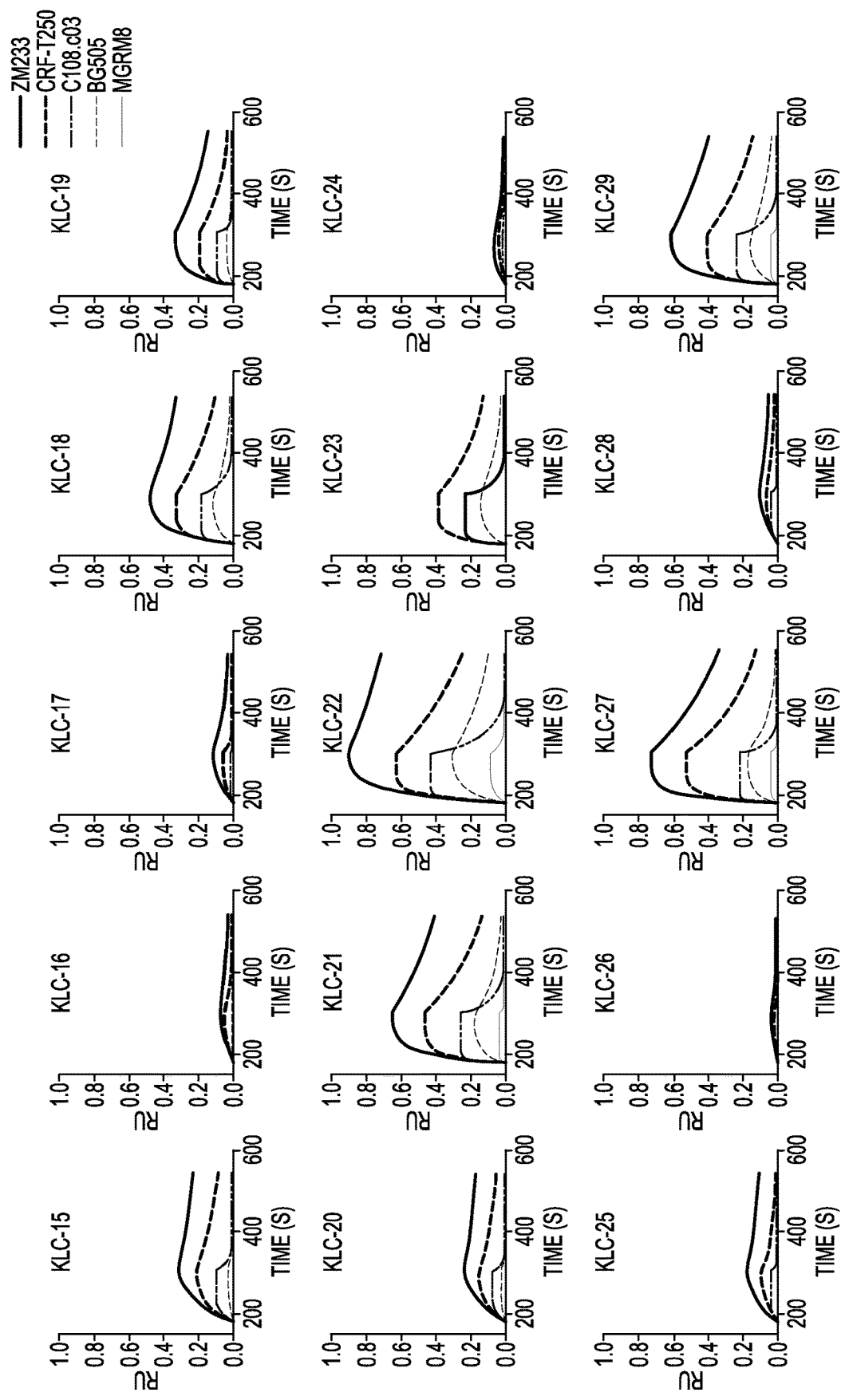
Figures 1, 2C:
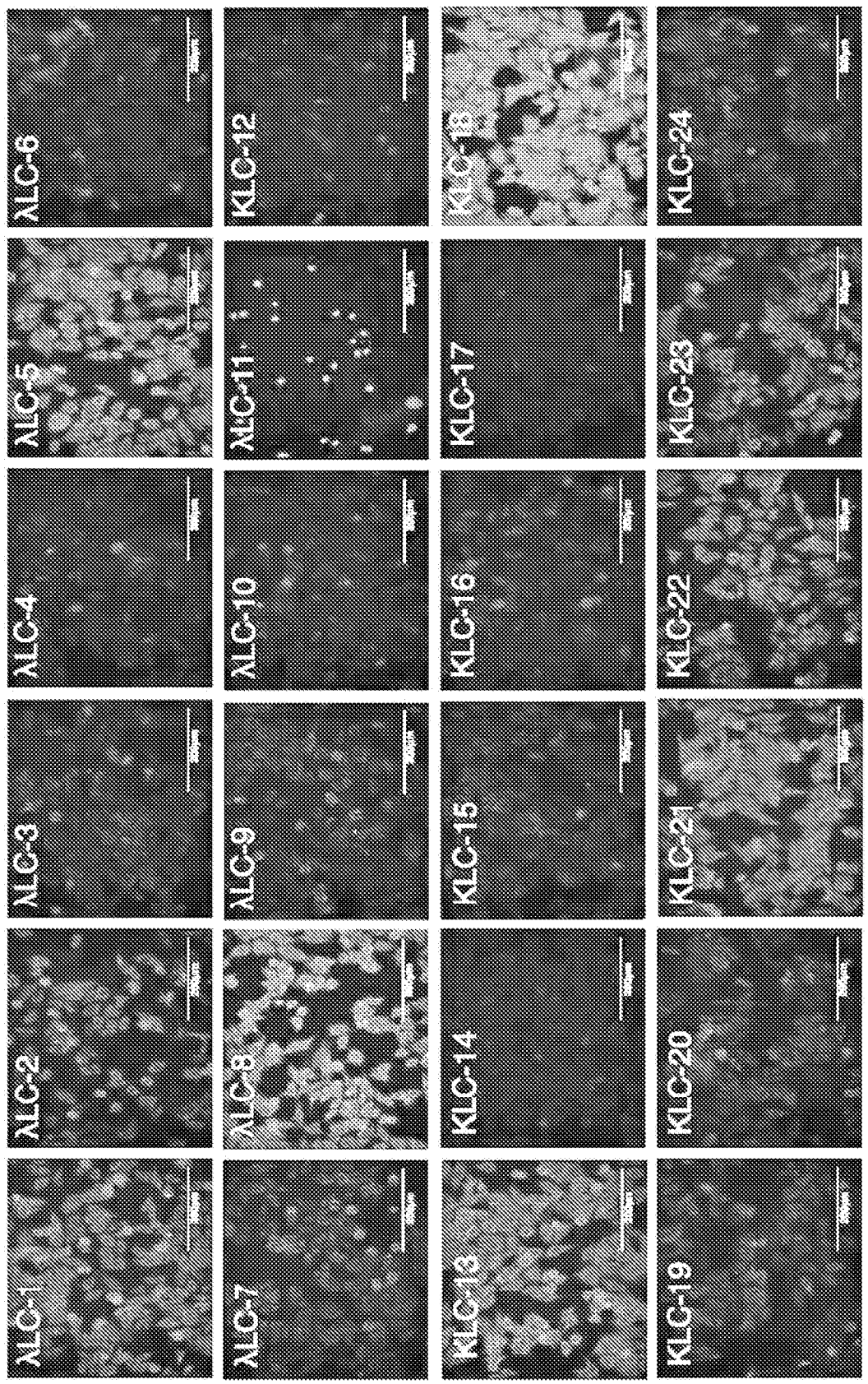
Figures 2, 2C:
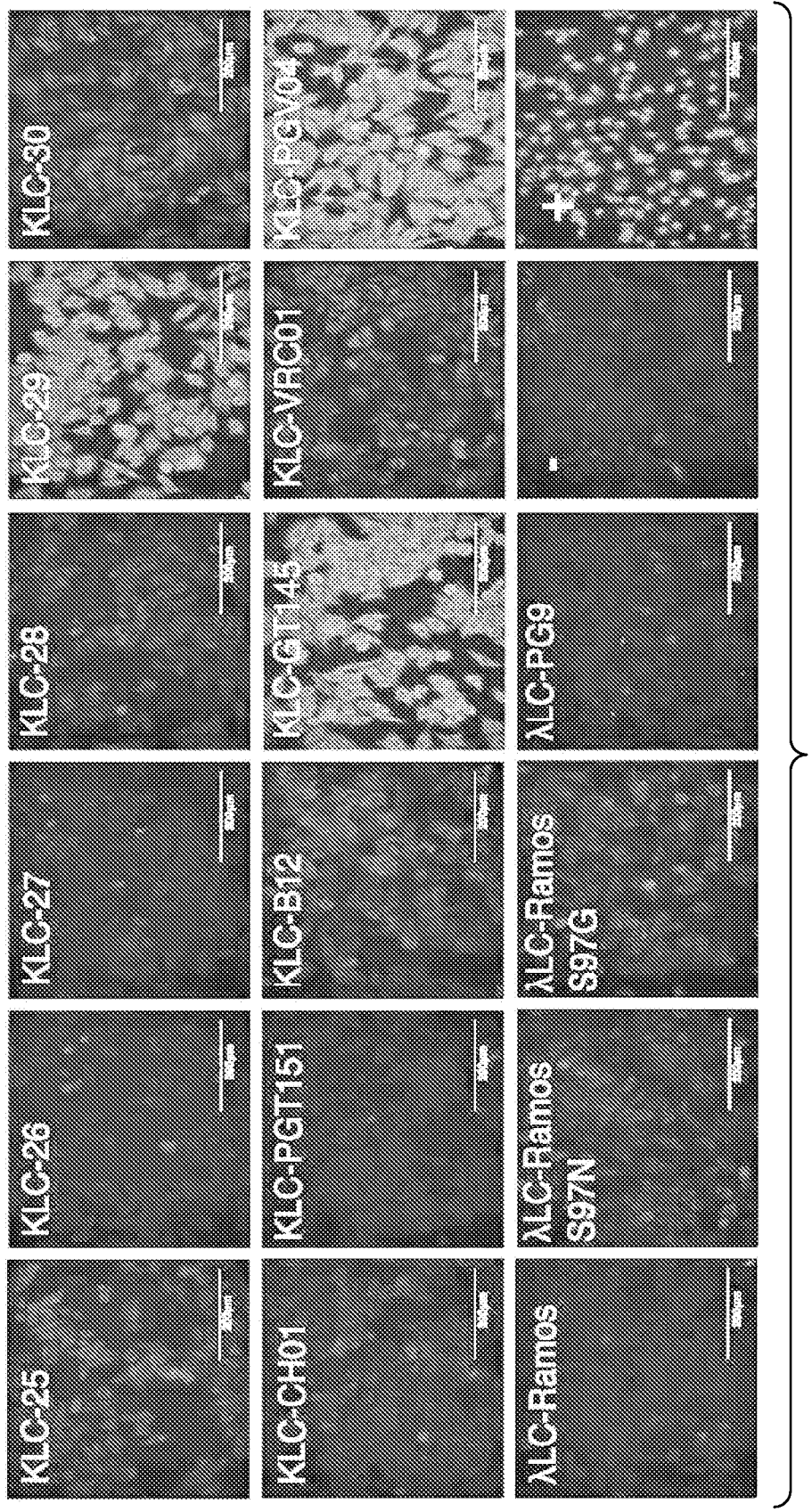
Figures 1, 2, 3D:
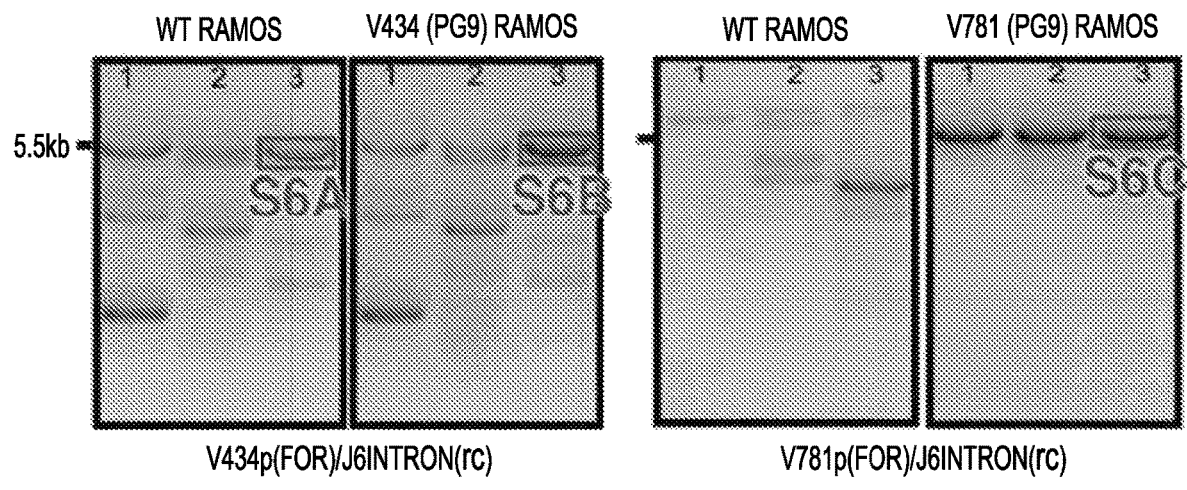

In particular, FIGS. 3D-1 and 3D-2 confirm that the native VDJ region is replaced with PG9 sequences in engineered cells. To show that the engineered cells had the expected genomic modifications, PCR reactions were done on engineered cell genomic DNA using three sets of forward and reverse primers designed to amplify across the entire engineered site including sequence outside of homology regions to ensure that new PG9 gene had engineered cell genomic sequences. Approximate primer annealing sites are indicated by red arrows in FIG. 3A. PCR products using V4-34 promoter/J6 intron primers sets amplified a 5.5 Kb fragment in both V4-34 engineered cells as well as in WT cells (outlined in red rectangular boxes in FIG. 3D). V781 promoter/J6 intron primer sets amplified a 5.5 Kb fragment in V7-81 engineered cells but not in WT cells. Sequences of these PCR products are shown in (FIGS. 3I-3Q). They show that both strategies successfully engineered the IGHV site.

FIG. 3I and FIG. 3M-1 to 3M-3 show shows an assembled 5.5 kb genomic human immunoglobulin heavy chain variable DNA sequence (SEQ ID NO:161) that was isolated by PCR amplification from wild type Ramos lymphoma B cells. The SEQ ID NO:161 sequence is also shown below.

```
TGCACATCTT CGTGTTACCT TCATGACACA GTCAACTCCC
ATTATGTAAG AAATGGTGAG TGCATTCCCA AGGGTCTTGC
ACAGTTATAA AAATAGACTT GATGAGGTGA GGAGTTGTTT
AAATTCCCCT CTGAAGAAGC AGCATCAACC CAACAAACCA
CTCTCTTCCC TCTGTGACTA GAGCTCTGTC ACAGGCCACA
TGGACCTAAA TCCTTGATGG AGATTACAGG ACTACGTAAA
TTGGACTGAT CGTTTTTATG CTGTTAAATT AATAGGTGAG
TCTGCACTCC AGCCTGGGCA ACAGAATAAT CTTGTCTGTA
AAATACAAAA GAAAGATAAA TTAATAGATA CTGACTTTGA
CATTTCGGAT AATAATATTT TCATAAACCG AATTTAATTA
TACCCACATT GTTACCTACA CCTTCACTGA AAAGTTCCTA
GTTATGTTGA GTTCCATCAA CACTCCACAT GTTCAAATCT
GGACATCCAA GAGAGTCTAG AGAATAAAAC GCAATGAGGG
CAGTGAAACT TGCGTATATT CAGCACCTCT TAACTCAGGA
GGACTCAATA CACCCTGGAA CACTCTGCTT TTCTGAATGG
CTCACAATGA CTCCAGCTCA CTCTCCAACC TCCTCAAACA
TCTGGCCTCT GTTTGCCCTA AGTTCACGCT CTGCTCTTAG
TCTATGTTCT GAAGTCTTTG TAAGTGAAAA TGAGCTGTCA
GATGGATCTT CCTTCTCACT GCAACATGGA ATTTGCTATT
TCACTTAATG ACCACTCTTT CCACAATGGT TGATTTCTTT
TGGCCTGTTC ATTACTGGTG ATTTTCAAGG AATCTCAGT
TGAATCTTTA CTGTTTTGCA TTTTGTCTCC ATGACAATGT
TGGGAAGTTT TTCTTCTAGC AGCATAACAT GATCTAGTGA
CCTGACACAT TTGCAGCAAA CAATACCTAC AAATTCAGAA
GCTCTTTGGT TTTCTTTCCA CGAAATATAA TTCTTGCTCT
TCTGTGTATG AGCACATCCT AGCATCCCTG TACACACCCA
CGTAGATGTC TACACGCCGA TGAAATATTC CCTGTAAATA
AAAAAAGTAT CTCAGTTTCT CTCAATGTTC ATAATTCTCC
TGAGGGTGAG GAAGGTACTT CTGGGTCTGC TCAAACAAAT
GGCCCAGAGA CCACCTGGTA GGTAGGTAAG GAGCTCACCT
CGCTCTGGAT ATTGAGTCTG TCTCTTTCCC TCTGTCGTCT
CATAGAAGGC CAGCCCACTT GTTCAGCTCC TAAGAAGAGA
GCCCAGGTTT ATCCAGATTA TACAACACAA CCAGCTTCTG
ATGACTCTCC TGTTACAACA TCCATGGAGA TATTTTGTGT
ATTATATAAT TCACCAAACT AATGTGAAAT GCCCAAGTTG
CAATACTGCA CACCCTAGGG TATGTTCTTG CAATTCAGCG
GAGGAGAAAT TCTTTCAGAG ACAGATGGAT CTGAATTGGT
AAATATGTGG GTACGAATTC TGGGCTTGAG TGTCATTGTC
CAGCCATGTT TCACAGGTGT GACCTGTCAG GGAAGAACCA
GAGTTCCTTG TTCTCTCAGA GGGTAGAGCT CACAGAGGTC
CTCTCTGGTT CCCAGGAAAG GTAATTTCAC TAATCTTGGT
GATGAGACTA TCCTCCAGTG CTGATGTACT ATAGAGTTTT
CATCTGAAGC TGTCACTGCT ATCCCCAATG TACATCTTTT
CACACAGAAA TGTTTAGAGG TCAGGCCATA TTCTCAGGGT
TACACATTGA GAAGGATGGA GATATATTCT ACTACCTTCT
CCTGAGATCT CACACACAAT CTCAAATTTC AAAAGGTCTC
AGAAGGGCAG CTCTCAGGTA CTATTTAAAA ATAACCCACT
TCCTGGGACA GGTAGCATCC TTCTAACCAT GATGGATGTT
CTGAAGTACA GTACACATTG CATGGATCCA GGTTTGTCTC
AATTCACTGT GATTATTACA CTCAGCAGCT GTTTCAATAT
GTCTGAAGGG GTAAATGACA ATTTAGGTGA CCTGGGTGTA
TGGTTGGTGT TATATGAATC TTTAAATGTA GAACAGTATT
AACTGTATTC CAAAATCTGT CTTTGATCCA TGATCACACT
TGTCTCCCAG ACCAGCTCCT TCAGCACATT TCCTACCTGG
```

```
AAGAAGAGGA CTCTGGGTTT GGTGAGGGGA GGCCACAGGA
AGAGAACTGA GTTCTCAGAG GGCACAGCCA GCATACACCT
CCCAGGGTGA GCCCAAAAGA CTGGGGCCTC CCTCATCCCT
TTTTACCTAT CCATACAAAG GCACCACCCA CATGCAAATC
CTCACTTAGG CACCCACAGG AAATGACTAC ACATTTCCTT
AAATTCAGGG TCCAGCTCAC ATGGGAAGTG CTTTCTGAGA
GTCATGGACC TCCTGCACAA GAACATGAAA CACCTGTGGT
TCTTCCTCCT CCTGGTGGCA GCTCCCAGAT GTGAGTGTCT
CAGGAATGCG GATATGAAGA TATGAGATGC TGCCTCTGAT
CCCAGGGCTC ACTGTGGGTT TTTCTGTTCA CAGGGGTCCT
GTCCCAGGTG CAGCTACAGC AGTGGGCGC AGGACTGTTG
AAGCCTTCGG AGACCCTGTC CCTCACCTGC GGTGTTTATG
GTGGGTCCTT CAGTGGTTAC TACTGGAGCT GGATCCGCCA
GCCCCCAGGG AAGGGGCTGG AGTGGATTGG GGAAATCAAT
CATAGTGGAA GCACCAACTA CAACCCGTCC CTCAAGAGTC
GAGTCACCAT ATCAGTAGAC ACGTCCAAGA AGCAGCTCTC
CCTGAAGTTG AGCTCTGTGA ACGCCGCGGA CACGGCTGTG
TATTACTGTG CGAGAGTTAT TACTAGGGCG AGTCCTGGCA
CAGACGGGAG GTACGGTATG GACGTCTGGG GCCAAGGGAC
CACGGTCACC GTCTCCTCAG GTGAGAATGG CCACTCTAGG
GCCTCTGTTC TCTGCTACTG CCTGTGGGGT TTCCTGAGCA
TTGCAGGTTG GTCCTCGGGG CATGTTCCGA GGGGACCTGG
GCGGACTGGC CAGGAGGGGA CGGGCACTGG GGTGCCTTGA
GGATCTGGGA GCCTCTGTGG ATTTTCCGAT GCCTTTGGAA
AATGGGACTC AGGTTGGGTG CGTCTGATGG AGTAACTGAG
CCTGGGGGCT TGGGGAGCCA CATTTGGACG AGATGCCTGA
ACAAACCAGG GGTCTTAGTG ATGGCTGAGG AATGTGTCTC
AGGAGCGGTG TCTGTAGGAC TGCAAGATCG CTGCACAGCA
GCGAATCGTG AAATATTTTC TTTAGAATTA CGAGGTGCGC
TGTGTGTCAA CCTGCATCTT AAATTCTTTA TTGGCTGGAA
AGAGAACTGT CGGAGTGGGT GAATCCAGCC AGGAGGGACG
CGTAGCCCCG GTCTTGATGA GAGCAGGGTT GGGGGCAGGG
GTAGCCCAGA AACGGTGGCT GCCGTCCTGA CAGGGGCTTA
GGGAGGCTCC AGGACCTCAG TGCCTTGAAG CTGGTTTCCA
TGAGAAAAGG ATTGTTTATC TTAGGAGGCA TGCTTACTGT
TAAAAGACAG GATATGTTTG AAGTGGCTTC TGAGAAAAAT
GGTTAAGAAA ATTATGACTT AAAAATGTGA GAGATTTTCA
AGTATATTAA TTTTTTTAAC TGTCCAAGTA TTTGAAATTC
TTATCATTTG ATTAACACCC ATGAGTGATA TGTGTCTGGA
ATTGAGGCCA AAGCAAGCTC AGCTAAGAAA TACTAGCACA
GTGCTGTCGG CCCCGATGCG GGACTGCGTT TTGACCATCA
TAAATCAAGT TTATTTTTTT AATTAATTGA GCGAAGCTGG
AAGCAGATGA TGAATTAGAG TCAAGATGGC TGCATGGGGG
TCTCCGGCAC CCACAGCAGG TGGCAGGAAG CAGGTGACCG
CGAGAGTCTA TTTTAGGAAG CAAAAAAACA CAATTGGTAA
ATTTATCACT TCTGGTTGTG AAGAGGTGGT TTTGCCCAGG
CCCAGATCTG AAAGTGCTCT ACTGAGCAAA ACAACACCTG
GACAATTTGC GTTTCTAAAA TAAGGCGAGG CTGACCGAAA
CTGAAAAGGC TTTTTTTAAC TATCTGAATT TCATTTCCAA
TCTTAGCTTA TCAACTGCTA GTTTGTGCAA ACAGCATATC
AACTTCTAAA CTGCATTCAT TTTTAAAGTA AGATGTTTAA
GAAATTAAAC AGTCTTAGGG AGACTTTATG ACTGTATTCA
AAAAGTTTTT TAAATTAGCT TGTTATCCCT TCATGTGATA
ACTAATCTCA AATACTTTTT CGATACCTCA GAGCATTATT
TTCATAATGA CTGTGTTCAC AATCTTTTTA GGTTAACTCG
TTTTCTCTTT GTGATTAAGG AGAAACACTT TGATATTCTG
ATAGAGTGGC CTTCATTTTA GTATTTTTCA AGACCACTTT
TCAACTACTC ACTTTAGGAT AAGTTTTAGG TAAAATGTGC
ATCATTATCC TGAATTATTT CAGTTAAGCA TGTTAGTTGG
TGGCATAAGA GAAAACTCAA TCAGATAGTG CTGAAGACAG
GACTGTGGAG ACACCTTAGA AGGACAGATT CTGTTCCGAA
TCACCGATGC GGCGTCAGCA GGACTGGCCT AGCGGAGGCT
CTGGGAGGGT GGCTGCCAGG CCCGGCCTGG GCTTTGGGTC
TCCCCGGACT ACCCAGAGCT GGGATGCGTG GCTTCTGCTG
CCGGGCGACT GGCTGCTCAG GCCCCAGCCC TGGTGAATGG
ACTTGGAGGA ATGATTCCAT GCCAAAGCTT TGCAAGGCTC
GCAGTGACCA TGCGCCCGAC ATGGTAAGAG ACAGGCAGCC
GCCGCTGCTG CATTTGCTTC TCTTAAAACT TTGTATTTGA
CGTCTTATTT CCACTAGAAG GGGAACTGGT CTTAATTGCT
T
```

FIG. 3K and FIGS. 3L-1 to 3L-3 shows a 5.5 kb genomic human immunoglobulin heavy chain variable DNA sequence (SEQ ID NO: 162) that was derived from Ramos B cells engineered using the 'V434' strategy and selected using C108 HIV Env via FACS. The SEQ ID NO: 162 sequence is also shown below.

```
TGGCTCCAGG CATTTTAAAT TCAACAGGTT ATGTAACCAG
GCTTTAAATT TGCACATCTT CGTGTTACCT TCATGACACA
GTCAACTCCC ATTATGTAAG AAATGGTGAG TGCATTCCCA
AGGGTCTTGC ACAGTTATAA AAATAGACTT GATGAGGTGA
GGAGTTGTTT AAATTCCCCT CTGAAGAAGC AGCATCAACC
CAACAAACCA CTCTCTTCCC TCTGTGACTA GAGCTCTGTC
```

-continued

```
ACAGGCCACA TGGACCTAAA TCCTTGATGG AGATTACAGG
ACTACGTAAA TTGGACTGAT CGTTTTTATG CTGTTAAATT
AATAGGTGAG TCTGCACTCC AGCCTGGGCA ACAGAATAAT
CTTGTCTGTA AAATACAAAA GAAAGATAAA TTAATAGATA
CTGACTTTGA CATTTCGGAT AATAATATTT TCATAAACCG
AATTTAATTA TACCCACATT GTTACCTACA CCTTCACTGA
AAAGTTCCTA GTTATGTTGA GTTCCATCAA CACTCCACAT
GTTCAAATCT GGACATCCAA GAGAGTCTAG AGAATAAAAC
GCAATGAGGG CAGTGAAACT TGCGTATATT CAGCACCTCT
TAACTCAGGA GGACTCAATA CACCCTGGAA CACTCTGCTT
TTCTGAATGG CTCACAATGA CTCCAGCTCA CTCTCCAACC
TCCTCAAACA TCTGGCCTCT GTTTGCCCTA AGTTCACGCT
CTGCTCTTAG TCTATCTTCT GAAGTCTTTG TAGAGGTGAA
AATGAGCTGT CAGATGGATC TTCCTTCTCA CTGCAACATG
GAATTTGCTA TTTCACTTAA TGACCACTCT TTCCACAATG
GTTGATTTCT TTTGGCCTGT TCATTACTGG TGATTTTCAA
GGGAATCTCA GTTGAATCTT TACTGTTTTG CATTTGTCT
CCATGACAAT GTTGGGAAGT TTTTCTTCTA GCAGCATAAC
ATGATCTAGT GACCTGACAC ATTTGCAGCA AACAATACCT
ACAAATTCAG AAGCTCTTTG GTTTTCTTTC CACGAAATAT
AATTCTTGCT CTTCTGTGTA TGAGCACATC CTAGCATCCC
TGTACACACC CACGTAGATG TCTACACGCC GATGAAATAT
TCCCTGTAAA TAAAAAAAGT ATCTCAGTTT CTCTCAATGT
TCATAATTCT CCTGAGGGTG AGGAAGGTAG TTCTGGGTCT
GCTCAAACAA ATGGCCCAGA GACCACCTGG TAGGTAGGTA
AGGAGCTCAC CTCGCTCTGG ATATTGAGTC TGTCTCTTTC
CCTCTGTCGT CTCATAGAAG GCCAGCCCAC TTGTTCAGCT
CCTAAGAAGA GAGCCCAGGT TTATCCAGAT TATACAACAC
AACCAGCTTC TGATGACTCT CCTGTTACAA CATCCATGGA
GATATTTGT GTATTATATA ATTCACCAAA CTAATGTGAA
ATGCCCAAGT TGCAATACTG CACACCCTAG GGTATGTTCT
TGCAATTCAG CGGAGGAGAA ATTCTTTCAG AGACAGATGG
ATCTGAATTG GTAAATATGT GGGTACGAAT TCTGGGCTTG
AGTGTCATTG TCCAGCCATG TTTCACAGGT GTGACCTGTC
AGGGAAGAAC CAGAGTTCCT TGTTCTCTCA GAGGGTAGAG
CTCACAGAGG TCCTCTCTGG TTCCCAGGAA AGGTAATTTC
ACTAATCTTG GTGATGAGAC TATCCTCCAG TGCTGATGTA
CTATAGAGTT TTCATCTGAA GCTGTCACTG CTATCCCCAA
TGTACATCTT TTCACACAGA AATGTTTAGA GGTCAGGCCA
TATTCTCAGG GTTACACATT GAGAAGGATG GAGATATATT
CTACTACCTT CTCCTGAGAT CTCACACACA ATCTCAAATT
```

```
TCAAAAGGTC TCAGAAGGGC AGCTCTCAGG TACTATTTAA
AAATAACCCA CTTCCTGGGA CAGGTAGCAT CCTTCTAACC
ATGATGGATG TTCTGAACTA CAGTACACAT TGCATGGATC
CAGGTTTGTC TCAATTCACT GTGATTATTA CACTCAGCAG
CTGTTTCAAT ATGTCTGAAG GGTAAATGA CAATTTAGGT
GACCTGGGTG TATGGTTGGT GTTATATGAA TCTTTAAATG
TAGAACAGTA TTAACTGTAT TCCAAAATCT GTCTTTGATC
CATGATCACA CTTGTCTCCC AGACCAGCTC CTTCAGCACA
TTTCCTACCT TTAAGAAGAG GACTCTGGGT TTGGTGAGGG
GAGGCACAG GAAGAGAACT GAGTTCTCAG AGGGCACAGC
CAGCATACAC CTCCCAGGGT GAGCCCAAAA GACTGGGGCC
TCCCTCATCC CTTTTTACCT ATCCATACAA AGGCACCACC
CACATGCAAA TCCTCACTTA GGCACCCACA GGAAATGACT
ACACATTTCC TTAAATTCAG GGTCCAGCTC ACATGGGAAG
TGCTTTCTGA GAGTCATGGA CCTCCTGCAC AAGAACATGG
AGTTTGGGCT GAGCTGGGTT TTCCTCGTTG CTCTTTTAAG
AGGTGATTCA TGGAGAAATA GAGAGACTGA GTGTGAGTGA
ACATGAGTGA GAAAAACTGG ATTTGTGTGG CATTTTCTGA
TAACGGTGTC CTTCTGTTTG CAGGTGGCCA GTGTCAGCGA
TTAGTGGAGT CTGGGGGAGG CGTGGTCCAG CCTGGGTCGT
CCCTGAGACT CTCCTGTGCA GCGTCCGGAT TCGACTTCAG
TAGACAAGGC ATGCACTGGG TCCGCCAGGC TCCAGGCCAG
GGGCTGGAGT GGGTGGCATT TATTAAATAT GATGGAAGTG
AGAAATATCA TGCTGACTCC GTATGGGGCC GACTCAGCAT
CTCCAGAGAC AATTCCAAGG ATACGCTTTA TCTCCAAATG
AATAGCCTGA GAGTCGAGGA CACGGCTACA TATTTTTGTG
TGAGAGAGGC TGGTGGGCCC GACTACCGTA ATGGGTACAA
CTATTACGAT TTCTATGATG GTTATTATAA CTACCACTAT
ATGGACGTCT GGGGCAAAGG GACCACGGTC ACCGTCTCCT
CAGGTAAGAA TGGCCACTCT AGGGCCTTTG TTTTCTGCTA
CTGCCTGTGG GGTTTCCTGA GCATTGCAGG TTGGTCCTCG
GGGCATGTTC CGAGGTTGGA CCTGGGCGGA CTGGCCAGGA
GGGGACGGGC ACTGGGGTGC CTTGAGGATC TGGGAGCCTC
TGTGGATTTT CCGATGCCTT TGGAAAATGG GACTCAGGTT
GGGTGCGTCT GATGGAGTAA CTGAGCCTGG GGGCTTGGGG
AGCCACATTT GGACGAGATG CCTGAACAAA CCAGGGGTCT
TAGTGATGGC TGAGGAATGT GTCTCAGGAG CGGTGTCTGT
AGGACTGCAA GATCGCTGCA CAGCAGCGAA TCGTGAAATA
TTTTCTTTAG AATTTATGAGG TGCGCTGTGT GTCAACCTGC
ATCTTAAATT CTTTATTGGC TGGAAAGAGA ACTGTCGGAG
```

```
TGGGTGAATC CAGCCAGGAG GGACGCGTAG CCCCGGTCTT
GATGAGAGCA GGGTTGGGGG CAGGGGTAGC CCAGAAACGG
TGGCTGCCGT CCTGACAGGG GCTTAGGGAG GCTCCAGGAC
CTCAGTGCCT TGAAGCTGGT TTCCATGAGA AAAGGATTGT
TTATCTTAGG AGGCATGCTT ACTGTTAAAA GACAGGATAT
GTTTGAAGTG GCTTCTGAGA AAAATGGTTA AGAAAATTAT
GACTTAAAAA TGTGAGAGAT TTTCAAGTAT ATTAATTTTT
TTAACTGTCC AAGTATTTGA AATTCTTATC ATTTGATTAA
CACCCATGAG TGATATGTGT CTGGAATTGA GGCCAAAGCA
AGCTCAGCTA AGAAATACTA GCACAGTGCT GTCGGCCCCG
ATGCGGGACT GCGTTTTGAC CATCATAAAT CAAGTTTATT
TTTTTAATTA ATTGAGCGAA GCTGGAAGCA GATGATGAAT
TAGAGTCAAG ATGGCTGCAT GGGGGTCTCC GGCACCCACA
GCAGGTGGCA GGAAGCAGGT CACCGCGAGA GTCTATTTTA
GGAAGCAAAA AAACACAATT GGTAAATTTA TCACTTCTGG
TTGTGAAGAG GTGGTTTTGC CCAGGCCCAG ATCTGAAAGT
GCTCTACTGA GCAAACAAC ACCTGGACAA TTTGCGTTTC
TAAAATAAGG CGAGGCTGAC CGAAACTGAA AAGGCTTTTT
TTAACTATCT GAATTTCATT TCCAATCTTA GCTTATCAAC
TGCTAGTTTG TGCAAACAGC ATATCAACTT CTAAACTGCA
TTCATTTTTA AAGTAAGATG TTTAAGAAAT TAAACAGTCT
TAGGGAGAGT TTATGACTGT ATTCAAAAAG TTTTTTAAAT
TAGCTTGTTA TCCCTTCATG TGATAACTAA TCTCAAATAC
TTTTTCGATA CCTCAGAGCA TTATTTTCAT AATGACTGTG
TTCACAATCT TTTTAGGTTA ACTCGTTTTC TCTTTGTGAT
TAAGGAGAAA CACTTTGATA TTCTGATAGA GTGGCCTTCA
TTTTAGTATT TTTCAAGACC ACTTTTCAAC TACTCACTTT
AGGATAAGTT TTAGGTAAAA TGTGCATCAT TATCCTGAAT
TATTTCAGTT AAGCATGTTA GTTGGTGGCA TAAGAGAAAA
CTCAATCAGA TAGTGCTGAA GACAGGAC
```

FIG. 3M and FIGS. 3N-1 to 3N-3 show the 5.5 kb genomic human immunoglobulin heavy chain variable genomic DNA sequence (SEQ ID NO: 163) that was derived from Ramos B cells engineered using the 'V781' strategy and selected using C108 HIV Env via FACS. The SEQ ID NO: 163 sequence is also shown below.

```
TCTCTATTAT AAAGGCATGT TGGCAAATAA AGACTACAGT
TTGTATTGAA TATTCATGCC AAAGAAGTTT TTTTCAAAAC
TTTTCAAGTA AAAAATTTTA TCTTGCCTAG TTTGAAAATT
ACCATCTAAA TTCAACAAAT AAGGTAATAC AGTTTTAAAA
GTGATGCTTG TCTTATTAGT TATTCAATTT ATTAACAACA
GACTGATATT TAAAATAAAT ACCATTGCAC ATTTAAGTGC
CATACTGTTC TGGGATTTTT TAAGGAATCA GAGAGACCGA
CTCTGTTCAG GAGGATATTT ATTATTTAGG TTCAGGAGGA
TATTTATTAT TTAGGTGCAC CGGCCAAGTC GAATTAACAT
CCAAAGGACT GAGCCCAGAA CAGAGTTCAG TTACCTTTTA
AGCATTTTGT GGGGTGGGAG AGGGGACATC TGTGCAGGGT
GAAGCATACT ACAGAAGTGA GAAACAAAGA CAGTTATTCA
ATTGAAACAT GTATTACATC ATTTCTTCCT TTTCAAGGAA
AAACATGTTT TGCGACTTGA GTTTATCTTT CTAGTGACCT
TGCAGCTACA CTGCTAGGGA ATCAGGGTCT TCAAAATGCC
TGAGAAGGGA GGAGAGGTAA GGCTCATTAG CCACAGAAAA
ACAGGCAGTT AGTATTTTAA AGGACTCCAG CTCTTTCTCT
TTTTCAGGGA GAATTGGGTT TTCTTACATA CAACTGAGTT
TCTGCTTACA CATTCTTTAA TTTCTTTTAA TTCCTGTTTC
AATACTTGAC AAGAATGGCA TTTACATACA GTTTTACCAA
AACATGTATT TAAATATATT TGTCTTTTTA ATATTGGAAT
AGGCAGACAT ACACGTAGAT CAGCATTATT TTGTACTAAA
ATCTCAAACT GCAAACACAA TTTAAATTCA ATTAAATAAT
TAGAATAATA TGAAACAAAT GGGTGTGTTG TTTTGGTGTT
TACGTATGCA TTCACTTTTG CATGGGCACA TGTATGAGTC
TTTGCTGGGC TGTTGTGCAC GTATGTGTGT TTGTATGACC
AGGAGGTTTT CAAATACATC ATTAAATTAC ATAGTTATAT
TAATCTTGGC AAGGCACTTG TATTCTGTTT TCTTTAATTC
TGTTTGCAGA AAGTAGACAC ATATTCAGTC TTAGTTCCAG
TGTAGGGAGT GCTTTTCATG AGAAAAATAC CAGAAAAAAG
GGCAAACATG GGGCCCACTA ATGTAAAAAT TAGCCACAAT
GTGTATGTGT GTGTGTGTGT GTGTGTGTGT GTGTCTGAGT
TGAATAGTAG AGTTGGAGTG GGCTTCTATC CACATGCACC
TGCGCCTACA GGTATTATCA GGTACAATAA TCAACTGCAG
AACCCTAAAG GAAATAAGAG TCCCCCCAAA CCCCTGAAGA
GTGTTTGGGT TCACCATGTG TCCAATGATT CAGTGCCTCT
CGAGCTCCAG GAAACGGCTC CCTGGTGATG CGTGAGATCT
TTTCTTGGGG TGTCCCTGCA GAGTTCGCTG GGTTTCCTAA
GGCTGATTCA CTATTTCAAA AGATGGTGTG AGAAGCATAT
GGTGTAAATA AAGCAGAATT CTGAGCCAGG GCACAGCCAC
TTTATACTGG GCTAGAGACA CTGGTAGGAA TATACTCTGT
CAGCTCAGAT AGAAACCTCC CTGCAGGGTG GGGGCAGGGC
TGCAGGGGGC GCTCAGGACA CATCGAGCAC AGTCTTCTGC
CCCAGAGCAG GTGCACATGA GGCTGGGGAG AGGTTCCTCT
CAGGGCCTGG GACTTCCTTT AAAAATATCT AAAATAAGTA
TTTCACAAGG ACTGCTGATG TTTGTATAAA TATCCTATTC
```

-continued

AATTGTGAGC ATTTATCAAA CTGGATGTTG TAATGAGAAC

CACTTTTATA ATGGCGATTT CAAACTCTGC TAGTTATCTT

AATAATAGCA GCTGGAGGTC AGGAAGAGAT TATTACTTAT

AAATAAGTGC AATTTTTGGA GAGACACACT CATTCCCAAA

ATAACACATT CACATATTAA GGTCTAGAAA TGGTTCACGT

TGCCCCTGAG ACATTCAAAT GTGGGTTCAA AGTGAGGTGC

TGTCCTCGGG GAGTTGTTCC TTAGTGGAGG AAGCGCTATC

AACACAGAGT TCAGGGATGG GTAGGGGATG CGTGGCCTCT

AACAGGATTA CGACTCGAAC CCTCAGCTCC TATAATTGTG

TCGTCCGTGT GTCATGGATT TCTCTTTCTC ATACTGGGTC

AGGAATTGGT CTATTAAATA GCATCCTTCA TGAATATGCA

AATAACTGAG GGGAATATAG TATCTCTGTA CCCTGAAAGC

ATCACCCAAC AACAACATCC CTCCTTGGGA GAATCCCCTA

GAGCACAGCT CCTCACATGG AGTTTGGGCT GAGCTGGGTT

TTCCTCGTTG CTCTTTTAAG AG*GTGATTCA TGGAGAAATA*

*GAGAGACTGA GTGTGAGTGA ACATGAGTGA GAAAAACTGG*

*ATTTGTGTGG CATTTTCTGA TAACGGTGTC CTTCTGTTTG*

*CAGGTGTCCA GTGTCAGCGA TTAGTGGAGT CTGGGGGAGG*

CGTGGTCCAG CCTGGGTCGT CCCTGAGACT CTCCTGTGCA

GCGTCCGGAT TCGACTTCAG TAGACAAGGC ATGCACTGGG

TCCGCCAGGC TCCAGGCCAG GGGCTGGAGT GGGTGGCATT

TATTAAATAT GATGGAAGTG AGAAATATCA TGCTGACTCC

GTATGGGGCC GACTCAGCAT CTCCAGAGAC AATTCCAAGG

ATACGCTTTA TCTCCAAATG AATAGCCTGA GAGTCGAGGA

CACGGCTACA TATTTTTGTG TGAGAGAGGC TGGTGGGCCC

GACTACCGTA ATGGGTACAA CTATTACGAT TTCTATGATG

GTTATTATAA CTACCACTAT ATGGACGTCT GGGGCAAAGG

GACCACGGTC ACCGTCTCCT CAGGTAAGAA TGGCCACTCT

AGGGCCTTTG TTTTCTGCTA CTGCCTGTGG GGTTTCCTGA

GCATTGCAGG TTGGTCCTCG GGGCATGTTC CGAGGTTGGA

CCTGGGCGGA CTGGCCAGGA GGGGACGGGC ACTGGGGTGC

CTTGAGGATC TGGGAGCCTC TGTGGATTTT CCGATGCCTT

TGGAAAATGG GACTCAGGTT GGGTGCGTCT GATGGAGTAA

CTGAGCCTGG GGGCTTGGGG AGCCACATTT GGACGAGATG

CCTGAACAAA CCAGGGGTCT TAGTGATGGC TGAGGAATGT

GTCTCAGGAG CGGTGTCTGT AGGACTGCAA GATCGCTGCA

CAGCAGCGAA TCGTGAAATA TTTTCTTTAG AATTATGAGG

TGCGCTGTGT GTCAACCTGC ATCTTAAATT CTTTATTGGC

TGGAAAGAGA ACTGTCGGAG TGGGTGAATC CAGCCAGGAG

GGACGCGTAG CCCCGGTCTT GATGAGAGCA GGGTTGGGGG

CAGGGGTAGC CCAGAAACGG TGGCTGCCGT CCTGACAGGG

-continued

GCTTAGGGAG GCTCCAGGAC CTCAGTGCCT TGAAGCTGGT

TTCCATGAGA AAAGGATTGT TTATCTTAGG AGGCATGCTT

ACTGTTAAAA GACAGGATAT GTTTGAAGTG GCTTCTGAGA

AAAATGGTTA AGAAAATTAT GACTTAAAAA TGTGAGAGAT

TTTCAAGTAT ATTAATTTTT TTAACTGTCC AAGTATTTGA

AATTCTTATC ATTTGATTAA CACCCATGAG TGATATGTGT

CTGGAATTGA GGCCAAAGCA AGCTCAGCTA AGAAATACTA

GCACAGTGCT GTCGGCCCCG ATGCGGGACT GCGTTTTGAC

CATCATAAAT CAAGTTTATT TTTTTAATTA ATTGAGCGAA

GCTGGAAGCA GATGATGAAT TAGAGTCAAG ATGGCTGCAT

GGGGGTCTCC GGCACCCACA GCAGGTGGCA GGAAGCAGGT

CACCGCGAGA GTCTATTTTA GGAAGCAAAA AAACACAATT

GGTAAATTTA TCACTTCTGG TTGTGAAGAG GTGGTTTTGC

CCAGGCCCAG ATCTGAAAGT GCTCTACTGA GCAAAACAAC

ACCTGGACAA TTTGCGTTTC TAAAATAAGG CGAGGCTGAC

CGAAACTGAA AAGGCTTTTT TTAACTATCT GAATTTCATT

TCCAATCTTA GCTTATCAAC TGCTAGTTTG TGCAAACAGC

ATATCAACTT CTAAACTGCA TTCATTTTTA AAGTAAGATG

TTTAAGAAAT TAAACAGTCT TAGGGAGAGT TTATGACTGT

ATTCAAAAAG TTTTTTAAAT TAGCTTGTTA TCCCTTCATG

TGATAACTAA TCTCAAATAC TTTTTCGATA CCTCAGAGCA

TTATTTTCAT AATGACTGTG TTCACAATCT TTTTAGGTTA

ACTCGTTTTC TCTTTGTGAT TAAGGAGAAA CACTTTGATA

TTCTGATAGA GTGGCCTTCA TTTTAGTATT TTTCAAGACC

ACTTTTCAAC TACTCACTTT AGGATAAGTT TTAGGTAAAA

TGTGCATCAT TATCCTGAAT TATTTCAGTT AAGCATGTTA

GTTGGTGGCA TAAGAGAAAA CTCAATCAGA TAGTGCTGAA

GAC

FIG. 3O and FIGS. 3P-1 to 3P-3 show the 5.5 kb genomic human immunoglobulin heavy chain variable genomic DNA sequence (SEQ ID NO: 164) that was derived from EBV transformed polyclonal cells engineered using the 'V781' strategy and selected using C108 HIV Env in FACS.

ACTACAGTTT GTATTGAATA TTCATGCCAA AGAAGTTTTT

TTCAAAACTT TTCAAGTAAA AAATTTTATC TTGCCTAGTT

TGAAAATTAC CATCTAAATT CAACAAATAA GGTAATACAG

TTTTAAAAGT GATGCTTGTC TTATTAGTTA TTCAATTTAT

TAACAACAGA CTGATATTTA ACATAAATAC CATTGCACAT

TTAAGTGCCA TACTGTTCTG GGATTTTTA AGGAATCAGA

GAGACCGACT CTGTTCAGGA GGATATTTAT TATTTAGGTT

CAGGAGGATA TTTATTATTT AGGTGCACCG GCCAAGTCGA

ATTAACATCC AAAGGACTGA GCCCAGAACA GAGTTCAGTT

ACCTTTTAAG CATTTTGTGG GGTGGGAGAG GGGACATCTG

TGCAGGGTGA ACATACTAC AGAAGTGAGA AACAAAGACA

GCTATTCAAA TGAAACATGT ATTACATCAT TTCTTCCTTT

TCAAGGAAAA ACATGTTTTG CGACTTGAGT TTATCTTTCT

AGTGACCTTG CAGCTACACA GCTAGGGAAT CAGGGTCTTC

AAAATGCCTG AGAAGGGAGG AGAGGTAAGG CTCATTAGCC

ACAGAAAAAC AGGCAGTTAG TATTTTAAAG GACTCCAGCT

CTTTCTCTTT TTCAGGGAGA ATTGGGTTTT CTTACATACA

ACAGAGTTTC TGCTTACACA TTCTTTAATT TCTTTTAATT

CCTGTTTCAA TACTTGACAA GAATGGCATT TACATACAGT

TTTACCAAAA CATGTATTTA AATATATTTG TCTTTTTAAT

ATTGGAATAG GCAGACATAC ACGTAGATCA GCATTATTTT

GTACTAAAAT CTCAAACTGC AAACACAATT TAAATTCAAT

TAAATAATTA GAATAATATG AAACAAATGG GTGTGTTGTT

TTGGTGTTTA CGTATGCATT CACTTTTGCA TGGGCACATG

TATGAGTCTT TGCTGGGCTG TTGTGCACGT ATGTGTGTTT

GTATGACCAG GAGGTTTTCA AATACATCAT TAAATTACAT

AGTTATATTA ATCTTGGCAA GGCACTTGTA TTCTGTTTTC

TTTAATTCTG TTTGCAGAAA GTAGACACAT ATTCAGTCTT

AGTTCCAGTG TAGCGAGTGC TTTTCATGAG AAAAATACCA

GAAAAAAGGG CAAACATGGG GCCCACTAAT GTAAAATTA

GCCACAATGT GTATGTGTGT GTGTGTGTGT GTGTGTGTGT

GTGTGTGTGT CTGAGTTGAA TAGTAGAGTT GGAGTGGGCT

TCTATCCACA TGCACCTGCG CCTACAGGTA TTATCAGGTA

CAATAATCAA CTGCAGAACC CTAAAGGAAA TAAGAGTCCC

CCCAAACCCC TGAAGAGTGT TTGGGTTCAC CATGTGTCCA

ATGATTCAGT GCCTCTCGAG CTCCAGGAAA CGGCTCCCTG

GTGATGCGTG AGATCTTTTC TTGGGGTGTC CCTGCAGAGT

TCGCTGGGTT TCCTAAGGCT GATTCACTAT TTCAAAAGAT

GGTGTGAGAA GCATATGGTG TAAATAAAGC AGAATTCTGA

GCCAGGGCAC AGCCACTTTA TACTGGGCTA GAGACACTGG

TAGGAATATA CTCTGTCAGC TCAGATAGAA ACCTCCCTGC

AGGGTGGGGG CAGGGCTGCA GGGGGCGCTC AGGACACATC

GAGCACAGTC TTCTGCCCCA GAGCAGGTGC ACATGAGGCT

GGGGAGAGGT TCCTCTCAGG GCCTGGGACT TCCTTTAAAA

ATATCTAAAA TAAGTAATTC ACAAGGACTG CTGATGTTTG

TAAAAATATC CAATTCAATT GTGAGCATTT ATCAAACTGG

AAGTTGTAAA GAACCACT TTTATAATGG CGATTTCAAA

CTCTGCTAGT TATCTTAATA ATAGCAGCTG GAGGTCAGGA

AGAGATTATT ACATATAAAT AAGTGCAATT TTTGGAGAGA

CACACACATT CCCAAAATAA CACATTCACA TATTAAGGTC

TAGAAATGGT TCACGTTGCC CCTGAGACAT TCAAATGTGG

GTTCAAAGTG AGGTGCTGTC CTCGGGGAGT TGTTCCTTAG

TGGAGGAAGC GCAAACAACA CAGAGTTCAG GGATGGGTAG

GGGATGCGTG GCCTCTAACA GGATTACGAC TCGAACCCTC

AGCTCCTATA ATTGTGTCGT CCGTGTGTCA TGGATTTCTC

TTTCTCATAC TGGGTCAGGA ATTGGTCTAT TAAATAGCAT

CCTTCATGAA TATGCAAATA ACTGAGGGGA ATATAGTATC

TCTGTACCCT GAAAGCATCA CCCAACAACA ACATCCCTCC

TTGGGAGAAT CCCCTAGAGC ACAGCTCCTC ACATGGAGTT

TGGGCTGAGC TGGGTTTTCC TCGTTGCTCT TTTAA*GAGGT*

*GATTCATGGA GAAATAGAGA GACTGAGTGT GAGTGAACAT*

*GAGTGAGAAA AACTGGATTT GTGTGGCATT TTCTGATAAC*

*GGTGTCCTTC TGTTTGCAGG* TGTCCAGTGT CAGCGATTAG

TGGAGTCTGG GGGAGGCGTG GTCCAGCCTG GGTCGTCCCT

GAGACTCTCC TGTGCAGCGT CCGGATTCGA CTTCAGTAGA

CAAGGCATGC ACTGGGTCCG CCAGGCTCCA GGCCAGGGGC

TGGAGTGGGT GGCATTTATT AAATATGATG GAAGTGAGAA

ATATCATGCT GACTCCGTAT GGGGCCGACT CAGCATCTCC

AGAGACAATT CCAAGGATAC GCTTTATCTC CAAATGAATA

GCCTGAGAGT CGAGGACACG GCTACATATT TTTGTGTGAG

AGAGGOTGGT GGGCCCGACT ACCGTAATGG GTACAACTAT

TACGATTTCT ATGATGGTTA TTATAACTAC CACTATATGG

ACGTCTGGGG CAAAGGGACC ACGGTCACCG TCTCCTCAGG

TAAGAATGGC CACTCTAGGG CCTTTGTTTT CTGCTACTGC

CTGTGGGGTT TCCTGAGCAT TGCAGGTTGG TCCTCGGGGC

ATGTTCCGAG GTTGGACCTG GGCGGACTGG CCAGGAGGGG

ACGGGCACTG GGGTGCCTTG AGGATCTGGG AGCCTCTGTG

GATTTTCCGA TGCCTTTGGA AAATGGGACT CAGGTTGGGT

GCGTCTGATG GAGTAACTGA GCCTGGGGGC TTGGGGAGCC

ACATTTGGAC GAGATGCCTG AACAAACCAG GGGTCTTAGT

GATGGCTGAG GAATGTGTCT CAGGAGCGGT GTCTGTAGGA

CTGCAAGATC GCTGCACAGC AGCGAATCGT GAAATATTTT

CTTTAGAATT ATGAGGTGCG CTGTGTGTCA ACCTGCATCT

TAAATTCTTT ATTGGCTGGA AAGAGAACTG TCGGAGTGGG

TGAATCCAGC CAGGAGGGAC GCGTAGCCCC GGTCTTGATG

AGAGCAGGGT TGGGGGCAGG GGTAGCCCAG AAACGGTGGC

TGCCGTCCTG ACAGGGGCTT AGGGAGGCTC CAGGACCTCA

GTGCCTTGAA GCTGGTTTCC ATGAGAAAAG GATTGTTTAT

CTTAGGAGGC ATGCTTACTG TTAAAAGACA GGATAGTTTT

```
GAAGTGGCTT CTGAGAAAAA TGGTTAAGAA AATTATGACT

TAAAAATGTG AGAGATTTTC AAGTATATTA ATTTTTTTAA

CTGTCCAAGT ATTTGAAATT CTTATCATTT GATTAACACC

CATGAGTGAT ATGTGTCTGG AATTGAGGCC AAAGCAAGCT

CAGCTAAGAA ATACTAGCAC AGTGCTGTCG GCCCCGATGC

GGGACTGCGT TTTGACCATC ATAAATCAAG TTTATTTTTT

TAATTAATTG AGCGAAGCTG GAAGCAGATG ATGAATTAGA

GTCAAGATGG CTGCATGGGG GTCTCCGGCA CCCACAGCAG

GTGGCAGGAA GCAGGTCACC GCGAGAGTCT ATTTTAGGAA

GCAAAAAAAC ACAATTGGTA AATTTATCAC TTCTGGTTGT

GAAGAGGTGG TTTTGCCCAG GCCCAGATCT GAAAGTGCTC

TACTGAGCAA AACAACACCT GGACAATTTG CGTTTCTAAA

ATAAGGCGAG GCTGACCGAA ACTGAAAAGG CTTTTTTTAA

CTATCTGAAT TTCATTTCCA ATCTTAGCTT ATCAACTGCT

AGTTTGTGCA AACAGCATAT CAACTTCTAA ACTGCATTCA

TTTTTAAAGT AAGATGTTTA AGAAATTAAA CAGTCTTAGG

GAGAGTTTAT GACTGTATTC AAAAAGTTTT TTAAATTAGC

TTGTTATCCC TTCATGTGAT AACTAATCTC AAATACTTTT

TCGATACCTC AGAGCATTAT TTTCATAATG ACTGTGTTCA

CAATCTTTTT AGGTTAACTC GTTTTCTCTT TGTGATTAAG

GAGAAACACT TTGATATTCT GATAGAGTGG CCTTCATTTT

AGTATTTTTC AAGACCACTT TTCAACTACT CACTTTAGGA

TAAGTTTTAG GTAAAATGTG CATCATTATC CTGAATTATT

TCAGTTAAGC ATGTTAGTTG GTGGCATAAG AGAAAACTCA

ATCAGATAGT GCTGAAGACA GGACTGTGGA GACACCTTAG

AAGGACAGAT TCTGTTCCGA ATCACCGATG CGGCGTC
```

In the vaccine enhancement strategy proposed herein, it is desirable for modified B cells to undergo affinity maturation after autologous engraftment (FIG. 1C). This Example describes experiments for assessing the ability of edited B cells to undergo two key steps in affinity maturation: class switching and somatic hypermutation.

Both of class switching and somatic hypermutation are mediated by activation-induced cytidine deaminase (AID), which is active in Ramos B cells and is regulated to act specifically within the immunoglobulin genomic locus. In vitro class switching occurs only in a specific Ramos subclone, 2G626 so the engineering strategy was repeated and PG9 heavy chain expressing cells were selected from the modified 2G626 cell. PCR amplification and sequencing of PG9 heavy chain mRNA showed that the engineered locus was successfully transcribed and spliced in the correct reading frame within either the native Ramos p constant gene (PG9-IgM) locus, or after culture with CD40 ligand-expressing feeder cells, IL-2 and IL-4. The native Ramos Y constant gene (PG9-IgG), showing the engineered locus retained the ability to class switch.

FIG. 3Q show sequences of PCR products amplified from cDNA derived from different Ramos cell lines and translated in the correct frame into amino acid sequence. The cell line in FIG. 3Q is indicated to the left of the sequence along with the PG9 VDJ reference. Either Ramos VDJ specific or PG9 VDJ forward primers were used with either IgM or IgG specific reverse primers, also indicated to the left of the sequence. HC VDJ numbering and CDRs are indicated in the linear diagram above the sequences. The sequences in FIG. 3Q are also shown below.

```
PG9 mature VDJ (reference; SEQ ID NO: 164):
QRLVESGGGVVQPGSSLRLSCAASGFDFSRQGMHWVRQAPGQGLEWVAF
IKYDGSEKYHADSVWGRLSISRDNSKDTLYLQMNSLRVEDTATYFCVRE
AGGPDYRNGYNYYDFYDGYYNYHYMDVWGKGTTVTVSS V781(PG9) stimulated PG9f/IgGrc (SEQ ID NO: 165):
QRLVESGGGVVQPGSSLRLSCAASGFDFSRQGMHWVRQAPGQGLEWVAF
IKYDGSEKYHADSVWGRLSISRDNSKDTLYLQMNSLRVEDTATYFCVRE
AGGPDYRNGYNYYDFYDGYYNYHYMDVWGKGTTVTVSSASTKGPSVFPL
APSSKSTSGGTAALGCLVKDYFPEPVTVSWNSGALTSGVHTFPAVLQSS
GLYSLSSVVTVPSS V434(PG9) stimulated PG9f/IgGrc (SEQ ID NO: 166):
QRLVESGGGVVQPGSSLRLSCAASGFDFSRQGMHWVRQAPGQGLEWVAF
IKYDGSEKYHADSVWGRLSISRDNSKDTLYLQMNSLRVEDTATYFCVRE
AGGPDYRNGYNYYDFYDGYYNYHYMDVWGKGTTVTVSSGSASAPTLFPL
VSCENSPSDTSSVAVGCLAQDFLPDSITFSWKYKNNSDISSTRGFPSVL
RG V781(PG9) stimulated PG9f/IgMrc (SEQ ID NO: 167):
QRLVESGGGVVQPGSSLRLSCAASGFDFSRQGMHWVRQAPGQGLEWVAF
IKYDGSEKYHADSVWGRLSISRDNSKDTLYLQMNSLRVEDTATYFCVRE
AGGPDYRNGYNYYDFYDGYYNYHYMDVWGKGTTVTVSSGSASAPTLFPL
VSCENSPSDTSSVAVGCLAQDFLPDSITFSWKYKNNSDISSTRGFPSVL
RG V434(PG9) stimulated PG9f/IgMrc (SEQ ID NO: 168):
DQLQQWGAGLLKPSETLSLTCGVYGGSFRGYYWSWIRQPPGKGLEWIGE
INHSGSTNYNPSLKSRVTISVDTSKKQLSLKLSSVNAADTAVYYCARVI
TRASPGTDGRYGMDVWGQGTTVTVSSGSASAPTLFPLVSCENSPSDTSS
VAVGCLAQDFLPDSITFSWKYKNNSDISSTRGFPSVLRG
```

While class switching is not inducible in Ramos RA1, random somatic hypermutation does occur due to constitutive activity of activation-induced cytidine deaminase. The ability of edited Ramos RA1 B cells to undergo somatic hypermutation and to produce higher affinity variants of the PG9-Ramos chimeric antibody was assessed in vitro by repeatedly selecting B cell populations with superior binding to Env using flow cytometry. Env SOSIP trimers derived from strains MGRM8 (clade AG) and WITO.4130 (clade B) were used as sorting probes because these proteins showed relatively weak binding to engineered cells (data not shown), and therefore gave the greatest scope for improvement. mRNA sequencing showed that the PG9 VDJ region accumulated mutations (FIG. 3F), so somatic hypermutation of the new gene was possible after genomic editing. However, three rounds of selection with the Env proteins, failed to enrich coding changes in the PG9 VDJ region. Amino acid changes in the Ramos LC gene were however enriched, with

Figures 1, 2, 3, 3E, 4, 5:
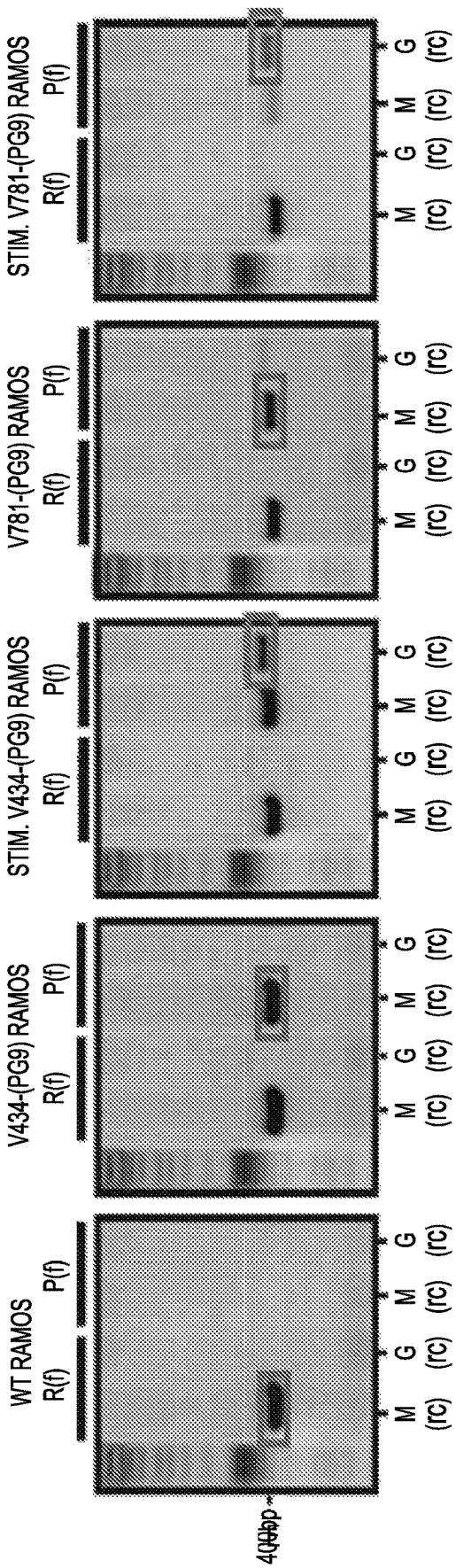
Figure 3G:
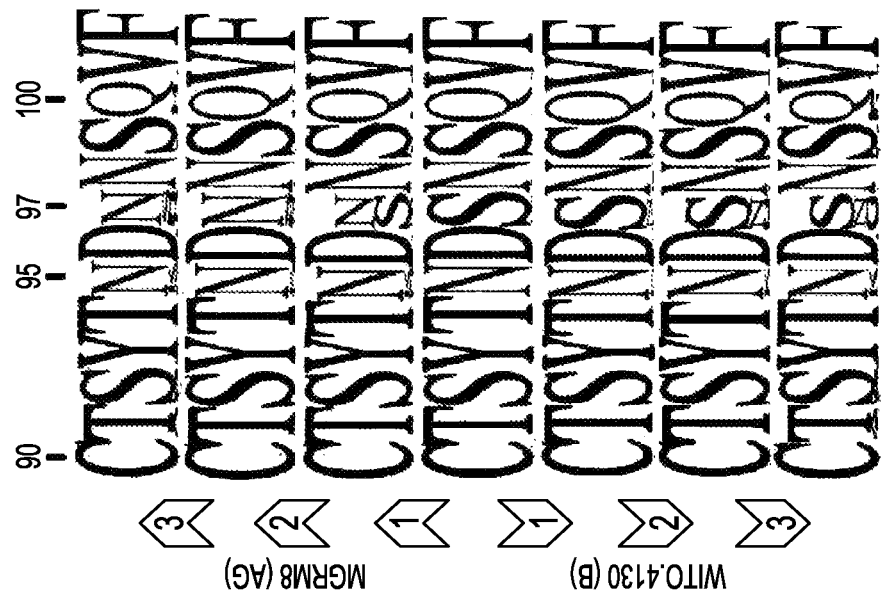
Figure 3F:
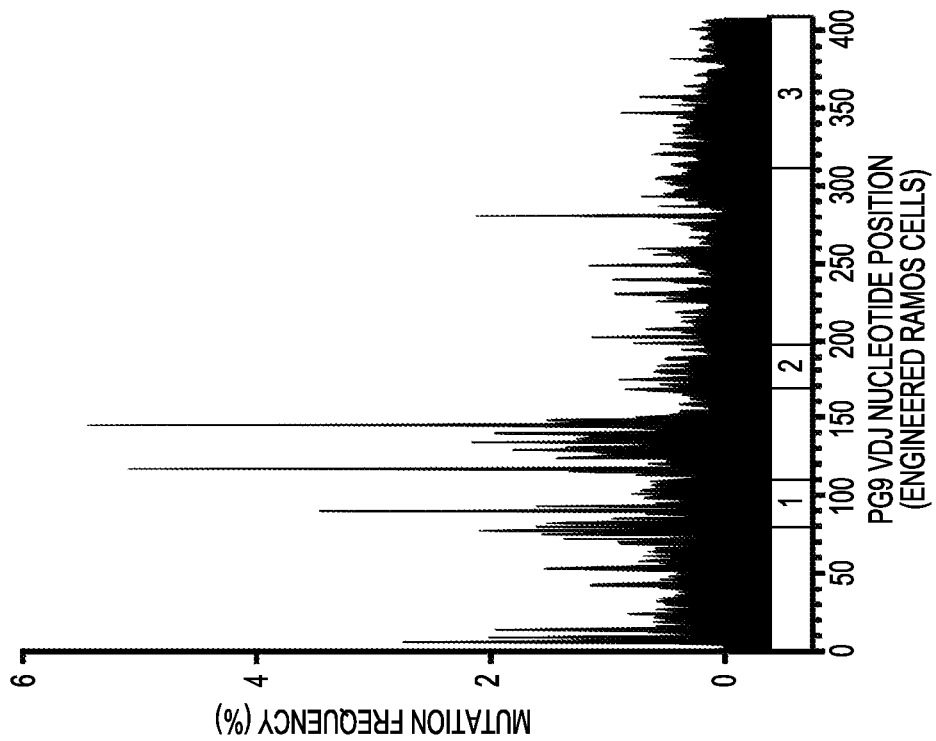
FIG. 3F graphically illustrates the positions of mutations occurring in the PG9 VDJ gene-V781 (universal strategy) engineered and Env-selected Ramos cells were passaged 16 times before havesting mRNA. The VDJ region was sequenced using next generation sequencing (NGS). The mutation frequencies (y-axis) at each nucleotide position (x-axis) in the engineered PG9 HC after correction for amplification and sequencing errors are shown as the percentage of the total sequenced reads. CDRH1, 2 and 3 positions are shown at the bottom of the plot.
Figures 1, 3H:
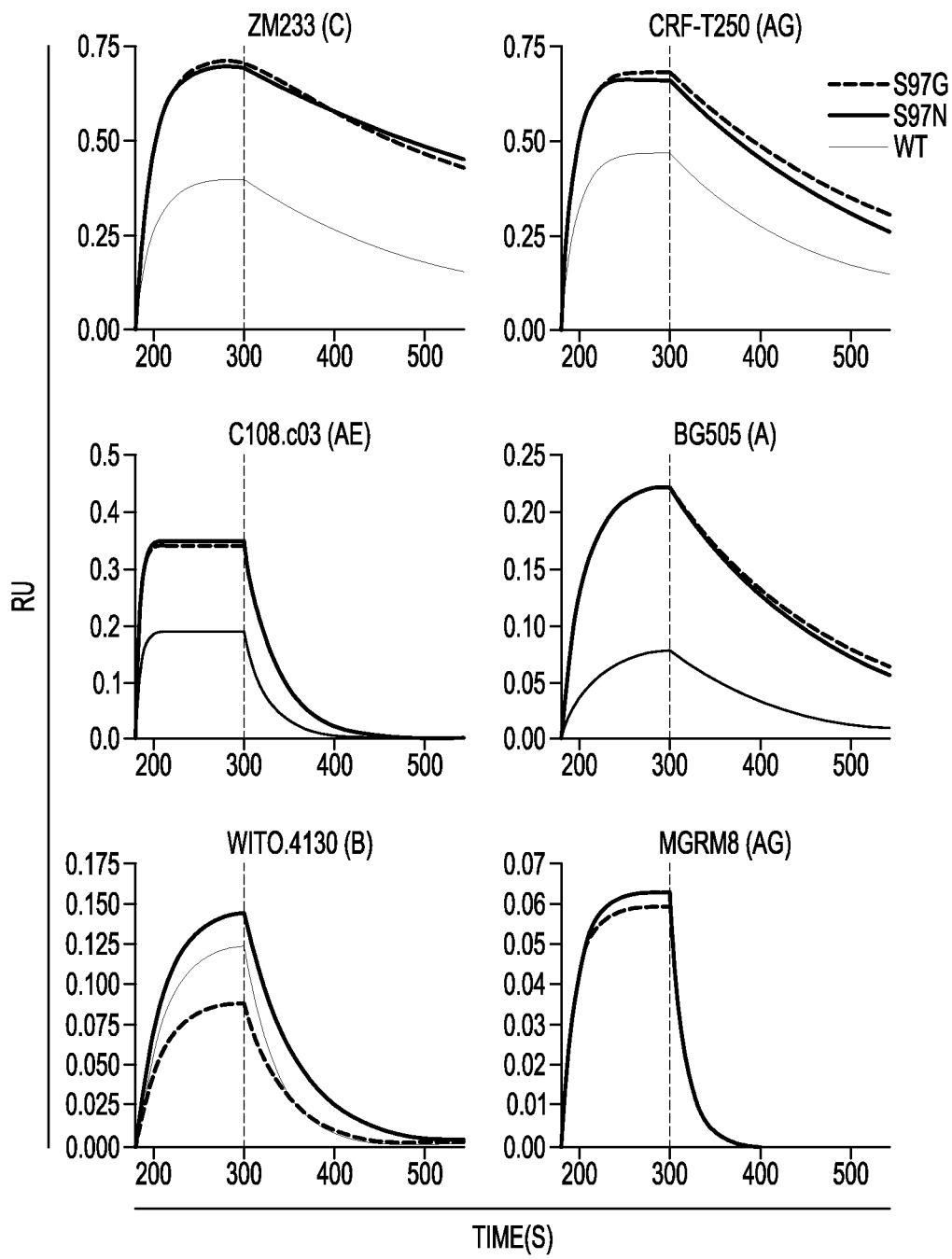
Figures 2, 3H:
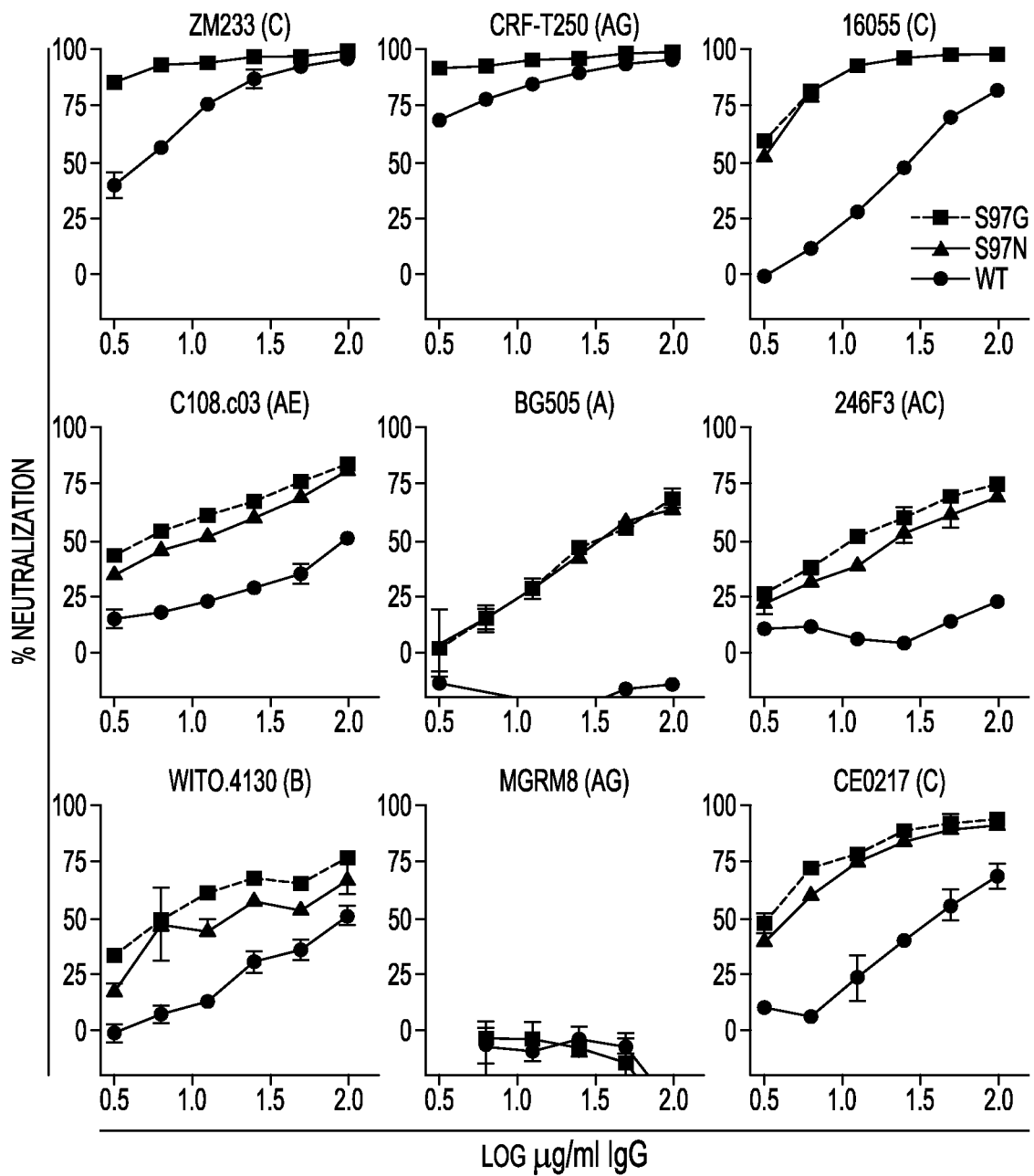
Figure 3I:
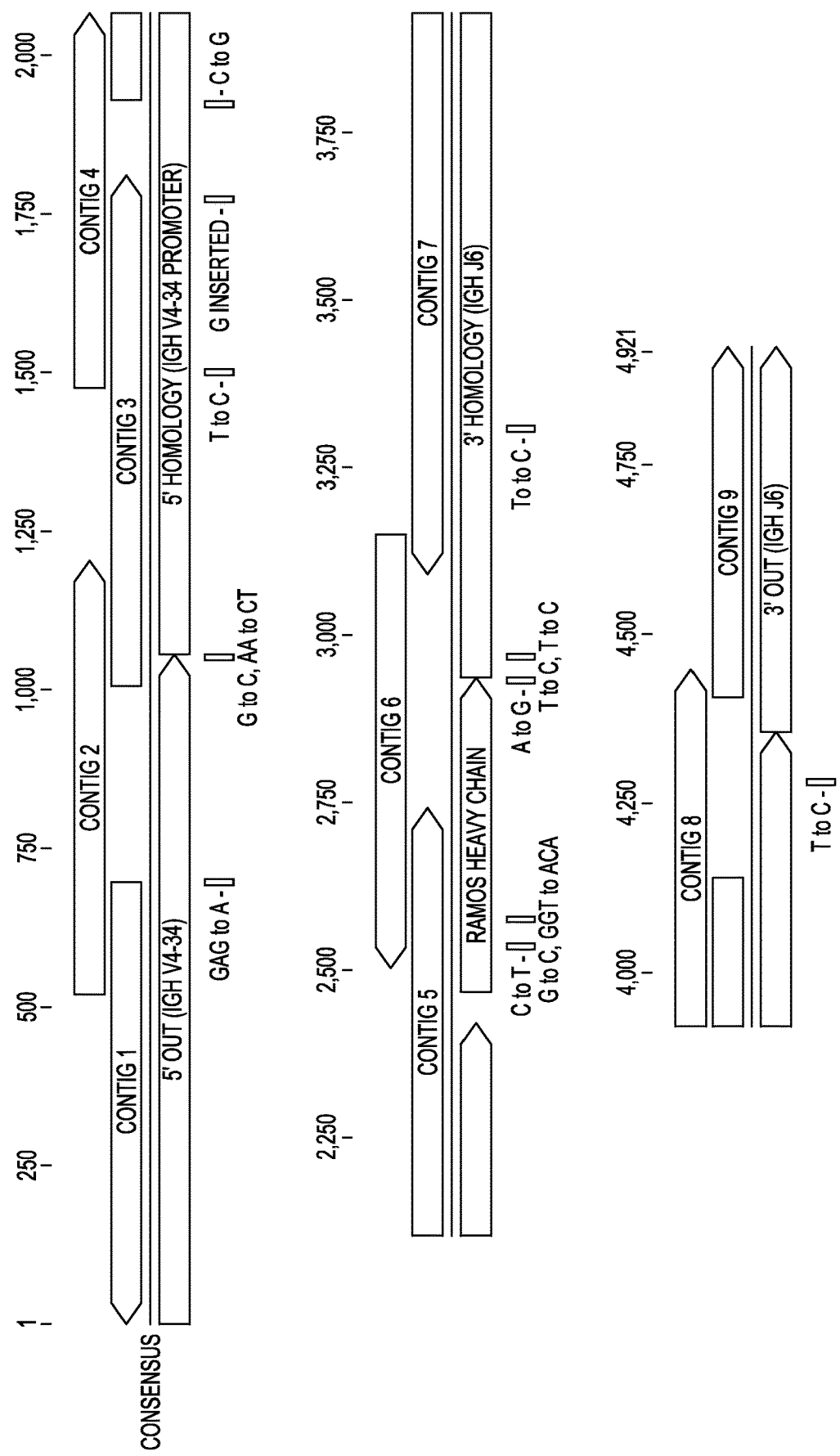
FIG. 3*i* (SEQ ID NO: 187) shows Ramos light chain CDR3 sequences following selection. Engineered Ramos cells were passaged and subjected to selection using WITO or MGRM8 Env trimers at effective concentration required to stain 10% of cells (EC10). The 5% of cells with the highest Env signal were selected for subsequent passage and two more rounds of sorting with selection for these same HIV Envs. mRNA was purified after each round of sorting and the variable heavy chain and light chain genes sequenced using next generation sequencing (NGS). Strong purifying selection of mutant BCRs that effectively moved an N-linked glycan site at position 95 in the CDRL3 to position 97 (MGRM8 selection) or shifted/eliminated the glycan site entirely (WITO) was observed and is shown as logos. The starting consensus sequence is at the center. The consensus sequence after one, two, or three selection steps with (upward arrows) MGRM8 or WITO (downward arrows) are above and below the starting consensus sequence, respectively.
Figure 3K:
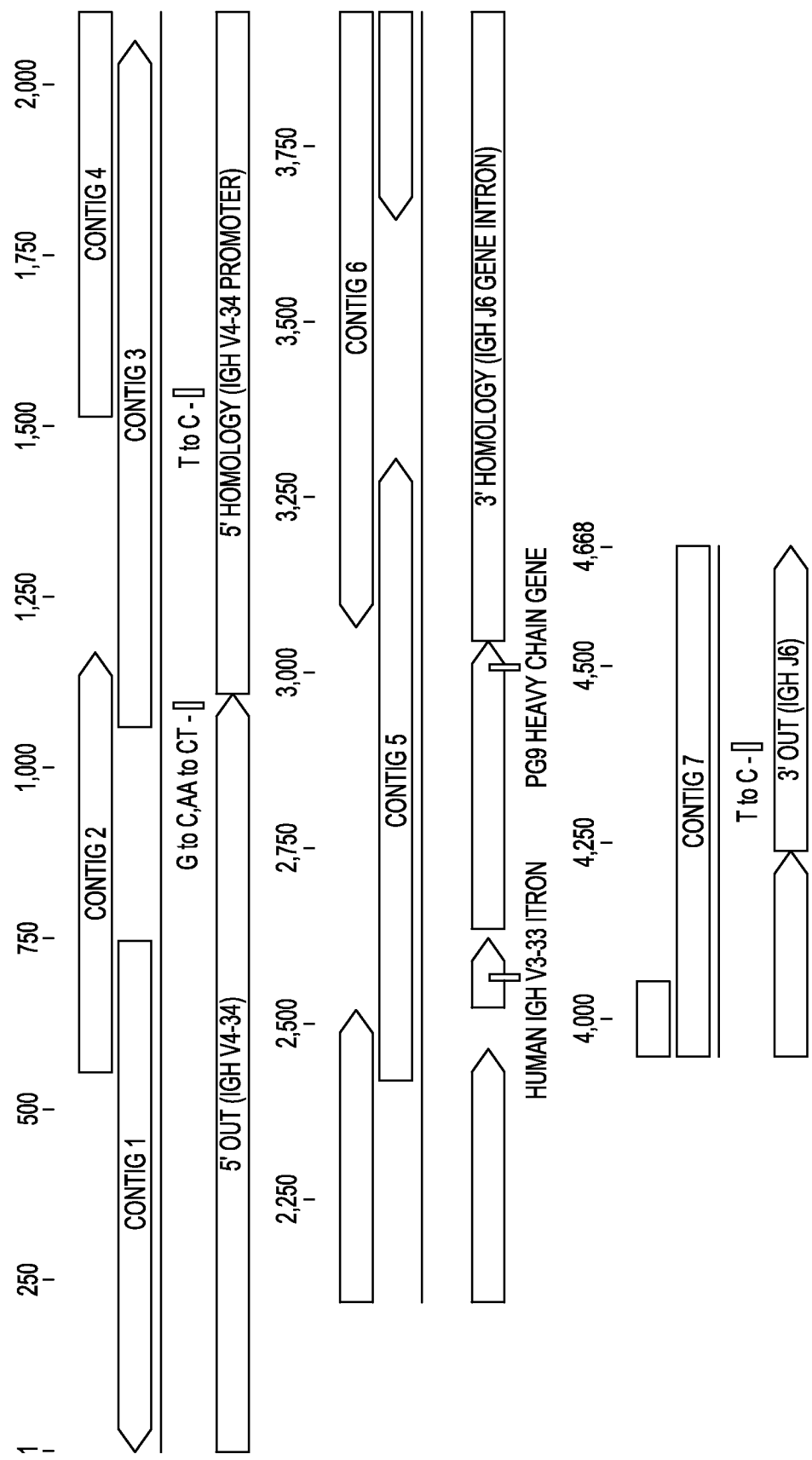
FIG. 3K shows a schematic diagram of an assembled 5.5 kb genomic human immunoglobulin heavy chain variable DNA sequence that was isolated by PCR amplification from Ramos lymphoma B cells engineered using the 'V434' strategy and selected using C108 HIV Env in FACS.
Figure 3M:
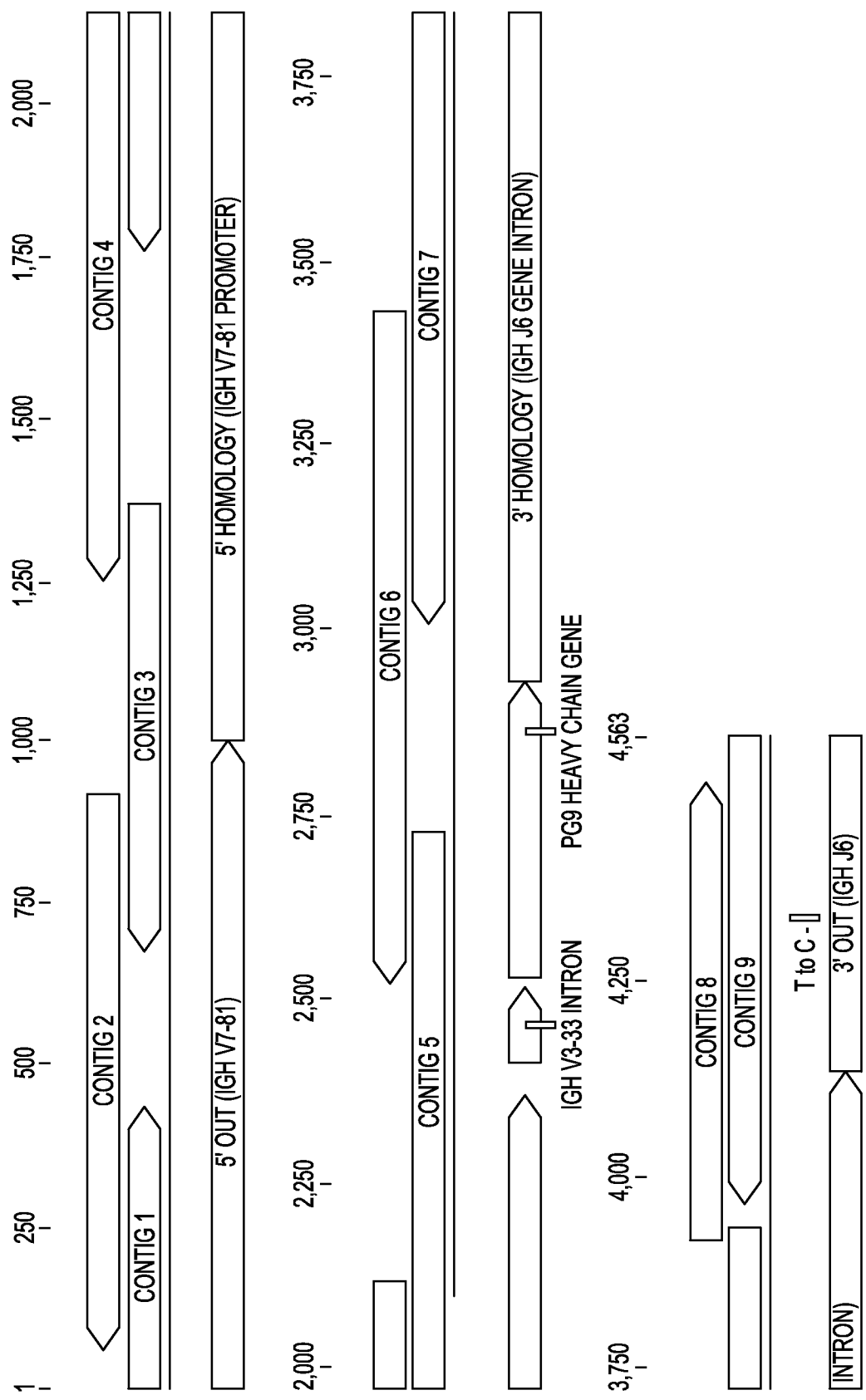
FIG. 3M shows a schematic diagram of an assembled 5.5 kb genomic human immunoglobulin heavy chain variable DNA sequence that was isolated by PCR amplification from Ramos lymphoma B cells engineered using the 'V781' strategy and selected using C108 HIV Env in FACS.
Figure 3O:
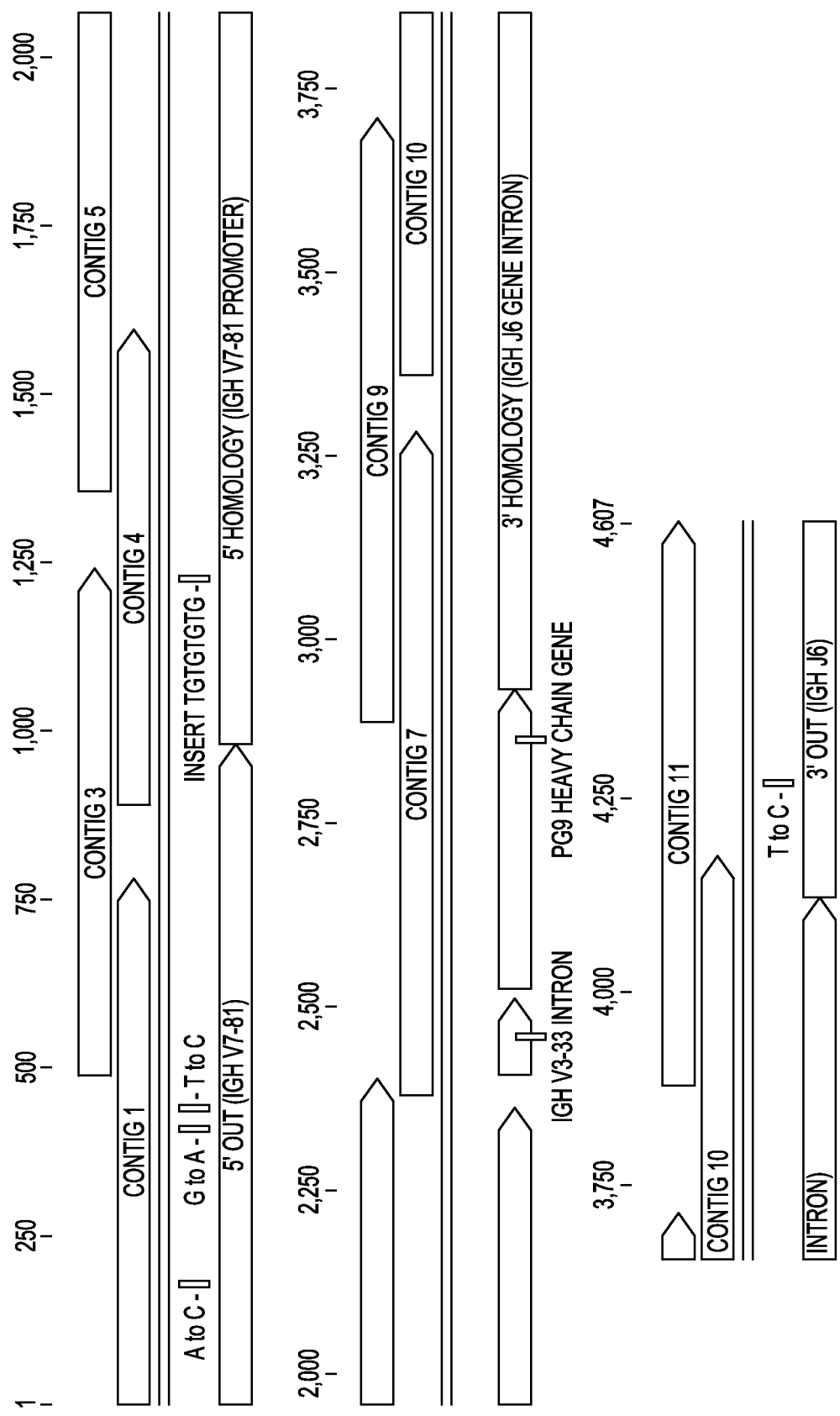
FIG. 3O shows a schematic diagram of an assembled 5.5 kb genomic human immunoglobulin heavy chain variable DNA sequence that was isolated by PCR amplification from EBV transformed polyclonal cells engineered using the 'V781' strategy and selected using C108 HIV Env in FACS.
Figure 3Q:
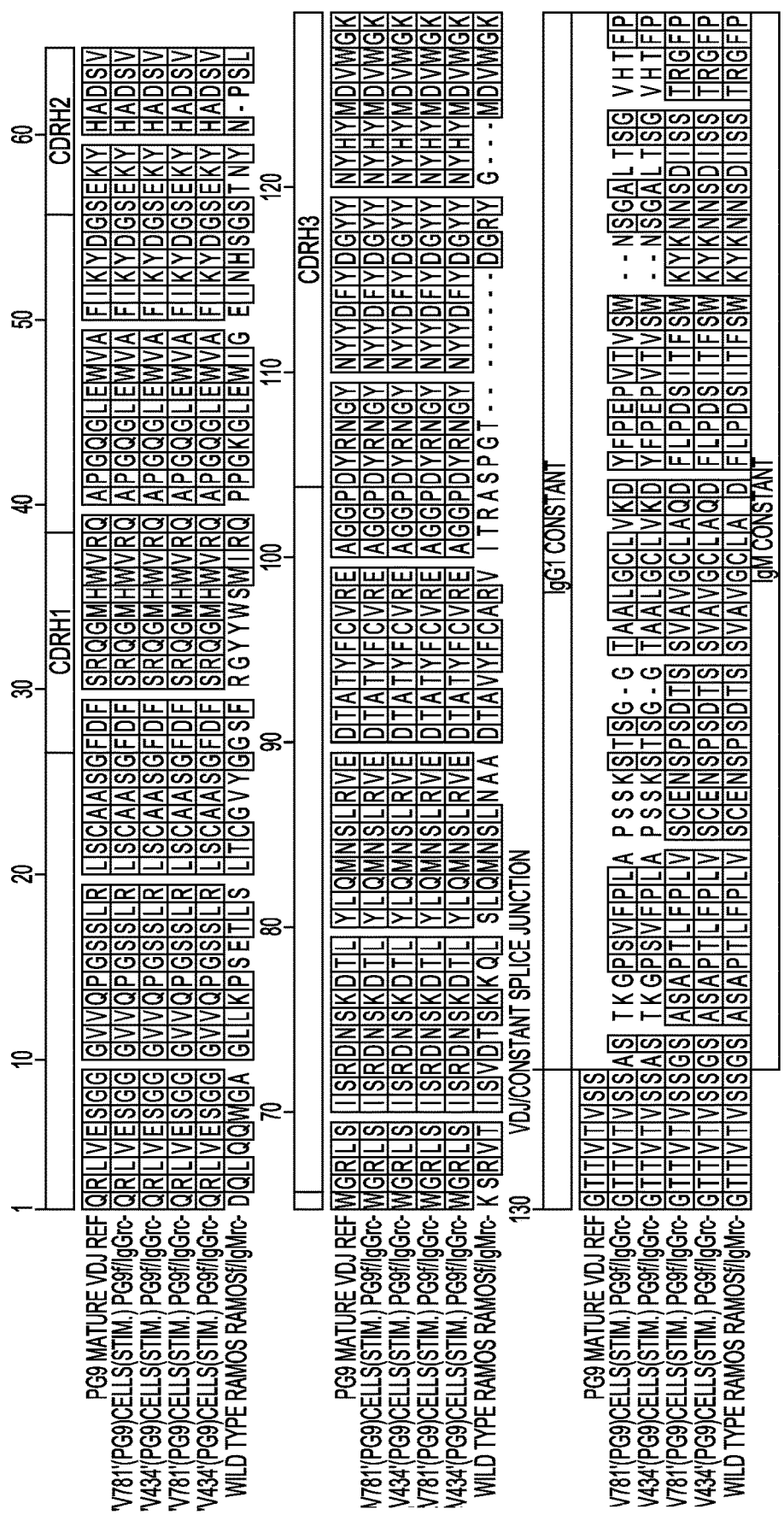

MGRM8 Env selecting a S97N substitution in the Ramos CDRL3. This mutation predicts a shift in a potential N-linked glycosylation site (PNGS) from N95 to N97. Similarly, selection with the WITO Env somewhat favored the elimination of the potential N-linked glycosylation site at N95 (mutations encoding N95K or S97G) or shifting the potential N-linked glycosylation site to N97 (FIG. 3G). To investigate whether these mutations had a functional effect, PG9-Ramos IgG chimeras were recombinantly produced as IgG with mutations to either remove or shift the potential N-linked glycosylation site to position 97 as selected (light chain S97G, S97N). Antibodies with either of these mutations generally improved affinity for HIV Env from different clades (FIG. 3H-1). Furthermore, these mutations resulted in more potent neutralization of a number of HIV strains, including a virus from the panel designed to represent global HIV diversity not neutralized by the original chimera (FIG. 3H-2). These results indicate that somatic mutation can overcome light chain restrictions to PG9 chimeric antibody neutralization breadth.

Figure 4A:
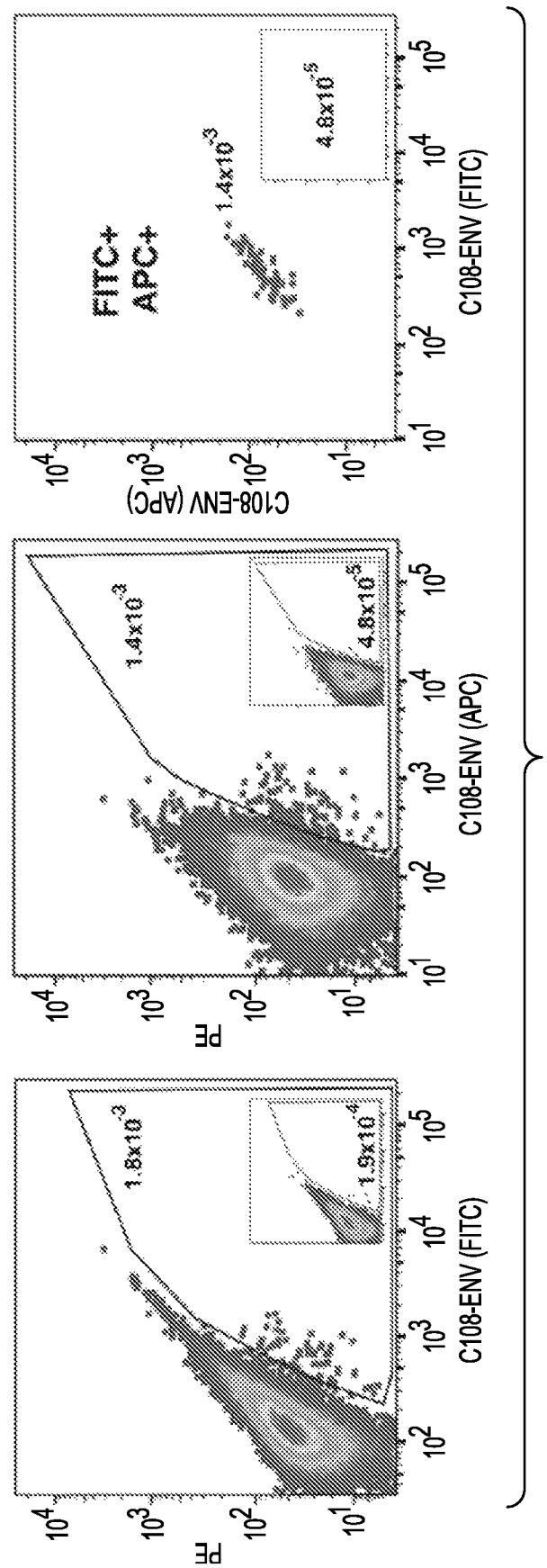
Figure 4B:
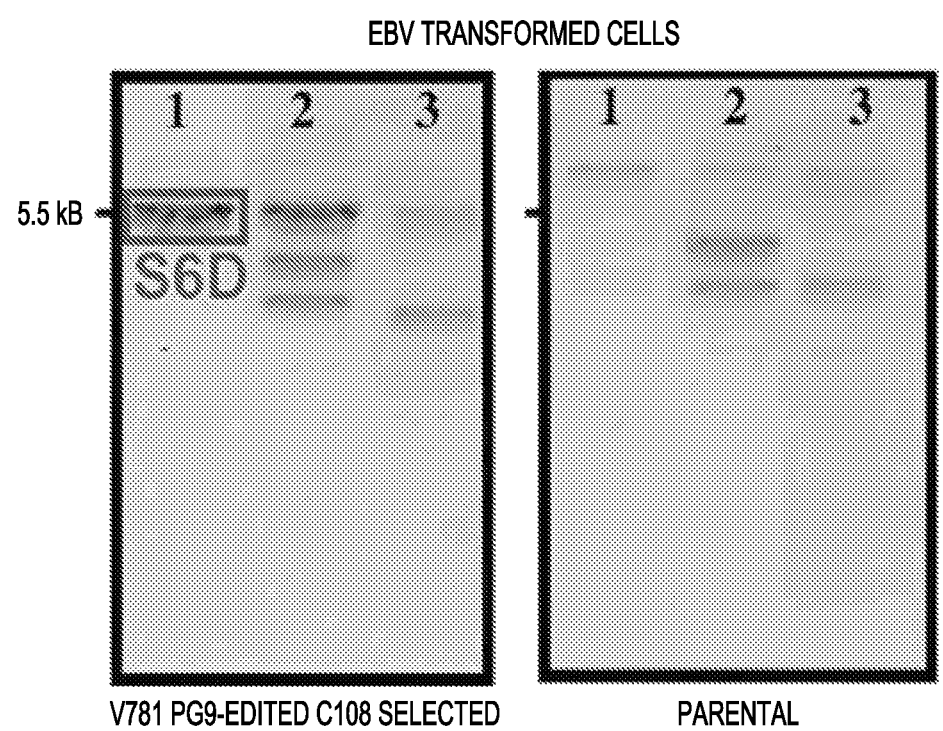

To assess the overall strategy in polyclonal cells that have undergone a diversity of VDJ recombination events and use different light chains, primary B cells were purified from human blood and transformed with Epstein-Barr virus (EBV) to allow long-term growth in culture. Nucleofection of the universal B cell editing plasmids and culture were performed as described for the monoclonal Ramos line. The C108.c03 Env trimer was used as a probe to enrich PG9 HC edited cells (FIG. 4A), because, while CRF-T250 Env trimer bound a broad diversity of PG9 chimeras (FIG. 2A), there was more non-specific binding with that trimer. C108.c03 trimer-selected cells were cultured and genomic DNA sequencing confirmed that the PG9 VDJ region was incorporated at the engineered site as predicted (FIGS. 4B, 30-3P). Heavy chain mRNA was sequenced using next generation sequencing (NGS) to identify the PG9 VDJ gene as the second most abundant species (FIG. 4C) that was not present in unengineered controls.

| V-gene | D-gene | J-gene | CDR lengths | AA JUNCTION | Read # (Before/After Engineering) |
|---|---|---|---|---|---|
| IGHV1-2*02 F | IGHD3-22*01 F | IGHJ4* 02 F | 8.8.13 | CARAPFYD SNLFDYW (SEQ ID NO: 178) | 37000/ 6048 |
| IGHV3-33*01 F | IGHD5-18*01 F | IGHJ4* 02 F | 8.8.13 | CARDLGKH IREIDFW (SEQ ID NO: 179) | 4382/ 24 |
| IGHV3-30*02 F* | IGHD3-10*01F | IGHJ4* 02 F* | 8.8.15 | CAKDPVGE NSGSYYIS W (SEQ ID NO: 180) | 2569/ 102 |
| IGHV3-30*02 F* | IGHD5-18*01 F | IGHJ3* 02 F | 8.8.14 | CAKGESYG PYDAFDMW (SEQ ID NO: 181) | 616"1/ 60 |
| IGHV3-30*02 F* | IGHD5-18*01 F | IGHJ3* 02 F | 8.8.14 | CAKGENYG PYDAFDM W (SEQ ID NO: 182) | 55"1/ 0 |
| IGHV1-8*01 F | IGHD2-2*01 F | IGHJ6* 03 F* | 8.8.16 | CARSPGYC SSNSCYPD VW (SEQ ID NO: 183) | 222/ 13 |
| IGHV3-33*01 F* | IGHD3-10*01 F | IGHJ4* 02 F* | 8.8.15 | CAKDPVGE NSGSYYIS W (SEQ ID NO: 184) | 54/ 0 |
| IGHV3-33*05 F | IGHD3-1*01 F | IGHJ6* 03 F* | 8.8.30 | CVREAGGP DYRNGYNY YDFYDGYY NYHYMDVW (SEQ ID NO: 185) | 0/ 574 |
| IGHV1-18*04 F | IGHD3-9*01 F | IGHJ6* 02 F | 8.8.16 | CARGSETV AAYSYGMD VW (SEQ ID NO: 186) | 0/ 29 |

These data illustrate a universal genome editing method that can introduce novel paratopes into the human antibody repertoire by replacing the VDJ region of B cells regardless of their original VDJ arrangement. Using endogenous light chains, these engineered cells can express B cell receptors with a defined specificity and are optimally poised to undergo antigen-stimulated expansion and affinity maturation. These data show that B cell receptor editing in primary cells, followed by autologous engraftment and immunogen boosting can successfully expand and mature protective antibody responses with memory subsets and tissue-appropriate, self-tolerant antibody expression from all classes of mature B-cells (FIG. 1C).

The human B cell editing strategy reported here has applications beyond induction of protective immune responses to antibody repertoire-resistant pathogens like HIV. Engineered cell lines could be used as directed evolution platforms to improve antibody binding properties or as in vitro tools to evaluate immunogens and complement in vivo approaches such as antibody knock-in mic.

Example 5: Replacement of the Heavy Chain Variable Locus in Ramos B Cells with PG9 HIV Neutralizing Antibody VDJ Open Reading Frame This Example illustrates replacement of a heavy locus with nucleic acids encoding a broadly neutralizing antibody (PG9) anti-HIV open reading from, followed by enrichment of the engineered Ramos cells for those that recognize the MGRM8 strain of HIV.

Figure 6A:
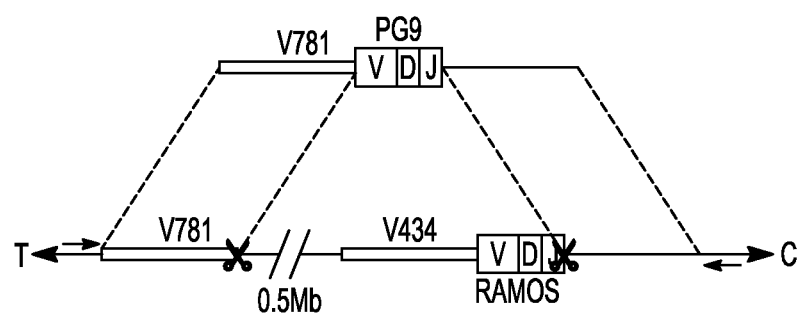

The human Ramos B cell line HC variable locus was replaced with the PG9 HIV broadly neutralizing antibody (bnAb) VDJ ORF by the 'universal' strategy using nucleases and HRs to the 5' most V gene promoter (V781) as well as the J6 intron (3' of the splice site) using a strategy outlined in FIG. 6A. The V781 promoter was used to drive expression of the PG9 heavy chain. The native cell IgM constant gene and Ramos lambda light chain (LLC) was expressed by these engineered Ramos cells. The engineered cell surface receptor was detected with HIV Env probes by FACS.

Figures 1, 6B:
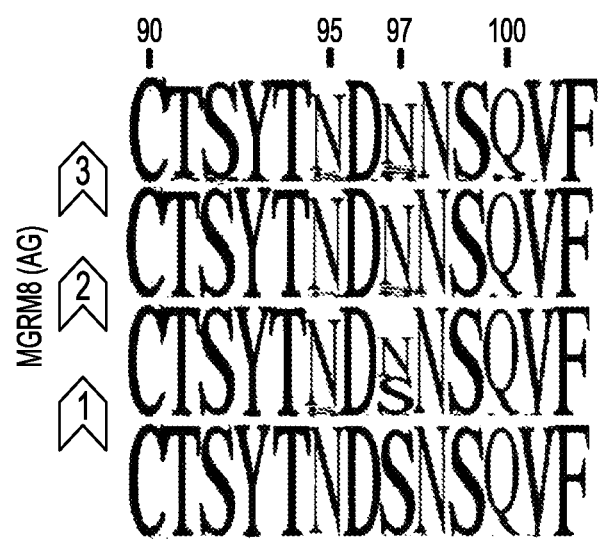
Figures 2, 6B:
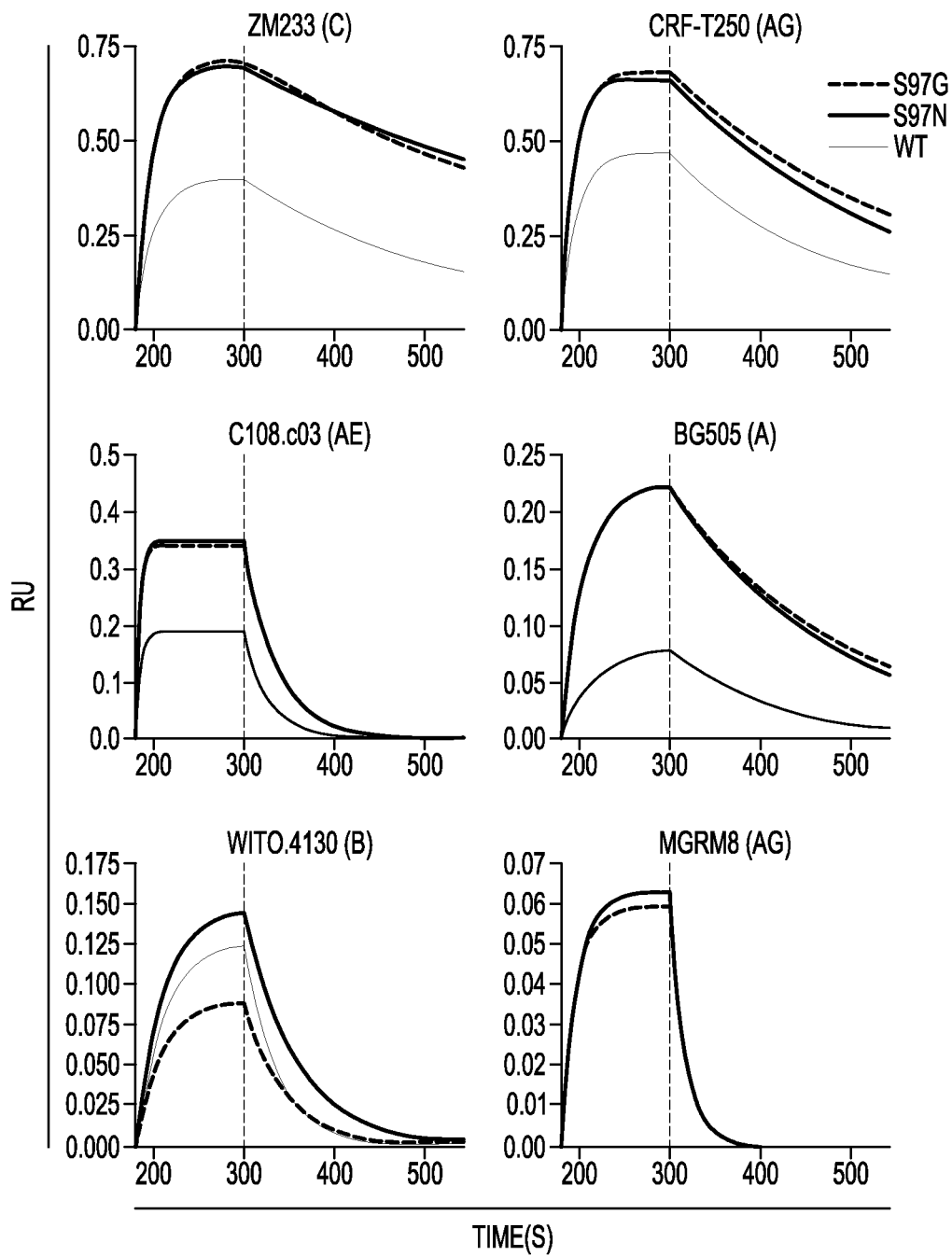
Figures 3, 6B:
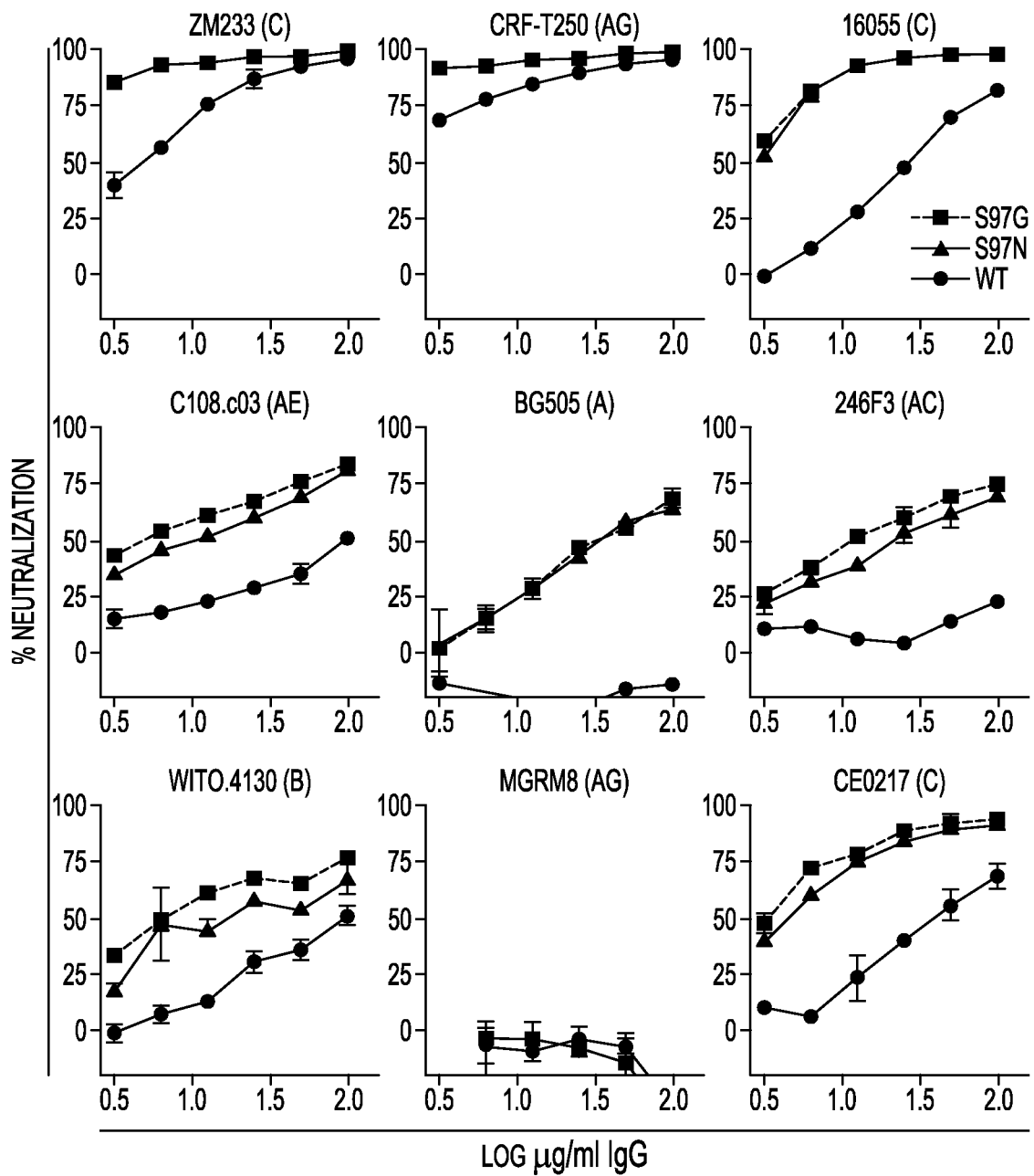
Figure 6C:
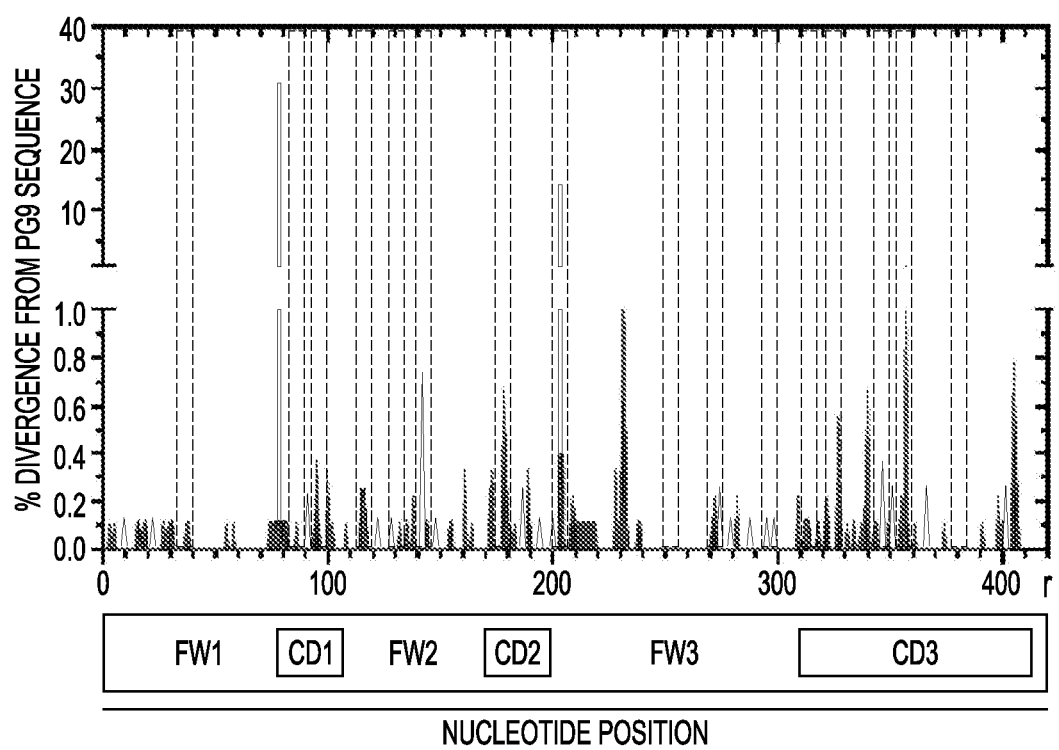

Activation-induced cytidine deaminase (AID) was used in engineered cells to generate variants of the PG9 IgM/Ramos LLC B cell receptor that had higher affinity to the MGRM8 strain of HIV Env which could be selected by FACS as illustrated in FIG. 6B. Three rounds of selection with MGRM8 probe highly enriched an LLC mutation at position 97 which deleted (N97G for example) or shifted (S97N) an N linked glycan from position 95 to position 97. The top panel of FIG. 6B illustrates next generation sequencing (NGS) consensus sequences from Ig cDNA after 3 each round of selection. These mutations improved binding (on rates and off rates shown for select strains of HIV Env as SOSIPS by Biolayer interferometry bottom left graphs) or virus neutralization (for select strains shown as a function of antibody concentration bottom right graphs).

Next generation sequencing of barcoded cDNA showed that an accumulation of mutations had occurred in the new PG9 VDJ region within a cell line selected three times with MGRM8 (shaded peaks) or passaged after initial enrichment of engineered cells without further selection (clear peaks), as a graph showing percent divergence from the initial PG9 VDJ sequence across the length of the gene (X axis) with activation-induced cytidine deaminase (AID) hotspot motifs highlighted by columns delineated with dashed lines.

Example 6: Engineering Both Light and Heavy Chains into B Cells

This Example illustrates engineering of the Ramos B cell line to express light and heavy chains of the precursor of the HIV broadly neutralizing antibodies (bnAbs) VRC01.

FIG. 7A illustrates the two-step strategy used for engineering both the light and heavy chains into the Ramos B cell line. A universal strategy was first used to engineer the light chain where an HA epitope tag for selection of successfully engineered cells was included in the donor DNA just after the leader and signal sequence cleavage site for the new light chain VJ gene. The enriched light chain engineered cells were then subjected to a second round of engineering of the heavy chain using the universal strategy. Antigen specific for the antibody engineered into this line was used to enrich fully engineered cells.

After engineering and selection of the light chain using HA probes, the engineered HC cells were selected with the 'GT8' VRC01 immunogen. After some time in culture, engineered cells acquired mutations allowing them to bind 'GT3-core' VRC01 boosting immunogen. These cells could be enriched by FACS as illustrated in FIG. 7B.

Figure 8A:
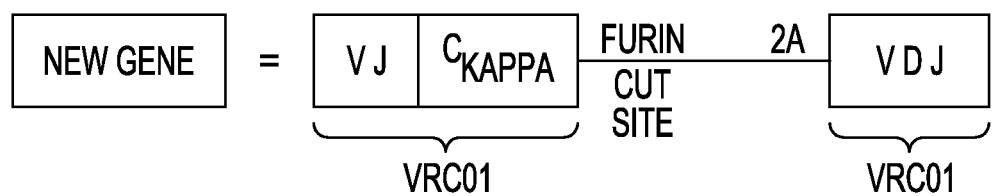
FIG. 8A-8B illustrate introduction of both light and heavy chains of an antibody into the heavy chain locus of B cells.
Figure 8B:
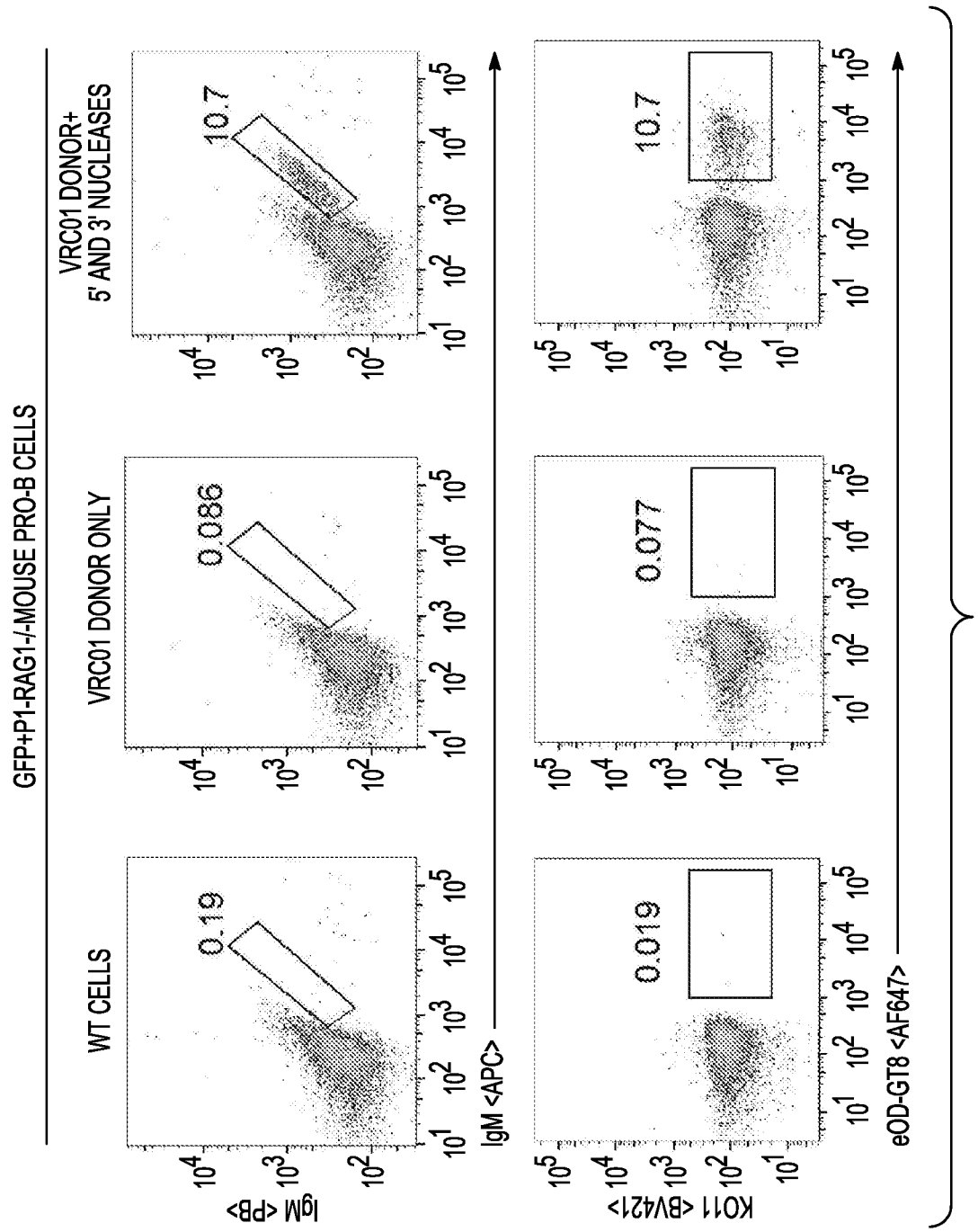

FIG. 8A-8B further illustrate introduction of both light and heavy chains of an antibody into the heavy chain locus of B cells. FIG. 8A shows a schematic diagram of the donor DNA for introducing both light and heavy chains of an antibody into the heavy chain locus of B cells by the universal BCR editing strategy. Light chain (in this case VRC01) DNA was used that included the constant region (shown in FIG. 8A to the left), followed by a furin cleavage and a ribosomal slip site, followed by the heavy chain VDJ.

FIG. 8B shows sorting of mouse pro-B cells 3 days post nucleofection with reagents designed to introduce the VRC01 at the HC variable locus using the universal BCR editing strategy. As shown, 10.7% of cells transfected with the VRC01 donor and two corresponding nucleases were IgM+ and bound to a probe that recognizes VRC01 'eOD-GT8' (but not to one where the VRC01 epitope is knocked out 'KO11'). WT or cells transfected with donor DNA only (without other reagents) are not recognized by these probes.

Example 7: Use of a Single Cut to Engineer a Ramos Heavy Chain Region

This example illustrates introduction of donor DNA at a single cut site, where the 5' end of the donor DNA is integrated through NHEJ and the 3' region is introduced by HDR.

Figure 9B:
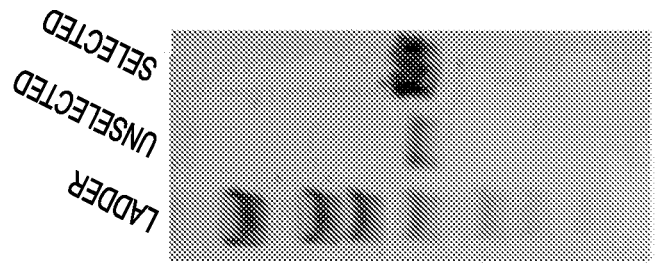
FIG. 9A-9B illustrate engineering of a Ramos heavy chain region using a single double-stranded cut where the 5' side of the donor DNA is introduced through NHEJ and the 3' region is introduced by HDR.
Figure 9A:
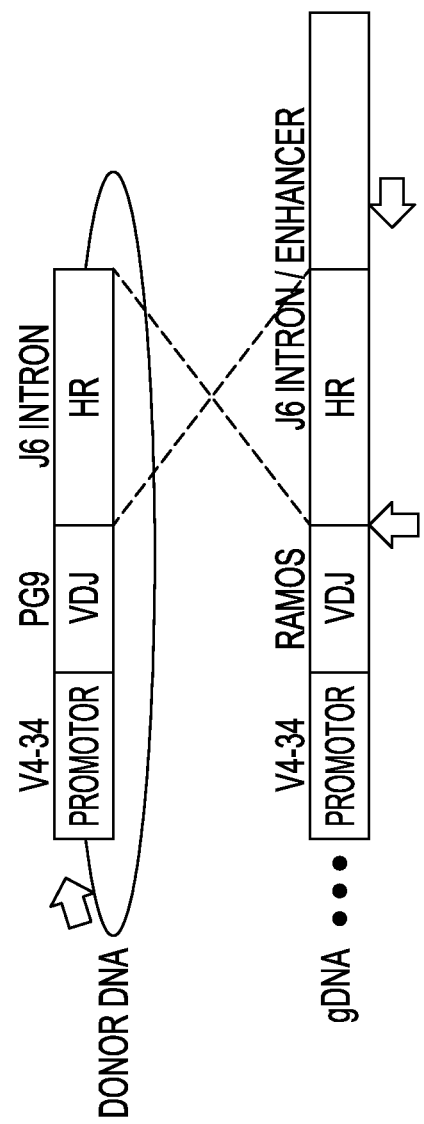

A schematic diagram provided in FIG. 9A illustrates donor DNA and genome structures as well as the engineering method. The genomic structure shown is the Ramos heavy chain region. The location of the nuclease cut site is depicted as vertical arrow pointing at the gDNA after the Ramos VDJ region. The homology region (HR) between the donor DNA and Ramos genome is also shown. The location of primers designed to amplify genome engineering events where the 5' side of the donor is introduced through NHEJ and the 3' region is introduced by HDR are shown as thick arrows with the forward primer located in the donor DNA plasmid backbone and the reverse compliment primer is located in the J6 intron/enhancer region downstream of the HR.

As shown in FIG. 9B, the amount of the engineered product is enriched in engineered cells selected for PG9 HC expression using H1V envelope probes. These PCR products were sequenced to confirm that the selected amplicon had the expected engineered structure.

Example 8: Engineering of Primary Human B cells to Express PG9 Antibodies

Primary human B cells were purified from human blood were nucleofected without (control) or with PG9 engineering plasmids using 2 ug V374 nuclease, 2 ug J6 nuclease and 2 ug PG9 VDJ donor plasmid/million cells. The cells were cultured and stained with HIV envelope-based probes to identify PG9HC chimeric B cell receptors on the cell surface.

Cells were analyzed by FACS. Live cells that bound to the PG9 probe but not to a mutant without the PG9 HC epitope (Pacific blue) were selected (FIG. 10A-10B). Of these, cells that bound to a second PG9 binding probe (FITC) were selected to remove non-specific binders (FIG. 10D-10E).

As illustrated in FIG. 10E, 0.13% of live cells transfected with engineering reagents appeared in the PG9 BCR gate (APC+, FITC+, Pacific blue-negative). However, only 0.02% of the unengineered controls appeared in the PG9 BCR gate (FIG. 10D). Hence, the methods provided herein can provide antibodies and antibody producing lines that have more than 5-fold greater affinity than control, unengineered antibodies and unengineered cell lines.

FIG. 10C shows amplification products from control unengineered cDNA samples (lanes 1 and 3) and from engineered cell cDNA samples (lanes 2 and 4). The primers used for the amplification were for PG9-IgM (lanes 1 and 2) or PG9-IgG1 (lanes 3 and 4). The bands seen in control (unengineered) cDNA lanes 1 and 3 were off target amplicons identified as RAD23 homolog A variant X1 and POU class 2 homeobox 2 respectively by next generation sequencing. The engineered cells yielded PG9-IgM (lane 2) or PG9-IgG (lane 4) PCR products as confirmed by next generation sequencing.

REFERENCES

1. Kepler, T. B. & Wiehe, K. Genetic and structural analyses of affinity maturation in the humoral response to HIV-1. *Immunol Rev* 275, 129-144, doi:10.1111/imr.12513 (2017).
2. Sui, J. et al. Structural and functional bases for broad-spectrum neutralization of avian and human influenza A viruses. *Nat Struct Mol Biol* 16, 265-273, doi:10.1038/nsmb.1566 (2009).
3. Heydarchi, B., Salazar-Quiroz, N. & Purcell, D. Broad Neutralizing Antibodies to HIV Env and Other Complex Viral Antigens from Vaccinated Cows. *Journal of Vaccines and Vaccination* 7 (2016).
4. Sok, D. L, K. M.; Vadnais, M.; Saye-Francisco, K.; Jardine, J. G.; Torres, J.; Berndsen, Z. T.; Kong, L.; Stanfield, R.; Ruiz, J; Ramos, A; Liang, C.; Chen, P. L.; Criscitiello, M. F.; Mwangi, W.; Wilson, I. A; Ward, A. B.; Smider, V. V.; Burton, D. R. Rapid elicitation of broadly neutralizing antibodies to HIV by envelope immunization in cows. *Nature (accepted for publication)* (2017).

Lee, J. H. et al. A Broadly Neutralizing Antibody Targets the Dynamic HIV Envelope Trimer Apex via a Long, Rigidified, and Anionic beta-Hairpin Structure. *Immunity* 46, 690-702, doi:10.1016/j.immuni.2017.03.017 (2017).

6. Feige, M. J., Hendershot, L. M. & Buchner, J. How antibodies fold. *Trends Biochem Sci* 35, 189-198, doi:10.1016/j.tibs.2009.11.005 (2010).
7. Doudna, J. A & Charpentier, E. Genome editing. The new frontier of genome engineering with CRISPR-Cas9. *Science* 346, 1258096, doi:10.1126/science.1258096 (2014).
8. Schwank, G. et al. Functional repair of CFTR by CRISPR/Cas9 in intestinal stem cell organoids of cystic fibrosis patients. *Cell stem cell* 13, 653-658, doi:10.1016/j.stem.2013.11.002 (2013).
9. Watson, C. T. & Breden, F. The immunoglobulin heavy chain locus: genetic variation, missing data, and implications for human disease. *Genes Immun* 13, 363-373, doi:10.1038/gene.2012.12 (2012).

Giudicelli, V., Chaume, D. & Lefranc, M. P. IMGT/GENE-DB: a comprehensive database for human and mouse immunoglobulin and T cell receptor genes. *Nucleic Acids Res* 33, D256-261, doi:10.1093/nar/gki010 (2005).

11. Gunilla B. Karlsson Hedstam, R. A M. F., Sanjay Phogat, Dennis R. Burton, Joseph Sodroski and Richard T. Wyatt The Challenges of eliciting neutralizing antibodies to HIV-1 and to influenza virus. *Nature Reviews Immunology* 6, 143-155 (2008).
12. McLellan, J. S. et al. Structure of HIV-1 gp120 V1/V2 domain with broadly neutralizing antibody PG9. *Nature* 480, 336-343, doi:10.1038/nature10696 (2011).
13. Julien, J. P. et al. Asymmetric recognition of the HIV-1 trimer by broadly neutralizing antibody PG9. *Proc Natl Acad Sci USA* 110, 4351-4356, doi:10.1073/pnas.1217537110 (2013).
14. Pejchal, R. et al. Structure and function of broadly reactive antibody PG16 reveal an H3 subdomain that mediates potent neutralization of HIV-1. *Proc Natl Acad Sci USA* 107, 11483-11488, doi:10.1073/pnas.1004600107 (2010).
15. deCamp, A et al. Global panel of HIV-1 Env reference strains for standardized assessments of vaccine-elicited neutralizing antibodies. *J Virol* 88, 2489-2507, doi:10.1128/JVI.02853-13 (2014).
16. Andrabi, R. et al. Identification of Common Features in Prototype Broadly Neutralizing Antibodies to HIV Envelope V2 Apex to Facilitate Vaccine Design. *Immunity* 43, 959-973, doi:10.1016/j.immuni.2015.10.014 (2015).
17. James E. Voss, R. A., Laura E. McCoy, Natalia de Val, Roberta P. Fuller, Terrence Messmer, Ching-Yao Su, Devin Sok, Salar N. Khan, Fernando Garces, Laura K. Pritchard, Richard T. Wyatt, Andrew B. Ward, Max Crispin, Ian A Wilson, Dennis R Burton. Elicitation of neutralizing antibodies targeting the V2 apex of the HIV Env trimer in a wild-type animal model. Cell Press under peer review (2017).
18. Carsetti, R., Kohler, G. & Lamers, M. C. Transitional B cells are the target of negative selection in the B cell compartment. *J Exp Med* 181, 2129-2140 (1995).
19. Russell, D. M. et al. Peripheral deletion of self-reactive B cells. *Nature* 354, 308-311, doi:10.1038/354308a0 (1991).

Goodnow, C. C., Crosbie, J., Jorgensen, H., Brink, R. A & Basten, A Induction of self-tolerance in mature peripheral B lymphocytes. *Nature* 342, 385-391, doi:10.1038/342385a0 (1989).

21. Borchert, G. M., Holton, N. W., Edwards, K. A, Vogel, L A & Larson, E. D. Histone H2A and H2B are monoubiquitinated at AID-targeted loci. *PLoS one* 5, e11641, doi:10.1371/journal.pone.0011641 (2010).
22. Montefiori, L et al. Extremely Long-Range Chromatin Loops Link Topological Domains to Facilitate a Diverse Antibody Repertoire. *Cell Rep* 14, 896-906, doi:10.1016/j.celrep.2015.12.083 (2016).
23. Ebert, A, Hill, L & Busslinger, M. Spatial Regulation of V-(D)J Recombination at Antigen Receptor Loci. *Adv Immunol* 128, 93-121, doi:10.1016/bs.ai.2015.07.006 (2015).
24. Jung, D., Giallourakis, C., Mostoslavsky, R. & Alt, F. W. Mechanism and control of V(D)J recombination at the immunoglobulin heavy chain locus. *Annu Rev Immunol* 24, 541-570, doi:10.1146/annurev.immunol.23.021704.115830 (2006).

Kato, T. et al. Creation of mutant mice with megabase-sized deletions containing custom-designed breakpoints by means of the CRISPR/Cas9 system. *Sci Rep* 7, 59, doi:10.1038/s41598-017-00140-9 (2017).

26. Ford, G. S., Yin, C. H., Barnhart, B., Sztam, K. & Covey, L R. CD40 ligand exerts differential effects on the expression of I gamma transcripts in subclones of an IgM+ human B cell lymphoma line. *J Immunol* 160, 595-605 (1998).
27. Sale, J. E. & Neuberger, M. S. TdT-accessible breaks are scattered over the immunoglobulin V domain in a constitutively hypermutating B cell line. *Immunity* 9, 859-869 (1998).
28. Baughn, L. B. et al. Recombinase-mediated cassette exchange as a novel method to study somatic hypermutation in Ramos cells. *MBio* 2, doi:10.1128/mBio.00186-11 (2011).
29. Ryan, J. L et al. Clonal evolution of lymphoblastoid cell lines. *Lab Invest* 86, 1193-1200, doi:10.1038/labinvest3700472 (2006).
30. Lim, W. A. & June, C. H. The Principles of Engineering Immune Cells to Treat Cancer. *Cell* 168, 724-740, doi:10.1016/j.cell.2017.01.016 (2017).
31. Wang, C. X. & Cannon, P. M. Clinical Applications of Genome Editing to HIV Cure. *AIDS Patient Care STDS* 30, 539-544, doi:10.1089/apc.2016.0233 (2016).
32. DeWitt, M. A et al. Selection-free genome editing of the sickle mutation in human adult hematopoietic stem/progenitor cells. *Sci Transl Med* 8, 360ra134, doi:10.1126/scitranslmed.aaf9336 (2016).

33 Shaw, K. L. et al. Clinical efficacy of gene-modified stem cells in adenosine deaminase-deficient immunodeficiency. *J Clin Invest* 127, 1689-1699, doi:10.1172/JCI90367 (2017).

34 Schumann, K. et al. Generation of knock-in primary human T cells using Cas9 ribonucleoproteins. *Proc Natl Acad Sci USA* 112, 10437-10442, doi:10.1073/pnas.1512503112 (2015).

Szeto, G. L. et al. Microfluidic squeezing for intracellular antigen loading in polyclonal B-cells as cellular vaccines. *Sci Rep* 5, 10276, doi:10.1038/srep10276 (2015).

36 June, C. H., Blazar, B. R. & Riley, J. L. Engineering lymphocyte subsets: tools, trials and tribulations. *Nature reviews. Immunology* 9, 704-716, doi:10.1038/nri2635 (2009).

37 Escolano, A. et al. Sequential Immunization Elicits Broadly Neutralizing Anti-HIV-1 Antibodies in Ig Knockin Mice. *Cell* 166, 1445-1458 e1412, doi:10.1016/j.cell.2016.07.030 (2016).

38 Sok, D. et al. Priming HIV-1 broadly neutralizing antibody precursors in human Ig loci transgenic mice. *Science* 353, 1557-1560, doi:10.1126/science.aah3945 (2016).

39 Seaman, M. S. et al. Tiered categorization of a diverse panel of HIV-1 Env pseudoviruses for assessment of neutralizing antibodies. *J Virol* 84, 1439-1452, doi: 10.1128/JVI.02108-09 (2010).

Walker, L M. et al. Broad neutralization coverage of HIV by multiple highly potent antibodies. *Nature* 477, 466-470, doi:10.1038/nature10373 (2011).

41 Lefranc, M. P. et al. IMGT®, the international ImMunoGeneTics information system® 25 years on. *Nucleic Acids Res* 43, D413-422, doi:10.1093/nar/gku1056 (2015).

42 Ran, F. A. et al. Genome engineering using the CRISPR-Cas9 system. *Nat Protoc* 8, 2281-2308, doi:10.1038/nprot.2013.143 (2013).

43 Mashiko, D. et al. Generation of mutant mice by pronuclear injection of circular plasmid expressing Cas9 and single guided RNA *Sci Rep* 3, 3355, doi:10.1038/srep03355 (2013).

44 McCoy, L E. et al. Holes in the Glycan Shield of the Native HIV Envelope Are a Target of Trimer-Elicited Neutralizing Antibodies. *Cell Rep* 16, 2327-2338, doi: 10.1016/j.celrep.2016.07.074 (2016).

Briney, B. et al. Tailored Immunogens Direct Affinity Maturation toward HIV Neutralizing Antibodies. *Cell* 166, 1459-1470 e1411, doi:10.1016/j.cell.2016.08.005 (2016).

46 Masella, A P., Bartram, A K., Truszkowski, J. M., Brown, D. G. & Neufeld, J. D. PANDAseq: paired-end assembler for illumina sequences. *BMC Bioinformatics* 13, 31, doi: 10.1186/1471-2105-13-31 (2012).

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements are intended to describe and summarize various embodiments of the invention according to the foregoing description in the specification.

Statements:
1. A method comprising:
   a. introducing double-stranded breaks on either side of a replaceable genomic segment within one or more B cells wherein the replaceable genomic segment encodes a recipient immunoglobulin variable region peptide;
   b. replacing the replaceable genomic segment with a segment of a donor nucleic acid, where the segment of a donor nucleic acid encodes a donor immunoglobulin variable peptide with at least one amino acid difference relative to the recipient immunoglobulin variable region peptide, to thereby generate a population of B cells comprising one or more modified B cells; and
   c. selecting one or more modified B cells from the population of B cells, each modified B cell with at least one modified immunoglobulin gene comprising a segment of a donor nucleic acid;
   to thereby generate one or more separate modified B cell(s) that express modified B cell receptors having high affinity for the antigen.
2. A method comprising:
   a. introducing double-stranded breaks on either side of a replaceable genomic segment within one or more antibody producing cell wherein the replaceable genomic segment encodes a recipient immunoglobulin variable region peptide;
   b. replacing the replaceable genomic segment with a segment of a donor nucleic acid, where the segment of a donor nucleic acid encodes a promoter, donor immunoglobulin variable peptide with at least one amino acid difference relative to the recipient immunoglobulin variable region peptide, or a combination thereof, to thereby generate a population of antibody producing cells comprising one or more modified antibody producing cells: and
   c. selecting one or more modified antibody producing cells from the population of antibody producing cells, each modified antibody producing cell with at least one modified immunoglobulin gene comprising a segment of a donor nucleic acid.
3. A method comprising
   a. introducing a single double-stranded cut within a genomic segment that is adjacent to a recipient immunoglobulin variable region peptide in one or more antibody producing cells;
   b. inserting a donor nucleic acid at the double-stranded cut site, where the donor nucleic acid includes a promoter, encodes a donor immunoglobulin variable peptide with at least one amino acid difference relative to the recipient immunoglobulin variable region peptide, or a combination thereof, to thereby generate a population of B cells comprising one or more modified antibody producing cells; and
   c. selecting one or more modified antibody producing cells from the population of cells, each modified antibody producing cell with at least one modified immunoglobulin gene comprising a segment of a donor nucleic acid.
4. The method of statement 1, 2, or 3, wherein the one or more cells are B cells, primary B cells, immortalized B cells, or a combination thereof.
5. The method of claim 1-3 or 4, wherein the genomic segment encodes an immunoglobulin light chain, or an immunoglobulin heavy chain.

6. The method of claim 1-3 or 4, wherein the donor DNA encodes an immunoglobulin light chain and an immunoglobulin heavy chain.
7. The method of statement 1-5 or 6, wherein the donor DNA encodes a complete or partial immunoglobulin variable region from a broadly neutralizing anti-HIV immunoglobulin.
8. The method of statement 1-6 or 7, wherein the modified antibody producing cell(s) produce antibodies or B cell receptors that selectively bind to at least one HIV antigen.
9. The method of statement 1-7 or 8, further comprising administering (e.g., engrafting) the modified antibody producing cell(s) to a subject.
10. The method of statement 1-8 or 9, further comprising:
    d. culturing one or more of the modified cells for a time and under conditions for inducing activation-induced cytidine deaminase (AID) activity in one or more modified cells;
    e. selecting at least one modified cell that expresses an engineered immunoglobulin, an engineered B cell receptor, or a combination thereof with high affinity for an antigen; and
    f. optionally repeating steps (d) and (e) two to 100 times;
    to thereby generate one or more separate engineered cell(s) that expresses engineered immunoglobulins, engineered B cell receptors, or a combination thereof having high affinity for the antigen.
11. The method of statement 1-9 or 10, further comprising culturing one or more of the modified cells or engineered cells for a time and under conditions for hypermutation to occur within a modified immunoglobulin genomic locus.
12. The method of statement 1-10 or 11, which generates one or more engineered B cells with a variant engineered B cell receptor.
13. The method of statement 1 to 11 or 12, further comprising separately culturing at least one engineered cell to generate a population of engineered cells.
14. The method of statement 1 to 12 or 13, further comprising separately culturing at least one engineered B cell to generate a population of engineered B cells and administering the population to a mammalian subject.
15. The method of statement 1 to 13 or 14, further comprising administering the engineered B cells to a mammalian subject, where the B cells are administered to the subject at the same time or at a separate time as a vaccine (e.g., a vaccine comprising an antigen).
16. The method of statement 1 to 14 or 15, wherein the modified immunoglobulin comprises at least one modified immunoglobulin chain expressed from a modified immunoglobulin heavy chain genomic locus, and an immunoglobulin light chain expressed from an endogenous immunoglobulin light chain genomic locus.
17. The method of statement 1 to 15 or 16, wherein the modified immunoglobulin comprises at least one modified immunoglobulin chain expressed from a modified immunoglobulin light chain genomic locus, and an immunoglobulin heavy chain expressed from an endogenous immunoglobulin light chain genomic locus.
18. The method of statement 1 to 16 or 17, wherein the modified immunoglobulin is an IgM modified immunoglobulin.
19. The method of statement 1 to 17 or 18, wherein the modified immunoglobulin is an IgG modified immunoglobulin.
20. The method of statement 1 to 18 or 19, wherein the replaceable genomic segment is flanked by one or two regions of sequence identity or complementarity that are at least about 15, or at least about 16, or at least about 17, or at least about 18, or at least about 19, or at least about 20, or at least about 21, or at least about 22, or at least about 23, or at least about 24, or at least about 25, or at least about 50, or at least about 100, or at least about 200, or at least about 300, or at least about 400, or at least about 500, or at least about 1000 nucleotides in length.
21. The method of statement 1 to 19 or 20, wherein the replaceable genomic segment comprises a VDJ segment or a VDJ/VJ segment.
22. The method of statement 1 to 20 or 21, wherein the replaceable genomic segment is flanked by one or two homology regions having at least 95%, or at least 96%, or at least 97%, or at least 98%, or at least 99%, or at least 99.5% sequence identity or complementarity to regions of the donor nucleic acids.
23. The method of statement 1 to 21 or 22, wherein the replaceable genomic segment is flanked by one or two homology regions that are near or can include a genomic 5' nuclease cut site (e.g., at V4-69, V7-81 or V3-74 5' UTR), a 3' cut site (e.g., at J7 or in the intron after J6).
24. The method of statement 1 to 22 or 23, wherein the donor nucleic acid comprises a region of divergent DNA, where the divergent DNA has a sequence that is homologous but not identical to the replaceable genomic segment sequence.
25. The method of statement 1 to 23 or 24, wherein the donor nucleic acid comprises a region of divergent DNA flanked one or two homology regions of sequence identity or complementarity relative to one or two segments of the recipient immunoglobulin variable region, where the one or two homology regions are at least about 15, or at least about 16, or at least about 17, or at least about 18, or at least about 19, or at least about 20, or at least about 21, or at least about 22, or at least about 23, or at least about 24, or at least about 25 nucleotides in length.
26. The method of statement 1 to 24 or 25, wherein the donor nucleic acid comprises one or two regions of sequence identity or complementarity that have at least 95%, or at least 96%, or at least 97%, or at least 98%, or at least 99%, or at least 99.5% sequence identity or complementarity to one or two regions of the recipient immunoglobulin variable genomic segment.
27. The method of statement 1 to 25 or 26, wherein the wherein the donor nucleic acid has a segment that has at least 30%, or at least 35%, or at least 40%, or least 45%, or at least 50%, at least 55%, or at least 60%, or at least 65%, or least 70%, or at least 75%, or at least 80%, or at least 85%, or at least 90%, or at least 95%, or at least 97%, or at least 98%, or at least 99%, or at least 99.5% sequence identity to any of SEQ ID NO:1-41, 48, 53, or 60.
28. The method of statement 1 to 26 or 27, wherein the wherein the donor nucleic acid has at least 30%, or at least 35%, or at least 40%, or least 45%, or at least 50%, at least 55%, or at least 60%, or at least 65%, or least 70%, or at least 75%, or at least 80%, or at least 85%, or at least 90%, or at least 95%, or at least 97%, or at least 98%, or at least 99%, or at least 99.5% sequence identity to SEQ ID NO:41, 48, 53, or 60.
29. The method of statement 1 to 27 or 28, wherein the donor genomic segment is less than about 5000, or less than about 4000, or less than about 3000, or less than about 2000, or less than about 1000, or less than about 500 nucleotides in length.
30. The method of statement 1 to 28 or 29, wherein at least one of the modified cells or at least one of the engineered cells expresses a modified immunoglobulin variable peptide or polypeptide with a sequence that has at least one amino acid difference compared to the recipient immunoglobulin variable region peptide or polypeptide.
31. The method of statement 1 to 29 or 30, wherein at least one of the modified cells or at least one of the engineered cells expresses a modified immunoglobulin variable peptide or polypeptide with a sequence that has at least one amino acid difference compared to the donor immunoglobulin variable peptide or polypeptide.
32. The method of statement 1 to 30 or 31, wherein the modified B cells, the modified antibody producing cells, or the engineered cells produce antibodies with specificities different from natural human repertoires of immunoglobulins.
33. The method of statement 1 to 31 or 32, wherein the modified B cells, the modified antibody producing cells, or the engineered cells express B cell receptors with specificities different from natural human repertoires of B cell receptors.
34. The method of statement 10 to 32 or 33, wherein the engineered cells produce antibodies with higher affinity and/or higher selectivity than the modified B cells, or the modified antibody producing cells of step (c).
35. The method of statement 10 to 32 or 34, wherein the engineered antibody producing cells produce neutralizing antibodies or neutralizing B cell receptor response where an immunogen alone cannot elicit protective responses from natural human repertoires of immunoglobulins.
36. A method comprising:
    a. introducing one or two double-stranded breaks on either side of a replaceable genomic segment within one or more primary or immortalized B cells wherein the replaceable genomic segment encodes a recipient immunoglobulin variable region peptide;
    b. replacing the replaceable genomic segment with a segment of a donor nucleic acid, where the segment of a donor nucleic acid encodes a donor immunoglobulin variable peptide with at least one amino acid difference relative to the recipient immunoglobulin variable region peptide, to thereby generate a population of B cells comprising one or more modified B cells;
    c. selecting one or more modified B cells for expression of antibodies with affinity to an antigen of interest and establishing separate modified B cell populations from the one or more selected modified B cells;
    d. culturing one or more modified B cell populations for a time and under conditions for activation-induced cytidine deaminase (AID) activity in one or more modified B cells in the modified B cell populations;
    e. selecting at least one modified B cell that expresses an engineered B cell receptor with higher affinity for an antigen than the primary or immortalized B cell of step (a) from one or more of the B cell populations of step (d) and separately establishing therefrom a second series of modified B cell populations; and
    f. optionally repeating steps (d) and (e) two to 100 times;
    g. sequencing one or more immunoglobulin genomic segments of modified B cells from at least one of the second series of modified B cell populations to identify one or more genomic modifications correlated with antibody affinity for the antigen of interest: and
    h. engineering at least one primary antibody producing cell to have the one or more genomic modifications correlated with antibody affinity for the antigen of interest, thereby generating at least one engineered primary antibody producing cell.
37. The method of statement 36, wherein the donor DNA encodes an immunoglobulin variable region from a broadly neutralizing anti-HIV immunoglobulin.
38. The method of statement 36 or 37, further comprising administering a population of the one engineered primary antibody producing cells to a subject.
39. The method of statement 36, 37 or 38, further comprising administering a population of the one or more engineered primary antibody producing cells to a subject, where the population of the one or more engineered primary antibody producing cells are administered to the subject at the same time or at a separate time as a vaccine.
40. The method of statement 1-37 or 38, further comprising isolating modified immunoglobulins from the modified cells or from the engineered cells.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential.

The methods and processes illustratively described herein suitably may be practiced in differing orders of steps, and the methods and processes are not necessarily restricted to the orders of steps indicated herein or in the claims. As used herein and in the appended claims, the singular forms "a," "an," and "the" include plural reference unless the context clearly dictates otherwise. Thus, for example, a reference to "a nucleic acid" or "a promoter" includes a plurality of such nucleic acids or promoters (for example, a solution of nucleic acids or a series of promoters), and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

What is claimed:

1. A method of producing modified antibody producing cells, said method comprising:
   (a) introducing only one double-stranded cut on a 3' side of a genomic segment within one or more antibody producing cells, wherein the genomic segment comprises sequences encoding a recipient immunoglobulin variable region, wherein said cut at the 3' side is located at a 3' side of the sequences encoding the recipient immunoglobulin variable region, downstream to a immunoglobulin Joining (J) gene and upstream of a constant region gene; and
   (b) inserting a donor nucleic acid into the cut of the genomic segment, said donor nucleic acid comprises a V gene promoter, a replacement variable region, and a J gene splice site followed by a sequence homologous to a J gene intron sequence to guide incorporation of the donor nucleic acid to said cut, wherein said donor nucleic acid comprises a J gene splice donor sequence located 3' to sequences encoding said replacement variable region and is post-transcriptionally spliced to a downstream endogenous constant region gene, thereby generating a population of cells comprising one or more modified antibody producing cells, wherein each modified antibody producing cell comprises the replacement variable region derived from a segment of the donor nucleic acid.

2. The method of claim 1, wherein the one or more antibody producing cells are primary B cells.

3. The method of claim 1, wherein the one or more antibody producing cells are immortalized B cells.

4. The method of claim 1, wherein the one or more modified antibody producing cells express modified B cell receptors encoded by the donor nucleic acid.

5. The method of claim 1, wherein the genomic segment comprises an immunoglobulin light chain variable region, or an immunoglobulin heavy chain variable region.

6. The method of claim 1, wherein the genomic segment comprises at least a portion of a VDJ segment or at least a portion of a VJ segment.

7. The method of claim 1, wherein the donor nucleic acid comprises sequences encoding one or both of an immunoglobulin light chain variable region (VJ) and an immunoglobulin heavy chain variable region (VDJ).

8. The method of claim 1, wherein the donor nucleic acid encodes an immunoglobulin variable region from a broadly neutralizing anti-HIV immunoglobulin.

9. The method of claim 1, wherein the modified antibody producing cell(s) produce antibodies or B cell receptors that selectively bind to at least one HIV antigen.

10. The method of claim 1, further comprising:
    (c) culturing one or more of the modified antibody producing cells for a time and under conditions for induction of activation-induced cytidine deaminase (AID) activity in said modified antibody producing cells;
    (d) selecting at least one modified antibody producing cell that expresses an engineered antibody or an engineered B cell receptor with high affinity for an antigen; and
    (e) optionally repeating steps (c) and (d) two to 100 times; thereby generating one or more modified antibody producing cells that express engineered antibodies or engineered B cell receptors with high affinity for the antigen.

11. The method of claim 10, wherein the modified antibody producing cells produce or express antibodies with higher affinity and/or higher selectivity than those antibodies produced by the modified antibody producing cells before mutation by AID activity.

12. The method of claim 4, wherein the modified B cell receptors have specificities different from those B cell receptors expressed by the antibody producing cells.

13. The method of claim 10, wherein the modified antibody producing cells produce engineered antibodies or engineered B cell receptors that cannot be readily elicited from natural human repertoires of immunoglobulins.

14. The method of claim 1, wherein the donor nucleic acid is flanked on one or both 5' and 3' ends thereof by homology arms that allow for specific insertion of said donor nucleic acid by homologous recombination, wherein said insertion of said donor nucleic acid comprises insertion at or downstream to the Ig J gene.

15. A population of modified antibody producing cells produced by the method of claim 1.

16. A method of treating a subject infected with a virus or a pathogen, comprising administering to said subject the population of modified antibody producing cells of claim 15.

* * * * *